(12) United States Patent
Barta et al.

(10) Patent No.: US 6,696,449 B2
(45) Date of Patent: Feb. 24, 2004

(54) SULFONYL ARYL HYDROXAMATES AND THEIR USE AS MATRIX METALLOPROTEASE INHIBITORS

(75) Inventors: Thomas E. Barta, Evanston, IL (US); Daniel P. Becker, Glenview, IL (US); Louis J. Bedell, Prospect Heights, IL (US); Gary A. DeCrescenzo, St. Charles, MO (US); John N Freskos, Clayton, MO (US); Daniel P. Getman, Chesterfield, MO (US); Joseph J. McDonald, Wildwood, MO (US); Brent V. Mischke, Defiance, MO (US); Shashidhar N. Rao, Saint Louis, MO (US); Clara I. Villamil, Glenview, IL (US)

(73) Assignee: Pharmacia Corporation, St. Louis, MO (US)

(*) Notice: Subject to any disclaimer, the term of this patent is extended or adjusted under 35 U.S.C. 154(b) by 0 days.

(21) Appl. No.: 09/909,227

(22) Filed: Jul. 19, 2001

(65) Prior Publication Data

US 2003/0073845 A1 Apr. 17, 2003

Related U.S. Application Data

(63) Continuation-in-part of application No. 09/569,034, filed on May 11, 2000, which is a continuation-in-part of application No. 09/310,813, filed on May 12, 1999, now abandoned, which is a continuation-in-part of application No. 09/230, 209, filed as application No. PCT/US98/04300 on Mar. 4, 1998, now Pat. No. 6,380,258, application No. 09/909,227, which is a continuation-in-part of application No. 09/728, 408, filed on Dec. 1, 2000, which is a continuation of application No. 09/310,813, filed on May 12, 2000, now abandoned.

(60) Provisional application No. 60/035,182, filed on Mar. 4, 1997.

(51) Int. Cl.$^7$ ..................... A61K 31/496; C07D 241/04

(52) U.S. Cl. ........................ 514/255.03; 514/252.12; 514/252.18; 514/309; 514/312; 514/331; 514/469; 514/575; 544/360; 544/383; 546/141; 546/153; 546/233; 546/234; 546/331

(58) Field of Search ............... 514/255.03, 252.12, 514/252.18, 309, 312, 331, 469, 575; 544/360, 383; 546/141, 153, 233, 234, 331

(56) References Cited

U.S. PATENT DOCUMENTS

| | | | |
|---|---|---|---|
| 4,148,801 A | 4/1979 | Santilli et al. | 548/131 |
| 4,595,700 A | 6/1986 | Donald et al. | 514/616 |
| 5,103,014 A | 4/1992 | Musser et al. | 548/204 |
| 5,424,279 A | 6/1995 | Sugai et al. | 504/282 |
| 5,455,258 A | 10/1995 | MacPherson et al. | 514/357 |
| 5,506,242 A | 4/1996 | MacPherson et al. | 514/336 |
| 5,552,419 A | 9/1996 | MacPherson et al. | 514/357 |
| 5,646,167 A | 7/1997 | MacPherson et al. | 514/357 |
| 5,932,595 A | 8/1999 | Bender | 514/317 |
| 6,013,649 A | 1/2000 | Freskos et al. | 514/237.8 |
| 6,118,001 A | 9/2000 | Owen et al. | 546/229 |
| 6,380,258 B2 | 4/2002 | Bedell et al. | 514/575 |
| 6,465,468 B1 * | 10/2002 | Baxter et al. | 514/252.12 |

FOREIGN PATENT DOCUMENTS

| | | | | |
|---|---|---|---|---|
| DE | 3738890 | 5/1989 | | |
| EP | 0 780 386 | 6/1997 | | C07D/309/08 |
| EP | 0 994 104 a1 | 4/2000 | | C07C/317/44 |
| EP | 1 081 137 A1 | 3/2001 | | C07D/211/96 |
| EP | 853255 | 5/2001 | | G03C/1/498 |
| WO | WO 90/05719 | 5/1990 | | C07C/323/62 |

(List continued on next page.)

OTHER PUBLICATIONS

Brown, P.D., "Synthetic Inhibitors of Matrix Metalloproteinases," in *Matrix Metalloproteinases*, pp. 243–261 (Edited by Parks, W.C. & Mecham, R.P., Academic Press, San Diego, CA (1998)).

Tang, B.L., "ADAMTS: A Novel Family of Extracellular Matrix Proteases," *Int'l Journal of Biochemistry & Cell Biology*, 33 pp. 33–44 (2001).

Woessner, J.F., "The Matrix Metalloprotease Family" in *Matrix Metalloproteinases*, pp. 1–14 (Edited by Parks, W.C. & Mecham, R.P., Academic Press, San Diego, CA (1998)).

(List continued on next page.)

*Primary Examiner*—Ceila Chang
(74) *Attorney, Agent, or Firm*—Julie M. Chappell; David Gryte

(57) ABSTRACT

This invention is directed to sulfonyl aromatic hydroxamic acid compounds and salts thereof that, inter alia, inhibit matrix metalloprotease (MMP) activity and/or aggrecanase activity. In some particularly preferred embodiments, the compound corresponds in structure to one of the following formulas:

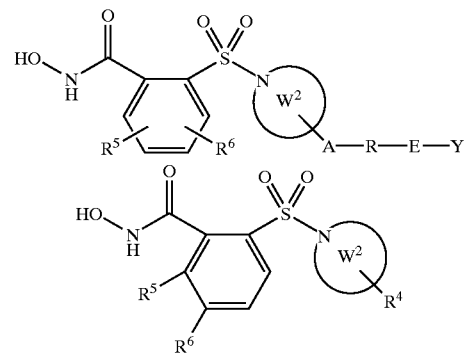

wherein $W^2$, the R groups, and —A—R—E—Y are described in more detail in Applicants' specification. This invention also is directed to a process that comprises administering such a compound or pharmaceutically acceptable salt thereof to a host animal having a condition associated with MMP activity.

39 Claims, No Drawings

FOREIGN PATENT DOCUMENTS

| | | | |
|---|---|---|---|
| WO | WO 93/20047 | 10/1993 | C07C/317/44 |
| WO | WO 94/02466 | 2/1994 | C07D/221/14 |
| WO | WO 94/24140 | 10/1994 | C07H/13/04 |
| WO | WO 95/09841 | 4/1995 | C07C/323/60 |
| WO | WO 95/13289 | 5/1995 | C07K/5/062 |
| WO | WO 95/29892 | 11/1995 | C07D/207/327 |
| WO | WO 96/06074 | 2/1996 | C07C/259/06 |
| WO | WO 96/11209 | 4/1996 | C07K/5/06 |
| WO | WO 97/20824 | 6/1997 | C07D/241/04 |
| WO | WO 97/24117 | 7/1997 | A61K/31/19 |
| WO | WO 97/49679 | 12/1997 | C07C/317/44 |
| WO | WO 98/06705 | 2/1998 | |
| WO | WO 98/37877 | 9/1998 | A61K/31/16 |
| WO | WO 98/38859 | 9/1998 | A01N/37/28 |
| WO | WO 99/09000 | 2/1999 | C07C/235/00 |
| WO | WO 99/25687 | 5/1999 | C07D/211/66 |
| WO | WO 00/37107 | 6/2000 | A61K/45/06 |
| WO | WO 00/46221 | 8/2000 | C07D/405/12 |
| WO | WO 00/50396 | 8/2000 | C07D/211/66 |
| WO | 00/56704 | * 9/2000 | |
| WO | WO 00/56704 | 9/2000 | C07C/311/21 |
| WO | WO 00/59874 | 10/2000 | C07D/259/06 |
| WO | WO 00/69819 | 11/2000 | C07D/211/16 |
| WO | WO 00/69821 | 11/2000 | C07D/211/66 |
| WO | WO0185680 | 11/2001 | A01N/37/28 |

OTHER PUBLICATIONS

Young, (1995) CA 123:83233.

Cramp, (1998) CA 128:208524.

Fujisawa, (1999) CA 131:73975.

Lombardino, XP-002179389—*Preparation of Substituted 1,2–Benzoisothiazolin–3–one 1, 1–Dioxides (o–Benzoic Sulfimides)* J. Org. Chem. vol. 36, No. 13, (1971), pp. 1843–1845.

Zawisza and Malinka, XP-002179391 *A Novel System: 2H–Pyrido [3,2–e]–1,2–Thiazine–1, 1–Dioxide. Synthesis and Properties of Some Derivatives,* II Farmaco—Ed. Sc. vol. 41, fasc. 10, (1986)pp. 819–826.

Arranz et al., XP-001024950—*Synthesis and Anti–HIV Activity of 1,1,3–Trioxo–2H,4H–thieno[3,4–e]thiadiazines (TTDs): A New Family of HIV–1 Specific Non–Nucleoside Reverse Transcriptase Inhibitors,* Bioorganic & Medicinal Chemistry 7 (1999), pp. 2811–2822.

Arranz et al., XP-002179390—*Novel 1, 1,3–Trioxo–2H, 4H–thieno[3,4–e][1,2,4]thiadiazine Derivatives as Non–Nucleoside Reverse Transcriptase Inhibitors That Inhibit Human Immunodeficiency Virus Type 1 Replication,* J. Med. Chem. (1998), 41, pp. 4109–4117.

Barta et al., *Synthesis and Activity of Selective MMP Inhibitors with an Aryl Backbone,* Bioorganic & Medicinal Chemistry Letters 10 (2000), pp 2815–2817.

Cremlyn et al., *Some heterocyclic sulfonyl chlorides and derivatives,* J. Heterocycl. Chem. 18(5):997–1006 (1981).

Denis et al., *Matrix metalloproteinase inhibitors: Present achievements and future prospects,* Invest. New Drugs, 15:175–185 (1997).

Gearing et al., *Processing of tumour necrosis factor–α precursor by metalloproteinases,* NATURE, 370:555–557 (1994).

Hannout et al., *Synthesis and screening of some new methyl salicylate–5–sulfonamides containing active units as analgesic agents,* J. Serb. Chem. Soc. 53(7):353–361 (1988).

Kenyon et al., *A model of angiogenesis in the mouse cornea,* Invest. Ophthalmol. Vis. Sci., 37(8):1625–1632 (1996).

Knight et al., *A novel coumarin–labelled peptide for sensitive continuous assays of the matrix metalloproteinases,* FEBS Lett. 296(3):263–266 (1992).

McGeehan et al., *Regulation of tumour necrosis factor–α processing by a metalloproteinase inhibitor,* NATURE, 370:558–561 (1994).

Mitchell et al., *Cloning, expression, and type II collagenolytic activity of matrix metalloproteinase–13 from human osteoarthritic cartilage,* J. Clin. Invest., 97(3):761–768 (1996).

Morphy et al., *Matrix metalloproteinase inhibitors: current status,* Cur. Med. Chem. 2:743–762 (1995).

Rasmussen et al., *Matrix metalloproteinase inhibition as a novel anticancer strategy: a review with special focus on batimastat and marimastat,* Pharmacol. Ther., 75(1):69–75 (1997).

Reboul et al., *The new collagenase, collagnease–3, is expressed and synthesized by human chondrocytes but not by synoviocytes,* J. Clin. Invest., 97(9):2011–2019 (1996).

Schwartz et al., *Synthetic inhibitors of bacterial and mammalian interstitial collagenases,* Prog. in Med. Chem., 29:271–334 (1992).

* cited by examiner

SULFONYL ARYL HYDROXAMATES AND THEIR USE AS MATRIX METALLOPROTEASE INHIBITORS

CROSS-REFERENCE TO RELATED PATENT APPLICATIONS

This patent is a continuation-in-part of U.S. patent application Ser. No. 09/569,034 (filed May 11, 2000), which, in turn, is a continuation-in-part of U.S. patent application Ser. No. 09/310,813 (filed May 12, 1999) now abandoned, which, in turn, is a continuation-in-part of U.S. patent application Ser. No. 09/230,209 (filed Jun. 24, 1999), which, in turn, is an application filed nationally from PCT Application No. PCT/US98/04300 (filed Mar. 4, 1998, published Sep. 11, 1998 as WIPO Int'l Publ. No. WO 98/38859) now U.S. Pat. No. 6,380,258, which, in turn, claims priority to U.S. Provisional Patent Application Serial No. 60/035,182 (filed Mar. 4, 1997). This patent also is a continuation-in-part of U.S. patent application Ser. No. 09/728,408 (filed Dec. 1, 2000), which, in turn, is a continuation of U.S. patent application Ser. No. 09/310,813 filed May 12, 2000 abandoned. The entire texts of all the above related patent applications are incorporated by referenced into this patent.

FIELD OF THE INVENTION

This invention is directed generally to proteinase (also known as "protease") inhibitors, and, more particularly, to sulfonyl aryl hydroxamates (also known as "sulfonyl aryl hydroxamic acids") that, inter alia, inhibit matrix metalloproteinase (also known as "matrix metalloprotease" or "MMP") and/or aggrecanase activity. This invention also is directed to compositions of such inhibitors, intermediates for the syntheses of such inhibitors, methods for making such inhibitors, and methods for preventing or treating conditions associated with MMP activity, particularly pathological conditions.

BACKGROUND OF THE INVENTION

Connective tissue is a required component of all mammals. It provides rigidity, differentiation, attachments, and, in some cases, elasticity. Connective tissue components include, for example, collagen, elastin, proteoglycans, fibronectin, and laminin. These biochemicals make up (or are components of) structures, such as skin, bone, teeth, tendon, cartilage, basement membrane, blood vessels, cornea, and vitreous humor.

Under normal conditions, connective tissue turnover and/or repair processes are in equilibrium with connective tissue production. Degradation of connective tissue is carried out by the action of proteinases released from resident tissue cells and/or invading inflammatory or tumor cells.

Matrix metalloproteinases, a family of zinc-dependent proteinases, make up a major class of enzymes involved in degrading connective tissue. Matrix metalloproteinases are divided into classes, with some members having several different names in common use. Examples are: MMP-1 (also known as collagenase 1, fibroblast collagenase, or EC 3.4.24.3); MMP-2 (also known as gelatinase A, 72 kDa gelatinase, basement membrane collagenase, or EC 3.4.24.24), MMP-3 (also known as stromelysin 1 or EC 3.4.24.17), proteoglycanase, MMP-7 (also known as matrilysin), MMP-8 (also known as collagenase II, neutrophil collagenase, or EC 3.4.24.34), MMP-9 (also known as gelatinase B, 92 kDa gelatinase, or EC 3.4.24.35), MMP-10 (also known as stromelysin 2 or EC 3.4.24.22), MMP-1 I (also known as stromelysin 3), MMP-12 (also known as metalloelastase, human macrophage elastase or HME), MMP-13 (also known as collagenase 111), and MMP-14 (also known as MT1-MMP or membrane MMP). See, generally, Woessner, J. F., "The Matrix Metalloprotease Family" in *Matrix Metalloproteinases*, pp. 1–14 (Edited by Parks, W. C. & Mecham, R. P., Academic Press, San Diego, Calif. 1998).

Excessive breakdown of connective tissue by MMPs is a feature of many pathological conditions. Inhibition of MMPs therefore provides a control mechanism for tissue decomposition to prevent and/or treat these pathological conditions. Such pathological conditions generally include, for example, tissue destruction, fibrotic diseases, pathological matrix weakening, defective injury repair, cardiovascular diseases, pulmonary diseases, kidney diseases, liver diseases, bone diseases, and diseases of the central nervous system. Specific examples of such conditions include, for example, rheumatoid arthritis, osteoarthritis, septic arthritis, multiple sclerosis, a decubitis ulcer, corneal ulceration, epidermal ulceration, gastric ulceration, tumor metastasis, tumor invasion, tumor angiogenesis, periodontal disease, liver cirrhosis, fibrotic lung disease, emphysema, otosclerosis, atherosclerosis, proteinuria, coronary thrombosis, dilated cardiomyopathy, congestive heart failure, aortic aneurysm, epidermolysis bullosa, bone disease, Alzheimer's disease, and defective injury repair (e.g., weak repairs, adhesions such as post-surgical adhesions, and scarring).

Matrix metalloproteinases also are involved in the biosynthesis of tumor necrosis factors (TNFs). Tumor necrosis factors are implicated in many pathological conditions. TNF-$\alpha$, for example, is a cytokine that is presently thought to be produced initially as a 28 kD cell-associated molecule. It is released as an active, 17 kD form that can mediate a large number of deleterious effects in vitro and in vivo. TNF-$\alpha$ can cause and/or contribute to the effects of inflammation (e.g., rheumatoid arthritis), autoimmune disease, graft rejection, multiple sclerosis, fibrotic diseases, cancer, infectious diseases (e.g., malaria, mycobacterial infection, meningitis, etc.), fever, psoriasis, cardiovascular diseases (e.g., post-ischemic reperfusion injury and congestive heart failure), pulmonary diseases, hemorrhage, coagulation, hyperoxic alveolar injury, radiation damage, and acute phase responses like those seen with infections and sepsis and during shock (e.g., septic shock and hemodynamic shock). Chronic release of active TNF-$\alpha$ can cause cachexia and anorexia. TNF-$\alpha$ also can be lethal.

Inhibiting TNF (and related compounds) production and action is an important clinical disease treatment. Matrix metalloproteinase inhibition is one mechanism that can be used. MMP inhibitors (e.g., inhibitors of collagenase, stromelysin, and gelatinase), for example, have been reported to inhibit TNF-$\alpha$ release. See, e.g., Gearing et al. *Nature*, 376, 555–557 (1994). See also, McGeehan et al. See also, *Nature* 376, 558–561 (1994). MMP inhibitors also have been reported to inhibit TNF-$\alpha$ convertase, a metalloproteinase involved in forming active TNF-$\alpha$. See, e.g., WIPO Int'l Pub. No. WO 94/24140. See also, WIPO Int'l Pub. No. WO 94/02466. See also, WIPO Int'l Pub. No. WO 97/20824.

Matrix metalloproteinases also are involved in other biochemical processes in mammals. These include control of ovulation, post-partum uterine involution, possibly implantation, cleavage of APP ($\beta$-amyloid precursor protein) to the ainyloid plaque, and inactivation of ($\alpha_1$-protease inhibitor (($\alpha_1$-PI). Inhibiting MMPs therefore may be, for example, a mechanism to control of fertility. In addition, increasing and maintaining the levels of an endogenous or administered serine protease inhibitor (e.g., $\alpha_I$-PI) supports the treatment and prevention of pathological conditions such as emphysema, pulmonary diseases, inflammatory diseases, and diseases of aging (e.g., loss of skin or organ stretch and resiliency).

Numerous metalloproteinase inhibitors are known. See, generally, Brown, P. D., "Synthetic Inhibitors of Matrix Metalloproteinases," in *Matrix Metalloproteinases,* pp. 243–61 (Edited by Parks, W. C. & Mecham, R. P., Academic Press, San Diego, Calif. 1998).

Metalloproteinase inhibitors include, for example, natural biochemicals, such as tissue inhibitor of metalloproteinase (TIMP), ($\alpha_2$-macroglobulin, and their analogs and derivatives. These are high-molecular-weight protein molecules that form inactive complexes with metalloproteinases.

A number of smaller peptide-like compounds also have been reported to inhibit metalloproteinases. Mercaptoamide peptidyl derivatives, for example, have been reported to inhibit angiotensin converting enzyme (also known as ACE) in vitro and in vivo. ACE aids in the production of angiotensin II, a potent pressor substance in mammals. Inhibiting ACE leads to lowering of blood pressure.

A wide variety of thiol compounds also have been reported to inhibit MMPs. See, e.g., W095/12389. See also, W096/11209. See also, U.S. Pat. No. 4,595,700. See also, U.S. Pat. No. 6,013,649.

A wide variety of hydroxamate compounds also have been reported to inhibit MMPs. Such compounds reportedly include hydroxamates having a carbon backbone. See, e.g., WIPO Int'l Pub. No. WO 95/29892. See also, WIPO Int'l Pub. No. WO 97/24117. See also, WIPO Int'l Pub. No. WO 97/49679. See also, European Patent No. EP 0 780 386. Such compounds also reportedly include hydroxamates having peptidyl backbones or peptidomimetic backbones. See, e.g, WIPO Int'l Pub. No. WO 90/05719. See also, WIPO Int'l Pub. No. WO 93/20047. See also, WIPO Int'l Pub. No. WO 95/09841. See also, WIPO Int'l Pub. No. WO 96/06074. See also, Schwartz et al., *Progr. Med. Chem.,* 29:271–334(1992). See also, Rasmussen et al., *PharmacoL Ther.,* 75(1): 69–75 (1997). See also, Denis et al., *Invest New Drugs,* 15(3): 175–185 (1997). Sulfamato hydroxamates have additionally been reported to inhibit MMPs. See, WIPO Int'l Pub. No. WO 00/46221. And various aromatic sulfone hydroxamates have been reported to inhibit MMPs. See, WIPO Int'l Pub. No. WO 99/25687. See also, WIPO Int'l Pub. No. WO 00/50396. See also, WIPO Int'l Pub. No. WO 00/69821. See also, WIPO Int'l Pub. No. WO 98/38859 (disclosing, for example, sulfonyl aryl and heteroaryl hydroxamates). See also, WIPO Int'l Publ. No. WO 00/69819 (same).

It is often advantageous for an MMP inhibitor drug to target a certain MMP(s) over another MMP(s). For example, it is typically preferred to inhibit MMP-2, MMP-3, MMP-9, and/or MMP-13 (particularly MMP-13) when treating and/or preventing cancer, inhibiting of metastasis, and inhibiting angiogenesis. It also is typically preferred to inhibit MMP-13 when preventing and/or treating osteoarthritis. See, e.g., Mitchell et al., *J Clin. Invest.,* 97:761–768 (1996). See also, Reboul et al., *J Clin. Invest.,* 97:2011–2019 (1996). Normally, however, it is preferred to use a drug that has little or no inhibitory effect on MMP-1 and MMP-14. This preference stems from the fact that both MMP-1 and MMP-14 are involved in several homeostatic processes, and inhibition of MMP-1 and/or MMP-14 consequently tends to interfere with such processes.

Many known MMP inhibitors exhibit the same or similar inhibitory effects against each of the MMPs. For example, batimastat (a peptidomimetic hydroxamate) has been reported to exhibit $IC_{50}$ values of from about 1 to about 20 nM against each of MMP-1, MMP-2, MMP-3, and MMP-9. Marimastat (another peptidomimetic hydroxamate) has been reported to be another broad-spectrum MMP inhibitor with an enzyme inhibitory spectrum similar to batimastat, except that Marimastat reportedly exhibited an $IC_{50}$ value against MMP-3 of 230 nM. See Rasmussen et al., *Pharmacol. Ther.,* 75(1): 69–75 (1997).

Meta analysis of data from Phase I/II studies using Marimastat in patients with advanced, rapidly progressive, treatment-refractory solid tumor cancers (colorectal, pancreatic, ovarian, and prostate) indicated a dose-related reduction in the rise of cancer-specific antigens used as surrogate markers for biological activity. Although Marimastat exhibited some measure of efficacy via these markers, toxic side effects reportedly were observed. The most common drug-related toxicity of Marimastat in those clinical trials was musculoskeletal pain and stiffniess, often commencing in the small joints in the hands, and then spreading to the arms and shoulder. A short dosing holiday of 1–3 weeks followed by dosage reduction reportedly permits treatment to continue. See Rasmussen et al., *Pharmacol. Ther.,* 75(1): 69–75 (1997). It is thought that the lack of specificity of inhibitory effect among the MMPs may be the cause of that effect.

Another enzyme implicated in pathological conditions associated with excessive degradation of connective tissue is aggrecanase, particularly aggrecanase-1 (also known as ADAMTS-4). Specifically, articular cartilage contains large amounts of the proteoglycan aggrecan. Proteoglycan aggrecan provides mechanical properties that help articular cartilage in withstanding compressive deformation during joint articulation. The loss of aggrecan fragments and their release into synovial fluid caused by proteolytic cleavages is a central pathophysiological event in osteoarthritis and rheumatoid arthritis. It has been reported that two major cleavage sites exist in the proteolytically sensitive interglobular domains at the N-terminal region of the aggrecan core protein. One of those sites has been reported to be cleaved by several matrix metalloproteases. The other site, however, has been reported to be cleaved by aggrecanase-1. Thus, inhibiting excessive aggrecanase activity provides an additional and/or alternative prevention or treatment method for inflammatory conditions. See generally, Tang, B. L., "ADAMTS: A Novel Family of Extracellular Matrix Proteases," *Int'l Journal of Biochemistry & Cell Biology,* 33, pp. 33–44 (2001). Such diseases reportedly include, for example, osteoarthritis, rheumatoid arthritis, joint injury, reactive arthritis, acute pyrophosphate arthritis, and psoriatic arthritis. See, e.g., European Patent Application Publ. No. EP 1 081 137 A1.

In addition to inflammatory conditions, there also is evidence that inhibiting aggrecanase may be used for preventing or treating cancer. For example, excessive levels of aggrecanase-1 reportedly have been observed with a ghoma cell line. It also has been postulated that the enzymatic nature of aggrecanase and its similarities with the MMPs would support tumor invasion, metastasis, and angiogenesis. See Tang, *Int'l Journal of Biochemistry & Cell Biology,* 33, pp. 33–44 (2001).

Various hydroxamate compounds have been reported to inhibit aggrecanase-1. Such compounds include, for example, those described in European Patent Application Publ. No. EP 1 081 137 A1. Such compounds also include, for example, those described in WIPO PCT Int'l Publ. No. WO 00/09000. Such compounds further include, for example, those described in WIPO PCT Int'l Publ. No. WO 00/59874.

In view of the importance of hydroxamate MMP inhibitors in the prevention and treatment of several pathological conditions and the lack of enzyme specificity exhibited by 2 of the more potent MMP-inhibitor drugs that have been in clinical trials, there continues to be a need for hydroxamates having greater enzyme specificity (preferably toward MMP-2, MMP-9 and/or MMP-13, and even more particularly MMP-13), while exhibiting little or no inhibition of MMP-1 and/or MMP-14. There also continues to be a need for hydroxamate aggrecanase inhibitors that may be used to prevent or treat conditions associated with aggrecanase activity. The following disclosure describes hydroxamate compounds that tend to exhibit such desirable activities.

SUMMARY OF THE INVENTION

This invention is directed to compounds that inhibit MMP activity, particularly compounds that inhibit MMP-2, MMP-9, and/or MMP-13, while generally exhibiting relatively little or no inhibition against MMP-1 and MMP-14 activity. This invention also is directed to compounds that additionally or alternatively inhibit aggrecanase activity. This invention is further directed to a method for inhibiting MMP activity, particularly pathological MMP activity. Such a method is particularly suitable to be used with mammals, such as humans, other primates (e.g., monkeys, chimpanzees, etc.), companion animals (e.g., dogs, cats, horses, etc.), farm animals (e.g., goats, sheep, pigs, cattle, etc.), laboratory animals (e.g., mice, rats, etc.), and wild and zoo animals (e.g., wolves, bears, deer, etc.).

Briefly, therefore, the invention is directed, in part, to a sulfonyl aryl hydroxamic acid compound or salt thereof (particularly a pharmaceutically acceptable salt thereof).

In one embodiment, the sulfonyl aryl hydroxamic acid compound corresponds in structure to Formula VIIC:

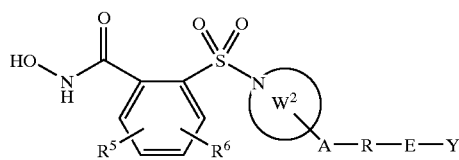

VIIC

In this embodiment:

$W^2$ is a 6-member heterocyclic ring comprising the sulfonyl-bonded nitrogen.

—A—R—E—Y is a substituent of $W^2$ bonded at the 4-position of $W^2$ relative to the sulfonyl-bonded nitrogen.

A is a bond, —O—, —S—, —S(O)—, —S(O)$_2$—, —N(R$^k$)—, —C(O)—N(R$^k$)—, —N(R$^k$)—C(O)—, —C(O)—O—, —O—C(O)—, —O—C(O)—O—, —C(H)=C(H)—, —C≡C—, —N=N—, —N(H)—N(H)—, —N(H)—C(O)—N(H)—, —C(S)—N(R$^k$)—, —N(R$^k$)—C(S)—, —C(H)$_2$—, —O—C(H)$_2$—, —C(H)$_2$—O—, —S—C(H)$_2$—, or —C(H)$_2$—S—.

R is alkyl, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, or heterocycloalkylthioalkyl. Here, the aryl, heteroaryl, cycloalkyl, or heterocycloalkyl optionally is substituted with 1 or 2 substituents selected from the group consisting of halogen, nitro, hydroxy, amino, alkyl, perfluoroalkyl, trifluoromethylalkyl, hydroxyalkyl, alkoxy, perfluoroalkoxy, perfluoroalkylthio, alkoxycarbonylalkyl, $C_1$-$C_2$-alkylenedioxy, hydroxycarbonylalkyl, hydroxycarbonylalkylamino, alkanoylamino, and alkoxycarbonyl.

E is a bond, —C(O)—, —C(O)—R$^g$—, —R$^g$—C(O)—, —C(O)—N(R$^k$)—, —N(R$^k$)—C(O)—, —S(O)$_2$—, —S(O)$_2$—R$^g$—, —R$^g$—S(O)$_2$—, —N(R$^k$)—S(O)$_2$—, or —S(O)$_2$—N(R$^k$)—.

Y is absent or hydrogen, hydroxy, nitrile, nitro, alkyl, haloalkyl, aminoalkyl, alkoxy, perfluoroalkoxy, cycloalkyl, aryl, aralkyl, heteroaryl, aryloxy, aralkoxy, heteroaryloxy, heteroaralkyl, R$^a$-oxyalkyl, perfluoroalkylthio, alkenyl, heterocycloalkyl, or alkoxycarbonyl. Here, the aryl, heteroaryl, aralkyl, or heterocycloalkyl optionally is substituted with 1 or 2 substituents independently selected from the group consisting of halogen, nitro, nitrile, alkyl, haloalkyl, alkoxy, perfluoroalkoxy, and aminoalkanoyl, aralkyl, and aryl. The amino nitrogen of the aminoalkanoyl optionally is substituted with 1 or 2 substituents independently selected from alkyl and aralkyl.

$R^5$ and $R^6$ are independently selected from the group consisting of hydrogen, halogen, nitro, hydroxy, carboxy, cyano, —N(R$^b$)(R$^c$), alkyl, haloalkyl, hydroxyalkyl, carboxyalkyl, acylalkyl, cycloalkyl, thiol, alkylthio, arylthio, cycloalkylthio, hydroxyalkylthio, alkoxy, haloalkoxy, cycloalkoxy, alkoxyalkyl, alkoxyalkoxy, heterocyclooxy, N(R$^b$)(R$^c$)-alkyl, N(R$^b$)(R$^c$)-alkoxy, N(R$^b$)(R$^c$)-carbonyl, N(R$^b$)(R$^c$)-alkylthio, and N(R$^b$)(R$^c$)-sulfonyl. Alternatively, $R^5$ and $R^6$, together with the atoms to which they are bonded, form an aliphatic or aromatic carbocyclic or heterocyclic ring having 5 to 7 members.

$R^a$ is hydrogen, alkyl, haloalkyl, N(R$^b$)(R$^c$)-alkyl, alkoxyalkyl, alkenyl, alkanoyl, haloalkanoyl, N(R$^b$)(R$^c$)-alkanoyl, aryl, arylalkyl, aroyl, arylalkylcarbonyl, or arylalkoxy.

$R^b$ and $R^c$ are independently selected from the group consisting of hydrogen, alkyl, haloalkyl, carboxyalkyl, hydroxyalkyl, aminoalkyl, alkenyl, alkynyl, alkoxyalkyl, bisalkoxyalkyl, perfluoroalkoxyalkyl, alkanoyl, haloalkanoyl, hydroxyalkanoyl, thiolalkanoyl, alkoxycarbonyl, alkoxycarbonylalkyl, aminocarbonyl, alkyliminocarbonyl, cycloalkyl, cycloalkylalkyl, aryl, arylalkyl, aryloxyalkyl, aryloxycarbonyl, arylsulfonyl, aralkanoyl, aroyl, aryliminocarbonyl, heterocyclo, heterocycloalkyl, heterocycloalkylcarbonyl, heteroaryl, heteroaryloxyalkyl, heteroarylalkoxyalkyl, heteroarylthioalkyl, alkylsulfonyl, heteroarylsulfonyl, heterocycloiminocarbonyl, arylthioalkyl, alkylthioalkyl, arylthioalkenyl, alkylthioalkenyl, heteroarylalkyl, aminoalkylcarbonyl, aminosulfonyl, and aminoalkylsulfonyl. Any amino nitrogen of R$^b$ or R$^c$ may be:

unsubstituted, substituted with 1 or 2 R$^d$ substituents, or substituted with substituents such that the substituents, taken together with the amino nitrogen, form either:
  a saturated or partially saturated heterocyclo optionally substituted with 1, 2, or 3 R$^d$ substituents, or
  a heteroaryl optionally substituted with 1, 2, or 3 R$^f$ substituents.

Each R$^d$ and R$^e$ is independently selected from the group consisting of hydrogen, alkyl, alkenyl, arylalkyl, aryl, alkanoyl, aroyl, arylalkylcarbonyl, alkoxycarbonyl, and arylalkoxycarbonyl.

Each R$^f$ is independently selected from the group consisting of halogen, cyano, nitro, hydroxy, alkyl, alkoxy, aryl, and —N(R$^d$)(R$^e$).

$R^g$ is hydrogen, halogen, hydroxy, cyano, amino, carboxy, alkyl, perfluoroalkyl, trifluoroalkyl, alkenyl, alkenyloxy, alkynyl, alkynyloxy, aldehydo, alkoxy, alkoxyalkyl, alkoxycarbonyl, alkanoyl, alkylthio, cycloalkyl, cycloalkenyl, aryl, heteroaryl, heterocyclo, aroyl, heteroaroyl, aryloxy, heteroaryloxy, alkoxyaryl, alkoxyheteroaryl, alkylenedioxy, aryloxyalkyl, arylthio, alkoxycarbonyloxy, aryloxycarbonyl, arylalkoxycarbonyl, arylalkoxycarbonylamino, aryloxycarbonyloxy, —N($R^h$)($R^i$), N($R^h$)($R^i$)-carbonyloxy, N($R^h$)($R^i$)-carbonyl, N($R^h$)($R^i$)-alkanoyl, hydroxyaminocarbonyl, N($R^h$)($R^i$)-sulfonyl, N($R^h$)($R^i$)-carbonyl-N($R^h$)—, trifluoromethylsulfonyl-N($R^h$)—, heteroarylsulfonyl-N($R^h$)—, arylsulfonyl-N($R^h$)—, arylsulfonyl-N($R^h$)-carbonyl, alkylsulfonyl-N($R^h$)—, arylcarbonyl-N($R^h$)-sulfonyl, or alkylsulfonyl-N($R^h$)-carbonyl.

Each $R^h$ is independently selected from the group consisting of alkyl, haloalkyl, hydroxyalkyl, carboxyalkyl, unsubstituted aminoalkyl, substituted aminoalkyl, alkenyl, alkynyl, alkoxyalkyl, alkoxycarbonyl, arylalkyl, alkanoyl, haloalkanoyl, unsubstituted aminoalkanoyl, substituted aminoalkanoyl, aryl, arylalkoxycarbonyl, aroyl, heteroaryl, and heterocyclo. Here, each such group (including the substituents of any substituted amino alkyl or aminoalkanoyl) optionally is substituted by 1 or 2 $R^j$ substituents $R^i$ is alkyl, haloalkyl, hydroxyalkyl, carboxyalkyl, unsubstituted aminoalkyl, substituted aminoalkyl, alkoxyalkyl,-alkoxycarbonyl, alkenyl, alkynyl, alkanoyl, haloalkanoyl, unsubstituted aminoalkanoyl, substituted aminoalkanoyl, aryl, arylalkyl, arylalkoxycarbonyl, aroyl, heteroaryl, or heterocyclo. Here, each such group optionally is substituted with 1 or 2 $R^j$ substituents.

Each $R^j$ is independently selected from the group consisting of alkyl, haloalkyl, hydroxyalkyl, carboxyalkyl, unsubstituted aminoalkyl, substituted aminoalkyl, alkenyl, alkynyl, alkoxyalkyl, alkoxycarbonyl, alkanoyl, haloalkanoyl, unsubstituted aminoalkanoyl, substituted aminoalkanoyl, aryl, arylalkyl, arylalkoxycarbonyl, aroyl, heteroaryl, and heterocyclo. The substituents of the substituted aminoalkyl or substituted aminoalkanoyl are independently selected from the group consisting of alkyl, alkenyl, alkoxycarbonyl, aryl, arylalkyl, aryloxycarbonyl, heteroaryl, and heteroarylalkyl.

$R^k$ is hydrogen, alkyl, alkenyl, alkoxycarbonyl, aryl, arylalkyl, aryloxycarbonyl, heteroaryl, heteroarylalkyl, N($R^c$)($R^d$)-carbonyl, N($R^c$)($R^d$)-sulfonyl, N($R^c$)($R^d$)-alkanoyl, or N($R^c$)($R^d$)-alkylsulfonyl.

In another embodiment, the sulfonyl aryl hydroxamic acid compound corresponds in structure to VIA-1:

VIA-1

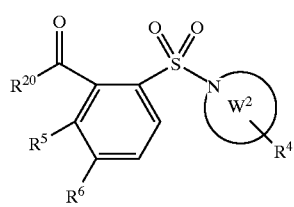

In this embodiment:

$W^2$ is a 6-member heterocyclic ring comprising the sulfonyl-bonded nitrogen.

$R^4$ is a substituent of $W^2$ bonded at the 4-position of $W^2$ relative to the sulfonyl-bonded nitrogen. $R^4$ has a chain length of from 3 to about 14 carbon atoms.

$R^5$ and $R^6$ are independently selected from the group consisting of hydrogen, halogen, nitro, hydroxy, carboxy, cyano, —N($R^b$)($R^c$), alkyl, haloalkyl, hydroxyalkyl, carboxyalkyl, acylalkyl, cycloalkyl, thiol, alkylthio, arylthio, cycloalkylthio, hydroxyalkylthio, alkoxy, haloalkoxy, cycloalkoxy, alkoxyalkyl, alkoxyalkoxy, heterocyclooxy, N($R^b$)($R^c$)-alkyl, N($R^b$)($R^c$)-alkoxy, N($R^b$)($R^c$)-carbonyl, N($R^b$)($R^c$)-alkylthio, and N($R^b$)($R^c$)-sulfonyl. Alternatively, $R^5$ and $R^6$, together with the atoms to which they are bonded, form a an aliphatic or aromatic carbocyclic or heterocyclic ring having 5 to 7 members.

$R^{20}$ is —N(H)(OH).

$R^b$ and $R^c$ are independently selected from the group consisting of hydrogen, alkyl, haloalkyl, carboxyalkyl, hydroxyalkyl, aminoalkyl, alkenyl, alkynyl, alkoxyalkyl, bisalkoxyalkyl, perfluoroalkoxyalkyl, alkanoyl, haloalkanoyl, hydroxyalkanoyl, thiolalkanoyl, alkoxycarbonyl, alkoxycarbonylalkyl, aminocarbonyl, alkyliminocarbonyl, cycloalkyl, cycloalkylalkyl, aryl, arylalkyl, aryloxyalkyl, aryloxycarbonyl, arylsulfonyl, aralkanoyl, aroyl, aryliminocarbonyl, heterocyclo, heterocycloalkyl, heterocycloalkylcarbonyl, heteroaryl, heteroaryloxyalkyl, heteroarylalkoxyalkyl, heteroarylthioalkyl, alkylsulfonyl, heteroarylsulfonyl, heterocycloiminocarbonyl, arylthioalkyl, alkylthioalkyl, arylthioalkenyl, alkylthioalkenyl, heteroarylalkyl, aminoalkylcarbonyl, aminosulfonyl, and aminoalkylsulfonyl. Any amino nitrogen of $R^b$ or $R^c$ may be:

unsubstituted, substituted with 1 or 2 $R^d$ substituents, or substituted with substituents such that the substituents, taken together with the amino nitrogen, form either:
  a saturated or partially saturated heterocyclo optionally substituted with 1, 2, or 3 $R^d$ substituents, or
  a heteroaryl optionally substituted with 1, 2, or 3 $R^f$ substituents.

Each $R^d$ and $R^e$ is independently selected from the group consisting of hydrogen, alkyl, alkenyl, arylalkyl, aryl, alkanoyl, aroyl, arylalkylcarbonyl, alkoxycarbonyl, and arylalkoxycarbonyl.

Each $R^f$ is independently selected from the group consisting of halogen, cyano, nitro, hydroxy, alkyl, alkoxy, aryl, and —N($R^d$)($R^e$).

This invention also is directed, in part, to a process for preventing or treating a condition associated with matrix metalloprotease activity in a host animal. The process comprises administering an above-described compound or pharmaceutically acceptable salt thereof to the host animal in an amount effective to prevent or treat the condition.

In one such embodiment, the condition comprises tissue destruction, a fibrotic disease, pathological matrix weakening, defective injury repair, a cardiovascular disease, a pulmonary disease, a bone disease, a central nervous system disease, or cancer. Specific examples of such conditions include osteoarthritis, rheumatoid arthritis, septic arthritis, tumor invasion, tumor metastasis, tumor angiogenesis, a gastric ulcer, a corneal ulcer, periodontal disease, multiple sclerosis, weak injury repair, an adhesion, scarring, congestive heart failure, coronary thrombosis, emphysema, proteinuria, and Alzheimer's disease. Other specific examples include decubitis ulcer, fibrotic lung disease, otosclerosis, atherosclerosis, dilated cardiomyopathy, epidermolysis bullosa, and aortic aneurysm.

In another such embodiment, the condition comprises a liver condition (e.g., liver cirrhosis) or kidney condition.

This invention also is directed, in part, to a process for preventing or treating a condition associated with matrix metalloprotease activity in a host animal, wherein the process comprises administering an above-described compound or pharmaceutically acceptable salt thereof to the host animal in an amount effective to inhibit MMP-2, MMP-9, and/or MMP-13.

This invention also is directed, in part, to a process for preventing or treating a condition associated with TNF-α activity (including TNF-α convertase activity) in a host animal. In one embodiment, the prevention or treatment process comprises administering an above-described compound or pharmaceutically acceptable salt thereof to the host animal in an amount effective to prevent or treat a condition associated with TNF-α activity. Examples of such a condition include inflammation, a pulmonary disease, a cardiovascular disease, an autoimmune disease, graft rejection, a fibrotic disease, cancer, an infectious disease, fever, psoriasis, hemorrhage, coagulation, radiation damage, acute-phase responses of shock and sepsis, anorexia, and cachexia.

This invention additionally is directed, in part, to pharmaceutical compositions comprising the above-described compounds or pharmaceutically acceptable salts thereof, and the use of those compositions in the above-described prevention or treatment processes for a condition related to MMP, TNF-α, and/or aggrecanase activity.

This invention further is directed, in part, to the use of the above-described compounds or pharmaceutically acceptable salts thereof for production of a medicament for use in the prevention or treatment of a condition related to MMP, TNF-α, and/or aggrecanase activity.

Further benefits of Applicants' invention will be apparent to one skilled in the art from reading this patent.

DETAILED DESCRIPTION OF THE PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating the preferred embodiments of this invention, are intended for purposes of illustration only. This invention, therefore, is not limited to the preferred embodiments described in this patent, and may be variously modified.

A. Compounds of This Invention

In accordance with this invention, it has been found that certain sulfonyl aryl or heteroaryl hydroxamates tend to be effective for inhibiting MMPs and/or aggrecanase. In the context of MMP inhibition, such hydroxamates tend to be particularly effective for inhibiting MMPs associated with excessive (or otherwise pathological) breakdown of connective tissue. More specifically, Applicants have found that these hydroxamates tend to be effective for inhibiting MMP-2 MMP-9, and/or MMP-13, which can be particularly destructive to tissue if present or generated in abnormally excessive quantities or concentrations. In addition, Applicants have discovered that these hydroxamates tend to be selective toward inhibiting MMP-2, MMP-9, and/or MMP-13 (as well as other MMPs associated with pathological condition conditions), and avoid excessive inhibition of other MMPs (particularly MMP-1 and MMP-14) essential to normal bodily function (e.g., tissue turnover and repair).

The present invention is directed, in part, to a sulfonyl aryl or heteroaryl hydroxamic acid compound, a salt of such a compound (such as a pharmaceutically acceptable salt, which can act as a matrix metalloprotease and/or aggrecanase inhibitor in a host animal), a precursor to such a compound, or a pro-drug form of such a compound.

The compounds used in this invention generally correspond in structure to Formula A:

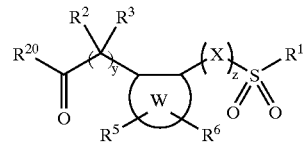

A

Here, the ring structure W is a 5- or 6-member aromatic or heteroaromatic ring. Contemplated aromatic or heteroaromatic rings include, for example, 1,2-phenylene; 2,3-pyridinylenel; 3,4-pyridinylene; 4,5-pyridinylene; 2,3-pyrazinylene; 4,5-pyrimidinylene; and 5,6-pyrimidinylene. 1,2-Phenylene (a 1,2-disubstituted phenyl ring) is a particularly preferred W ring, and is therefore sometimes used illustratively herein as W.

Each of the variables y and z are zero or one such that the sum of x and y is either zero or 1.

Thus, when z is 1, the compound corresponds in structure to Formula A2:

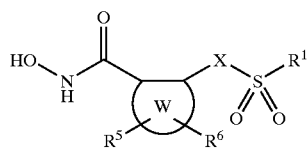

A2

Here, X is —CH$_2$— or —N(R$^9$)—, wherein R$^9$ is hydrogen, aryl, alkyl, or arylalkyl. In an often preferred embodiment, X is —CH$_2$—, i.e., the compound corresponds in structure to Formula A3:

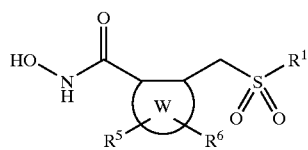

A3

When y is 1, the compound corresponds in structure to Formula A1:

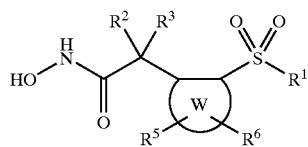

A1

In one such embodiment, R$^2$ and R$^3$ are independently selected from the group consisting of hydrogen, hydroxy, thiol, alkyl, haloalkyl, hydroxyalkyl, alkenyl, alkynyl, R$^a$-oxyalkyl, R$^a$-thioalkyl, —N(R$^b$)(R$^c$), N(R$^b$)(R$^c$)-alkyl, N(R$^d$)(R$^e$)-alkanoyl-N(R$^b$)-alkyl, N(R$^b$)(R$^c$)-alkoxy, N(R$^b$)

($R^c$)-alkoxyalkyl, heterocyclo, heterocycloalkyl, heterocyclooxy, heterocyclothio, heteroaryl, heteroarylalkyl, heteroaryloxy, and heteroarylthio. In another embodiment, $R^2$ and $R^3$ are independently selected from the group consisting of hydrogen, hydroxy, $C_1$–$C_4$-alkyl, and amino.

Alternatively, $R^2$ and $R^3$, together with the carbon to which they are both bonded, form a 4- to 8-member (more preferably 5- to 6-member) carbocyclic or heterocyclic ring. Where such a ring is a heterocyclic ring, the heteroatom(s) in the ring is/are oxygen, sulfur, and/or nitrogen. Any such sulfur ring atom optionally may be substituted with 1 or 2 oxygens, and any such nitrogen ring atom may be substituted with $C_1$–$C_4$-hydrocarbyl, $C_3$–$C_6$-cyclohydrocarbyl, $C_1$–$C_4$-hydrocarbylcarbonyl, or $C_1$–$C_4$-hydrocarbylsulfonyl.

In an often particularly preferred embodiment, both y and z are zero so that the compound corresponds in structure to Formula C:

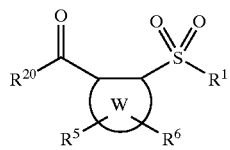

C $R^5$ and $R^6$, together with the atoms to which $R^5$ and $R^6$ are both bonded, may form an aliphatic or aromatic carbocyclic or heterocyclic ring having from 5 to 7 members.

Alternatively, $R^5$ and $R^6$ are independently selected from the group consisting of hydrogen, halogen, nitro, hydroxy, carboxy, cyano, unsubstituted or substituted amino (i.e., —N($R^b$)($R^c$)), alkyl, haloalkyl, hydroxyalkyl, carboxyalkyl, acylalkyl, cycloalkyl, thiol, alkylthio, arylthio, cycloalkylthio, hydroxyalkylthio, alkoxy, haloalkoxy, cycloalkoxy, alkoxyalkyl, alkoxyalkoxy, heterocyclooxy, $R^b R^c$ aminoalkyl (i.e., N($R^b$)($R^c$)-alkyl), $R^b R^c$aminoalkoxyl (i.e., N($R^b$)($R^c$)-alkoxy), $R^b R^c$ aminocarbonyl (i.e., N($R^b$)($R^c$)-carbonyl), $R^b R^c$aminoalkylthio (i.e., N($R^b$)($R^c$)-alkylthio), and $R^b R^c$aminosulfonyl (i.e., N($R^b$)($R^c$)-sulfonyl).

In another embodiment, $R^5$ and $R^6$ are independently selected from the group consisting of hydrogen, halogen, nitro, hydroxy, cyano, alkyl, haloalkyl, hydroxyalkyl, acylalkyl, cycloalkyl, alkoxy, haloalkoxy, and $R^b R^c$aminoalkyl.

In still another embodiment, $R^5$ and $R^6$ are independently selected from the group consisting of hydrogen, hydrocarbyl (preferably $C_1$–$C_4$-hydrocarbyl), hydroxyhydrocarbyl, hydroxy, amino, dihydrocarbylamino, heterocyclo, heterocyclohydrocarbyl, heterocyclooxy, and heterocyclothio.

$R^b$ and $R^c$ are independently selected from the group consisting of hydrogen, alkyl, haloalkyl (preferably perfluoroalkyl or trifluoromethylalkyl), carboxyalkyl, hydroxyalkyl, aminoalkyl, alkenyl, alkynyl, alkoxyalkyl, bisalkoxyalkyl, perfluoroalkoxyalkyl, alkanoyl, haloalkanoyl, hydroxyalkanoyl, thiolalkanoyl, alkoxycarbonyl, alkoxycarbonylalkyl, aminocarbonyl, alkyliminocarbonyl, cycloalkyl, cycloalkylalkyl, aryl, arylalkyl, aryloxyalkyl, aryloxycarbonyl, arylsulfonyl, aralkanoyl, aroyl, aryliminocarbonyl, heterocyclo, heterocycloalkyl, heterocycloalkylcarbonyl, heteroaryl, heteroaryloxyalkyl, heteroarylalkoxyalkyl, heteroarylthioalkyl, alkylsulfonyl, heteroarylsulfonyl, heterocycloiminocarbonyl, arylthioalkyl, alkylthioalkyl, arylthioalkenyl, alkylthioalkenyl, heteroarylalkyl, aminoalkylcarbonyl, aminosulfonyl, and aminoalkylsulfonyl. Any amino nitrogen of $R^b$ or $R^c$ may be:
unsubstituted,
substituted with 1 or 2 $R^d$ substituents, or
substituted with substituents such that the substituents, taken together with the amino nitrogen, form either:
a saturated or partially saturated heterocyclo optionally substituted with 1, 2, or 3 $R^d$ substituents, or
a heteroaryl optionally substituted with 1, 2, or 3 $R^f$ substituents.

Each $R^d$ and $R^e$ is independently selected from the group consisting of hydrogen, alkyl, alkenyl, arylalkyl, aryl, alkanoyl, aroyl, arylalkylcarbonyl, alkoxycarbonyl, and arylalkoxycarbonyl.

Each $R^f$ is independently selected from the group consisting of halogen, cyano, nitro, hydroxy, alkyl, alkoxy, aryl, and —N($R^d$)($R^e$).

In one embodiment, $R^{20}$ is —O—$R^{21}$, wherein $R^{21}$ is hydrogen, $C_1$–$C_6$-alkyl, aryl, aryl-$C_1$–$C_6$-alkyl, or a pharmaceutically acceptable cation.

In another embodiment, $R^{20}$ is —N$R^{13}$—O—$R^{22}$, wherein $R^{22}$ is a selectively removable protecting group; and $R^{13}$ is hydrogen, $C_1$–$C_6$-alkyl, or benzyl.

In another embodiment, $R^{20}$ is —N$R^{23}R^{24}$. $R^{23}$ and $R^{24}$ may independently be selected from the group consisting of hydrogen, $C_1$–$C_6$-alkyl, amino-$C_1$–$C_6$-alkyl, hydroxy-$C_1$–$C_6$-alkyl, aryl, and aryl-$C_1$–$C_6$-alkyl. Alternatively, $R^{23}$ and $R^{24}$, together with the nitrogen to which they are both bonded, may form a 5- to 8-member ring optionally containing an additional heteroatom that is oxygen, nitrogen, or sulfur.

In still another embodiment, $R^{20}$ is —N$R^{13}$—O—$R^{14}$, wherein $R^{13}$ is hydrogen, $C_1$–$C_6$-alkyl, or benzyl; and $R^{14}$ is hydrogen, a pharmaceutically acceptable cation, or —C(V) $R^{15}$. Here, V is O or S; and $R^{15}$ is $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, aryl-$C_1$–$C_6$-alkoxy, aryl-$C_1$–$C_6$-alkyl, heteroaryl, or amino-$C_1$–$C_6$-alkyl. As to the amino-$C_1$–$C_6$-alkyl nitrogen:
the amino-$C_1$–$C_6$-alkyl nitrogen may be unsubstituted;
the amino-$C_1$–$C_6$-alkyl nitrogen may be substituted with 1 or 2 substituents independently selected from the group consisting of $C_1$–$C_6$-alkyl, aryl, aryl-$C_1$–$C_6$-alkyl, $C_3$–$C_8$-cycloalkyl-$C_1$–$C_6$-alkyl, aryl-$C_1$–$C_6$-alkoxycarbonyl, $C_1$–$C_6$-alkoxycarbonyl, and $C_1$–$C_6$-alkanoyl; or
the amino-$C_1$–$C_6$-alkyl nitrogen, together with the 2 substituents bonded thereto, may form a 5- to 8-member heterocyclo or heteroaryl ring.

In one such particularly preferred embodiment, $R^{20}$ is N(H)(OH), and the compound corresponds in structure to Formula C4:

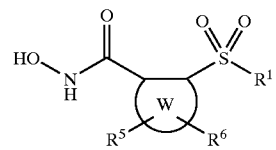

C4

$R^1$ is a substituent (i.e., radical, group, or moiety) that: (a) contains a 5- or 6-member cyclohydrocarbyl, heterocyclo, aryl, or heteroaryl bonded directly to the depicted $SO_2$ group; (b) has a length greater than about that of a hexyl group and less than about that of an eicosyl group; and (c) has a rotational width of from about that of a furanyl ring to about that of 2 phenyl rings. Initial studies indicate that so long as the $R^1$ substituent falls within these criteria, the $R^1$ substituent can be extremely varied.

Exemplary 5- or 6-member cyclohydrocarbyl, heterocyclo, aryl, or heteroaryl groups that may bonded directly to the depicted $SO_2$ group as part of $R^1$ (and are themselves substituted as discussed herein) include phenyl; 2-, 3-, or 4-pyridyl; 2-naththyl; 2-pyrazinyl; 2- or 5-pyrimidinyl; 2- or 3-benzo(b)thienyl; 8-purinyl; 2 or 3-furyl; 2- or 3-pyrrolyl; 2-imidazolyl; cyclopentyl; cyclohexyl; 2-or 3-piperidinyl; piperazinyl, 2- or 3-morpholinyl; 2- or 3-tetrahydropyranyl; 2-imidazolidinyl; 2- or 3-pyrazolidinyl; and the like. Phenyl, piperidinyl, and piperazinyl are often particularly preferred, and are therefore sometimes used illustratively herein.

When examined along its longest chain of atoms, $R^1$ has a total length equivalent to a length that is greater than that of a fully extended, saturated straight chain of 6 carbon atoms (i.e., a length greater than that of a hexyl group, or, in other words, a length of at least a heptyl chain in staggered conformation or longer), and a length that is less than that of a fully extended, saturated straight chain of about 20 carbons (i.e., a length less than that of an eicosyl group). Preferably, the length is from about 8 to about 18 carbon atoms (and often more preferably at least that of an octyl group and no greater than that of a palmityl group), even though many more atoms may be present in ring structures or substituents.

The $R^1$ length is measured along the longest linear atom chain in the $R^1$ substituent, following the skeletal atoms of a ring where necessary. Each atom in the chain (e.g., carbon, oxygen, or nitrogen) is presumed to be carbon for ease in calculation. Such lengths can be readily determined by using published bond angles, bond lengths, and atomic radii, as needed, to draw and measure a chain, or by building models using commercially available kits whose bond angles, lengths, and atomic radii are in accord with accepted, published values. $R^1$ substituent lengths also can be determined somewhat less exactly by presuming, as is done here, that all atoms have bond lengths of saturated carbon, that unsaturated and aromatic bonds have the same lengths as saturated bonds, and that bond angles for unsaturated bonds are the same as those for saturated bonds, although the above-mentioned modes of measurement are preferred. To illustrate, a 4-phenyl or 4-pyridyl group has a length of a four carbon chain, as does a propoxy group. A biphenyl group, on the other hand, has a length of about an 8-carbon chain. Because a single-ring or fused-ring system cyclohydrocarbyl, heterocyclo, aryl, or heteroaryl is generally not itself long enough to fulfill the length requirement for a preferred compound (particularly where $R^1$ is —N($R^7$)($R^8$)), the $R^1$ cyclohydrocarbyl, heterocyclo, aryl, or heteroaryl bonded to directly to the sulfonyl is preferably itself substituted.

The length of $R^1$ is believed to play a role in the overall activity of a contemplated inhibitor compound against MMP enzymes generally. Specifically, a compound having an $R^1$ that is shorter in length than a heptyl group (e.g., 4-methoxyphenyl) typically exhibits moderate to poor inhibitory activity against all the MMP enzymes, whereas compounds containing an $R^1$ substituent with a length of about an heptyl chain or longer (e.g., 4-phenoxyphenyl, which has a length of about a nine-carbon chain), typically exhibit good to excellent potencies against MMP-13 and/or MMP-2, and also selectivity against MMP-1. Exemplary data are provided in the Inhibition Tables hereinafter in which the activities of the two compounds mentioned above can be compared.

In addition to the preferred length, an $R^1$ substituent also has a preferred rotational width. More specifically, an $R^1$ substituent containing a 6-member ring bonded directly to the depicted $SO_2$ group preferably has geometric dimensions such that if the $R^1$ substituent were to be rotated about an axis drawn through the $SO_2$-bonded 1-position and the 4-position of the $SO_2$-bonded $R^1$ ring, the 3-dimensional volume defined by the rotation would have a widest dimension in a direction transverse to the axis of rotation of from about that of a furanyl ring to about that of 2 phenyl rings. Likewise, an $R^1$ substituent containing a 5-member ring bonded directly to the depicted $SO_2$ group preferably has geometric dimensions such that if the $R^1$ substituent were to be rotated about an axis drawn through the $SO_2$-bonded 1-position and the center of the 3,4-bond of the $SO_2$-bonded $R^1$ ring, the 3-dimensional volume defined by the rotation would have a widest dimension in a direction transverse to the axis of rotation of from about that of a furanyl ring to about that of 2 phenyl rings. In this context, a fused ring system (e.g., naphthyl or purinyl) is considered to be a 6- or 5 member ring that is substituted at appropriate positions numbered from the $SO_2$-linkage that is deemed to be at the 1-position. Thus, a 2-naphthyl substituent or an 8-purinyl substituent is an appropriately sized $R^1$ radical as to the rotational width criterion. On the other hand, a 1-naphthyl group or a 7- or 9-purinyl group is too large upon rotation and therefore is excluded.

As a consequence of these preferred length and rotational width criteria, $R^1$ substituents such as 4-(phenyl)phenyl [biphenyl], 4-(4'-methoxyphenyl)phenyl, 4-(phenoxy) phenyl, 4-(thiophenyl)phenyl [4-(phenylthio)phenyl], 4-(phenylazo)phenyl, 4-(phenylureido)phenyl, 4-(anilino) phenyl, 4-(nicotinamido)phenyl, 4-(isonicotinamido) phenyl, 4-(picolinamido)phenyl, and 4-(benzamido)phenyl, are among particularly preferred $R^1$ substituents, with 4-(phenoxy)phenyl and 4-(thiophenyl)phenyl often being most preferred.

In some embodiments, $R^1$ is —N($R^7$)($R^8$). In one such embodiment, $R^7$ and $R^8$ are independently selected from the group consisting of hydrogen, hydrocarbyl, aryl, substituted aryl, arylhydrocarbyl, and substituted arylhydrocarbyl. In a more preferred embodiment:

$R^7$ and $R^8$ are independently selected from the group consisting of hydrogen, alkyl, alkenyl, alkynyl, alkoxyalkyl, haloalkyl, $R^a$-oxyalkyl, cycloalkyl, cycloalkylalkyl, aryl, arylalkyl, heteroaryl, heteroarylalkyl, and heterocyclo, each of which substituent optionally is independently substituted with an —A—R—E—Y substituent (i.e., the substituent is unsubstituted or substituted with an —A—R—E—Y substituent); or $R^7$ and $R^8$, together with the nitrogen to which they are both attached, form a substituent —G—A—R—E—Y, wherein G is an N-heterocyclo group substituted with an —A—R—E—Y substituent.

With respect to the —A—R—E—Y substituent, A is a bond, —O—, —S—, —S(O)—, —S(O)$_2$—, —N($R^k$)—, —C(O)—N($R^k$)—, —N($R^k$)—C(O)—, —C(O)—O—, —O—C(O)—, —O—C(O)—O—, —C(H)=C(H)—, —C≡C—, —N=N—, —N(H)—N(H)—, —N(H)—C(O)—N (H)—, —C(S)—N($R^k$)—, —N($R^k$)—C(S)—, —C(H)$_2$—, —O—C(H)$_2$—, —O—C(H)$_2$—, —C(H)$_2$—O—, —S—C (H)$_2$—, or —C(H)$_2$—S—.

R is alkyl, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, or heterocycloalkylthioalkyl. The aryl, heteroaryl, cycloalkyl, or heterocycloalkyl optionally is substituted with 1 or 2 substituents selected from the group consisting of halogen (or "halo"; F, Cl, Br, I), nitro, hydroxy, amino, alkyl, perfluoroalkyl, trifluoromethylalkyl, hydroxyalkyl, alkoxy, perfluoroalkoxy, perfluoroalkylthio, alkoxycarbonylalkyl, $C_1$-$C_2$-alkylenedioxy, hydroxycarbonylalkyl, hydroxycarbonylalkylamino, alkanoylamino, and alkoxycarbonyl.

E is a bond, —C(O)—, —C(O)—$R^g$—, —$R^g$—C(O)—, —C(O)—N($R^k$)—, —N($R^k$)—C(O)—, —S(O)$_2$—, —S(O)$_2$—$R^g$—, —$R^g$—S(O)$_2$—, —N($R^k$)—S(O)$_2$—, or —S(O)$_2$—N($R^k$)—.

Y is absent or hydrogen, hydroxy, nitrile, nitro, alkyl, haloalkyl (preferably trifluoromethylalkyl or trifluoromethyl), aminoalkyl, alkoxy, perfluoroalkoxy, cycloalkyl, aryl, aralkyl, heteroaryl, aryloxy, aralkoxy, heteroaryloxy, heteroaralkyl, $R^a$-oxyalkyl, perfluoroalkylthio, alkenyl, heterocycloalkyl, or alkoxycarbonyl. Here, the aryl, heteroaryl, aralkyl, or heterocycloalkyl optionally is substituted with 1 or 2 substituents independently selected from the group consisting of halogen, nitro, nitrile, alkyl, haloalkyl (preferably perfluoroalkyl), alkoxy, perfluoroalkoxy, and aminoalkanoyl, aralkyl, and aryl. The amino nitrogen optionally is substituted with 1 or 2 substituents independently selected from alkyl and aralkyl.

$R^a$ is hydrogen, alkyl, alkenyl, alkenyl, arylalkyl, aryl, alkanoyl, aroyl, arylalkylcarbonyl, $R^b R^c$aminoalkanoyl, haloalkanoyl, $R^b R^c$aminoalkyl, alkoxyalkyl, haloalkyl, or arylalkoxy.

$R^g$ is hydrogen, halogen, hydroxy, cyano, amino, carboxy, alkyl, perfluoroalkyl, trifluoroalkyl, alkenyl, alkenyloxy, alkynyl, alkynyloxy, aldehydo (CHO, formyl), alkoxy, alkoxyalkyl, alkoxycarbonyl, alkanoyl, alkylthio, cycloalkyl, cycloalkenyl, aryl, heteroaryl, heterocyclo, aroyl, heteroaroyl, aryloxy, heteroaryloxy, alkoxyaryl, alkoxyheteroaryl, alkylenedioxy, aryloxyalkyl, arylthio, alkoxycarbonyloxy, aryloxycarbonyl, arylalkoxycarbonyl, arylalkoxycarbonylamino, aryloxycarbonyloxy, —N($R^h$)($R^i$), N($R^h$)($R^i$)-carbonyloxy, N($R^h$)($R^i$)-carbonyl, N($R^h$)($R^i$)-alkanoyl, hydroxyaminocarbonyl, N($R^h$)($R^i$)-sulfonyl, N($R^h$)($R^i$)-carbonyl-N($R^h$)—, trifluoromethylsulfonyl-N($R^h$)—, heteroarylsulfonyl-N($R^h$)—. arylsulfonyl-N($R^h$)—, arylsulfonyl-N($R^h$)-carbonyl, alkylsulfonyl-N($R^h$)—, arylcarbonyl-N($R^h$)-sulfonyl, or alkylsulfonyl-N($R^h$)-carbonyl.

Each $R^h$ is independently selected from the group consisting of alkyl, haloalkyl, hydroxyalkyl, carboxyalkyl, unsubstituted aminoalkyl, substituted aminoalkyl, alkenyl, alkynyl, alkoxyalkyl, alkoxycarbonyl, arylalkyl, alkanoyl, haloalkanoyl, unsubstituted aminoalkanoyl, substituted aminoalkanoyl, aryl, arylalkoxycarbonyl, aroyl, heteroaryl, and heterocyclo. Each such group (including the substituents of any substituted amino alkyl or aminoalkanoyl) optionally is substituted by 1 or 2 $R^j$ substituents.

$R^i$ is alkyl, haloalkyl, hydroxyalkyl, carboxyalkyl, unsubstituted aminoalkyl, substituted aminoalkyl, alkoxyalkyl, alkoxycarbonyl, alkenyl, alkynyl, alkanoyl, haloalkanoyl, unsubstituted aminoalkanoyl, substituted aminoalkanoyl, aryl, arylalkyl, arylalkoxycarbonyl, aroyl, heteroaryl, or heterocyclo. Each such group optionally is substituted with 1 or 2 $R^j$ substituents.

Each $R^j$ is independently selected from the group consisting of alkyl, haloalkyl, hydroxyalkyl, carboxyalkyl, unsubstituted aminoalkyl, substituted aminoalkyl, alkenyl, alkynyl, alkoxyalkyl, alkoxycarbonyl, alkanoyl, haloalkanoyl, unsubstituted aminoalkanoyl, substituted aminoalkanoyl, aryl, arylalkyl, arylalkoxycarbonyl, aroyl, heteroaryl, and heterocyclo. The substituents of the substituted aminoalkyl or substituted aminoalkanoyl are independently selected from the group consisting of alkyl, alkenyl, alkoxycarbonyl, aryl, arylalkyl, aryloxycarbonyl, heteroaryl, and heteroarylalkyl.

$R^k$ is hydrogen, alkyl, alkenyl, alkoxycarbonyl, aryl, arylalkyl, aryloxycarbonyl, heteroaryl, heteroarylalkyl, N($R^c$)($R^d$)-carbonyl, N($R^c$)($R^d$) sulfonyl, N($R^c$)($R^d$)-alkanoyl, or N($R^c$)($R^d$)-alkylsulfonyl.

Some embodiments of this invention contemplate a compound that corresponds in structure to Formula VI-1 below:

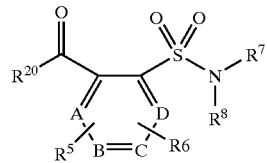

VI-1

Here, $R^5$, $R^6$, $R^7$, $R^8$, and $R^{20}$ are as defined above. Each of A, B, C, and D is carbon, nitrogen, sulfur, or oxygen, and is present or absent so that the depicted ring has 5- or 6-members. A hydroxamate compound of Formula VI-1 tends to be a selective inhibitor of MMP-2 over both of MMP-1 and MMP-13. That is, a hydroxamate compound of Formula VI-1 tends to exhibit greater activity in inhibiting MMP-2 than in inhibiting either MMP-1 and usually also MMP-13. In one such embodiment, the compound corresponds in structure to Formula VIB:

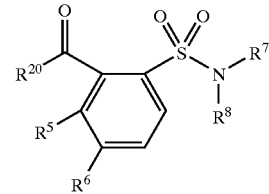

VIB

Again, $R^{20}$, $R^5$, $R^6$, $R^7$, and $R^8$ are as defined above.

In a particularly preferred embodiment, the compound corresponds in structure to either Formula VIA or Formula VIA-1:

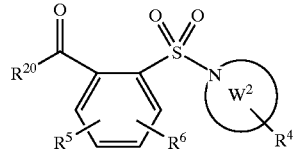

VIA

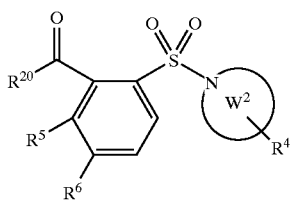

VIA-1

Here, $R^{20}$, $R^5$, and $R^6$ are as defined above.

Ring structure $W^2$, including the depicted nitrogen atom (i.e., the sulfonyl-bonded nitrogen), is a heterocyclic ring that contains 5 or 6 ring members (with 6 ring members often being more preferred). In a particularly preferred embodiment, the ring structure $W^2$ is N-piperidinyl. In a another particularly preferred embodiment, the ring structure $W^2$ is N-piperazinyl.

$R^4$ is a substituent that preferably is bonded at the 4-position of $W^2$ (relative to the depicted nitrogen atom) when $W^2$ is a 6-member ring, and at the 3-or 4-position of $W^2$ (relative to the depicted nitrogen) when $W^2$ is a 5-member ring. $R^4$ preferably is a substituent that has a chain length of from 3 to about 14 carbon atoms. More specifically, $R^4$ preferably is an optionally-substituted (i. e., unsubstituted or substituted) single-ring cyclohydrocarbyl, single-ring heterocyclo, single-ring aryl, single-ring heteroaryl, or other substituent having a chain length of from 3 to about 14 carbon atoms, such as hydrocarbyl (e.g., $C_3$–$C_{14}$ hydrocarbyl), hydrocarbyloxy (e.g., $C_2$–$C_{14}$-hydrocarbyloxy), phenyl, phenoxy (—O—$C_6H_5$), thiophenoxy (phenylsulfanyl; —S—$C_6H_5$), anilino (—NH—$C_6H_5$), phenylazo (—$N_2$-$C_6H_5$), phenylureido (aniline carbonylamino; —NHC(O)NH—$C_6H_5$), benzamido (—NHC(O)—$C_6H_5$), nicotinamido (-3—NHC(O)$C_5H_4N$), isonicotinamido (-4—NHC(O)$C_5H_4N$), or picolinamido (-2—NHC(O)$C_5H_4N$). Additional contemplated $R^4$ substituents include optionally-substituted heterocyclo, heterocyclohydrocarbyl, arylhydrocarbyl, arylheterocyclohydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, or heteroarylthio. Where these groups are substituted, they preferably are substituted with one or more substituents selected from the group consisting of halogen, hydrocarbyl, hydrocarbyloxy, nitro, cyano, perfluorohydrocarbyl, trifluoromethyl hydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarylhydrocarbyl, hydrocarbyloxycarbonyl hydrocarbyl, heterocyclooxy, hydroxycarbonyl hydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroaryl hydrocarbylamino, arylhydrocarbyloxy, arylhydrocarbylthio, arylhydrocarbylamino, heterocyclic, heteroaryl, hydroxycarbonylhydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxy hydrocarbyloxy, hydrocarbylthio, hydrocarbyloxy hydrocarbylthio, hydrocarbyloxycarbonyl, hydroxycarbonylhydrocarbyloxy, hydrocarbyloxy carbonylhydrocarbyl, hydrocarbylhydroxycarbonyl hydrocarbylthio, hydrocarbyloxycarbonyl hydrocarbyloxy, hydrocarbyloxycarbonyl hydrocarbylthio, amino, hydrocarbylcarbonylamino., arylcarbonylamino, cyclohydrocarbylcarbonylamino, heterocyclohydrocarbylcarbonylamino, arylhydrocarbylcarbonylamino, heteroaryl carbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbyl sulfonylamino, cyclohydrocarbylsulfonylamino, heterocyclohydrocarbylsulfonylamino, and N-mono substituted or N,N-disubstituted aminohydrocarbyl. The substituent(s) on the mono or di-substituted aminohydrocarbyl nitrogen are selected from the group consisting of hydrocarbyl, aryl, arylhydrocarbyl, cyclohydrocarbyl, arylhydrocarbyloxycarbonyl, hydrocarbyloxycarbonyl, and hydrocarboyl. Alternatively, in the case of a disubstituted aminohydrocarbyl, the substituents, together with the aminohydrocarbyl nitrogen, form a 5- to 8-member heterocyclic or heteroaryl ring group.

Where $R^4$ is a substituted 6-member ring, the 6-member ring preferably is substituted at the meta- or para-position (or both) with a single atom or a substituent containing a longest chain of up to 10 atoms, excluding hydrogen. For example, $R^4$ may be a phenyl, phenoxy, thiophenoxy, phenylazo, phenylureido, anilino, nicotinamido, isonicotinamido, picolinamido, or benzamido that optionally is itself substituted at its own meta or para-position (or both) with a substituent(s) that is selected from the group consisting of halogen, halohydrocarbyl, halo-$C_1$–$C_9$ hydrocarbyloxy, perfluoro-$C_1$–$C_9$ hydrocarbyl, $C_1$–$C_9$ hydrocarbyloxy (—O—$C_1$–$C_9$-hydrocarbyl), $C_1$–$C_{10}$-hydrocarbyl, di-$C_1$–$C_9$-hydrocarbylamino (—N($C_1$–$C_9$ hydrocarbyl)($C_1$–$C_9$ hydrocarbyl)), carboxy-$C_1$–$C_8$-hydrocarbyl, $C_1$–C4-hydrocarbyloxy carbonyl-$C_1$–$C_4$-hydrocarbyl ($C_1$–$C_4$-hydrocarbyl-O—(CO)—$C_1$–$C_4$-hydrocarbyl), $C_1$–$C_4$-hydrocarbyloxycarbonyl-$C_1$–$C_4$-hydrocarbyl ($C_1$–$C_4$-hydrocarbyl-O—(CO)—$C_1$–$C_4$ hydrocarbyl), and $C_1$–$C_8$-hydrocarbyl carboxamido (—NH (CO)—$C_1$–$C_8$-hydrocarbyl); or is substituted at the meta- and para-positions by 2 methyl groups or by a $C_1$–$C_2$-alkylenedioxy group (e.g., methylenedioxy).

In still a further embodiment of this invention, $R^1$ is an $SO_2$-linked 5- or 6-member cyclohydrocarbyl, heterocyclo, aryl, or heteroaryl that is itself substituted with an $R^4$ substituent. When the $SO_2$-linked cyclohydrocarbyl, heterocyclo, aryl, or heteroaryl is a 6-member ring, it is preferably substituted by the $R^4$ substituent at its own 4-position. When the $SO_2$-linked cyclohydrocarbyl, heterocyclo, aryl, or heteroaryl is a 5-member ring, it is preferably substituted by the $R^4$ substituent at its own 3 or 4-position.

Inasmuch as a contemplated $SO_2$-linked cyclohydrocarbyl, heterocyclo, aryl, or heteroaryl of $R^1$ is itself preferably substituted with a 6-member aromatic ring, two nomenclature systems are used together herein for ease in understanding substituent positions. The first system uses position numbers for the ring directly bonded to the $SO_2$-group, whereas the second system uses ortho, meta, or para for the position of one or more substituents of a 6-member ring bonded to an $SO_2$-linked cyclohydrocarbyl, heterocyclo, aryl, or heteroaryl radical. When an $R^4$ substituent is other than a 6-member ring, substituent positions are numbered from the position of linkage to the aromatic or heteroaromatic ring. Formal chemical nomenclature is used in naming particular compounds. Thus, the I-position of an above-discussed $SO_2$-linked cyclohydrocarbyl, heterocyclo, aryl, or heteroaryl is the position at which the $SO_2$ group is bonded to the ring. The 4- and 3-positions of the rings discussed here are numbered from the sites of substituent bonding from the $SO_2$-linkage as compared to formalized ring numbering positions used in heteroaryl nomenclature.

A compound of Formula A (and more preferably Formula C) embraces a useful precursor compound, a pro-drug form of a hydroxamate, and the hydroxamate itself, as well as amide compounds that can be used as intermediates and also as MMP inhibitor compounds. Thus, for example, where $R^{20}$ is $—O—R^{21}$ (in which $R^{21}$ is selected from the group consisting of a hydrogen, $C_1$-$C_6$-alkyl, aryl, aryl-$C_1$-$C_6$-alkyl group, and a pharmaceutically acceptable cation), a precursor carboxylic acid or ester is defined that can be readily transformed into a hydroxamic acid, as is illustrated in several Examples hereinafter. It should be recognized that such a precursor compound also can have activity as an inhibitor of MMP enzymes and/or aggrecanase.

Another useful precursor compound is defined when $R^{20}$ is $—NR^{13}—O—R^{22}$, wherein $R^{22}$ is a selectively removable protecting group, and $R^{13}$ is a hydrogen or benzyl (preferably hydrogen). Examples of selectively removable protecting groups include 2-tetrahydropyranyl (THP), benzyl, p-methoxybenzyloxycarbonyl (MOZ), benzyloxycarbonyl (BOC), $C_1$-$C_6$-alkoxycarbonyl, $C_1$-$C_6$-alkoxy—$CH_2$—, $C_1$-$C_6$-alkoxy-$C_1$-$C_6$-alkoxy—$CH_2$—, trisubstituted silyl, o-nitrophenyl, peptide synthesis resin, and the like.

A contemplated trisubstituted silyl group is a silyl group substituted with $C_1$-$C_6$-alkyl, aryl, aryl-$C_1$-$C_6$-alkyl, or a mixture thereof. Examples include trimethylsilyl, triethylsilyl, butyldiphenylsilyl, diphenylmethylsilyl, a tribenzylsilyl group, and the like. Exemplary trisubstituted silyl protecting groups and their uses are discussed at several places in Greene et al., *Protective Groups In Organic Synthesis,* 2 nd ed. (John Wiley & Sons, Inc., New York, 1991).

A contemplated peptide synthesis resin is solid phase support also known as a so-called Merrifield's Peptide Resin that is adapted for synthesis and selective release of hydroxamic acid derivatives as is commercially available from Sigma Chemical Co., St. Louis, Mo. An exemplary peptide synthesis resin so adapted and its use in the synthesis of hydroxamic acid derivatives is discussed in Floyd et al., *Tetrahedron Let.,* 37 (44), pp. 8048–8048 (1996).

A 2-tetrahydropyranyl protecting group is a particularly preferred selectively removable protecting group and is often used when $R^{13}$ is hydrogen. A contemplated THP-protected hydroxamate compound of Formula C can be prepared by reacting the carboxylic acid precursor compound of Formula C (where $R^{20}$ is —OH) in water with O—(tetrahydro-2H-pyran-2-yl)hydroxylamine in the presence of N-methylmorpholine, N-hydroxybenzotriazole hydrate, and a water-soluble carbodiimide (e.g., 1-(3dimethylaminopropyl)-3-ethylcarbodiimide hydrochloride). The resulting THP-protected hydroxamate corresponds in structure to Formula C3 (below), wherein W, $R^1$, $R^5$, and $R^6$ are as defined previously and more fully hereinafter. The THP protecting group is readily removable in an aqueous acid solution such as an aqueous mixture of p-toluenesulfonic acid or HCl and acetonitrile or methanol.

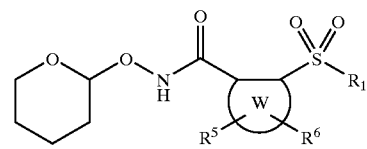

C3

In view of the above-discussed preferences, compounds corresponding in structure to particular formulas constitute particularly preferred embodiments.

For example, taking into account the before-stated preference that W be a 1,2-phenylene radical, particularly preferred compounds correspond in structure to Formulas VIIC and VIII below, wherein the above definitions for —A—R—E—Y, —$W^2$, $R^5$, and $R^6$ also apply:

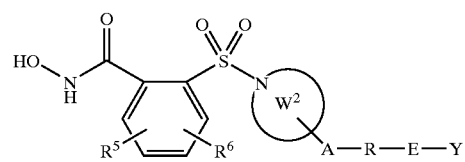

VIIC

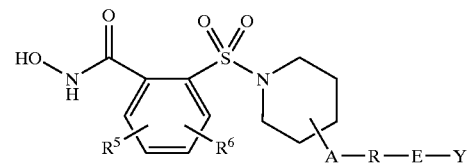

VIII

The compounds that correspond in structure to Formulas D, D1, D2, D3, D4 below are also among the particularly preferred compounds contemplated herein:

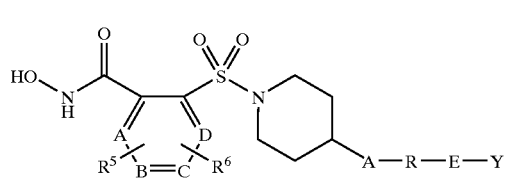

D

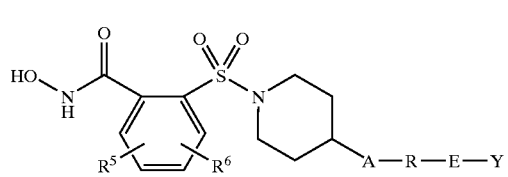

D1

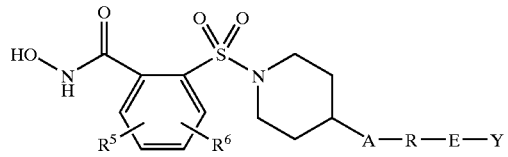

D2

-continued

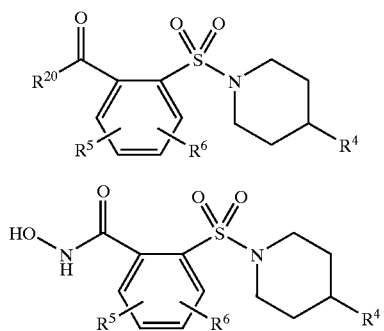
D3

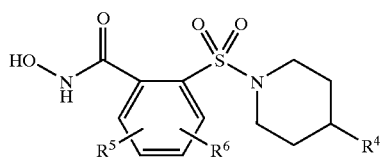
D4

In each of these formulas, the above definitions for —A—R—E—Y, $R^4$, $R^5$, $R^6$, and $R^{20}$ apply and each of A, B, C, and D is independently carbon, nitrogen, sulfur, or oxygen that is present or absent so that the depicted ring has 5- or 6-members. The compound of Example 24, for example, has a structure corresponding to Formula D2. In that compound, $R^5$ and $R^6$ are both methoxy, A is a sulfur atom (i.e., —S—), R is 1,4-phenylene, E is a bond, and Y is hydrogen. The compound of Example 27 also, for example, corresponds in structure to Formula D2. There, $R^5$ and $R^6$ are again both methoxy, A is an oxygen atom (i.e., —O—), R is 1,4-phenylene, E is a bond, and Y is a dialkoxy-substituted phenyl.

The compounds that correspond in structure to Formulas E1, E2, E3, E4, and E5 below are also among the particularly preferred compounds contemplated herein:

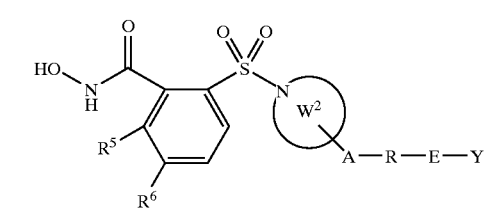
E1

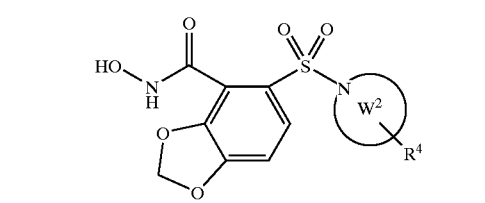
E2

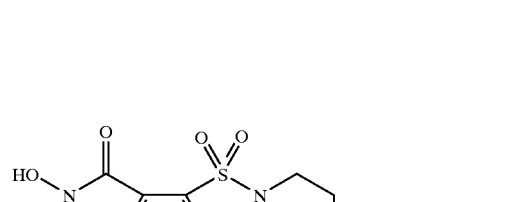
E3

-continued

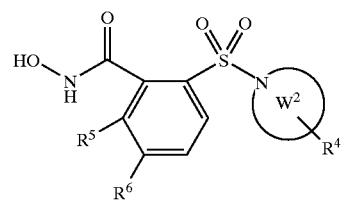
E4

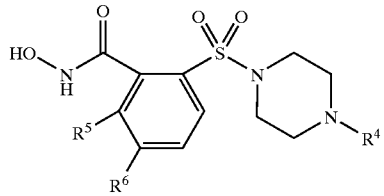
E5

In each of these formulas, the above definitions for $W^2$, —A—R—E—Y, $R^4$, $R^5$, $R^6$, and $R^{20}$ apply.

In some other particularly preferred embodiments, the compound corresponds in structure to Formula F1, F2, F3, F4, F5, F6, F7, F8, F9, F10, F11, F12, F13, or F14:

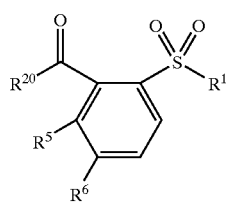
F1

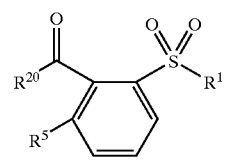
F2

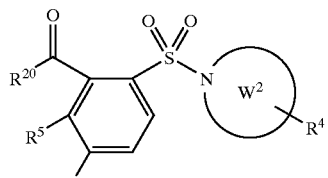
F3

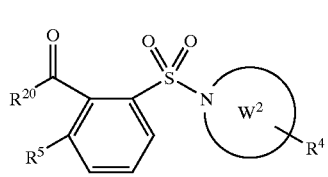
F4

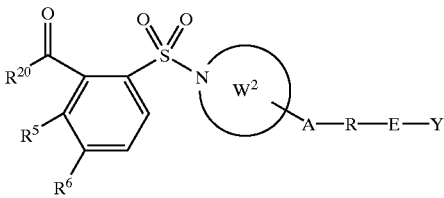
F5

-continued

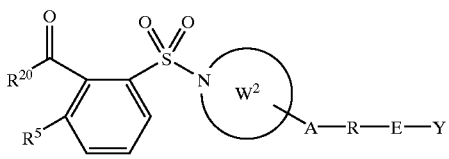
F6

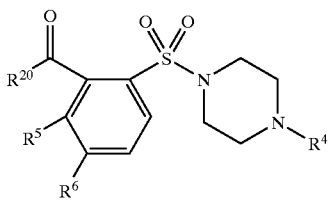
F7

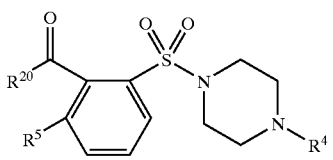
F8

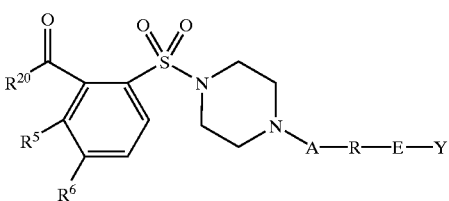
F9

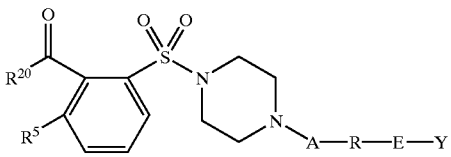
F10

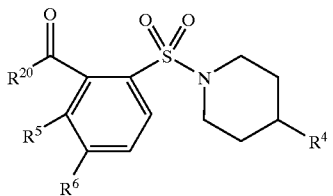
F11

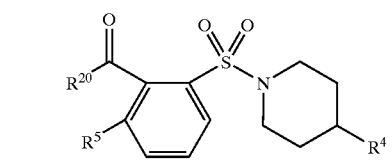
F12

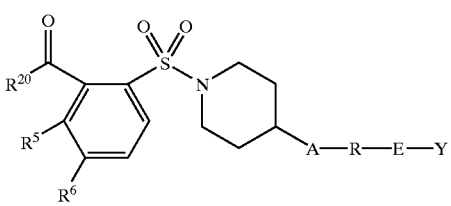
F13

-continued

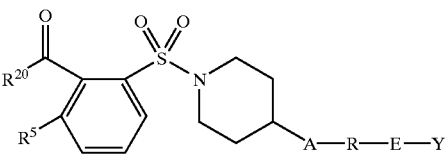
F14

Here, $R^1$, $R^4$, $R^6$, $R^{20}$, $W^2$, and —A—R—E—Y are as defined herein, while $R^5$ is any of the possible substituents listed herein for $R^5$ except hydrogen. Applicants have found that compounds having such an $R^5$ substituent (particularly a polar substituent) tend to exhibit more favorable half-life properties, especially where $R^{20}$ is —N(H)(OH).

Particularly preferred compounds (and salts thereof) contemplated herein are illustrated herein below (see also the Example section below for a further description of several particularly preferred compounds):

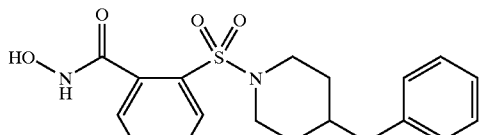

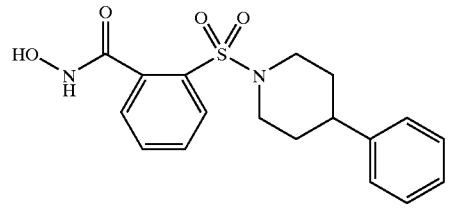

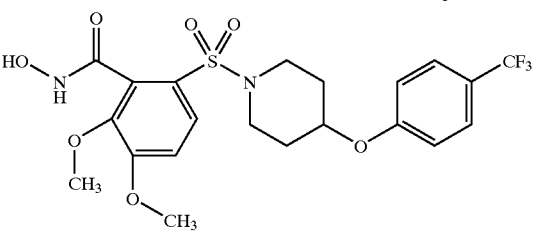

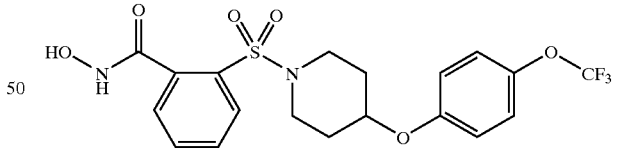

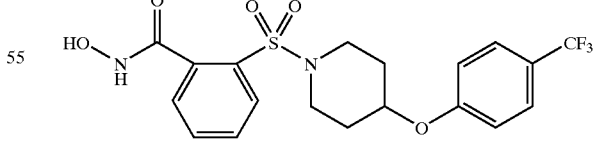

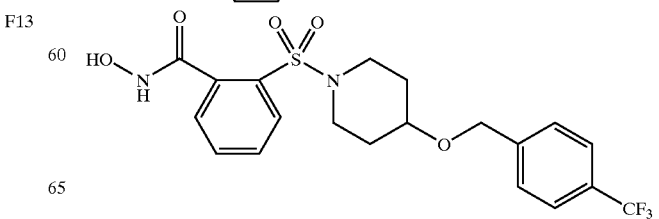

-continued
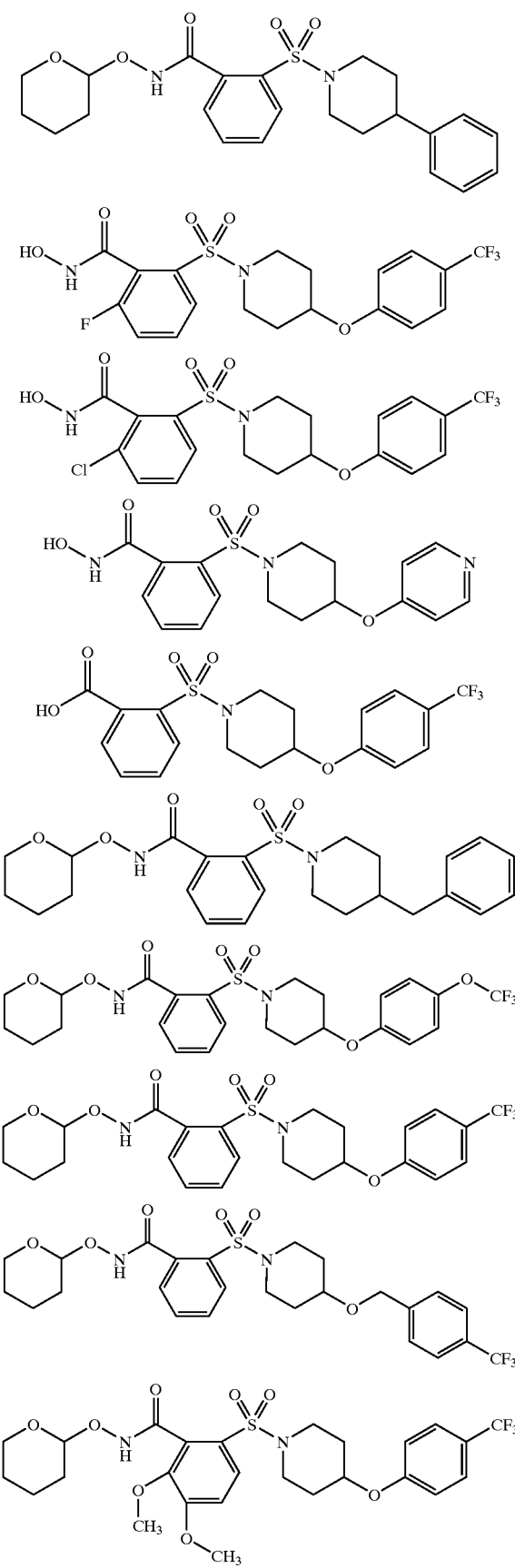
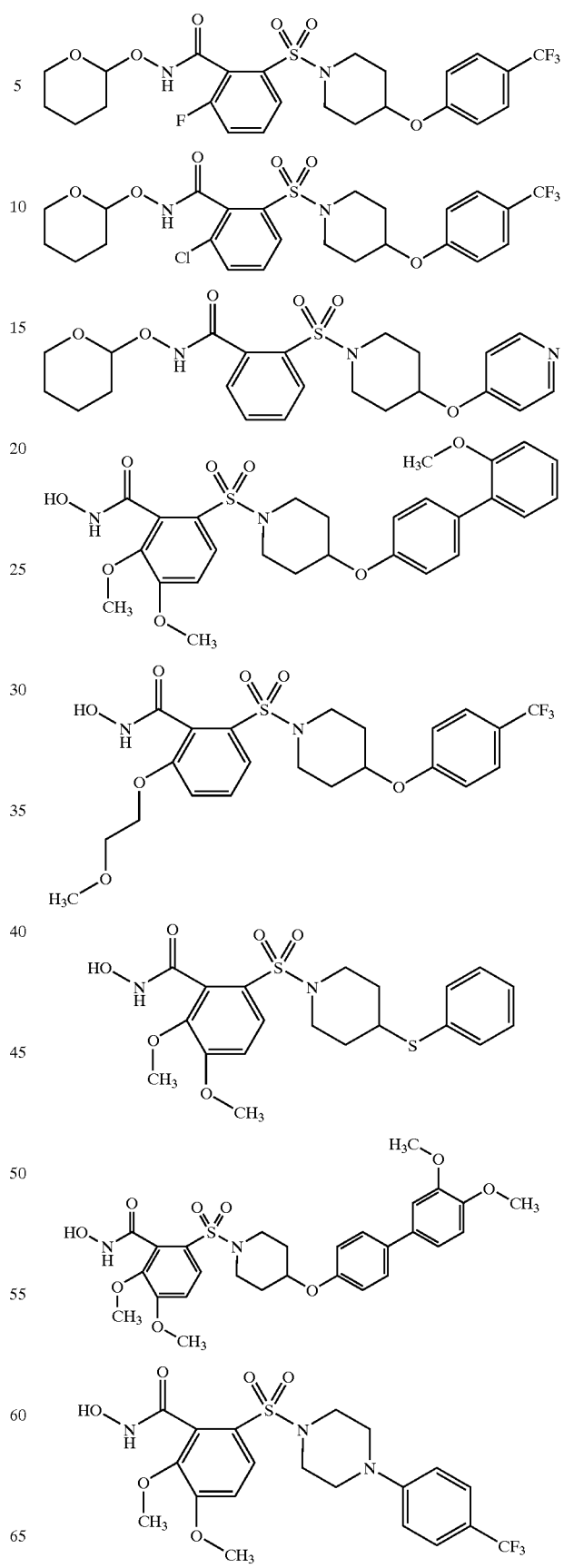

-continued
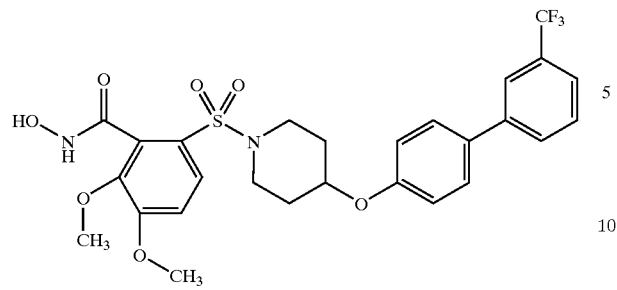
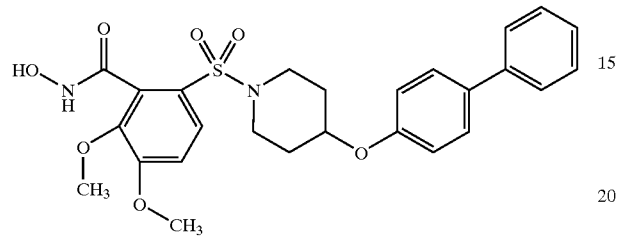
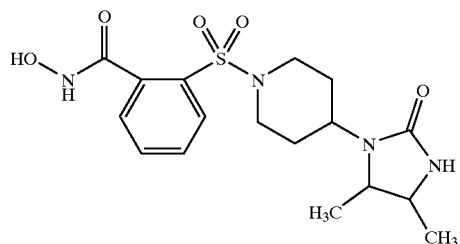
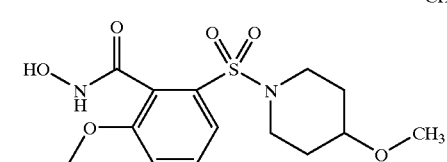
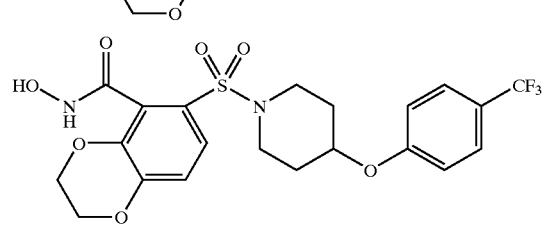
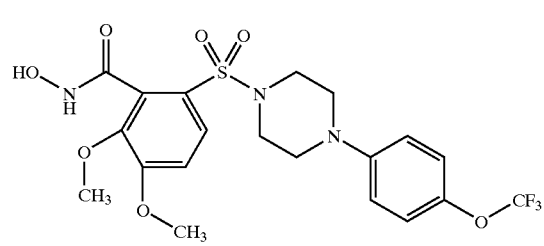
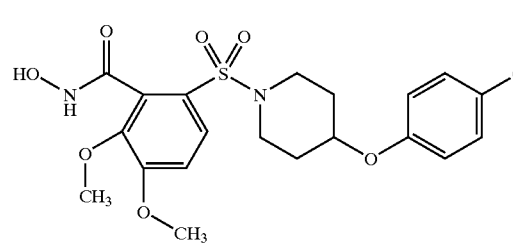
-continued
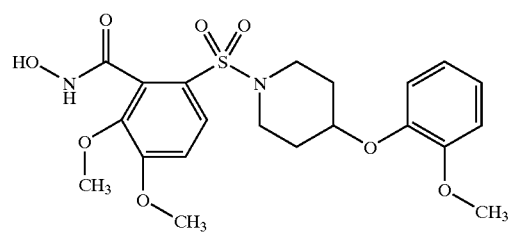
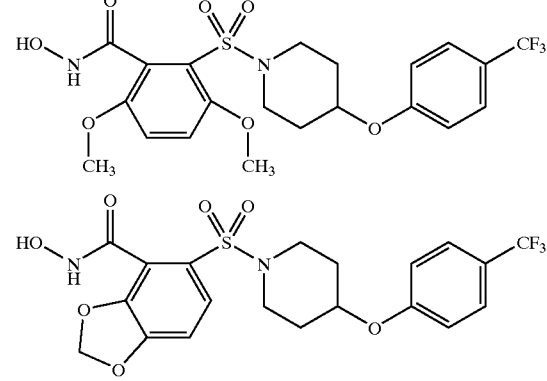
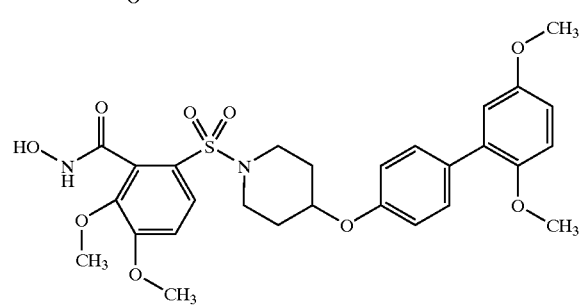
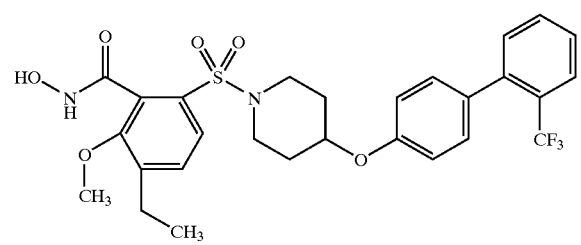
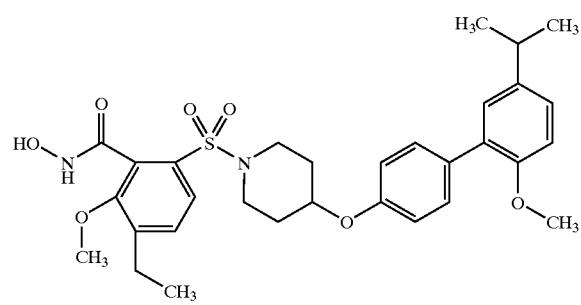
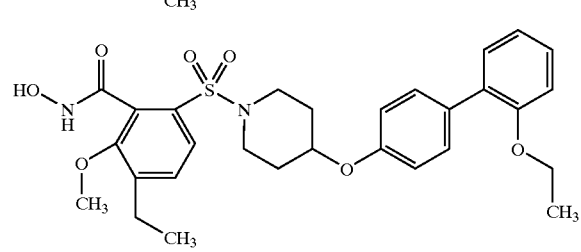

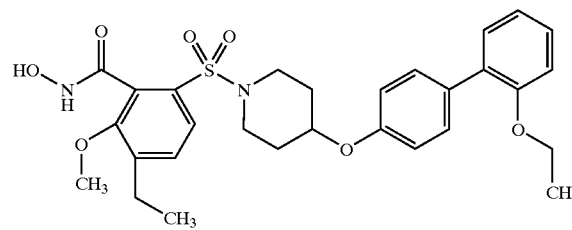
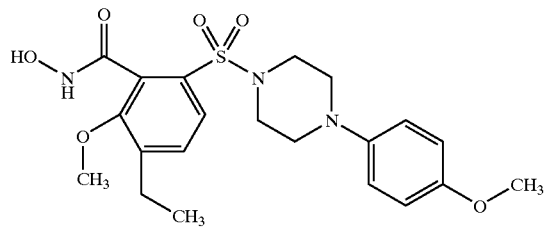
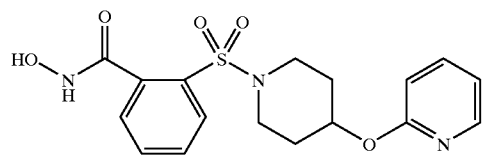
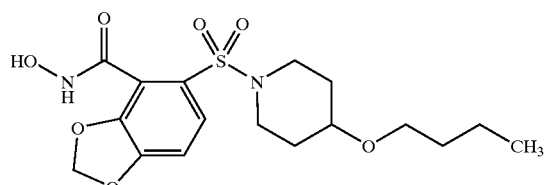
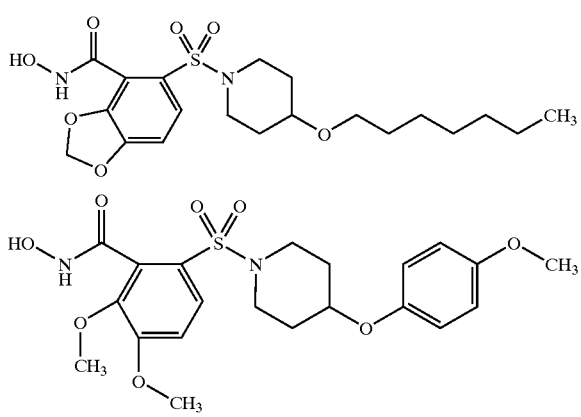
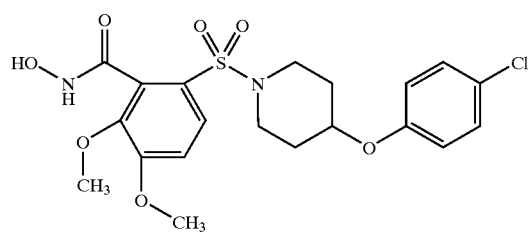
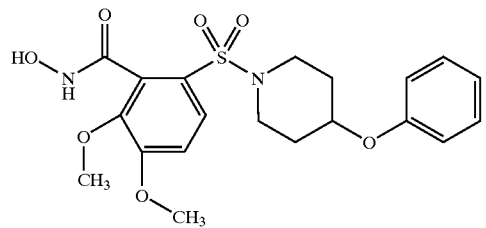
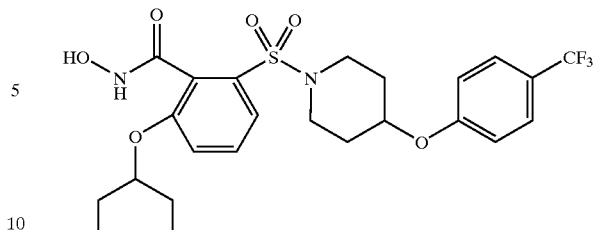
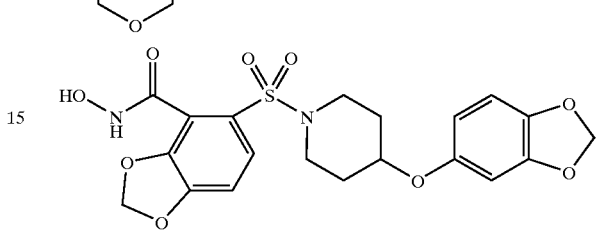
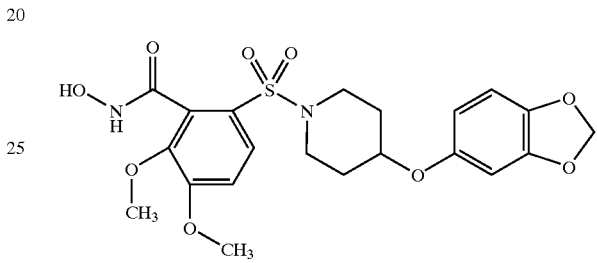
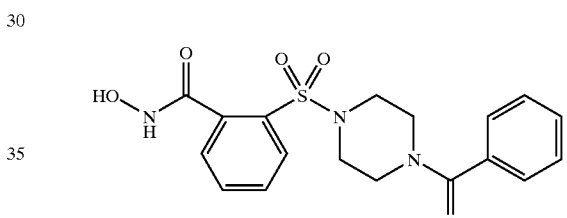
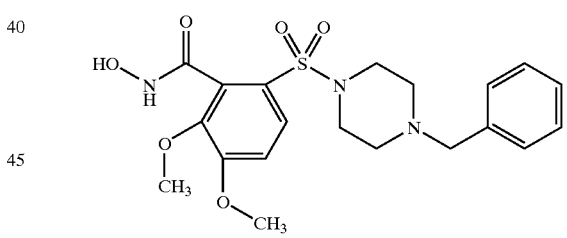
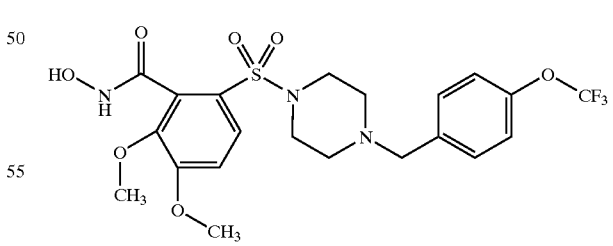
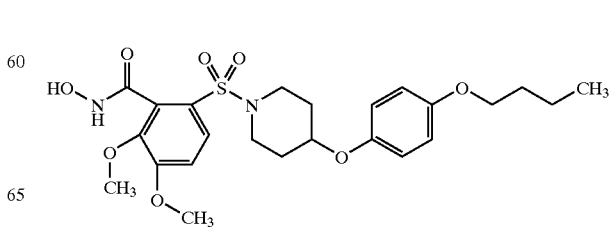

31

-continued

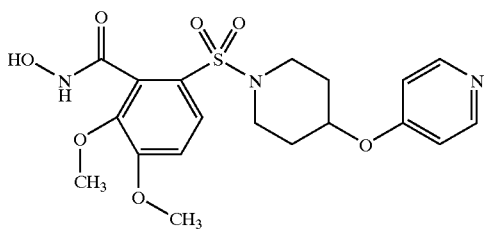

32

-continued

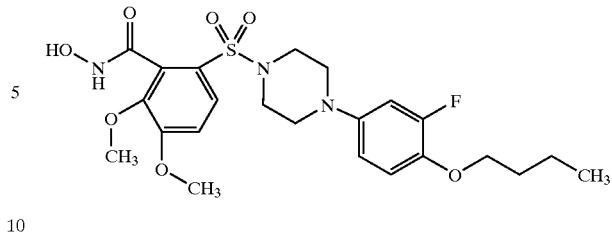

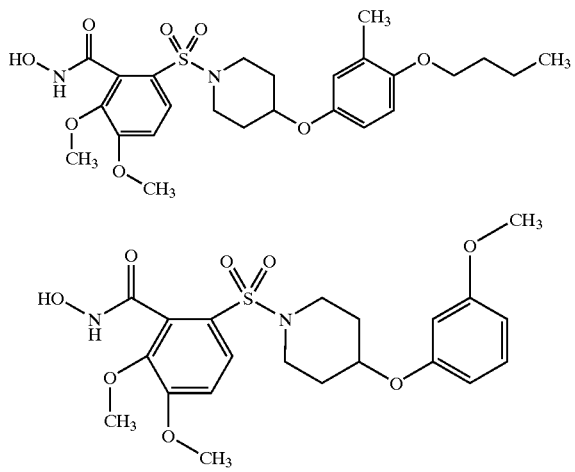

The following Tables 1–58 show several contemplated sulfonyl aryl or heteroaryl hydroxamic acid compounds as structural formulas that illustrate substituent groups. Each group of compounds of Tables 1–58 is illustrated by a generic formula, followed by a series of preferred moieties or groups that constitute various substituents that can be attached at the position shown in the generic structure. One or two bonds (straight lines) are shown with those substituents to indicate the respective positions of attachment in the illustrated compound. This system is well known in the chemical communication arts, and is widely used in scientific papers and presentations. The substituent symbols (e.g., $R^4$, Ar, and X) in these Tables may sometimes be different from those shown in formulas elsewhere in this patent.

Tables 59–73 illustrate specific compounds of the previous tables, as well as other contemplated compounds, using complete molecular formulas.

TABLE 1

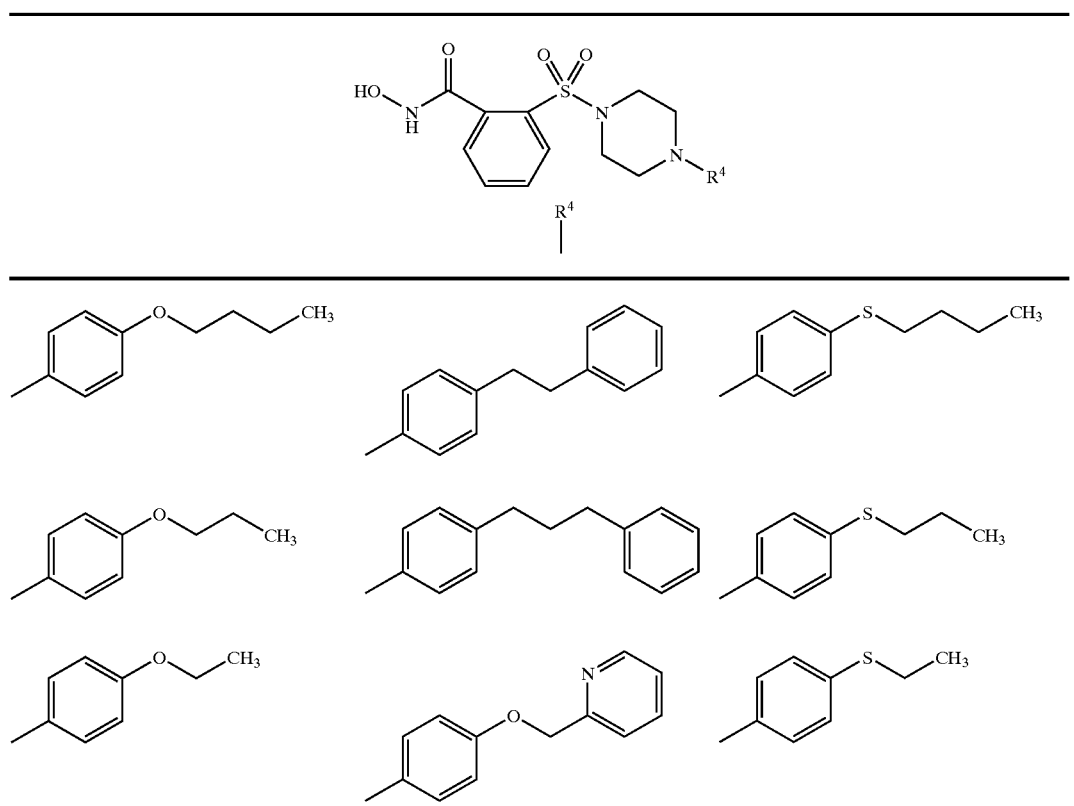

TABLE 1-continued
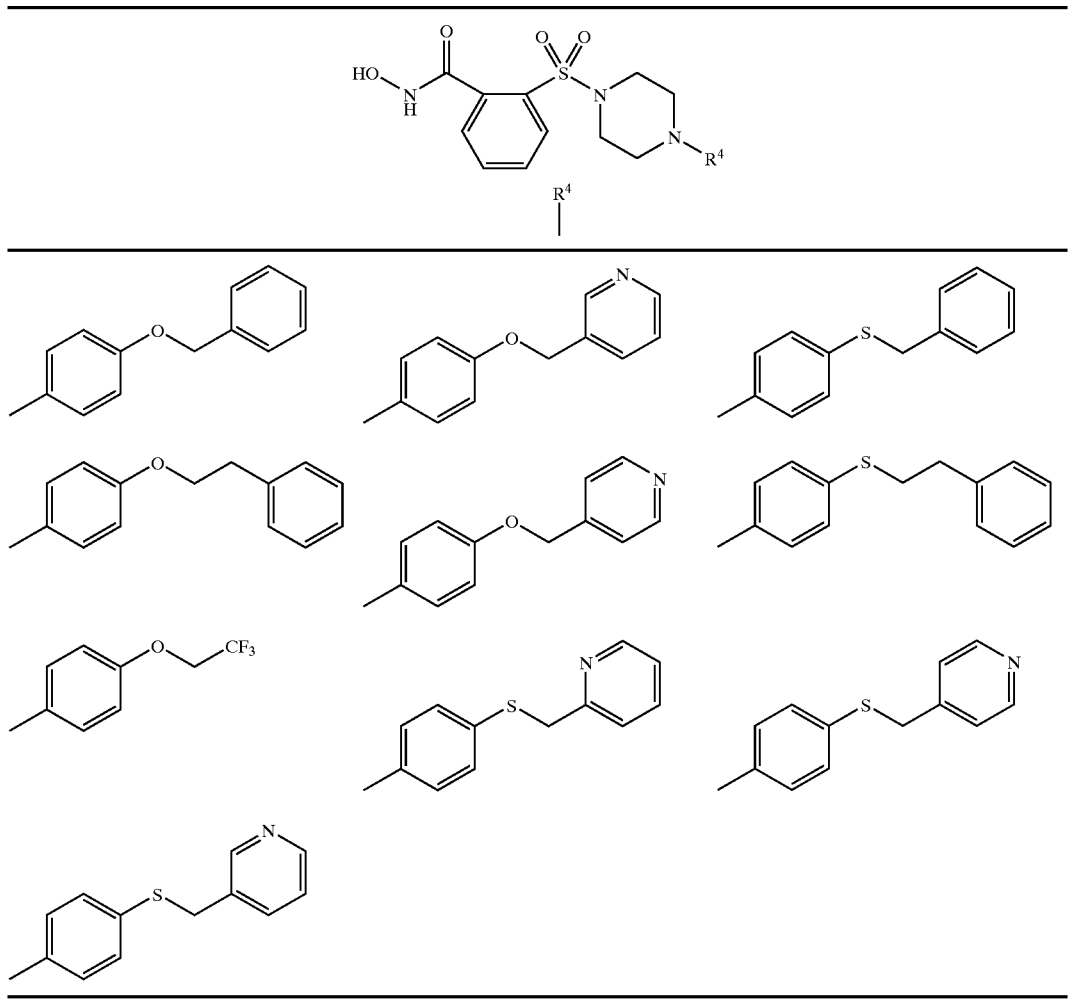
TABLE 2
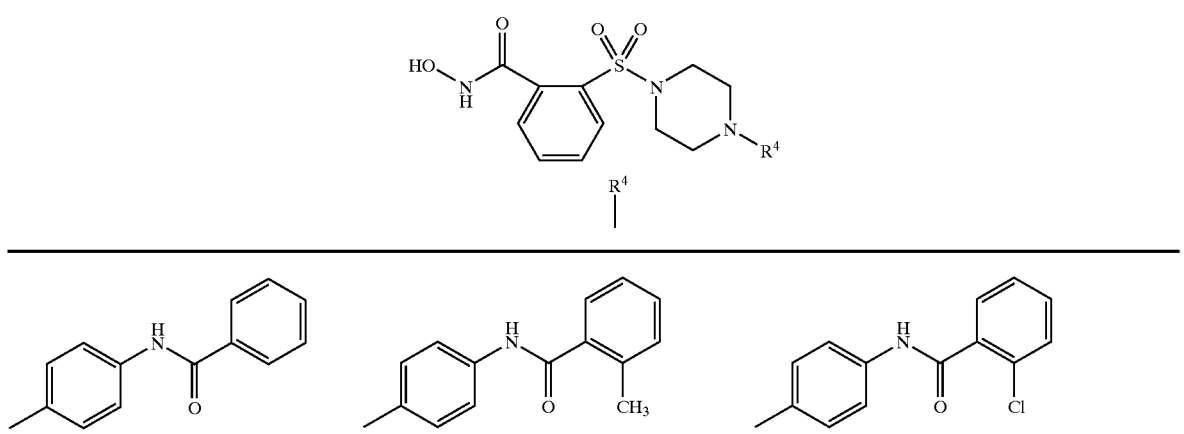

TABLE 2-continued
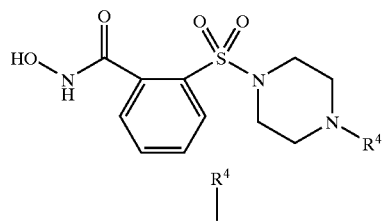
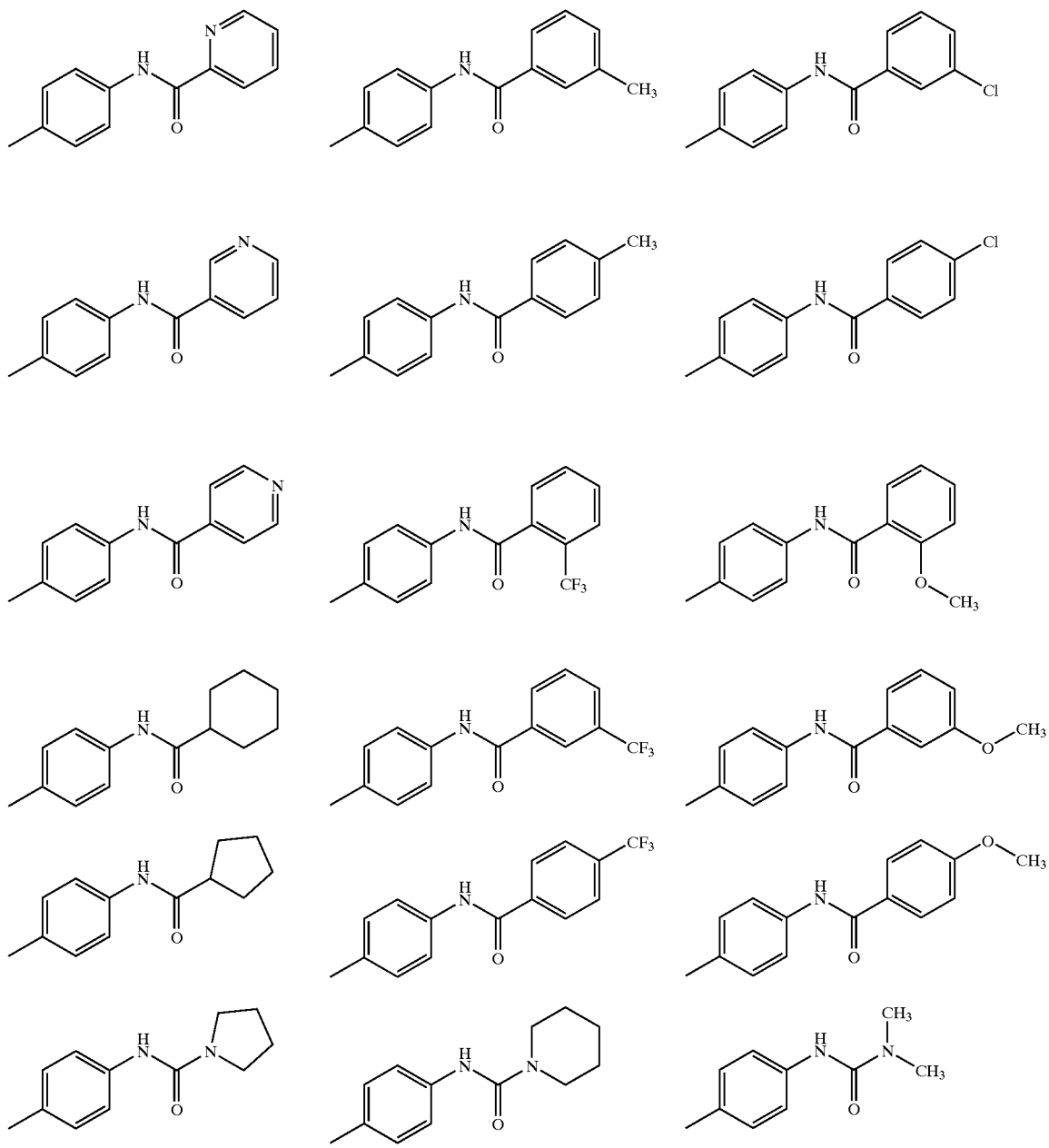

TABLE 3
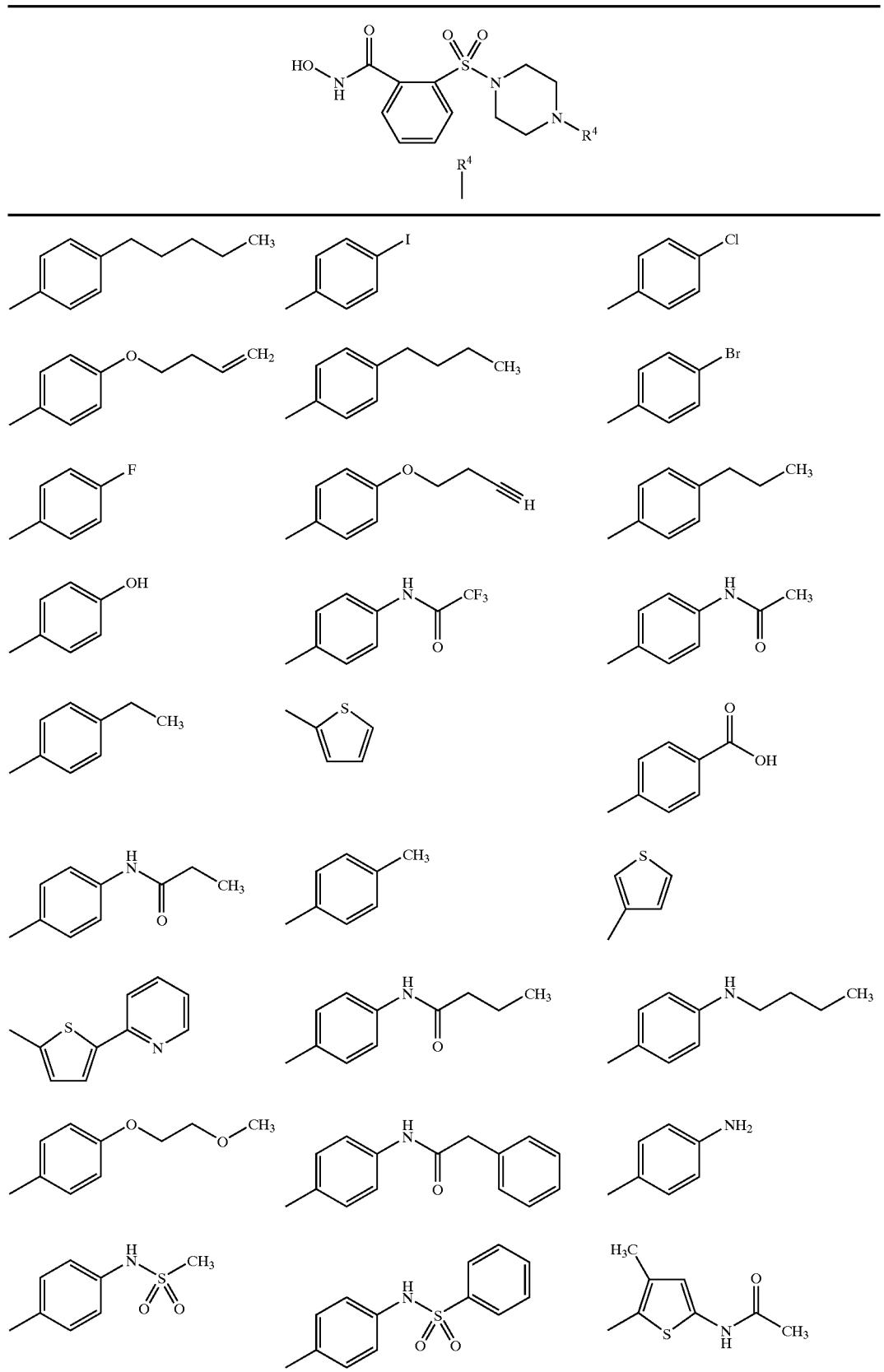

TABLE 3-continued
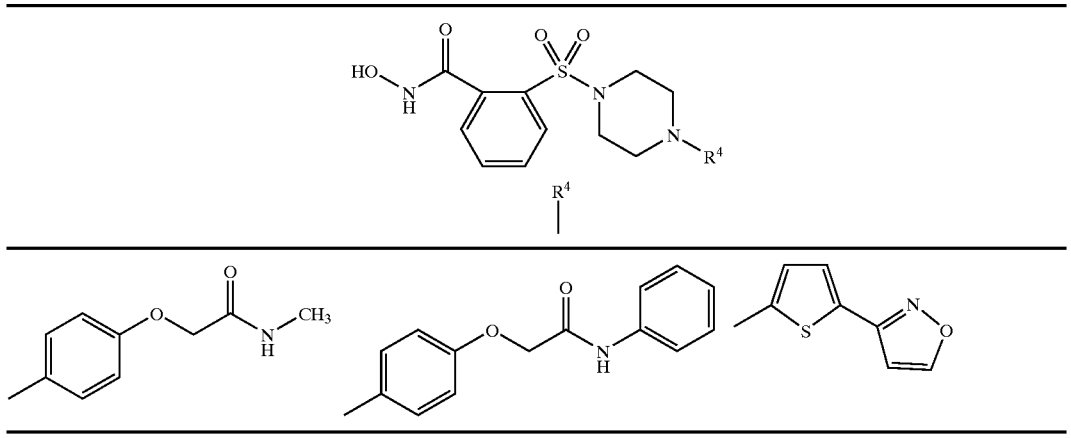
TABLE 4
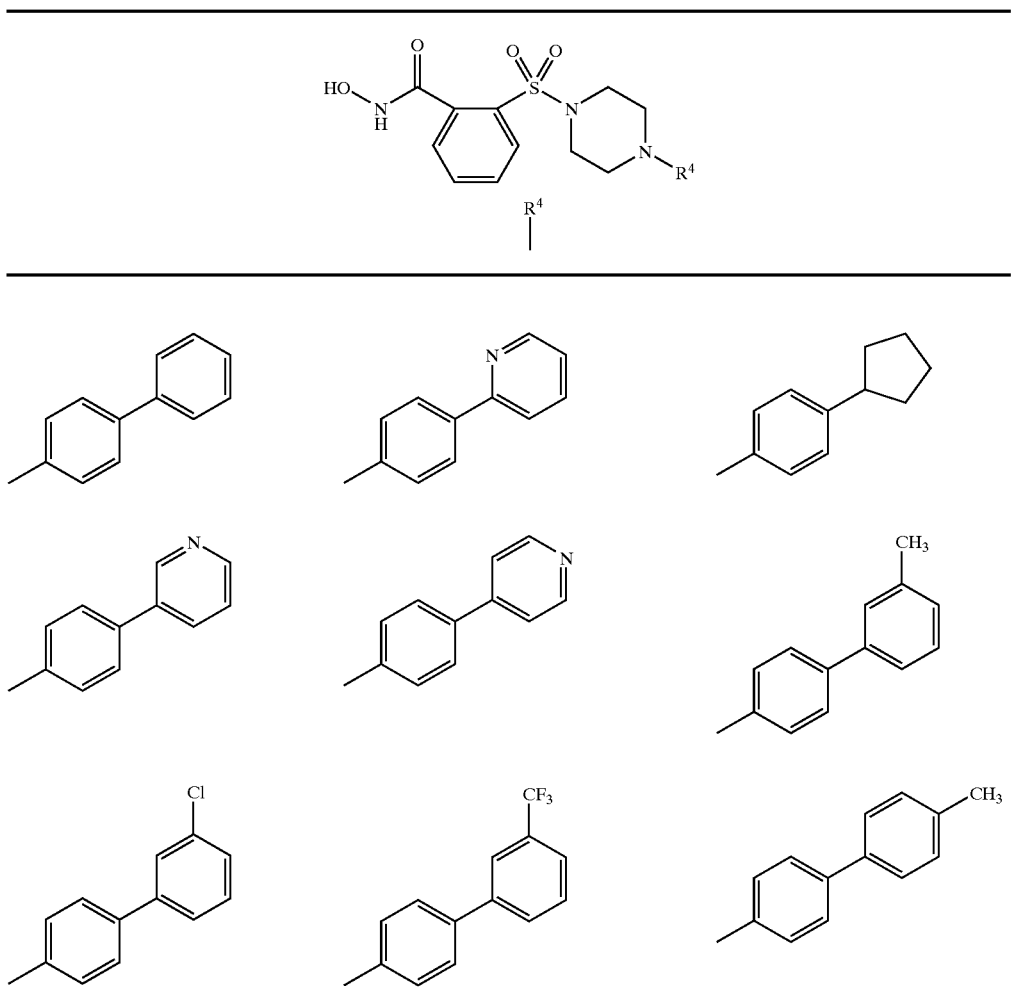

TABLE 4-continued
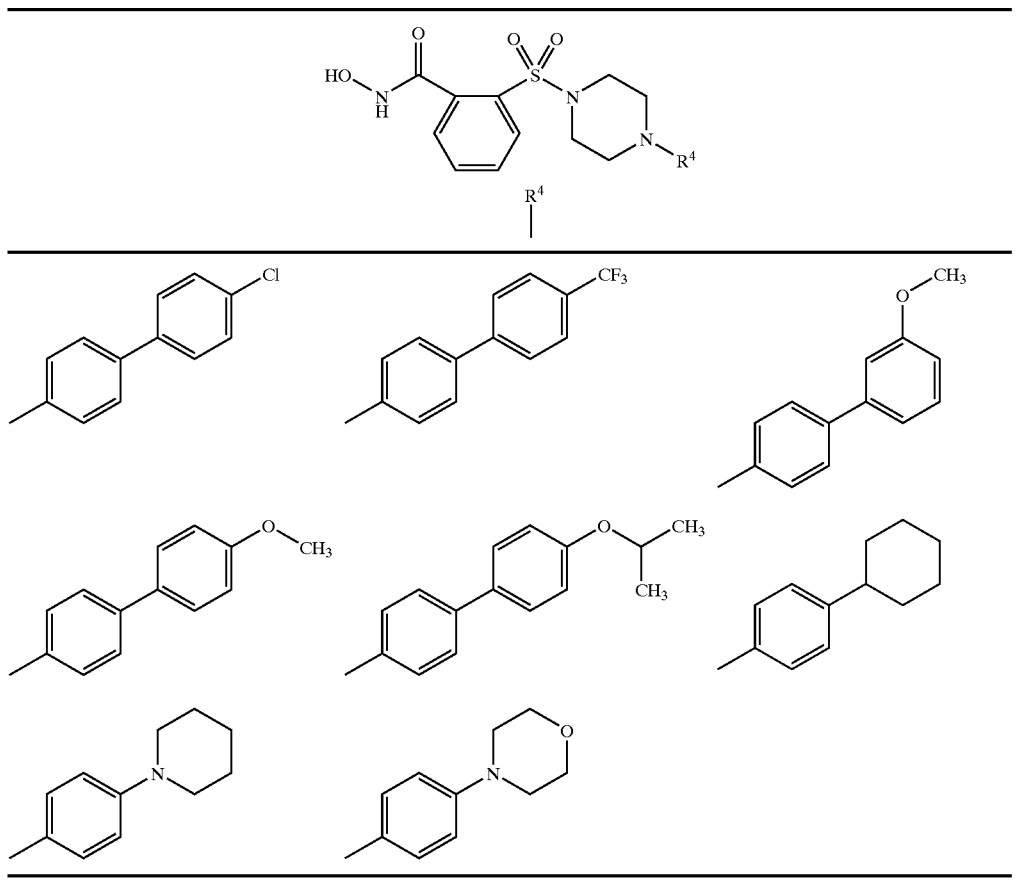
TABLE 5
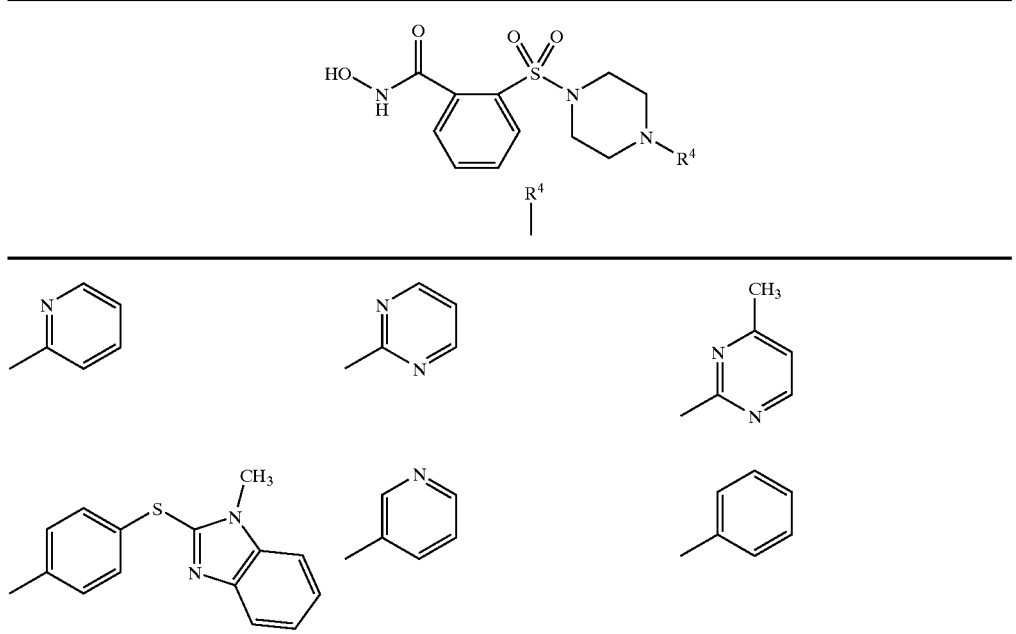

TABLE 5-continued
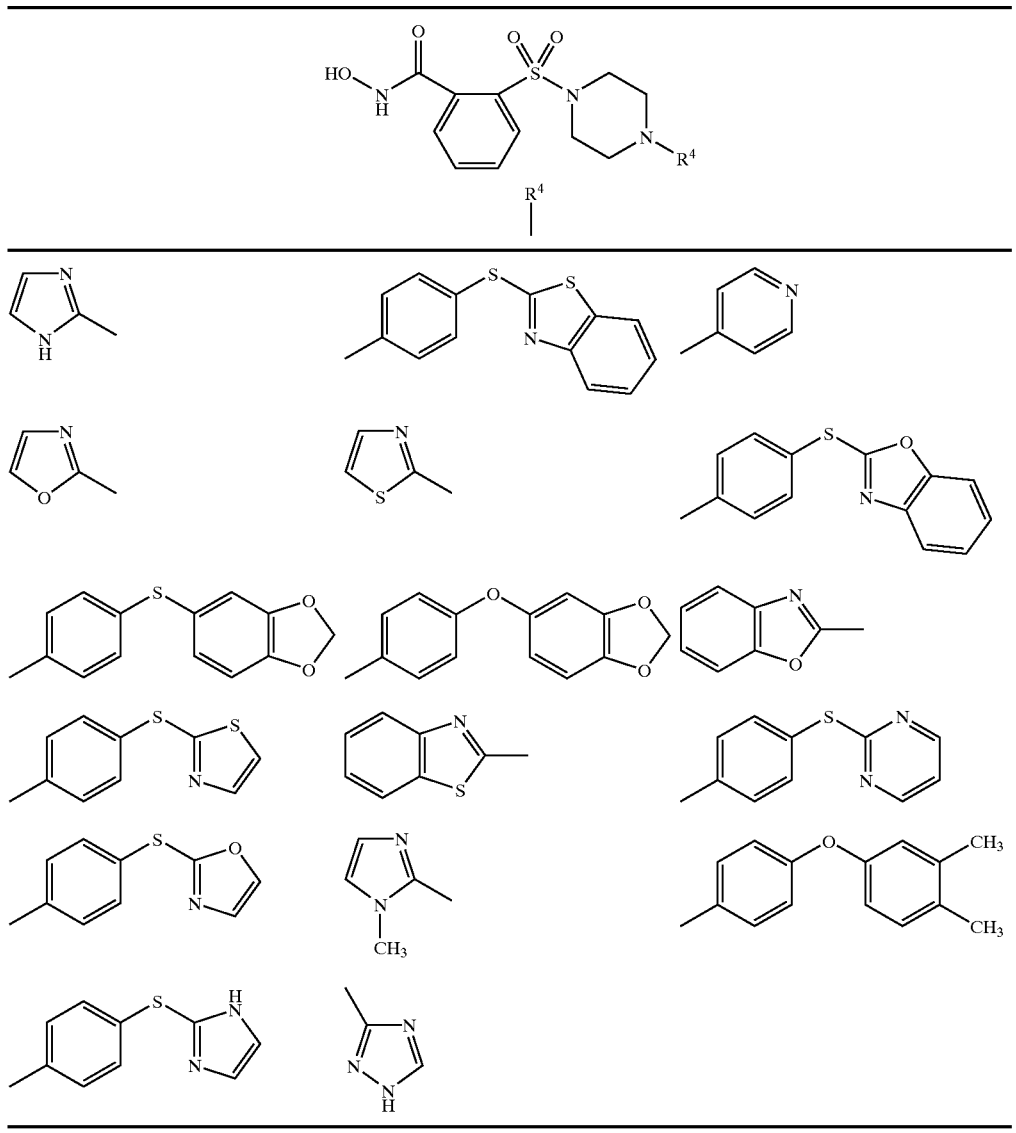
TABLE 6
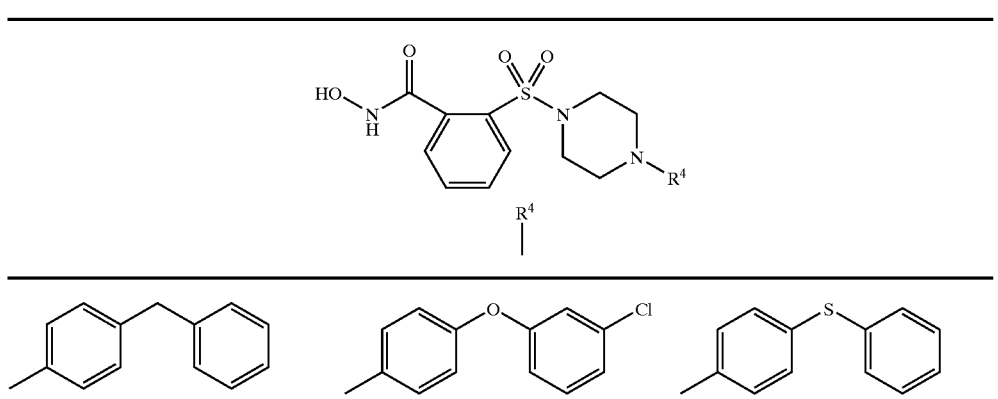

TABLE 6-continued

[Structure: 2-(piperazin-1-ylsulfonyl)-N-hydroxybenzamide with R⁴ substituent on piperazine nitrogen]

R⁴ groups shown:
- 4-methylphenyl benzoyl (benzophenone-type)
- 4-methylphenyl cyclopentyl sulfide
- 4-methylphenyl cyclohexyl sulfide
- 4-methylphenyl phenyl ether
- 4-methylphenyl (4-chlorophenyl) ether
- 4-methylphenyl (pyridin-2-yl) sulfide
- 4-methylphenyl (2-methylphenyl) ether
- 4-methylphenyl (pyridin-2-yl) ether
- 4-methylphenyl (pyridin-3-yl) sulfide
- 4-methylphenyl (3-methylphenyl) ether
- 4-methylphenyl (pyridin-3-yl) ether
- 4-methylphenyl (pyridin-4-yl) sulfide
- 4-methylphenyl (4-methylphenyl) ether
- 4-methylphenyl (pyridin-4-yl) ether
- 4-methylphenyl (3-chlorophenyl) ether
- 4-methylphenyl (3-trifluoromethylphenyl) ether
- 4-methylphenyl (4-trifluoromethylphenyl) ether
- 4-methylphenyl cyclohexyl ether

TABLE 7

[Structure: 2-(piperazin-1-ylsulfonyl)-N-hydroxybenzamide with R⁴ substituent on piperazine nitrogen]

R⁴ groups shown:
- N-(4-methylphenyl)-4-ethylbenzamide
- N-(4-methylphenyl)-4-methoxybenzamide TABLE 7-continued
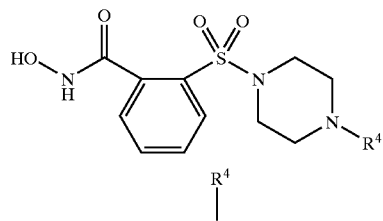
R[4]
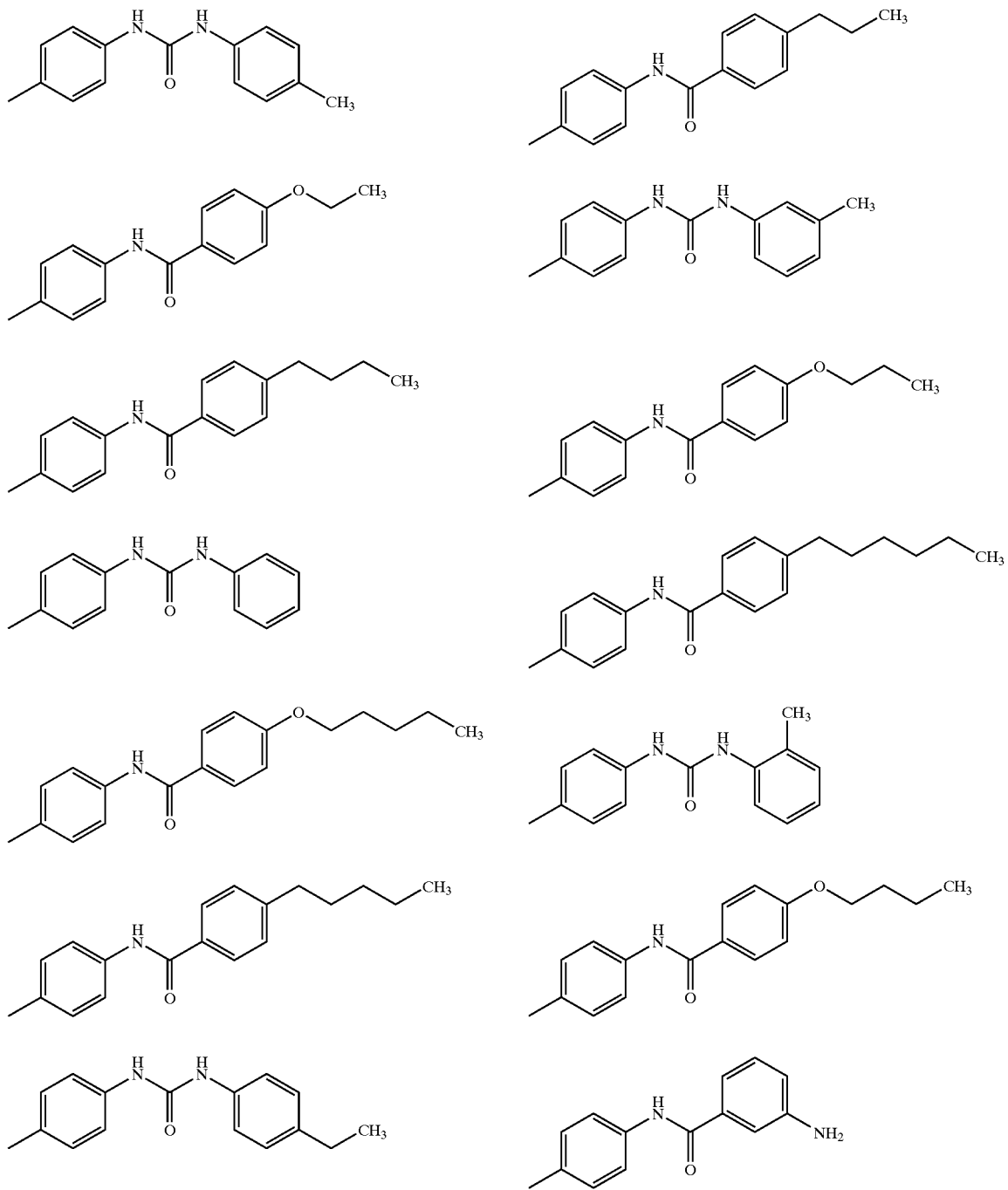

TABLE 7-continued
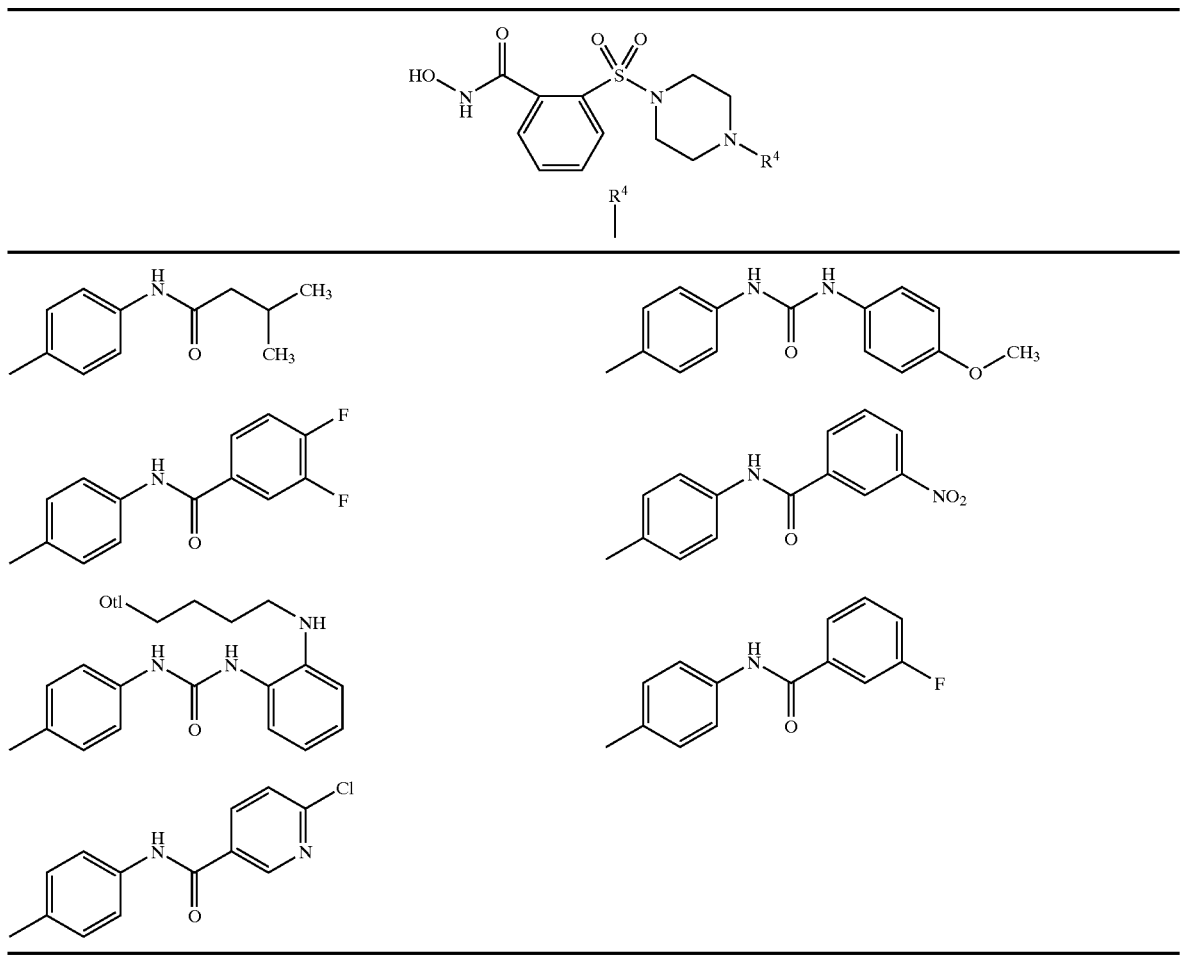
TABLE 8
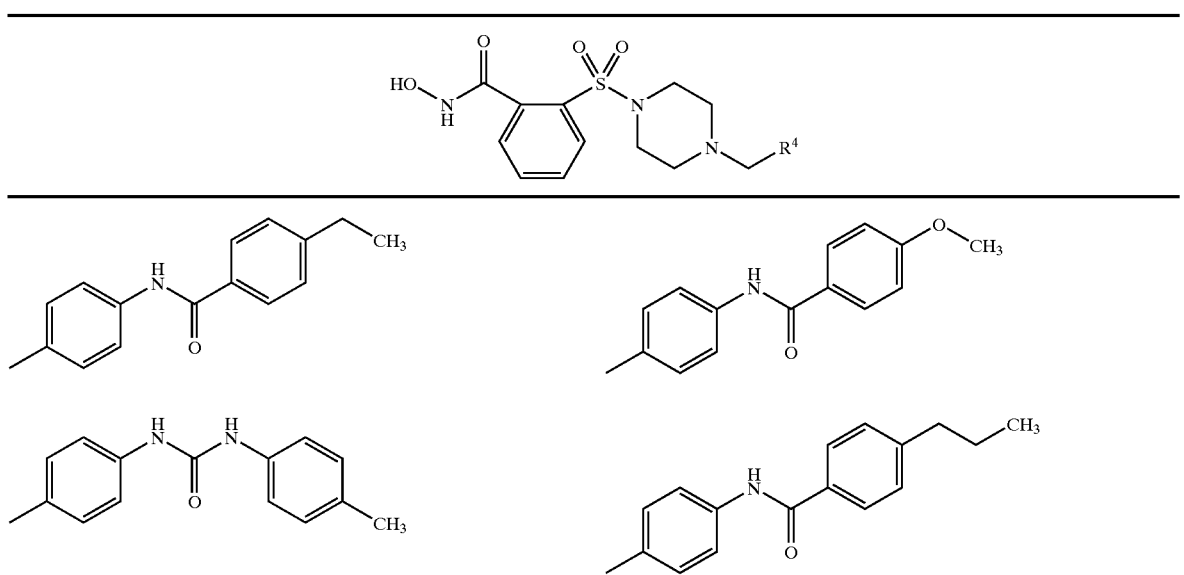

TABLE 8-continued
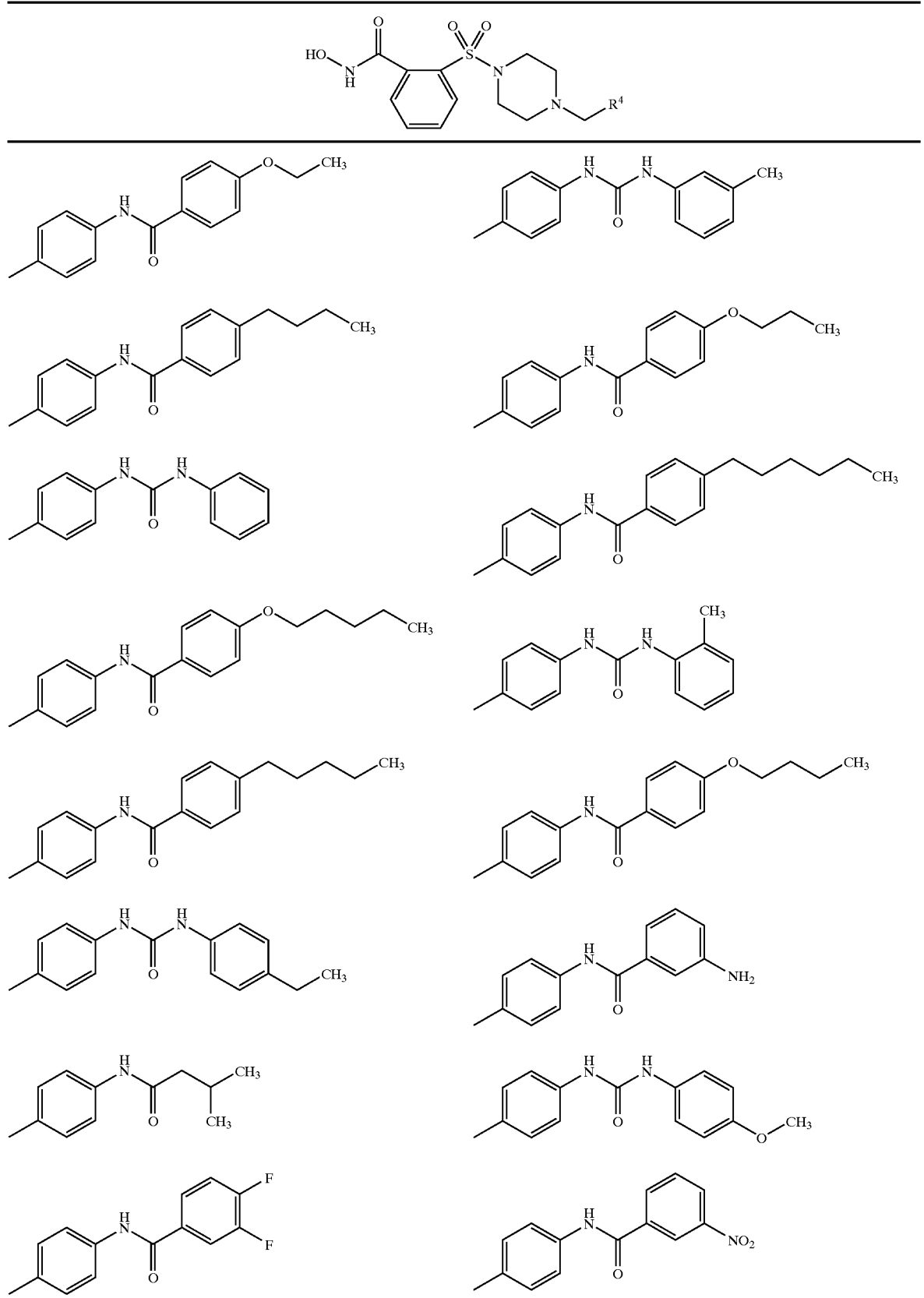

TABLE 8-continued
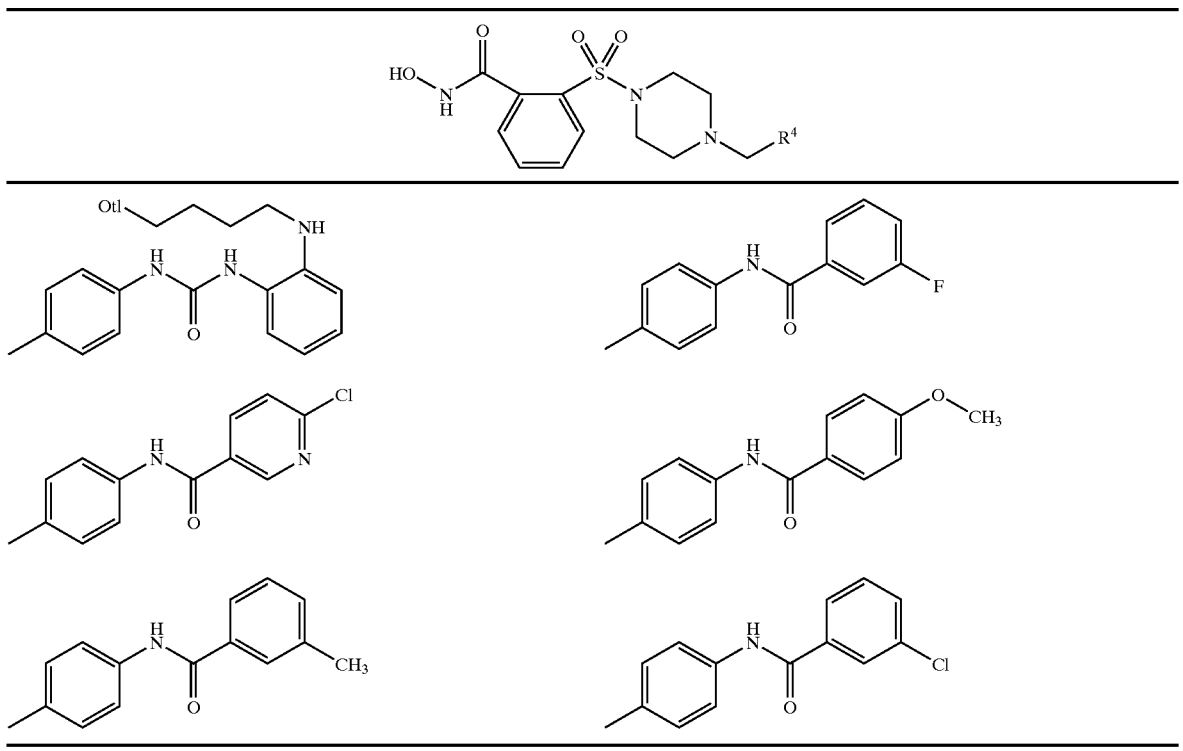
TABLE 9
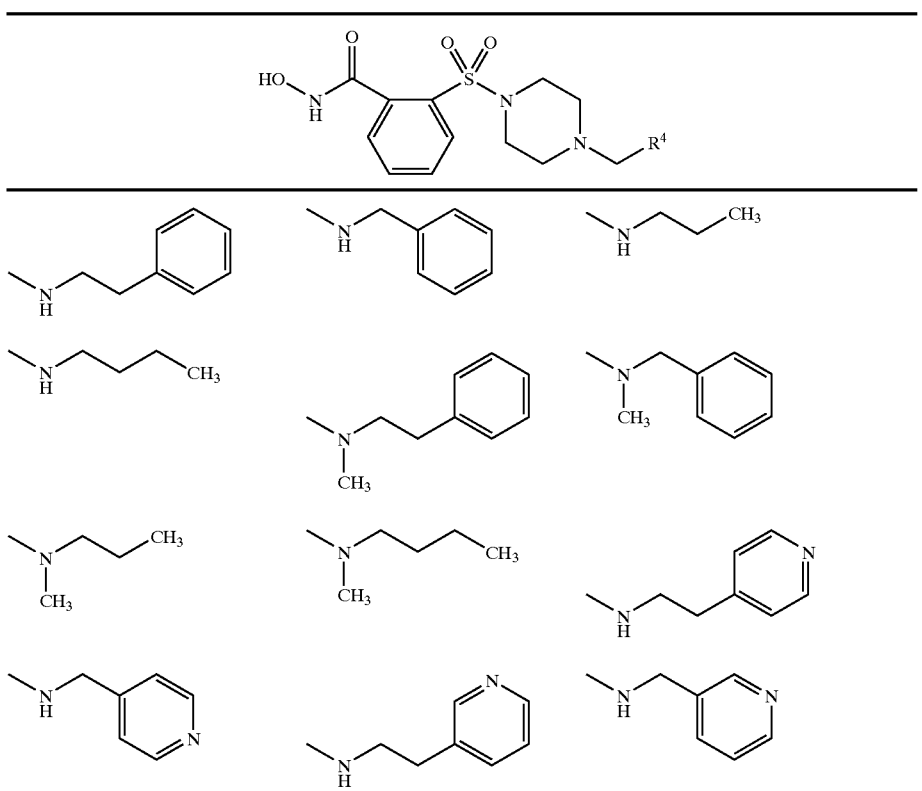

TABLE 9-continued
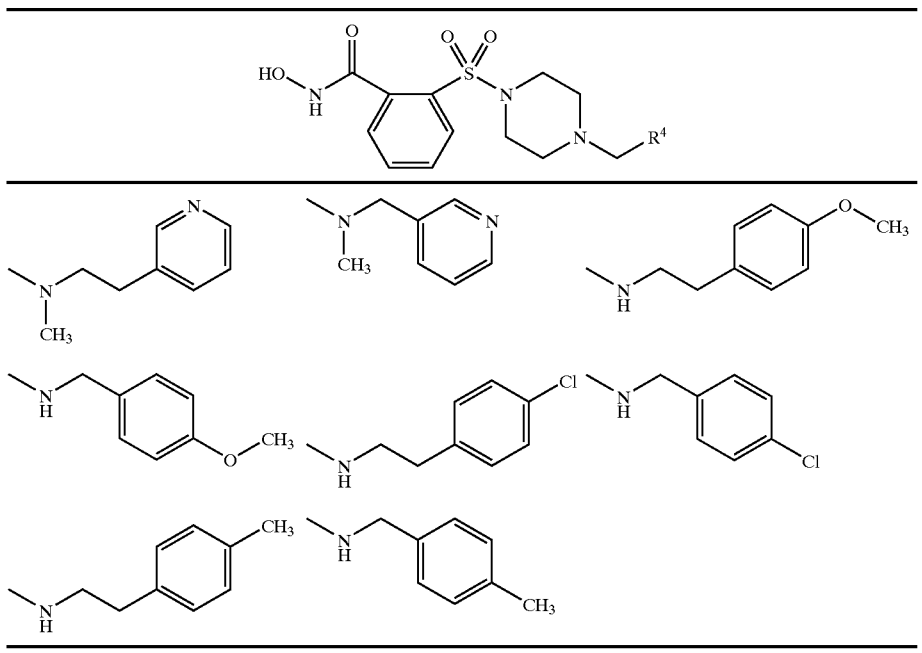
TABLE 10
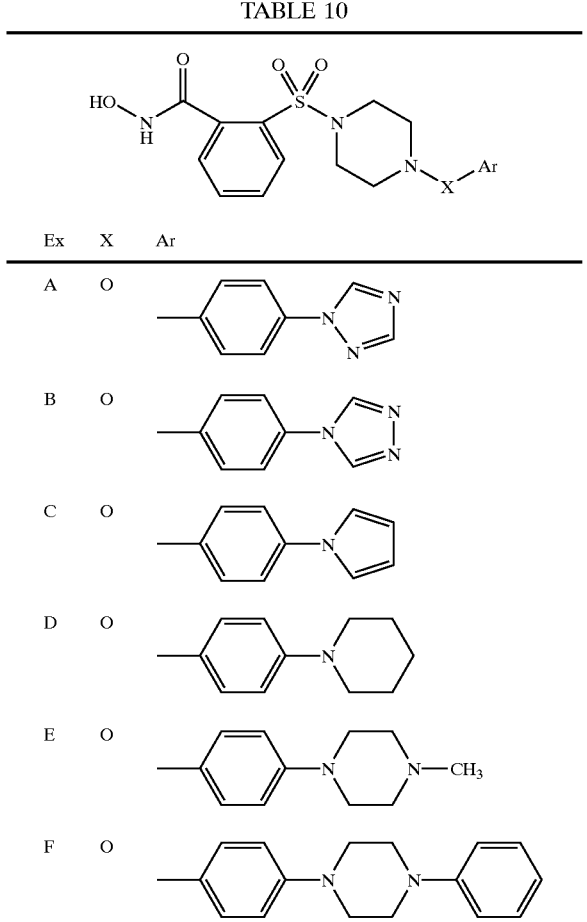
TABLE 10-continued
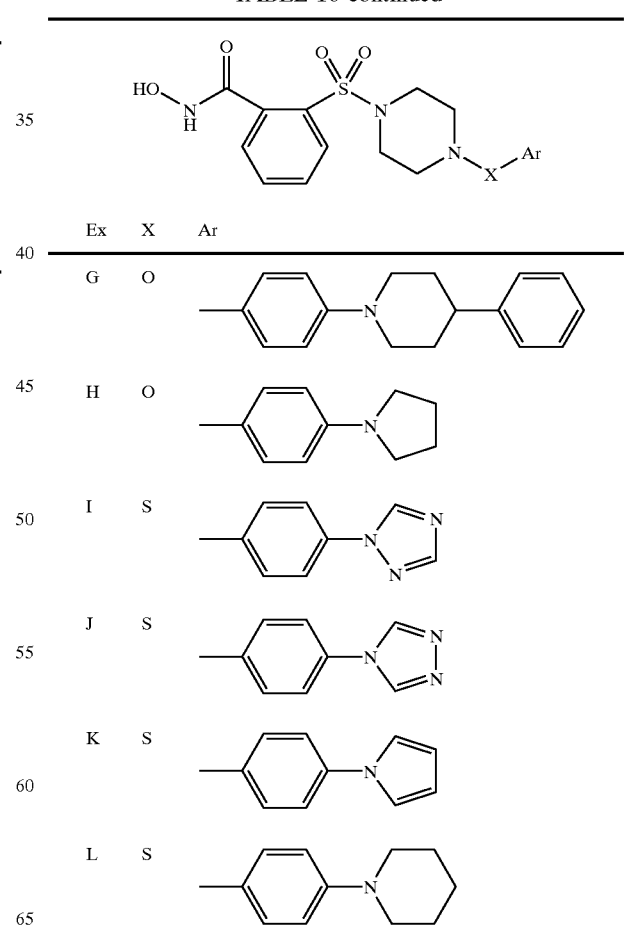

TABLE 10-continued
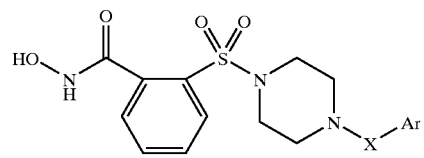
| Ex | X | Ar |
|---|---|---|
| M | S | 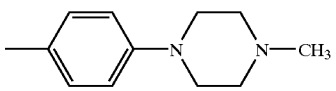 |
| N | S | 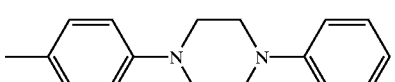 |
| O | S | 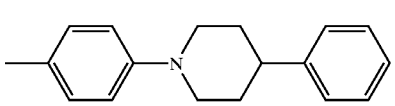 |
| P | S | 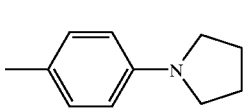 |
TABLE 11
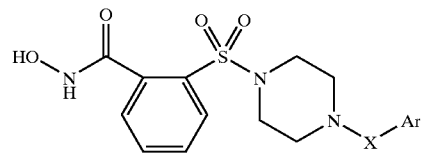
| Ex | X | Ar |
|---|---|---|
| A | O | 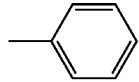 |
| B | O |  |
| C | O | 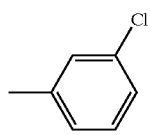 |
| D | O | 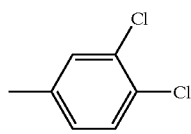 |
| E | O | 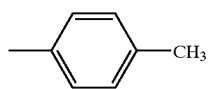 |
TABLE 11-continued
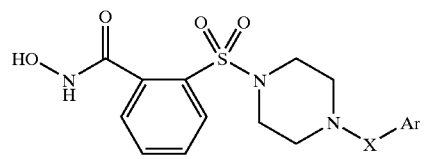
| Ex | X | Ar |
|---|---|---|
| F | O | 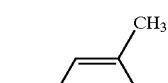 |
| G | O | 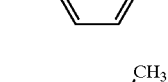 |
| H | O | 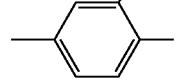 |
| I | O | 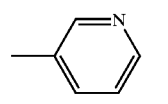 |
| J | O | 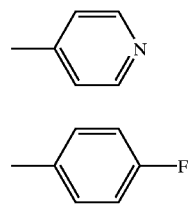 |
| K | O | 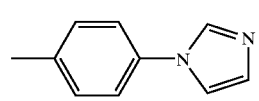 |
| L | S | 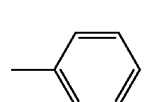 |
| M | S |  |
| N | S | 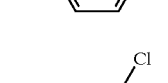 |
| O | S | 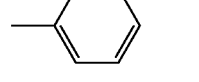 |
| P | S | 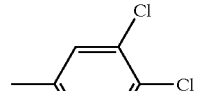 |

TABLE 11-continued
| Ex | X | Ar |
|---|---|---|
| Q | S | 3,5-dimethylphenyl (shown as 3-methyl with methyl) |
| R | S | 2,4-dimethylphenyl |
| S | S | 3-pyridyl |
| T | S | 4-pyridyl |
| U | S | 4-fluorophenyl |
| V | S | 4-(1-imidazolyl)phenyl |
TABLE 12
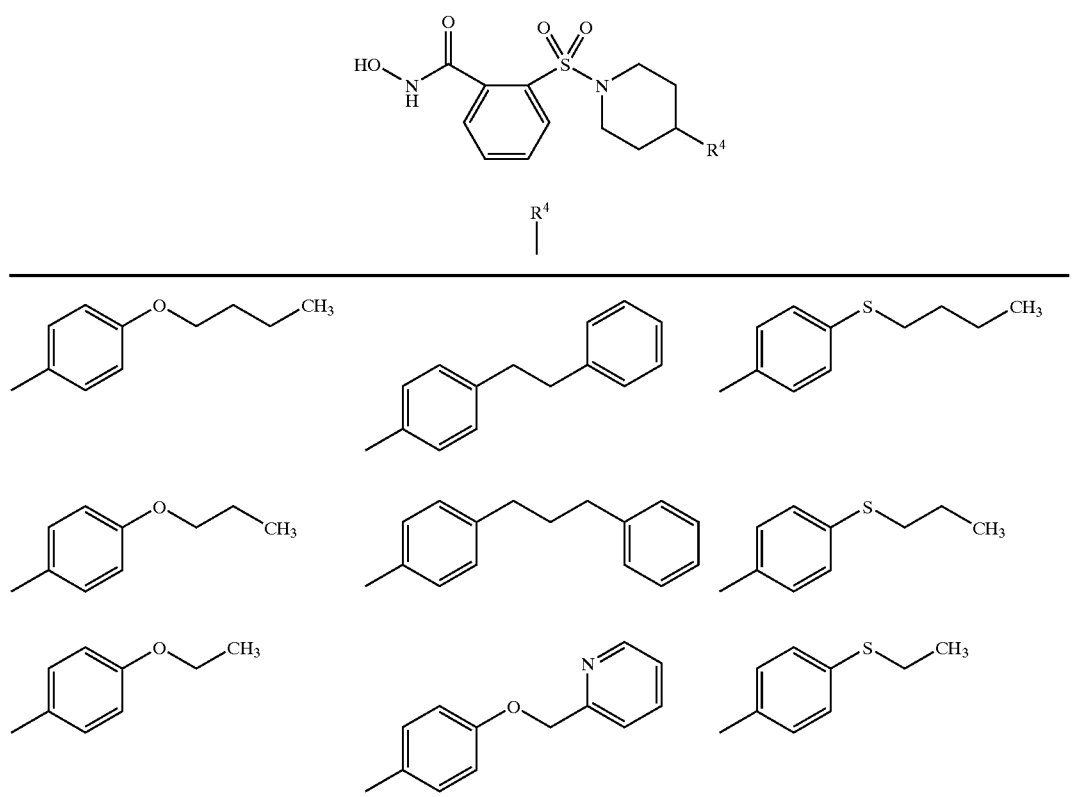

TABLE 12-continued
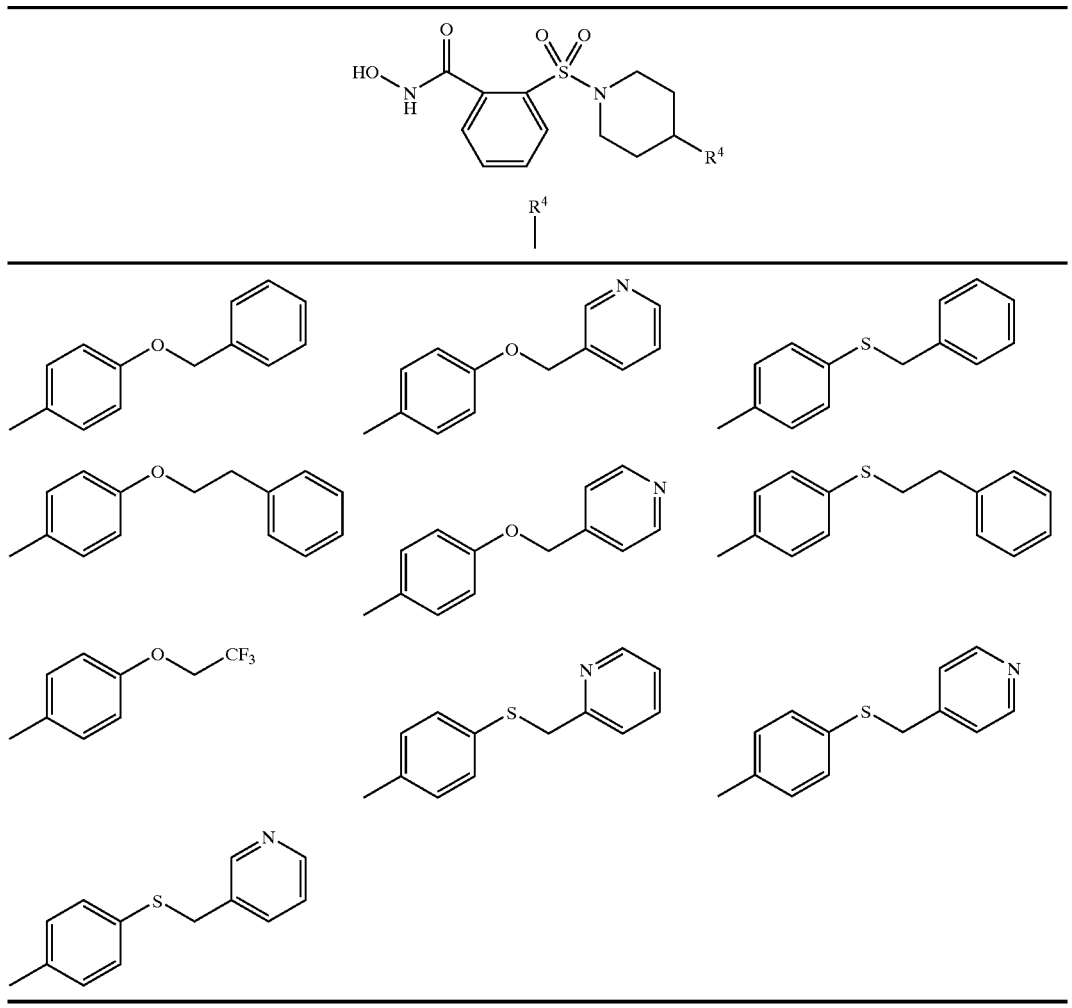
TABLE 13
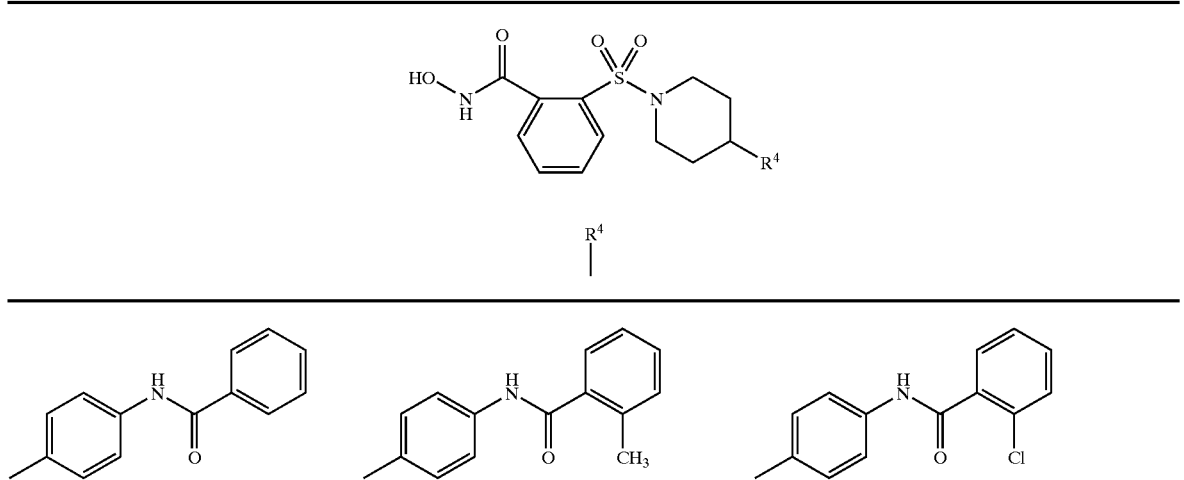

TABLE 13-continued
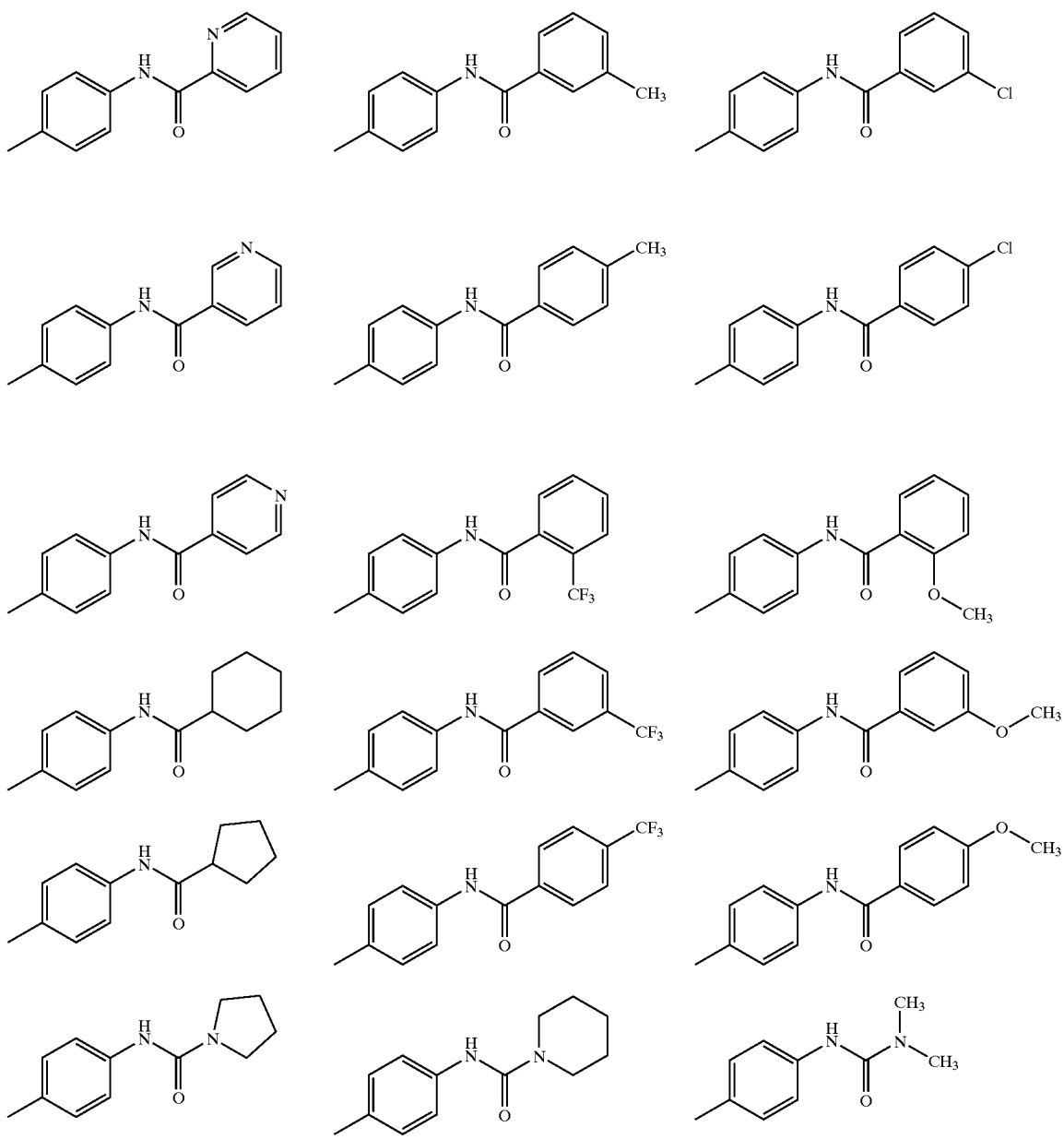

TABLE 14
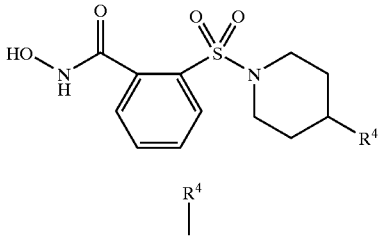

TABLE 14-continued
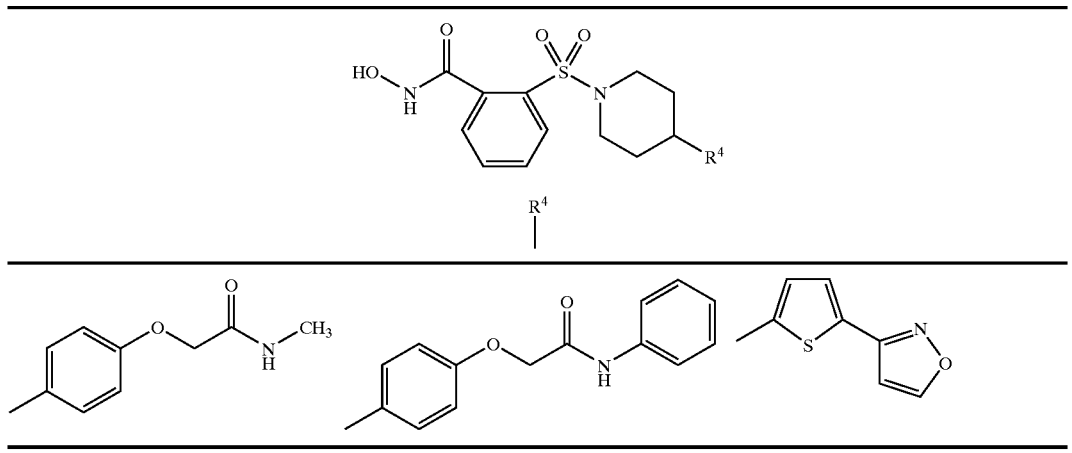
TABLE 15
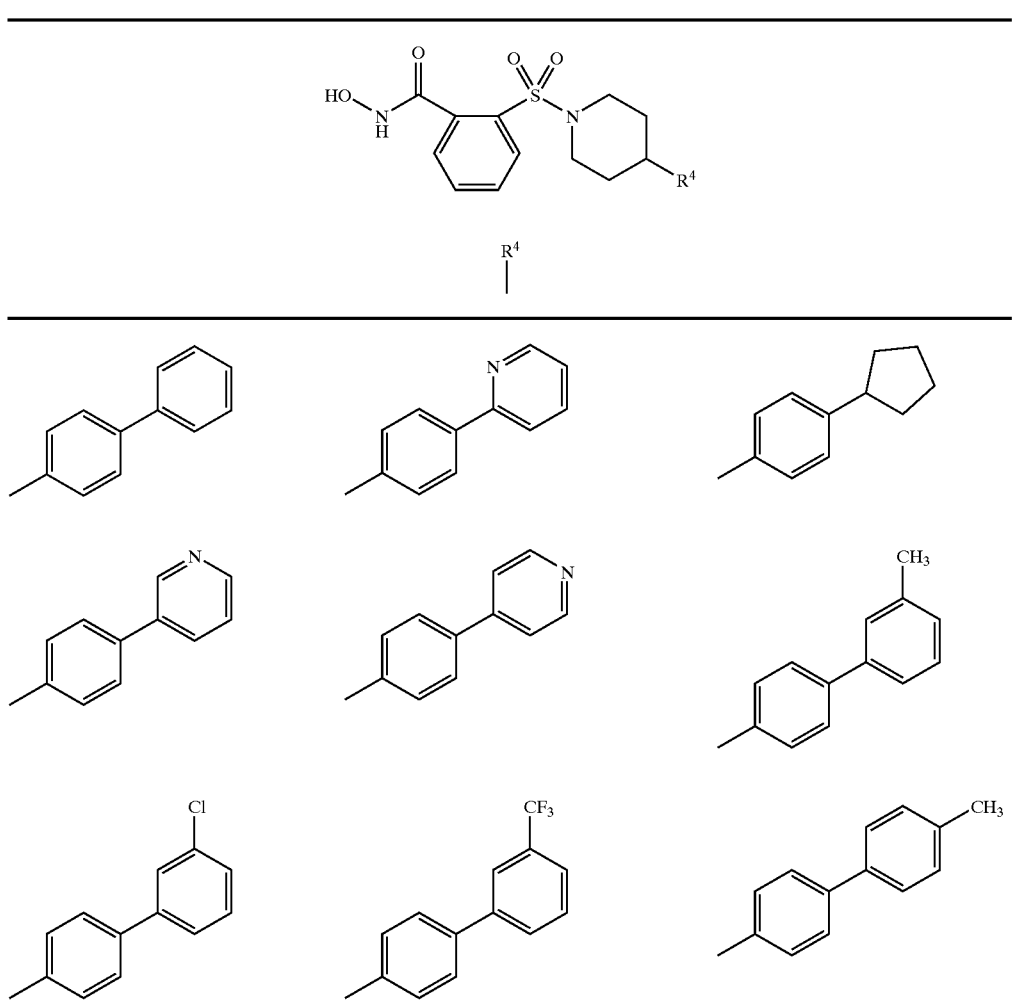

TABLE 15-continued
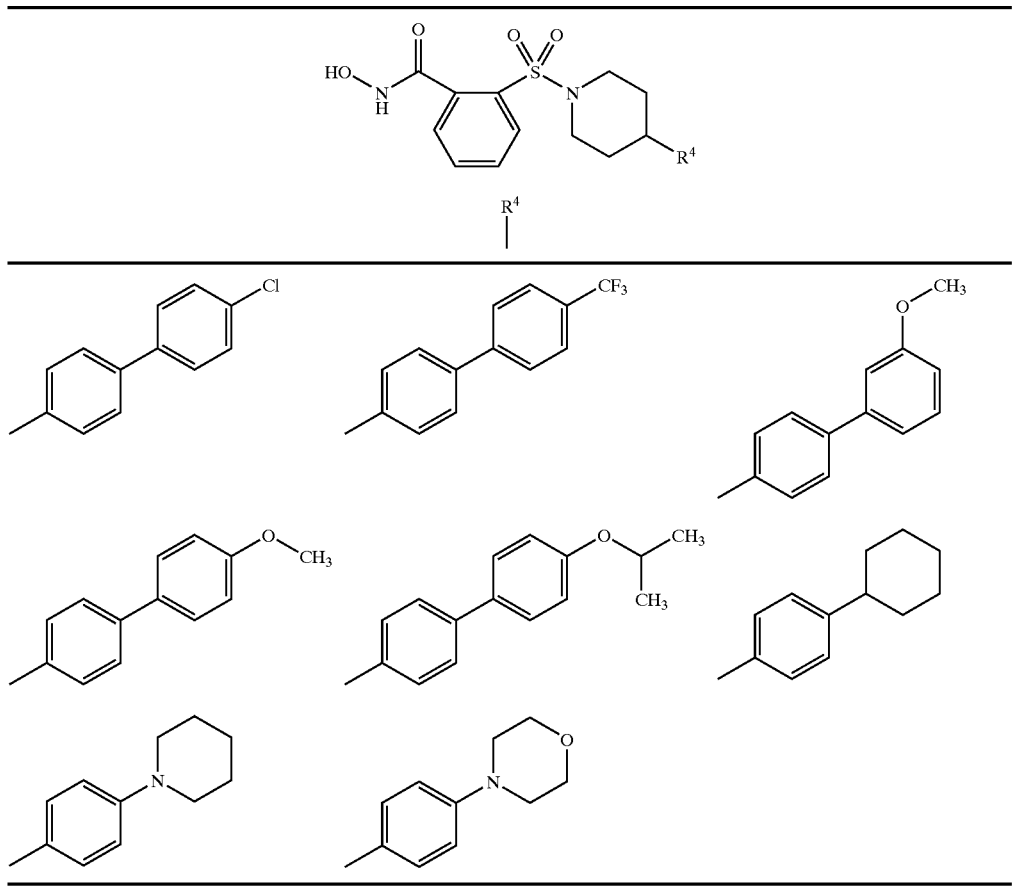
TABLE 16
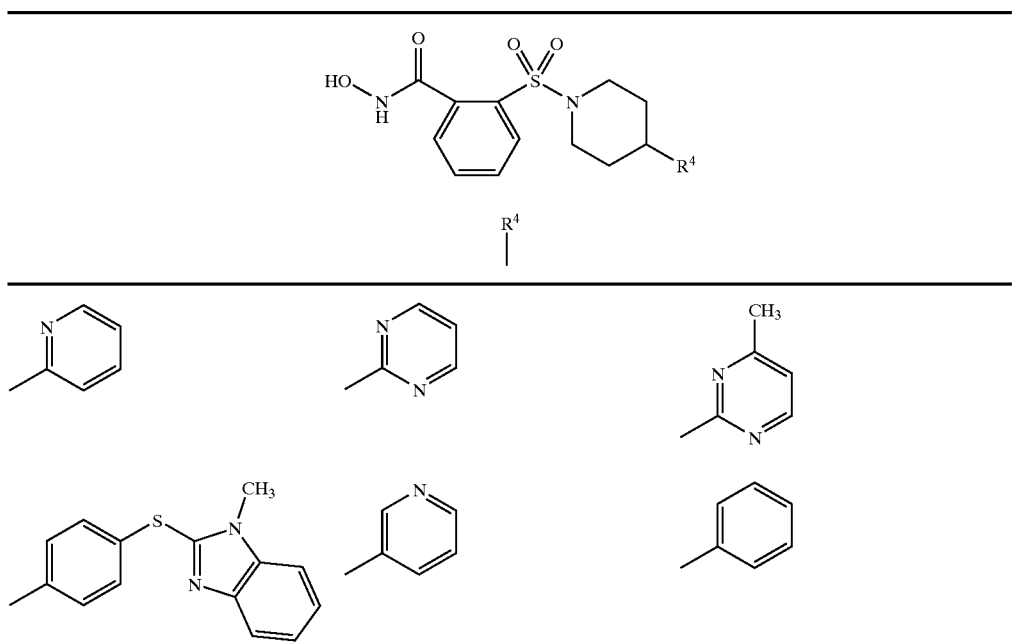

TABLE 16-continued
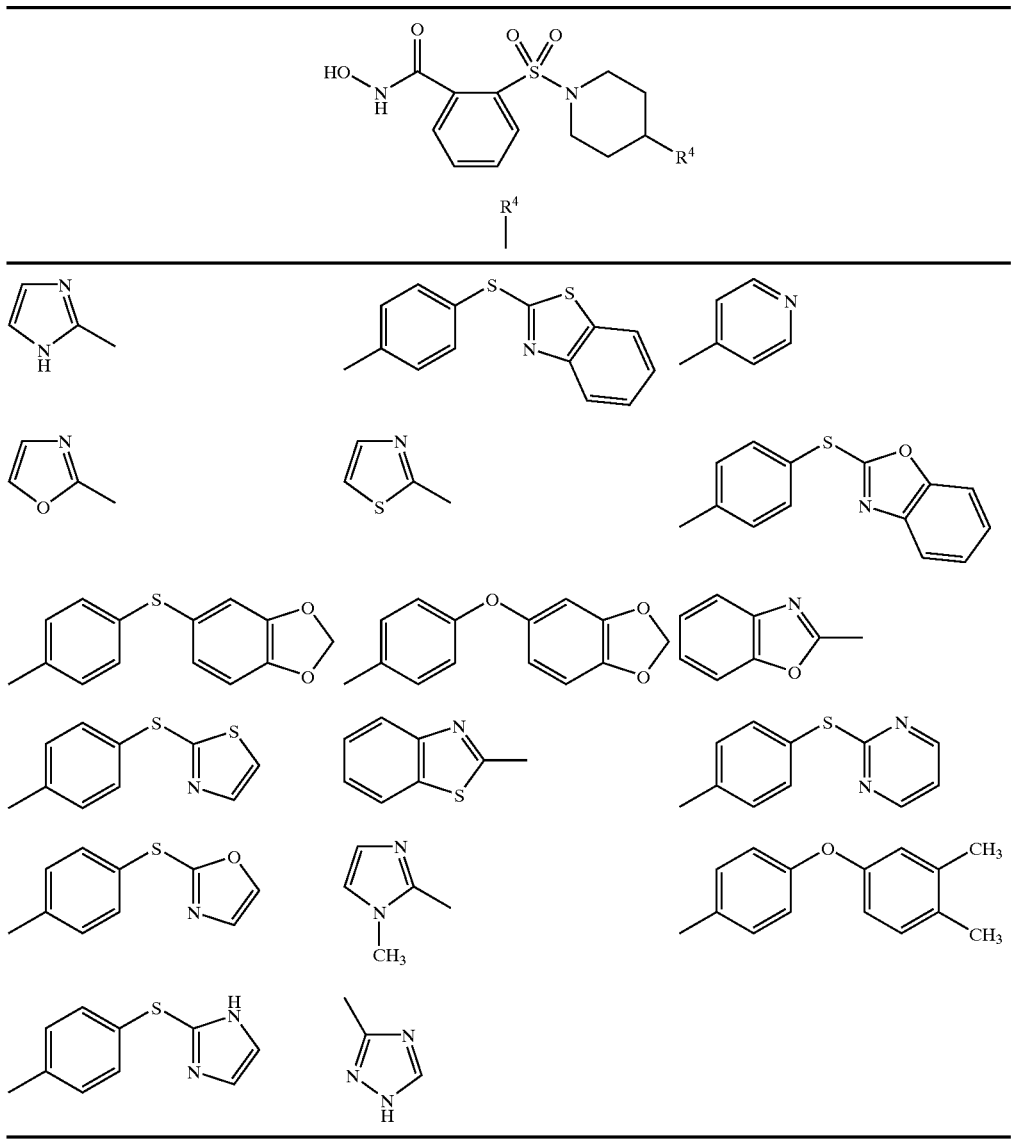
TABLE 17
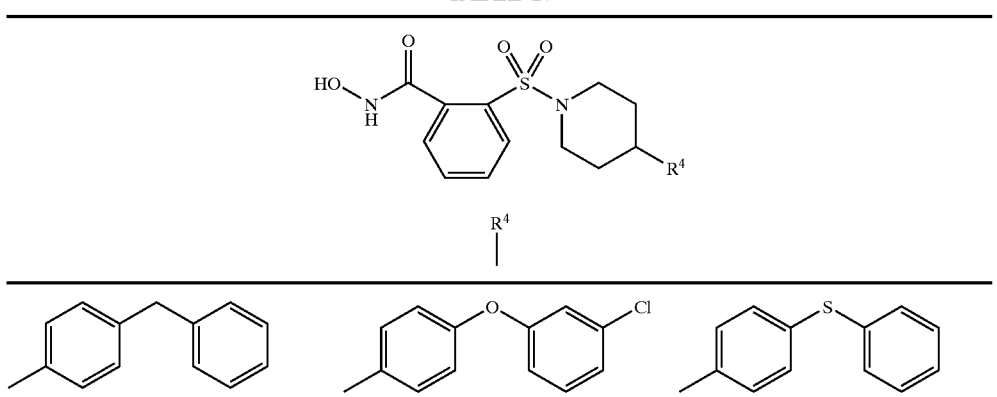

TABLE 17-continued
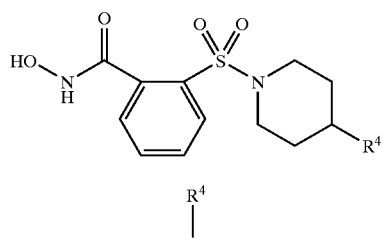
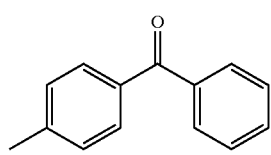 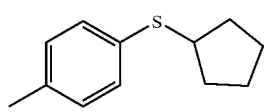 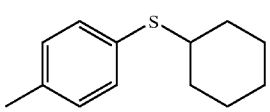
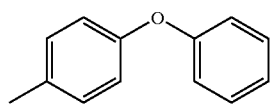 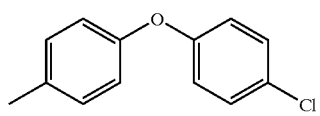 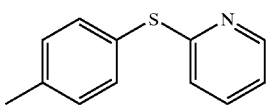
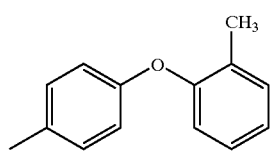 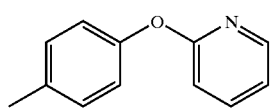 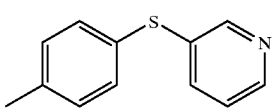
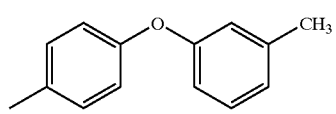 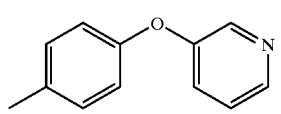 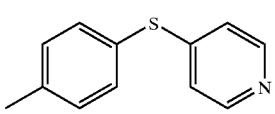
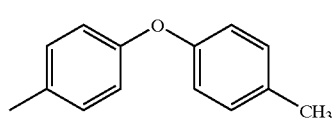 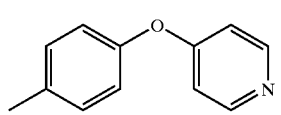 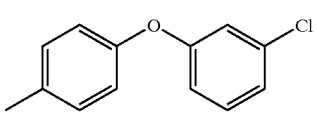
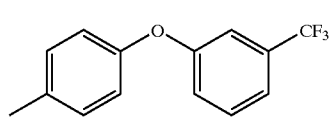 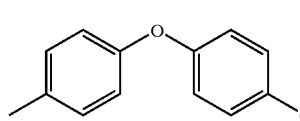 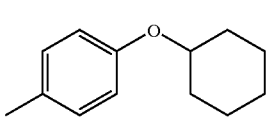

TABLE 18
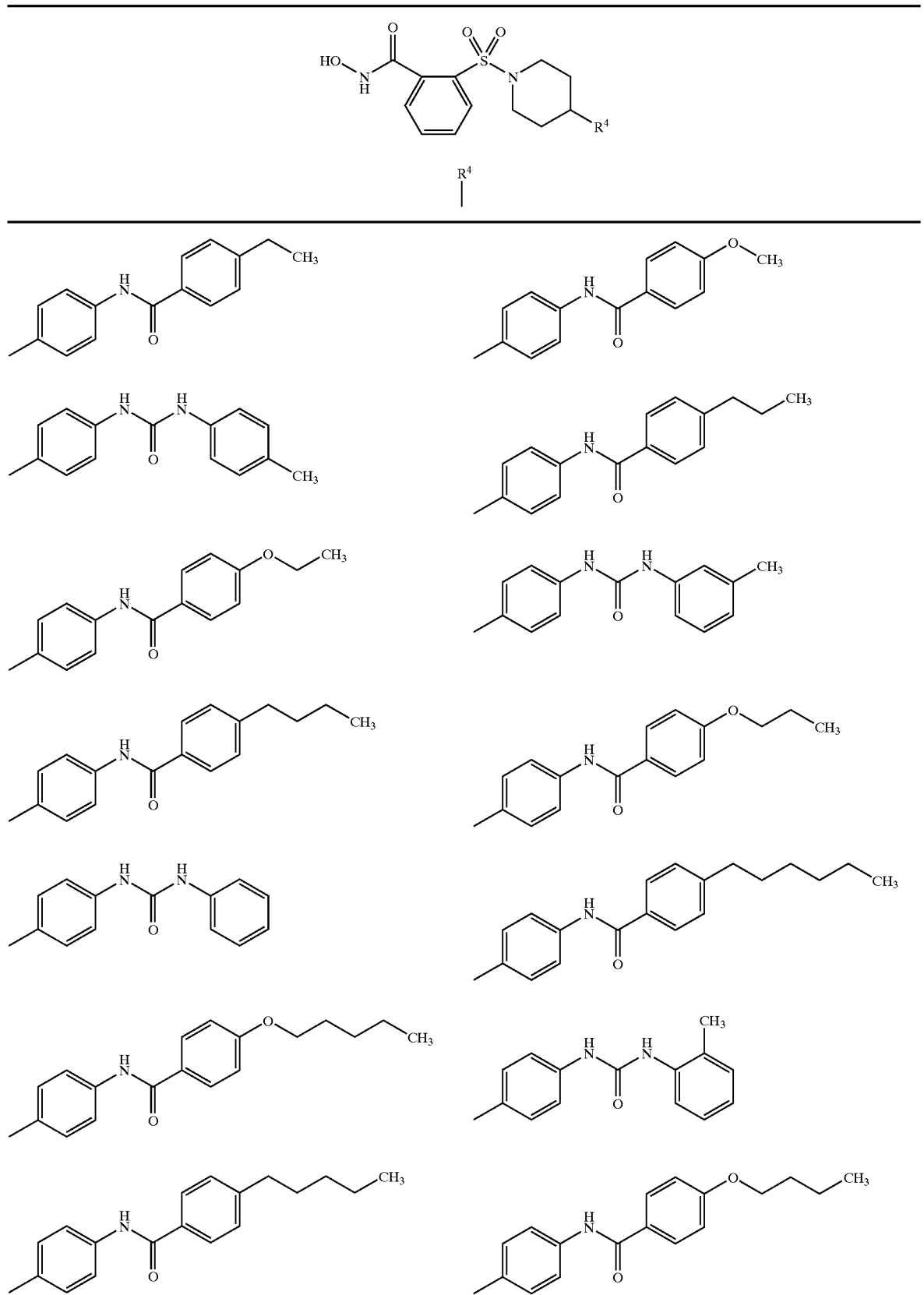

TABLE 18-continued
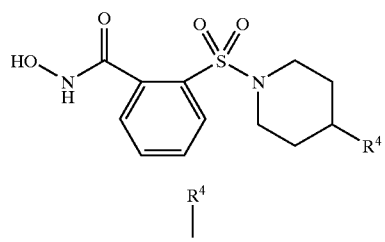
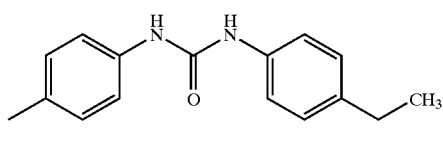 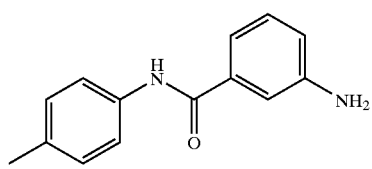
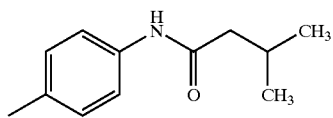 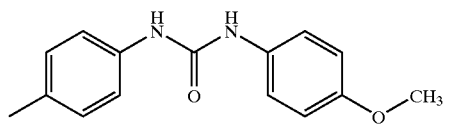
 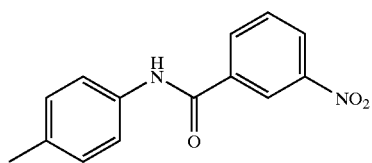
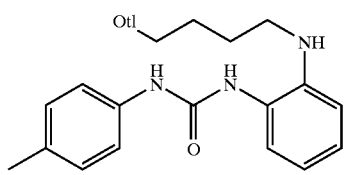 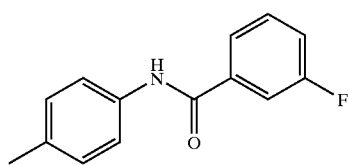
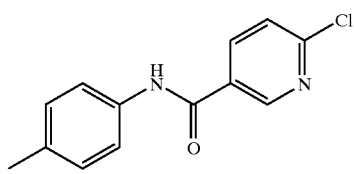 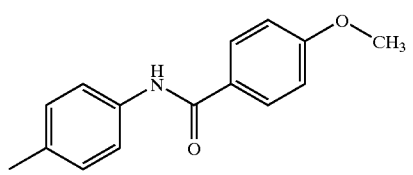
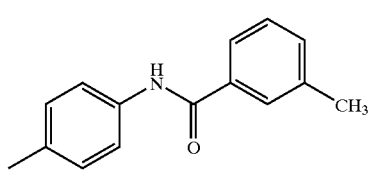 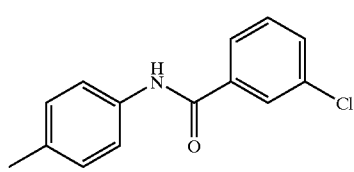

TABLE 19
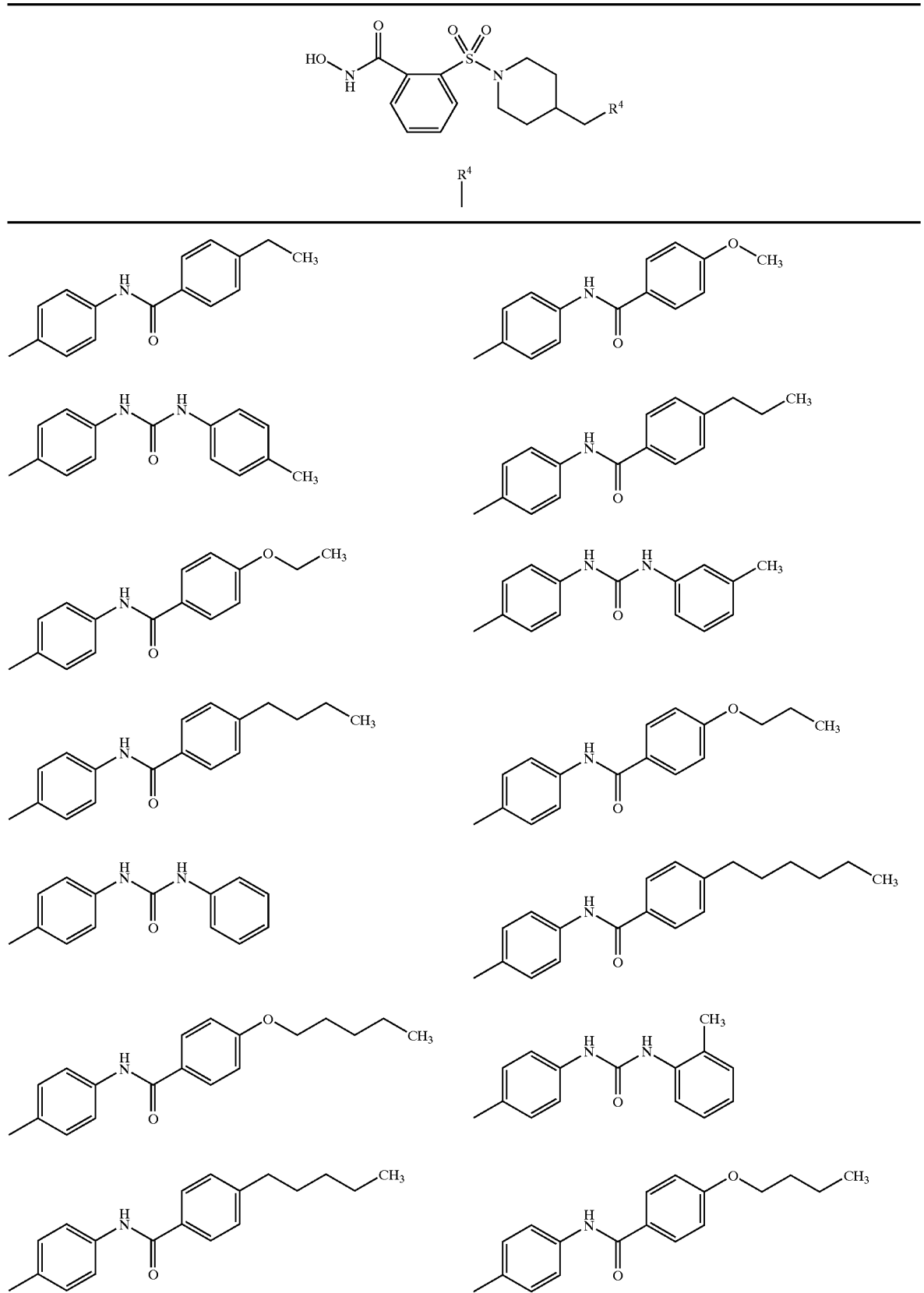

TABLE 19-continued
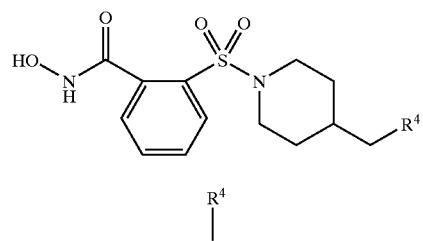
| R⁴ |  |
|---|---|
| 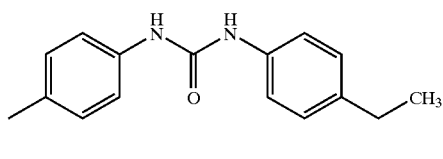 | 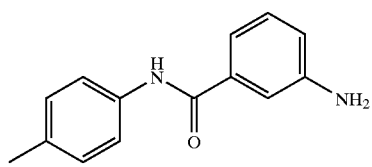 |
| 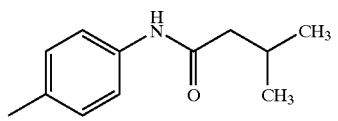 | 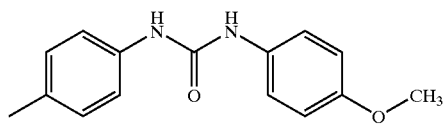 |
| 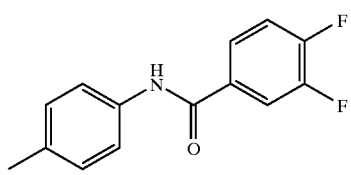 | 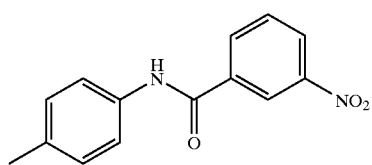 |
| 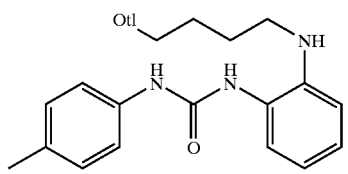 | 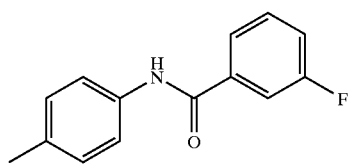 |
| 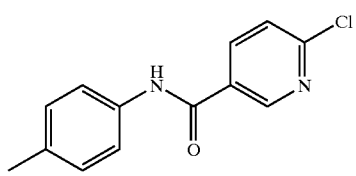 | 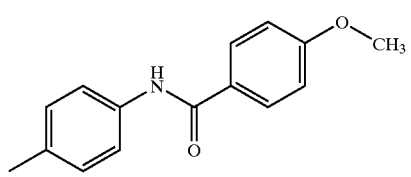 |
| 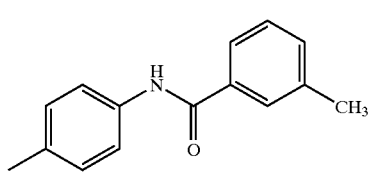 | 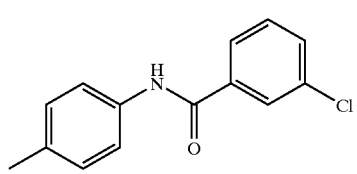 |

TABLE 20
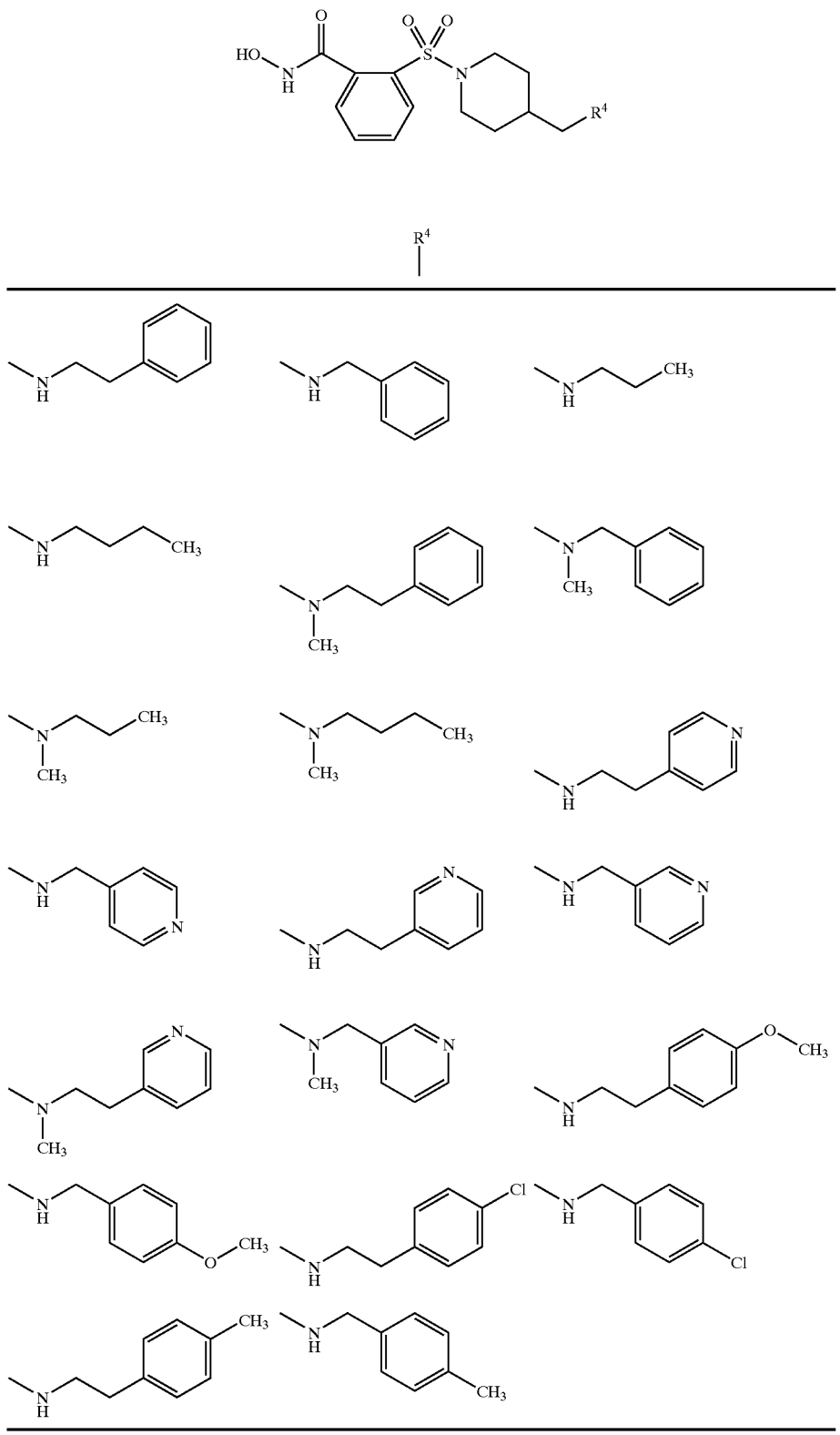

TABLE 21

[Structure: HO-NH-C(=O)-phenyl-SO2-N(piperidine)-X-Ar]

| Ex | X | Ar |
|----|---|-----|
| A | O | 4-(1,2,4-triazol-1-yl)phenyl |
| B | O | 4-(1,2,4-triazol-4-yl)phenyl |
| C | O | 4-(pyrrol-1-yl)phenyl |
| D | O | 4-(piperidin-1-yl)phenyl |
| E | O | 4-(4-methylpiperazin-1-yl)phenyl |
| F | O | 4-(4-phenylpiperazin-1-yl)phenyl |
| G | O | 4-(4-phenylpiperidin-1-yl)phenyl |
| H | O | 4-(pyrrolidin-1-yl)phenyl |
| I | S | 4-(1,2,4-triazol-1-yl)phenyl |
| J | S | 4-(1,2,4-triazol-4-yl)phenyl |
| K | S | 4-(pyrrol-1-yl)phenyl |
| L | S | 4-(piperidin-1-yl)phenyl |
| M | S | 4-(4-methylpiperazin-1-yl)phenyl |

TABLE 21-continued

[Structure: HO-NH-C(=O)-phenyl-SO2-N(piperidine)-X-Ar]

| Ex | X | Ar |
|----|---|-----|
| N | S | 4-(4-phenylpiperazin-1-yl)phenyl |
| O | S | 4-(4-phenylpiperidin-1-yl)phenyl |
| P | S | 4-(pyrrolidin-1-yl)phenyl |

TABLE 22

[Structure: HO-NH-C(=O)-phenyl-SO2-N(piperidine)-X-Ar]

| Ex | X | Ar |
|----|---|-----|
| A | O | phenyl |
| B | O | 4-chlorophenyl |
| C | O | 3-chlorophenyl |
| D | O | 3,4-dichlorophenyl |
| E | O | 4-methylphenyl |

TABLE 22-continued

| Ex | X | Ar |
|---|---|---|
| F | O | 3-methylphenyl |
| G | O | 2,4-dimethylphenyl |
| H | O | pyridin-3-yl |
| I | O | pyridin-4-yl |
| J | O | 4-fluorophenyl |
| K | O | 4-(1-imidazolyl)phenyl |
| L | S | phenyl |
| M | S | 4-chlorophenyl |
| N | S | 3-chlorophenyl |
| O | S | 3,4-dichlorophenyl |
| P | S | 4-methylphenyl |
| Q | S | 3-methylphenyl |
| R | S | 2,4-dimethylphenyl |
| S | S | pyridin-3-yl |
| T | S | pyridin-4-yl |
| U | S | 4-fluorophenyl |
| V | S | 4-(1-imidazolyl)phenyl |

TABLE 23
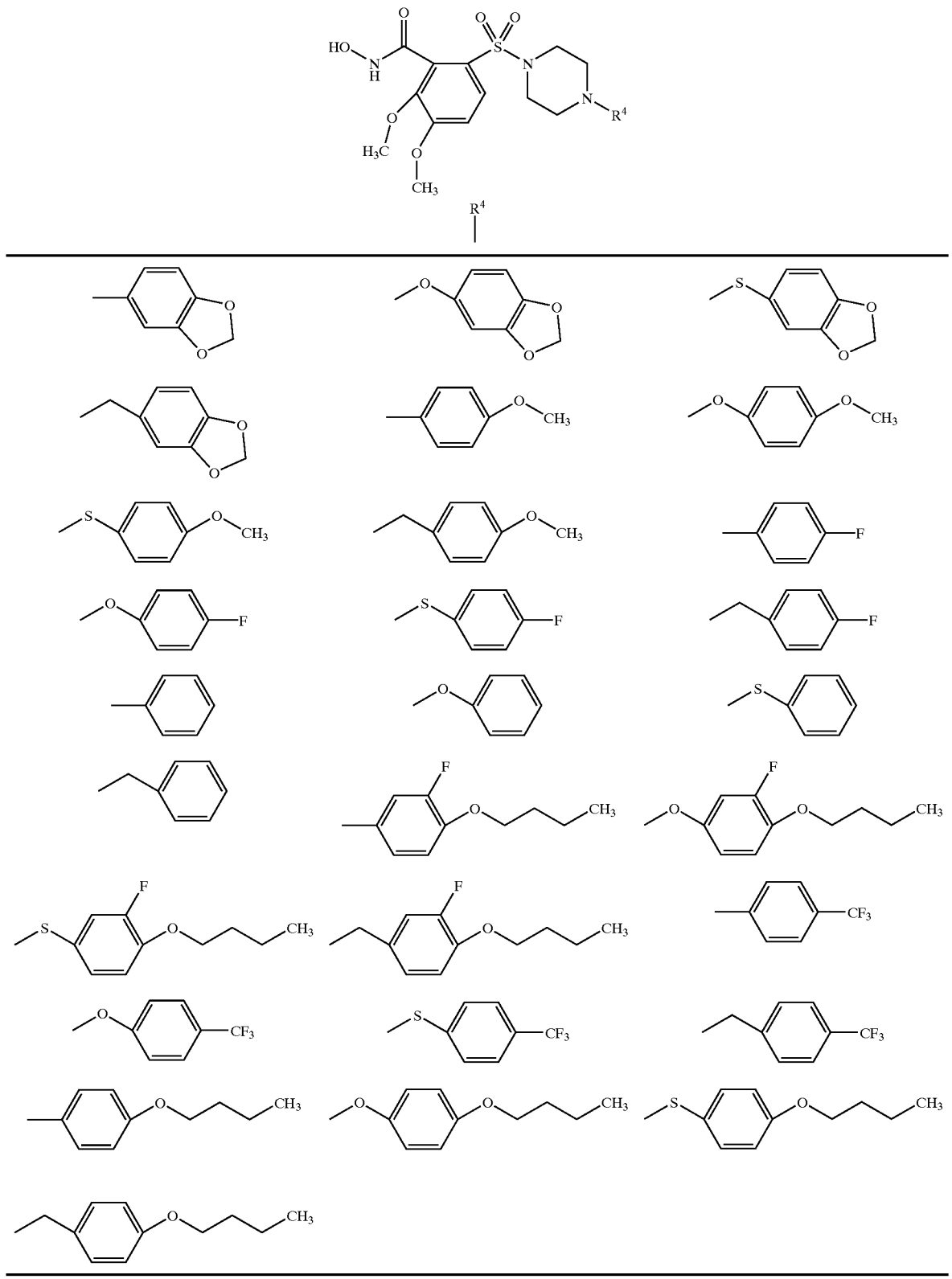

TABLE 24
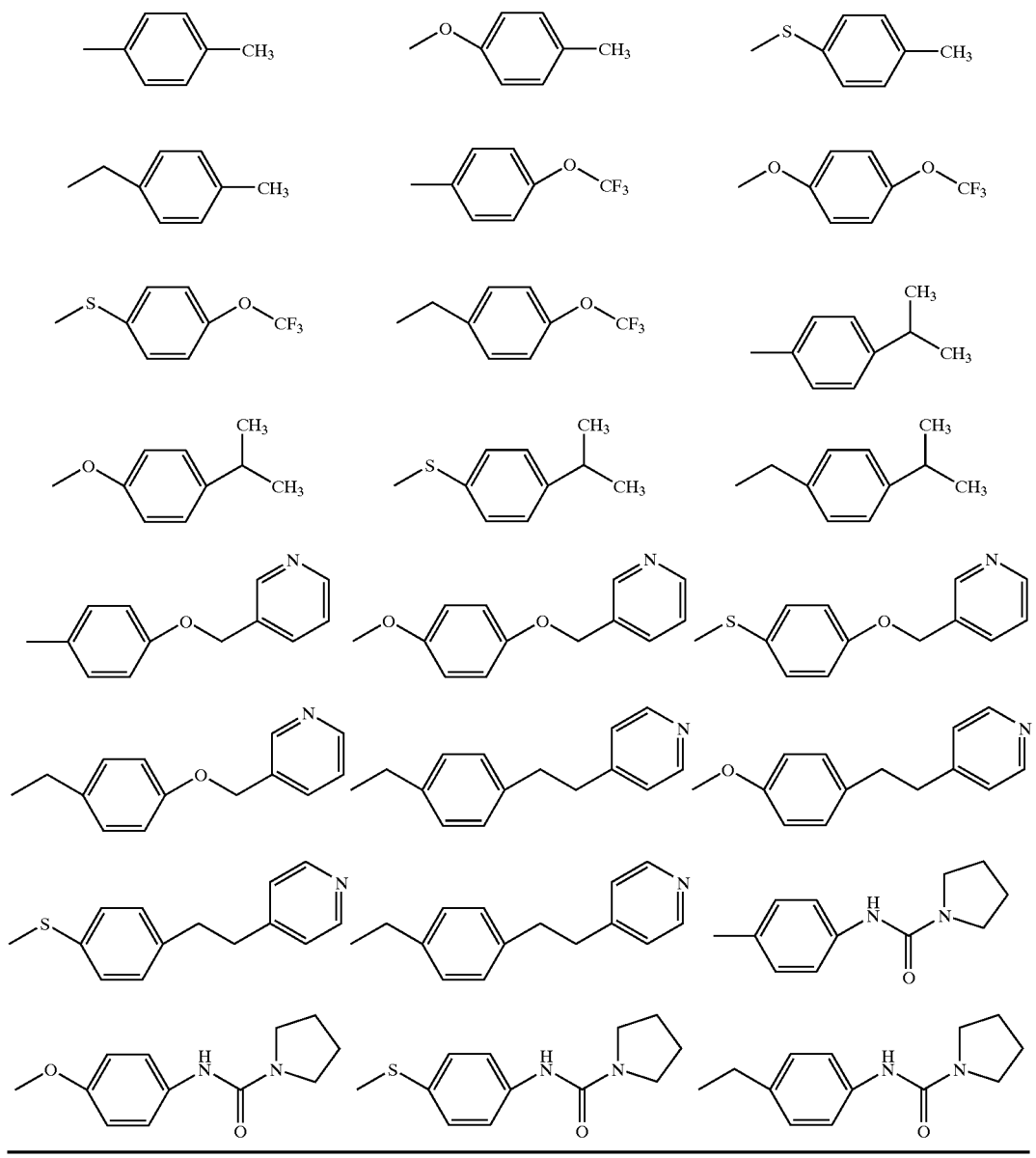

TABLE 25
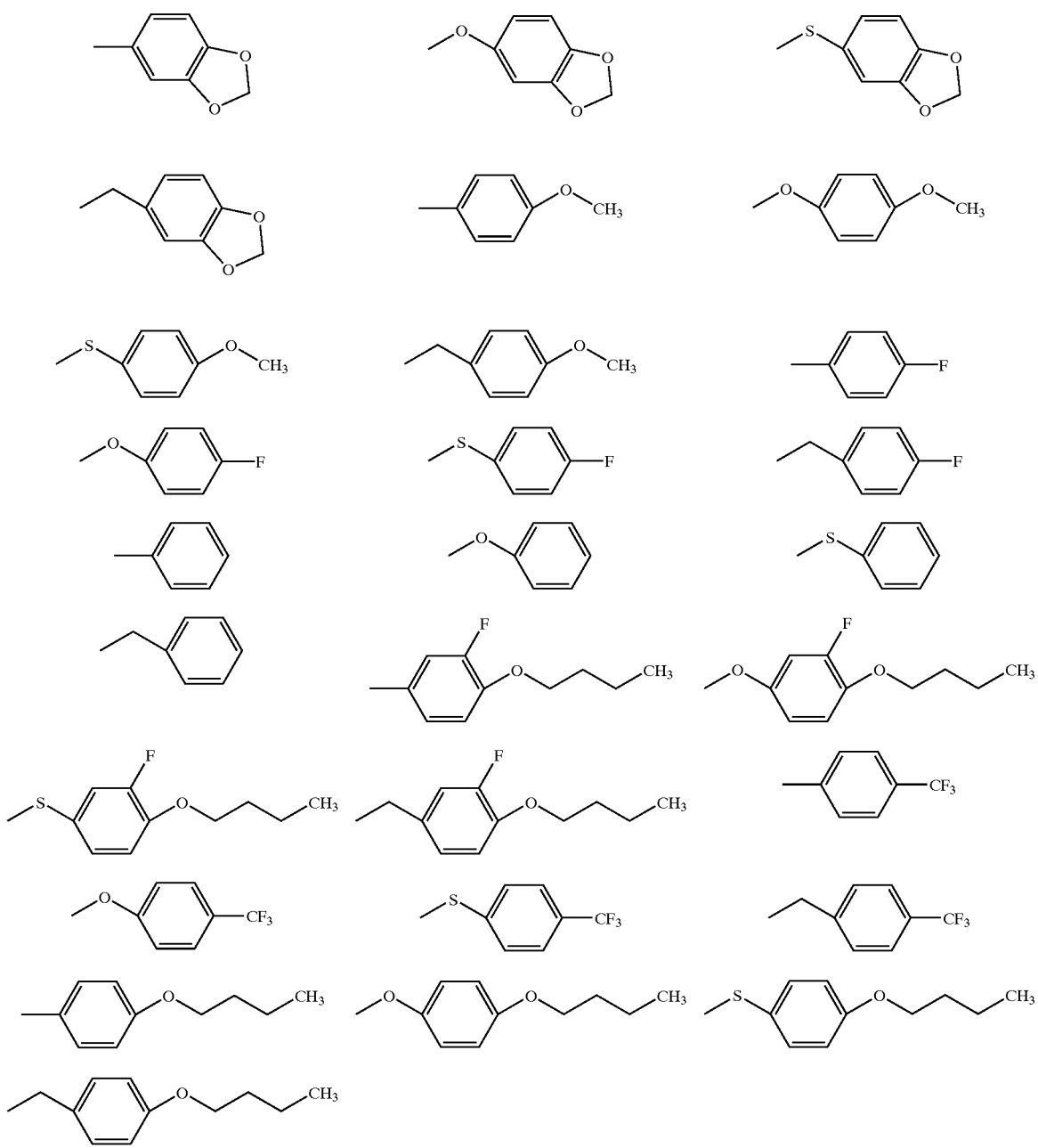

TABLE 26
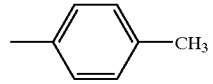

TABLE 27
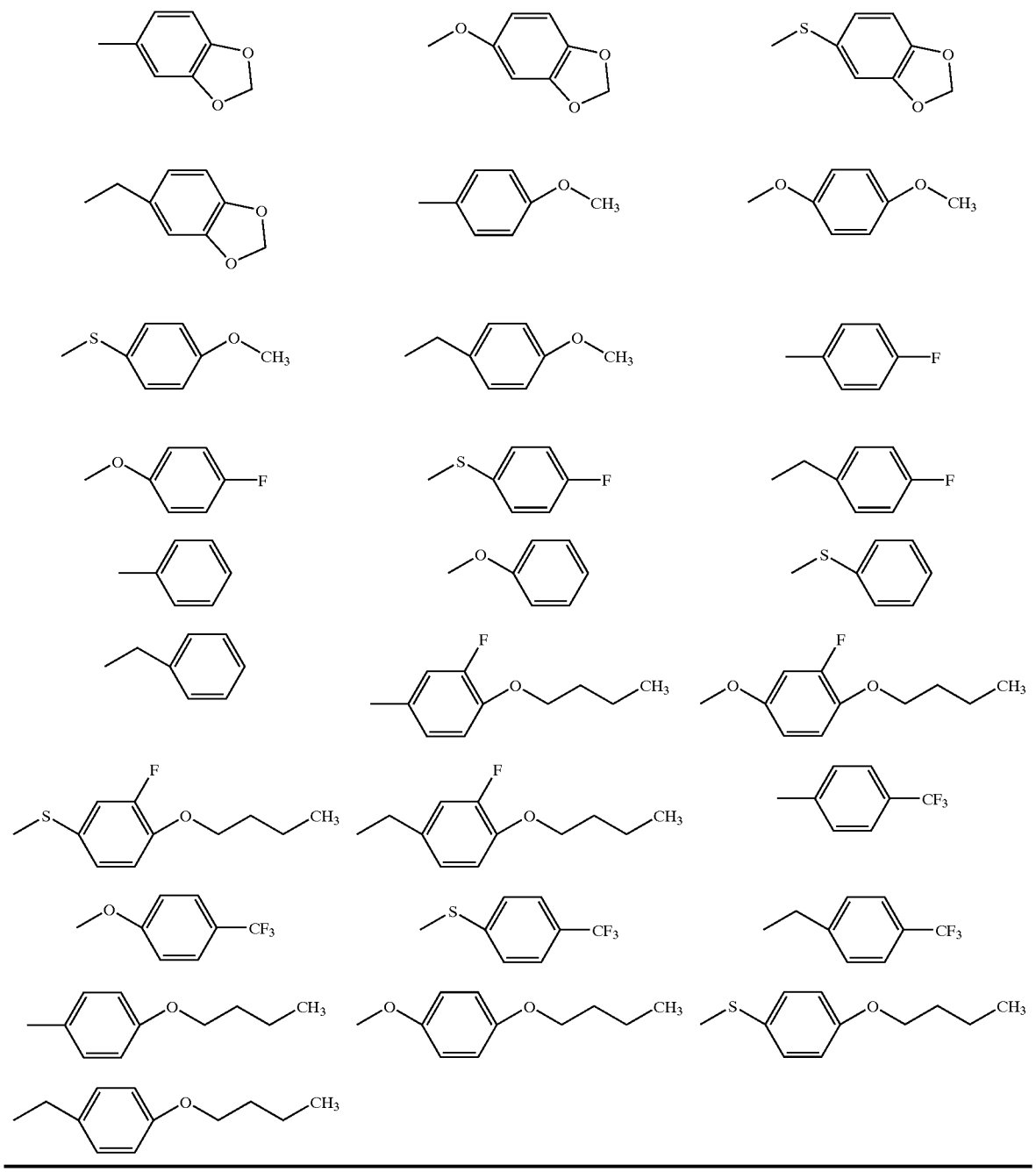

TABLE 28
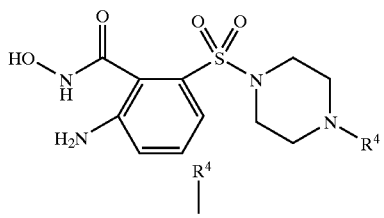
| | | |
|---|---|---|
| 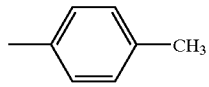 | 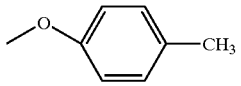 | 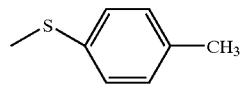 |
| 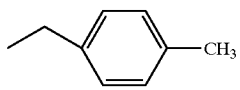 | 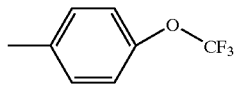 | 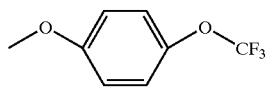 |
| 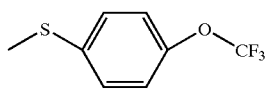 | 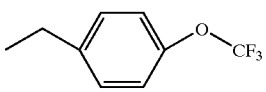 | 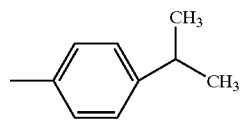 |
| 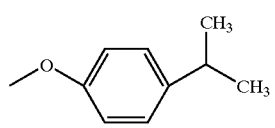 | 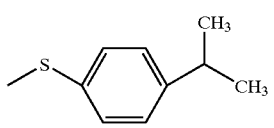 | 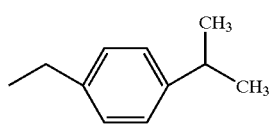 |
| 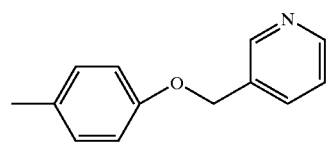 | 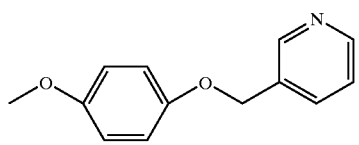 | 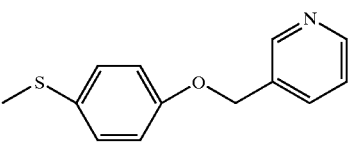 |
| 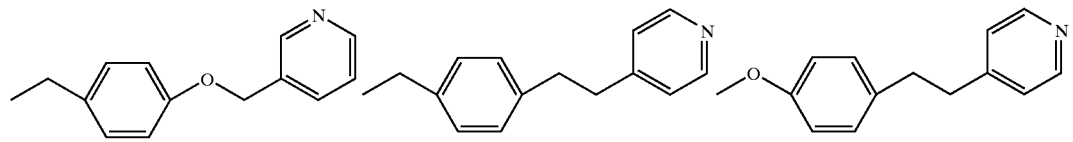 | | |
| 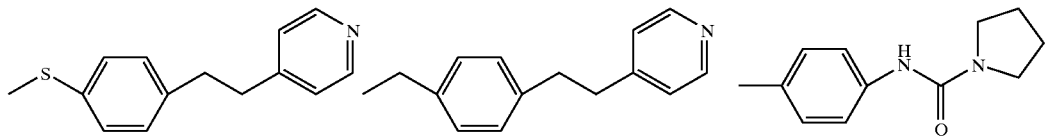 | | |
| 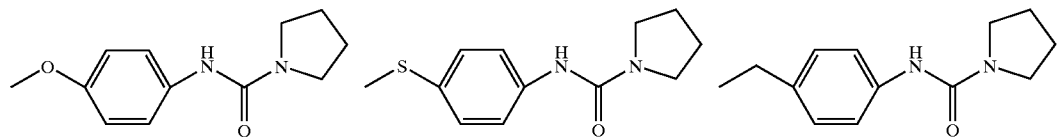 | | |

TABLE 29
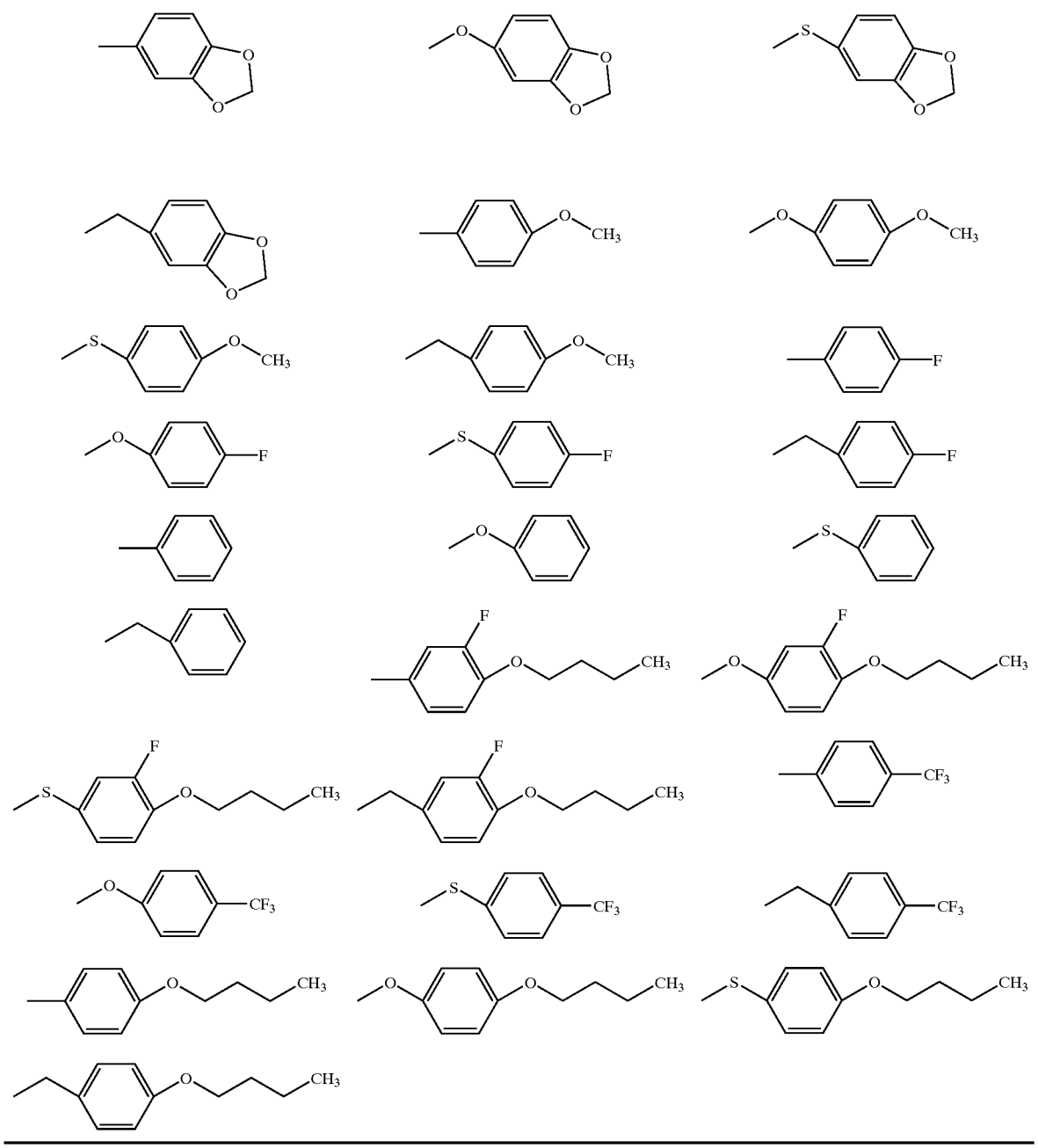

TABLE 30
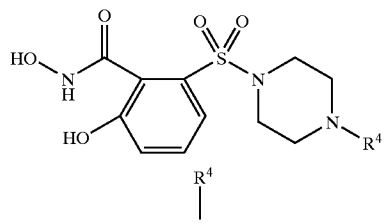
| | | |
|---|---|---|
| 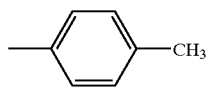 | 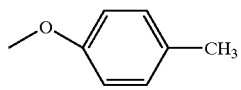 | 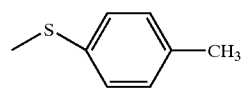 |
| 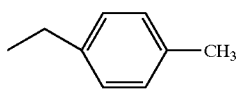 | 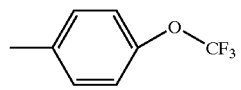 | 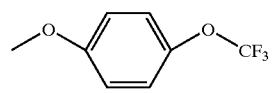 |
| 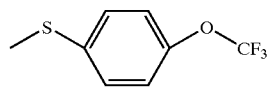 | 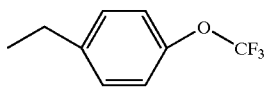 | 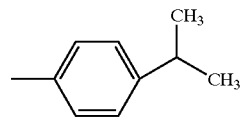 |
| 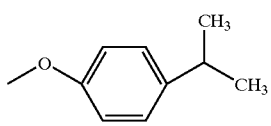 | 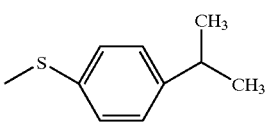 | 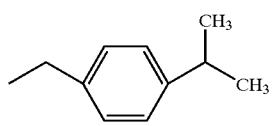 |
| 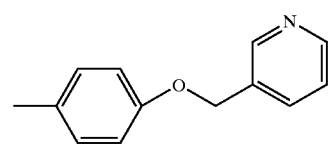 | 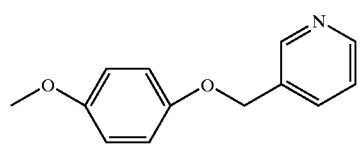 | 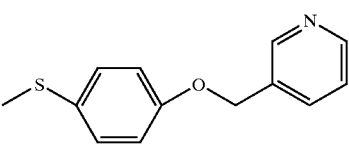 |
| 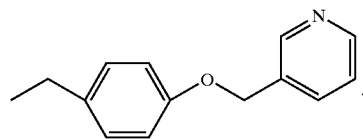 | 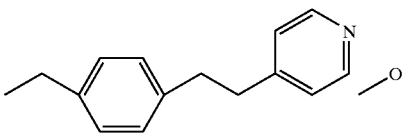 | 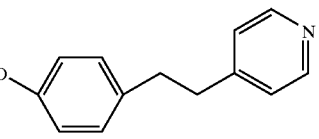 |
| 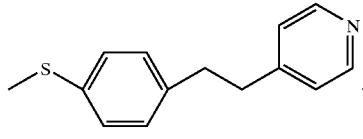 | 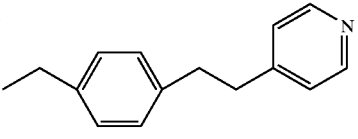 | 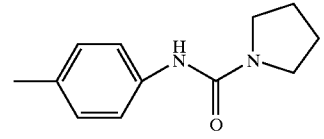 |
| 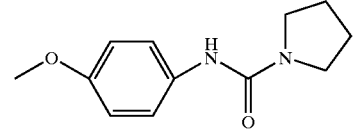 | 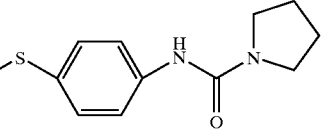 | 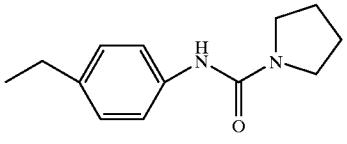 |

TABLE 31
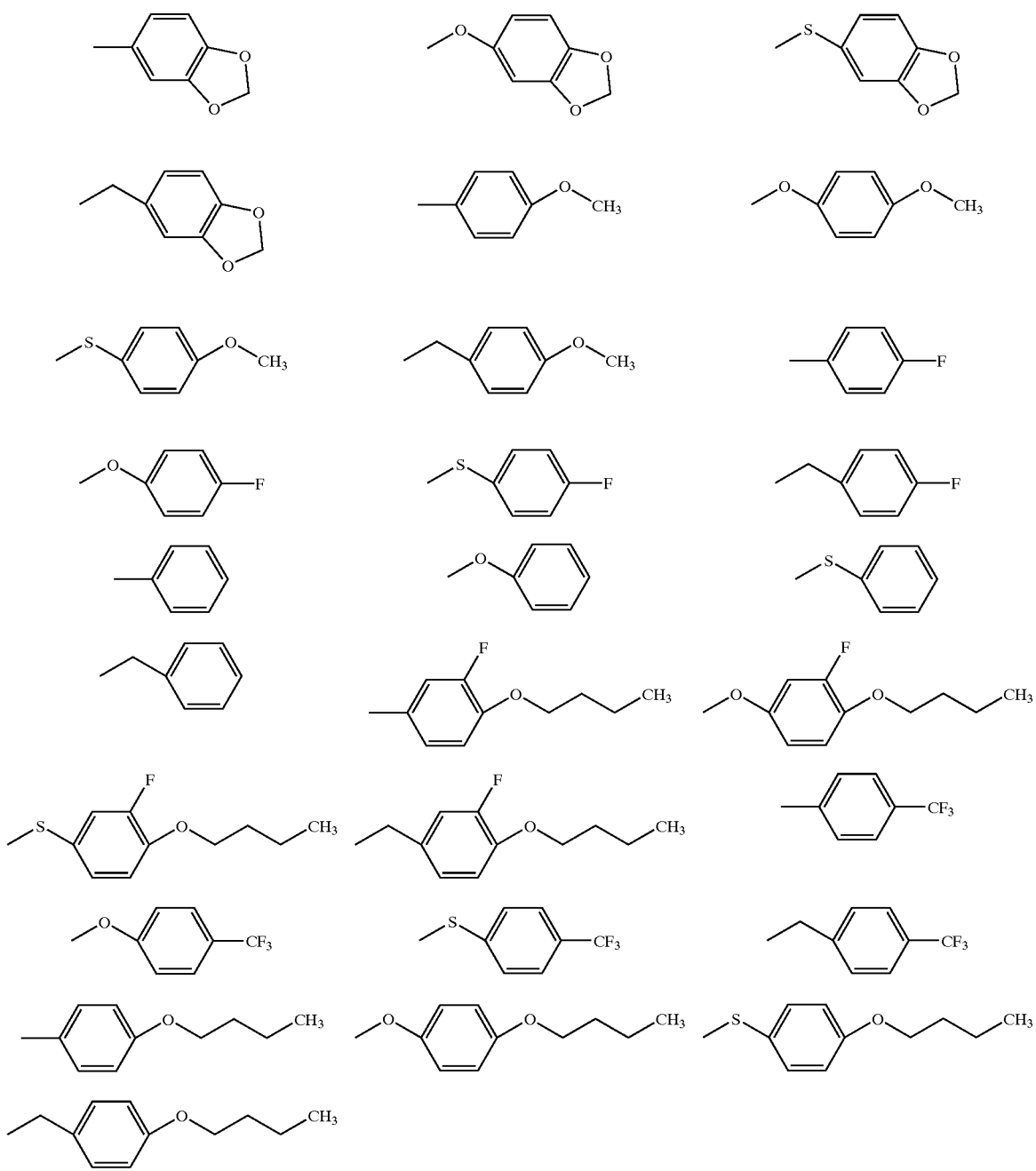

TABLE 32
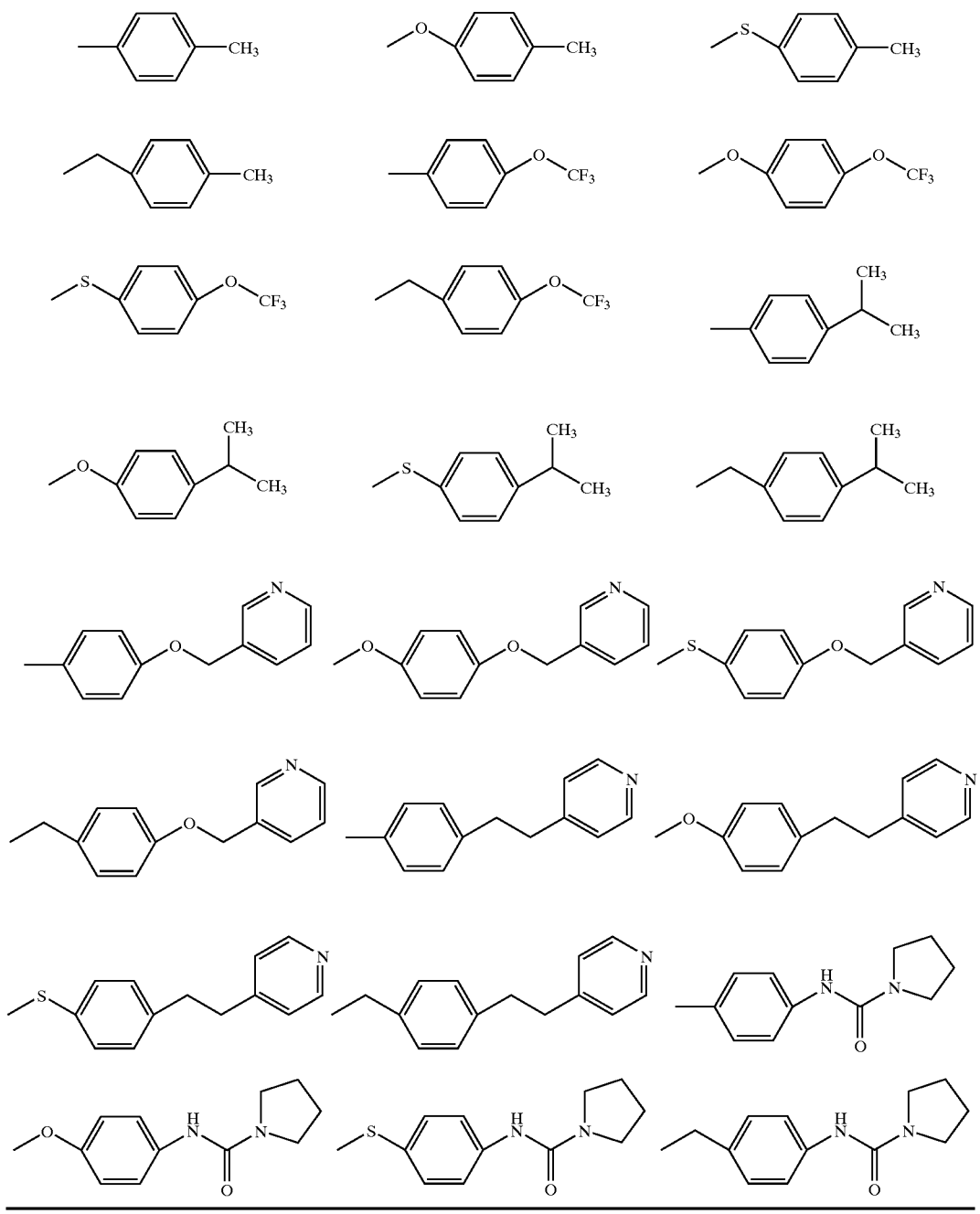

TABLE 33
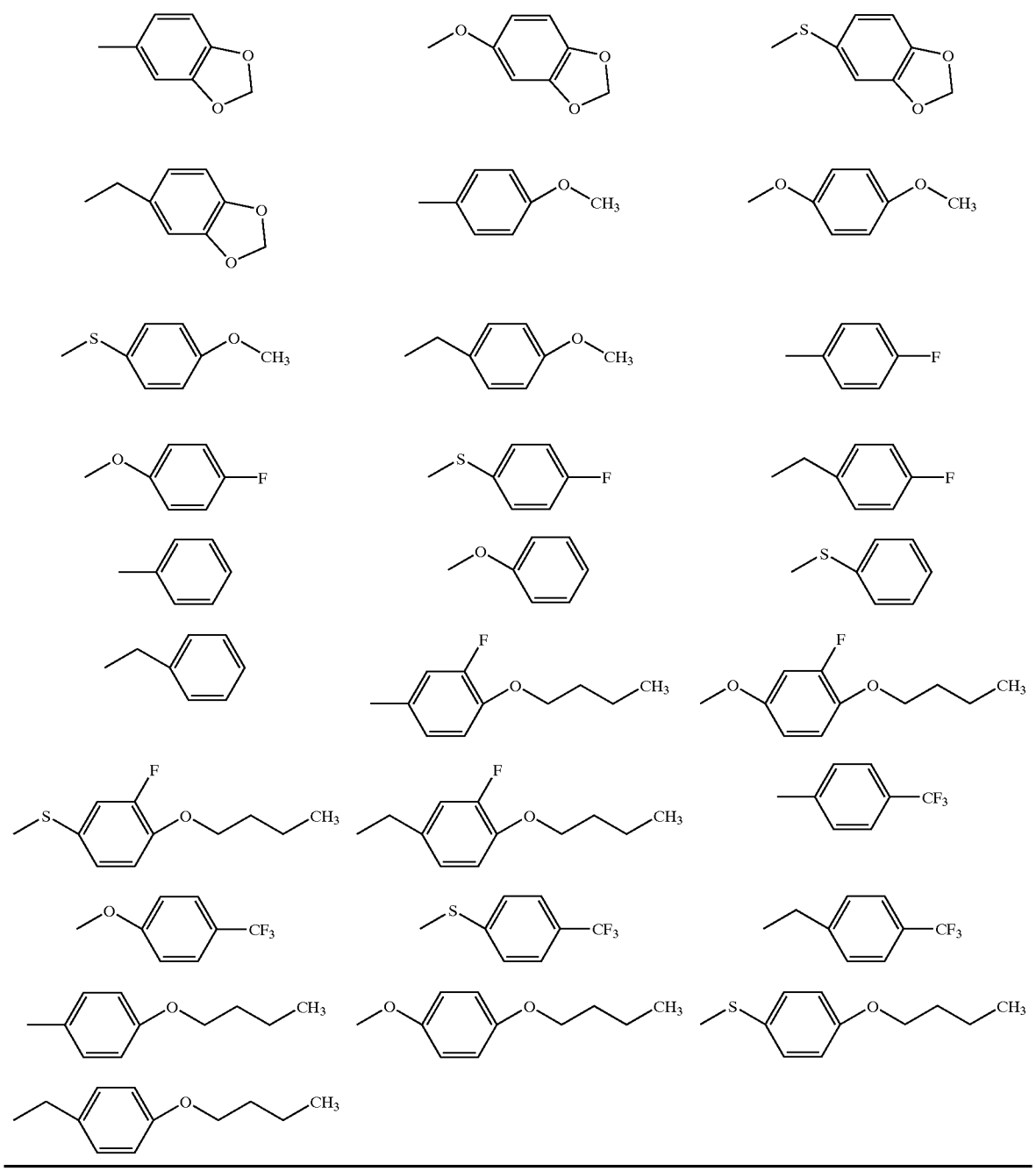

TABLE 34
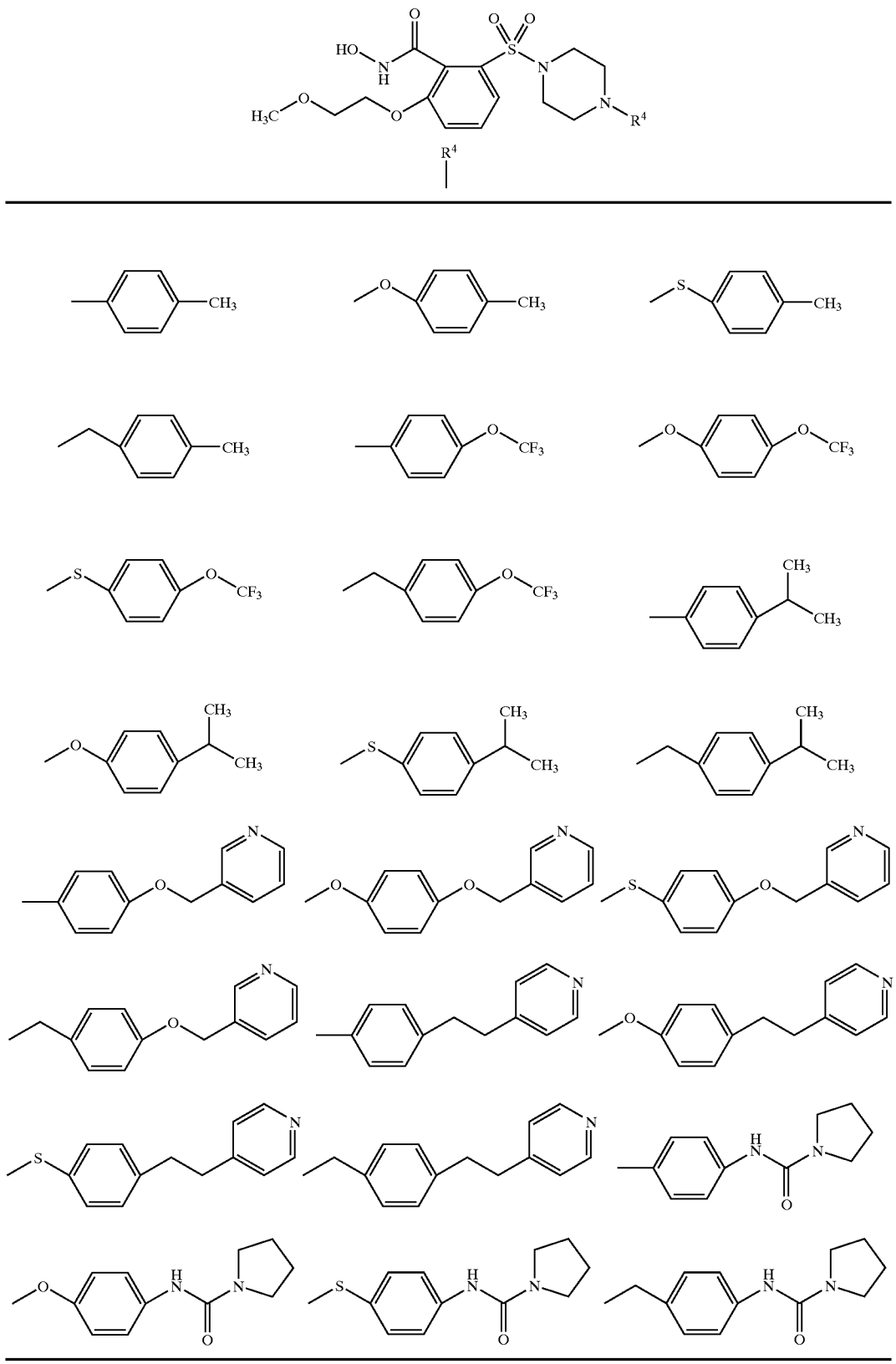

TABLE 35
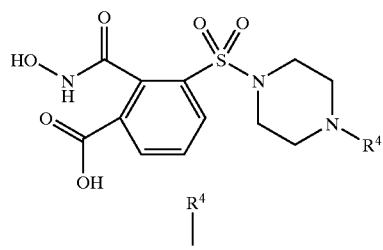
R⁴|||
---|---|---
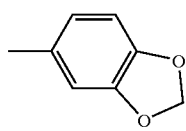 | 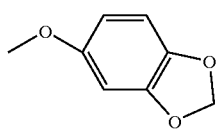 | 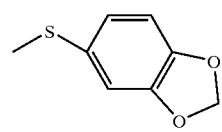
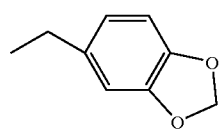 | 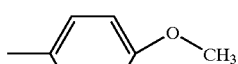 | 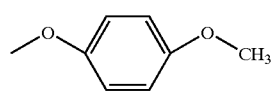
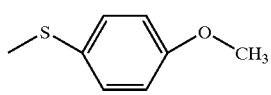 | 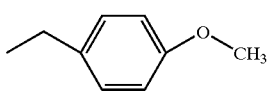 | 
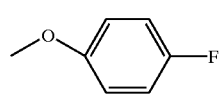 | 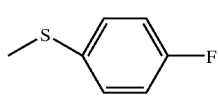 | 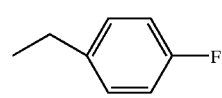
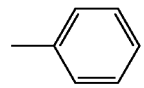 | 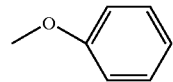 | 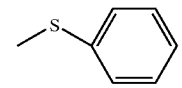
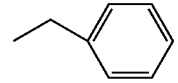 | 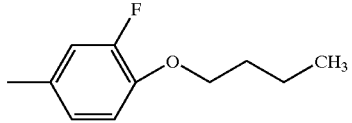 | 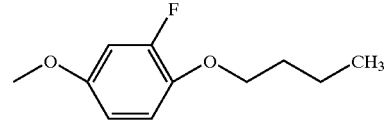
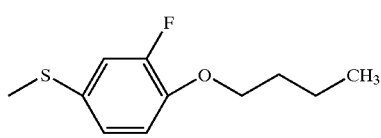 | 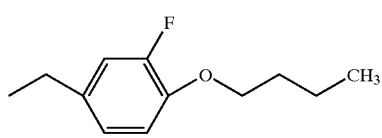 | 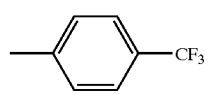
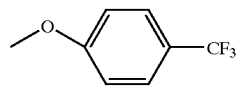 | 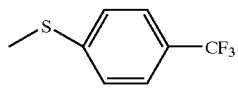 | 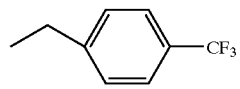
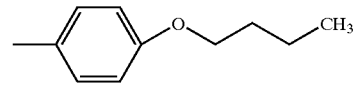 | 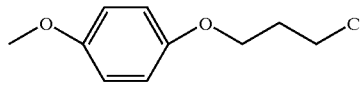 | 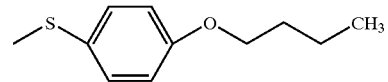
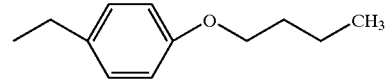 | |

TABLE 36
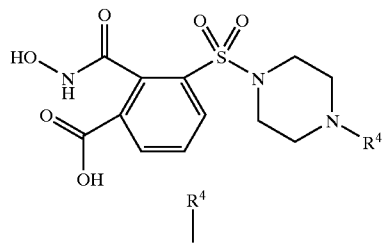
R⁴
| | | |
|---|---|---|
| 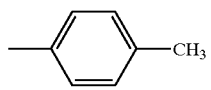 |  | 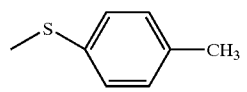 |
| 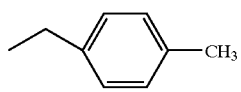 | 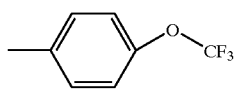 | 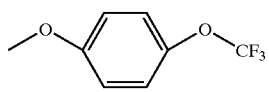 |
| 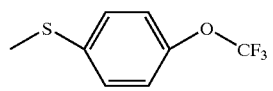 | 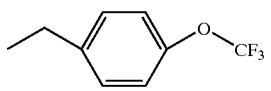 | 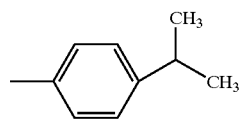 |
| 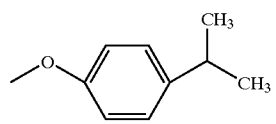 | 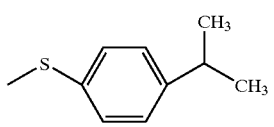 | 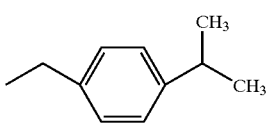 |
| 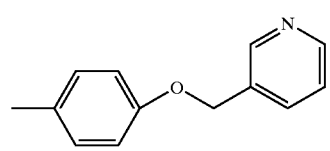 | 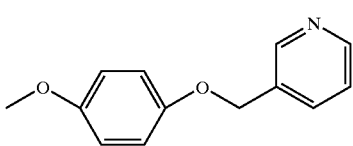 | 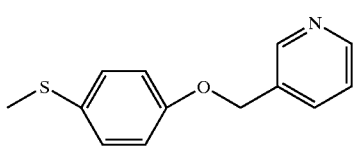 |
| 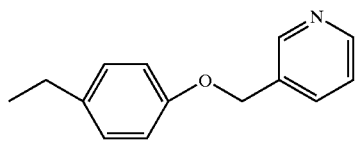 | 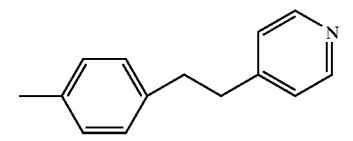 | 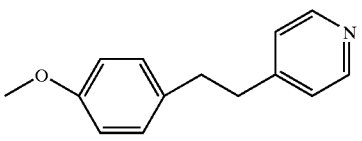 |
| 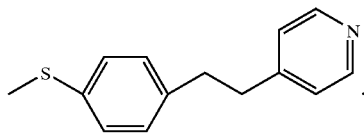 | 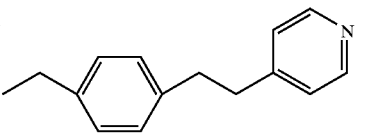 | 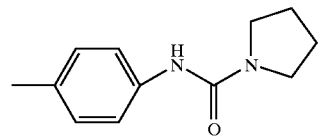 |
| 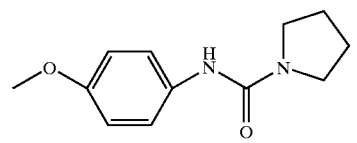 | 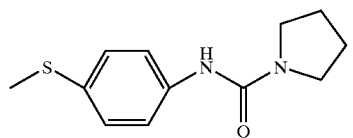 | 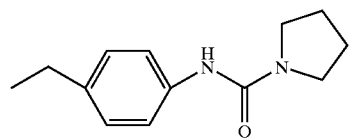 |

TABLE 37
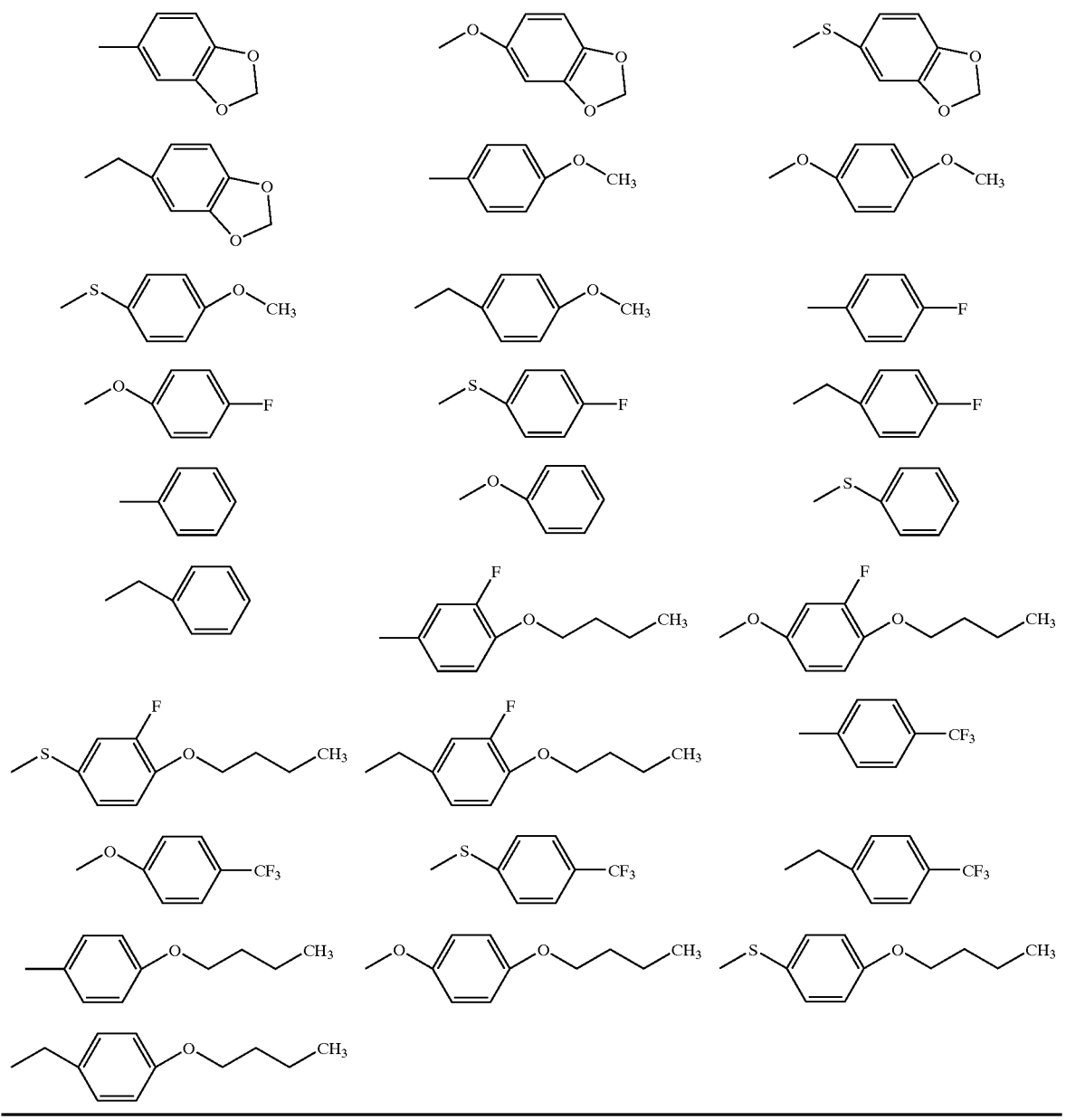

TABLE 38
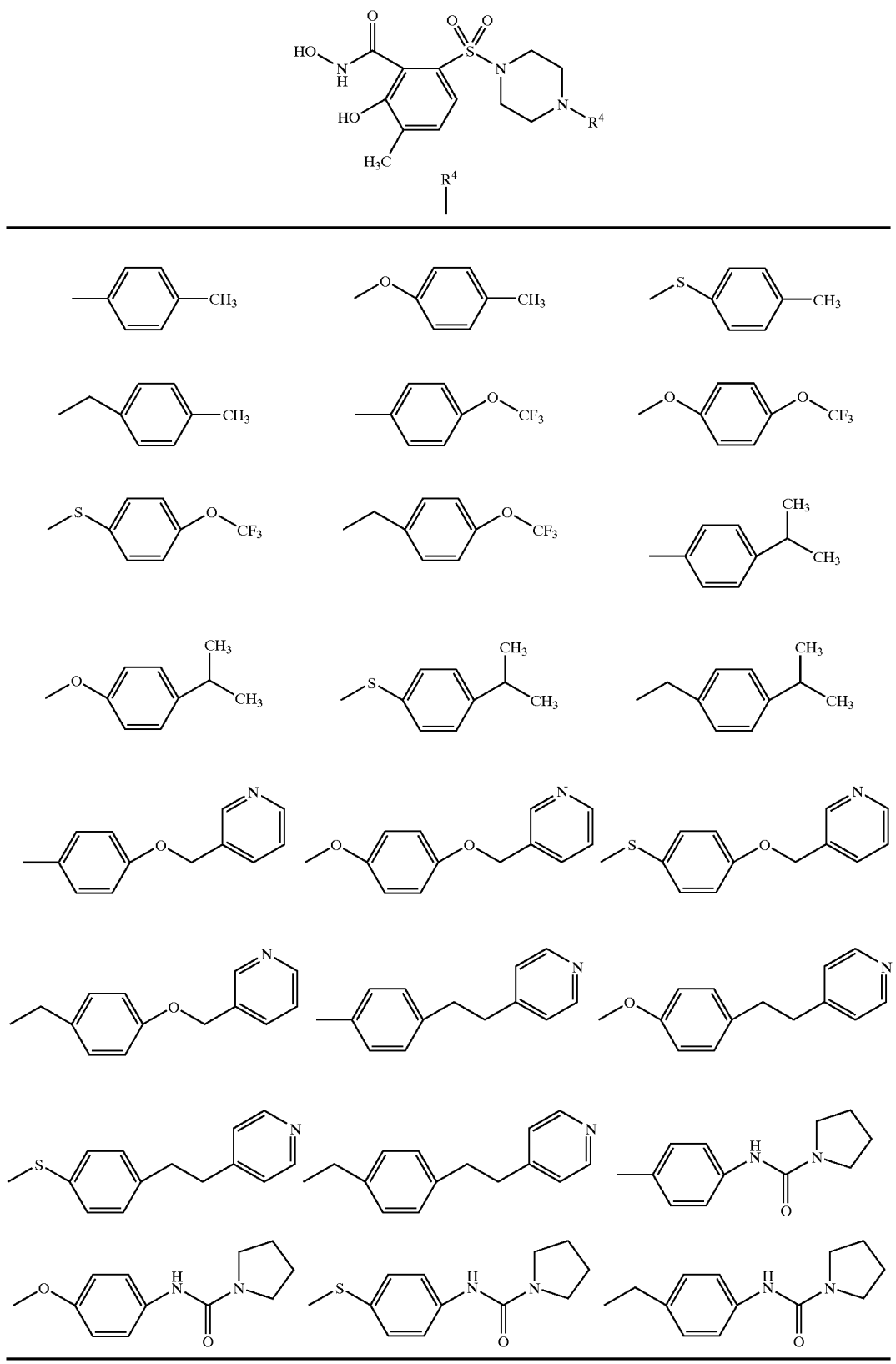

TABLE 39
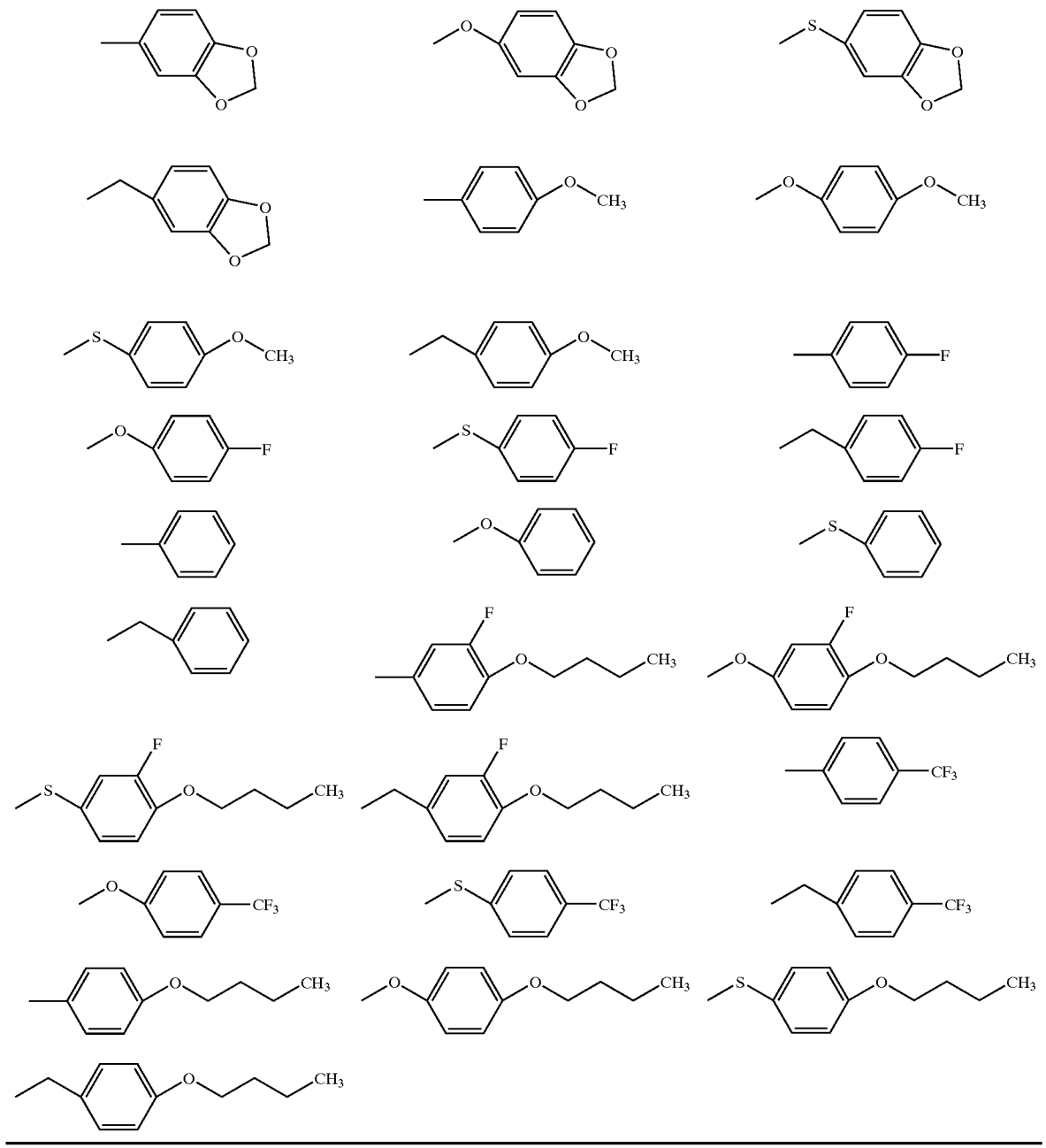

TABLE 40
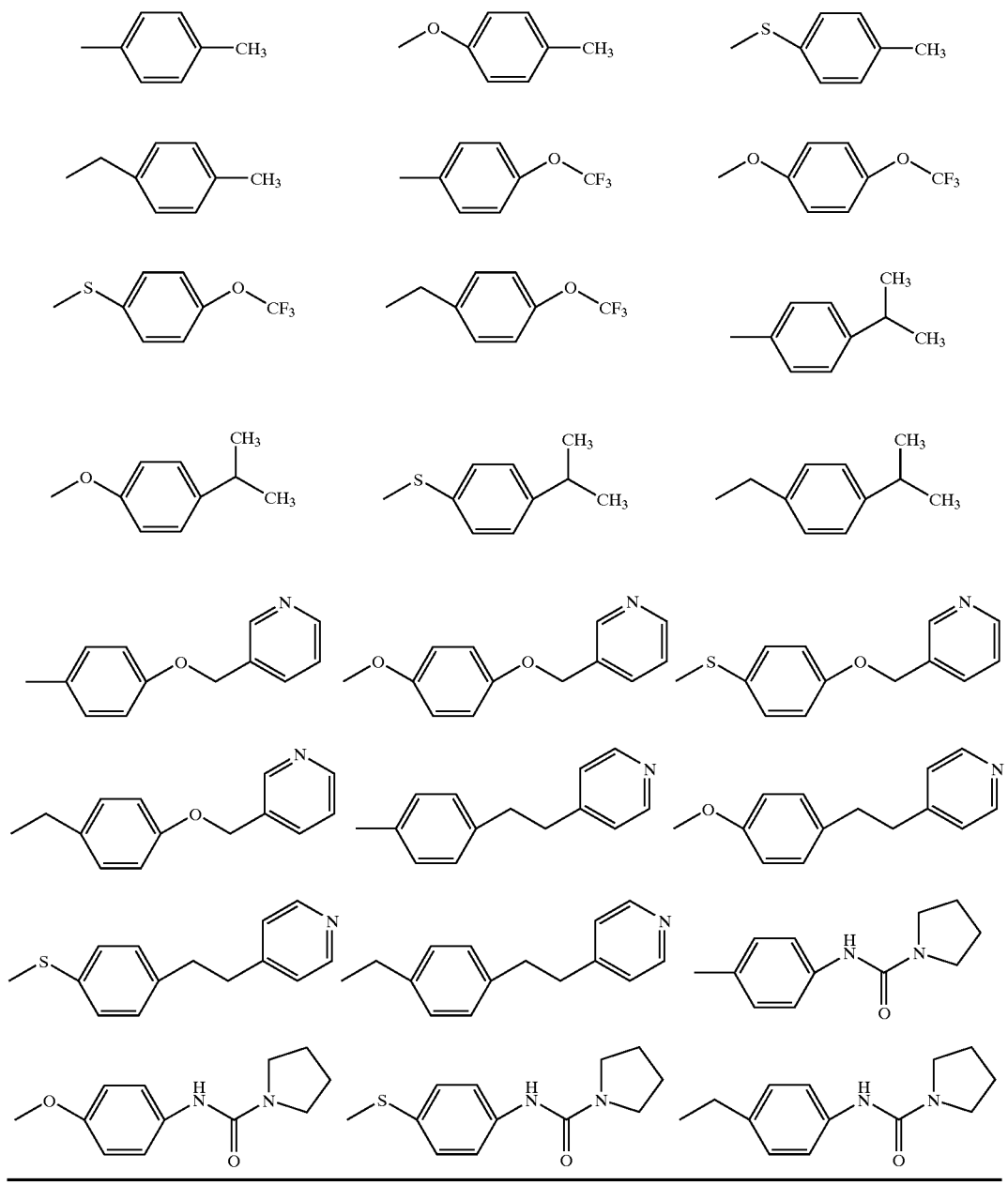

TABLE 41
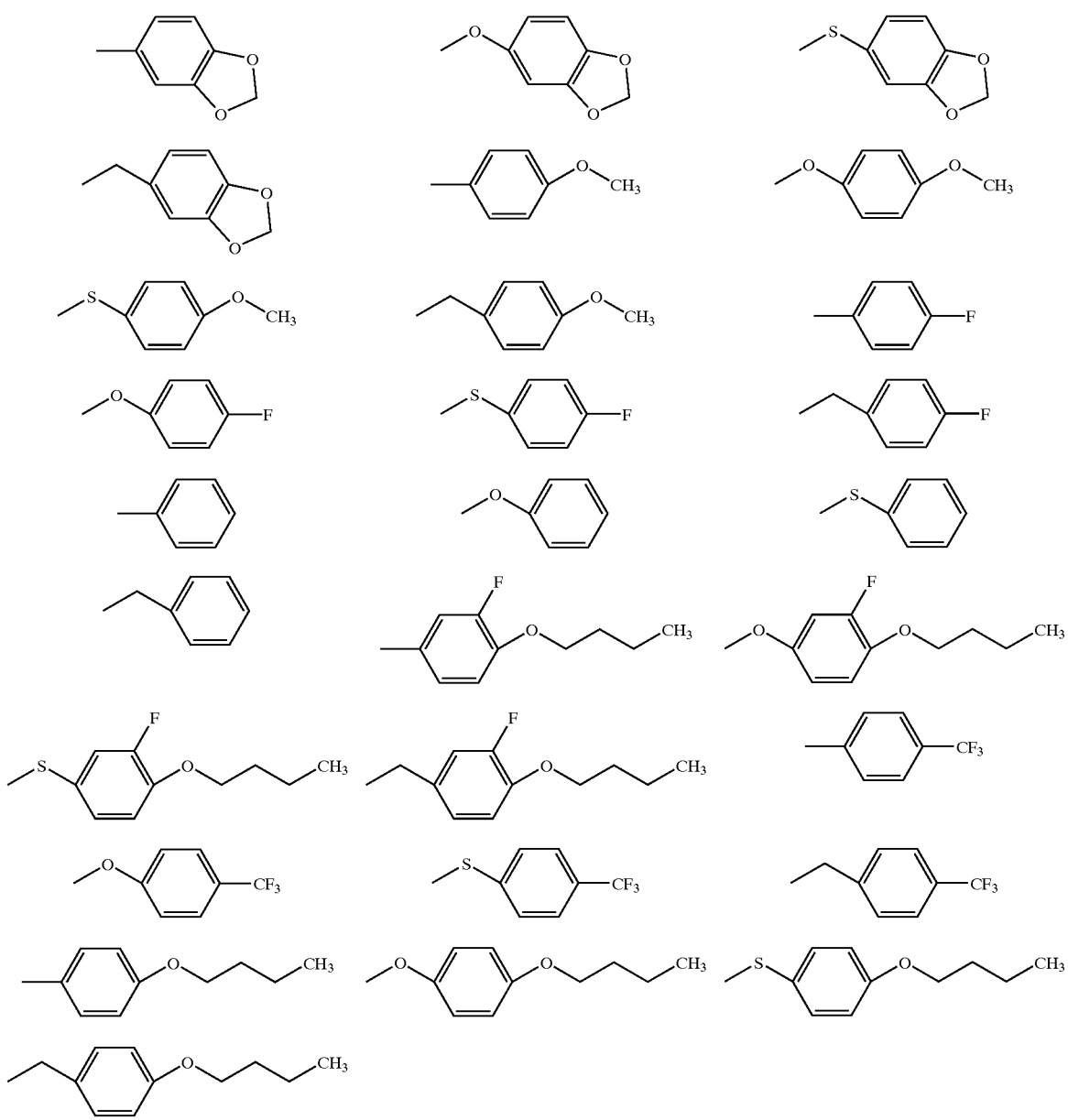

TABLE 42
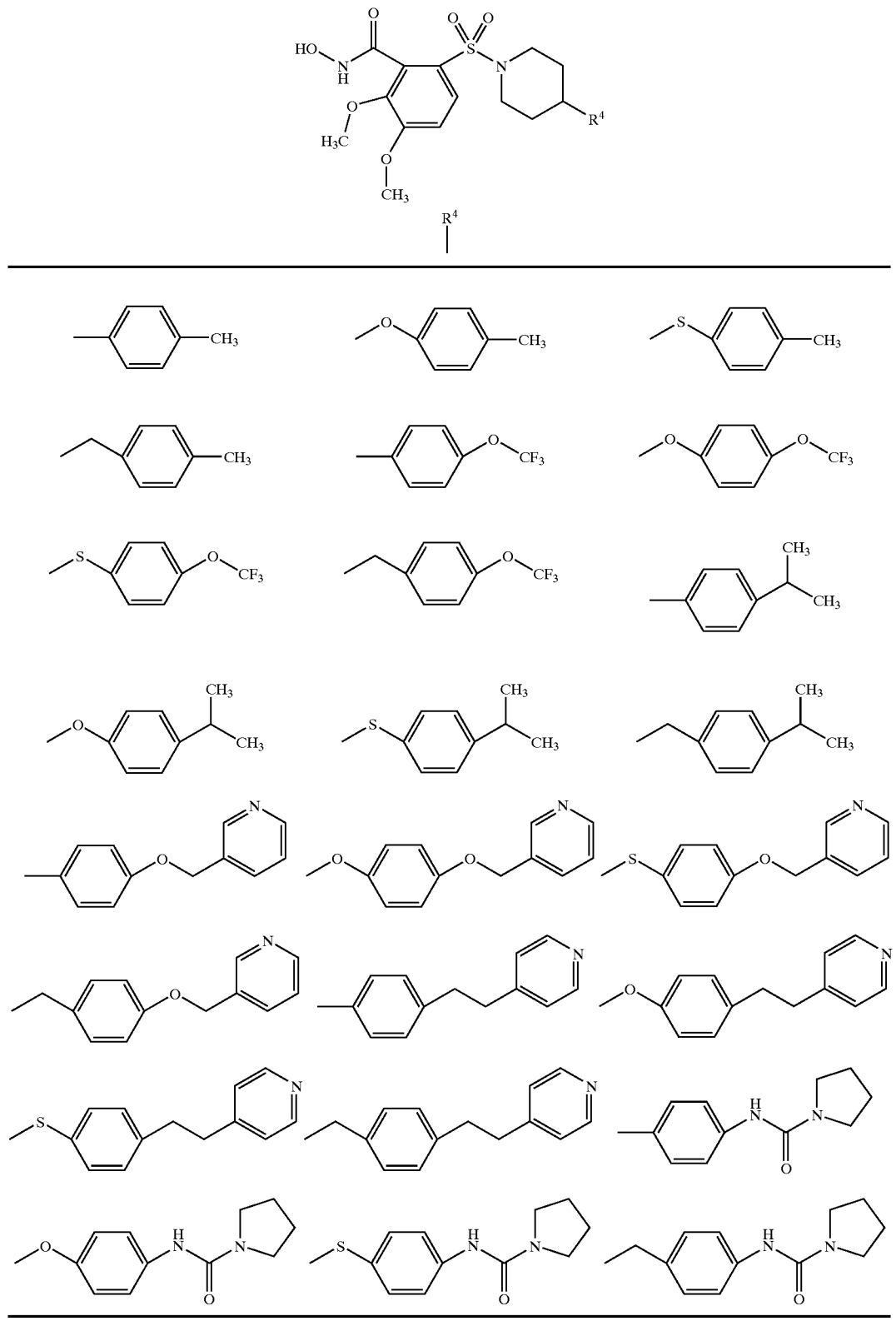

TABLE 43
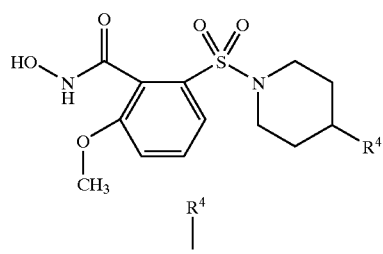
| R⁴ | | |
|---|---|---|
| 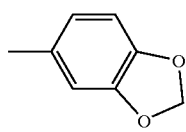 | 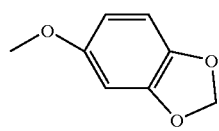 | 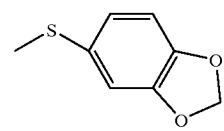 |
| 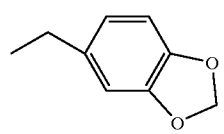 | 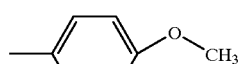 | 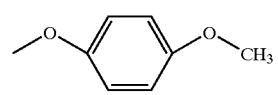 |
| 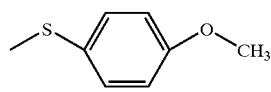 | 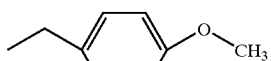 |  |
| 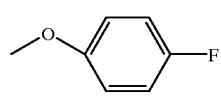 | 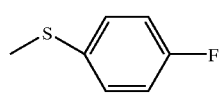 | 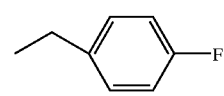 |
| 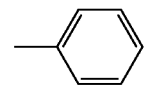 | 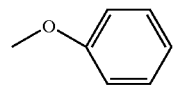 | 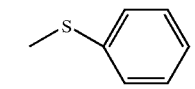 |
| 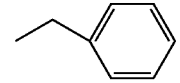 | 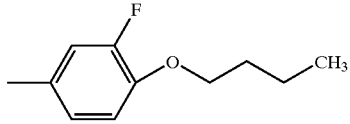 | 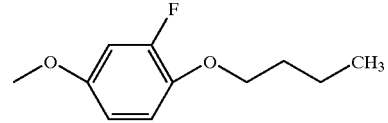 |
| 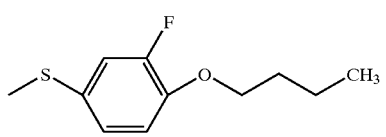 | 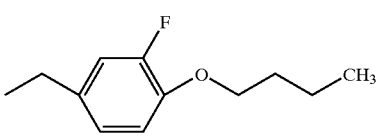 | 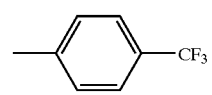 |
| 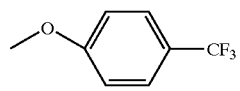 | 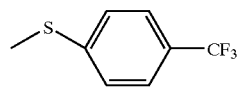 | 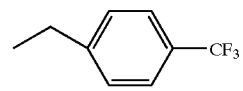 |
| 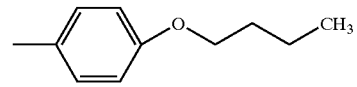 | 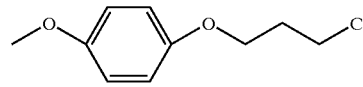 | 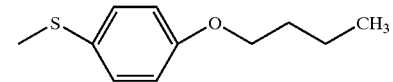 |
| 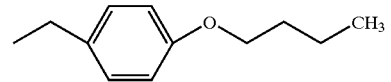 | | |

TABLE 44
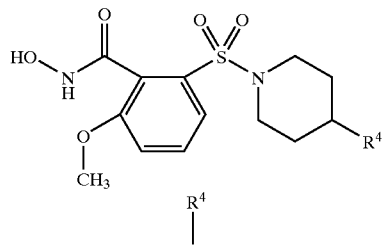
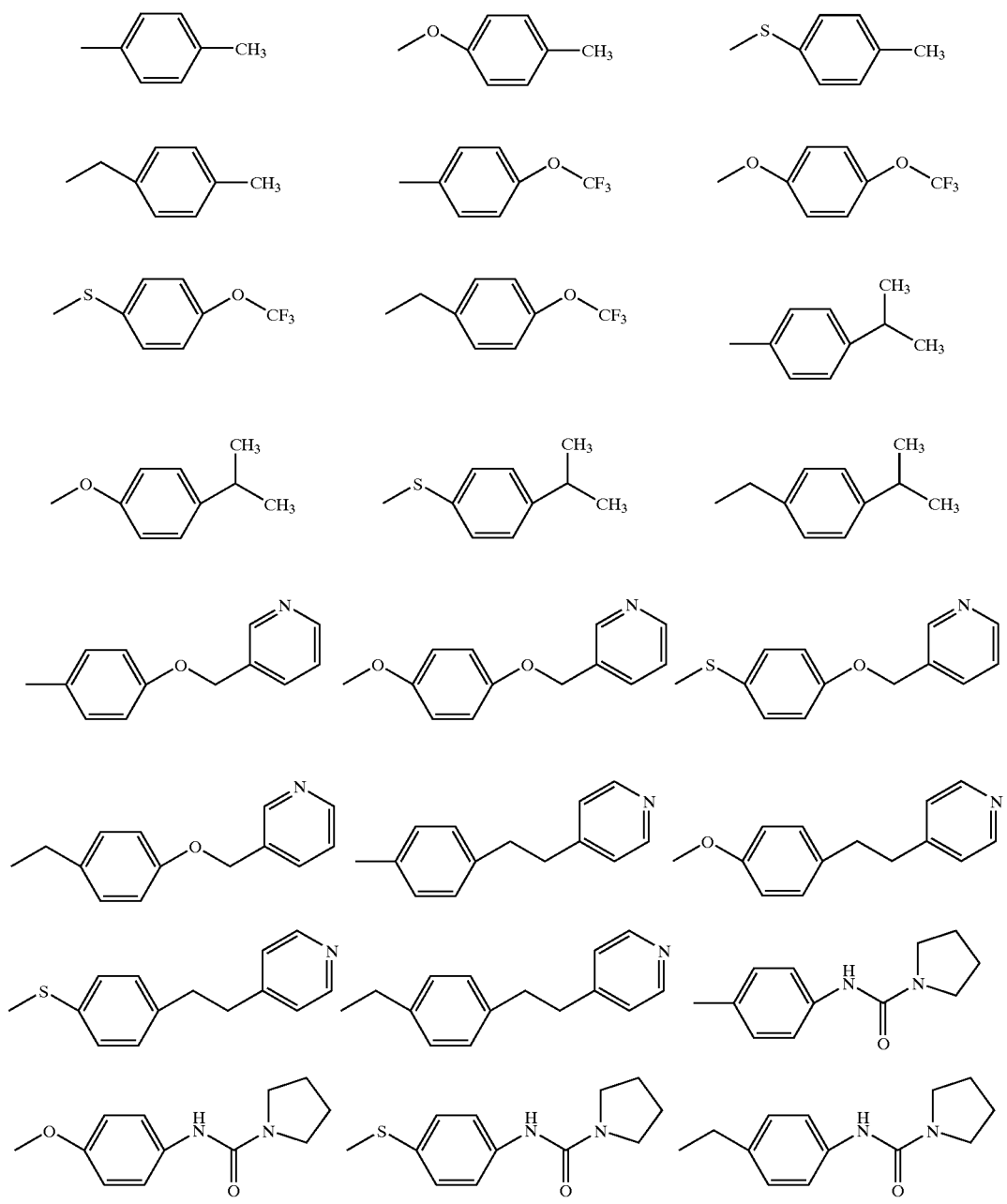

TABLE 45

TABLE 46
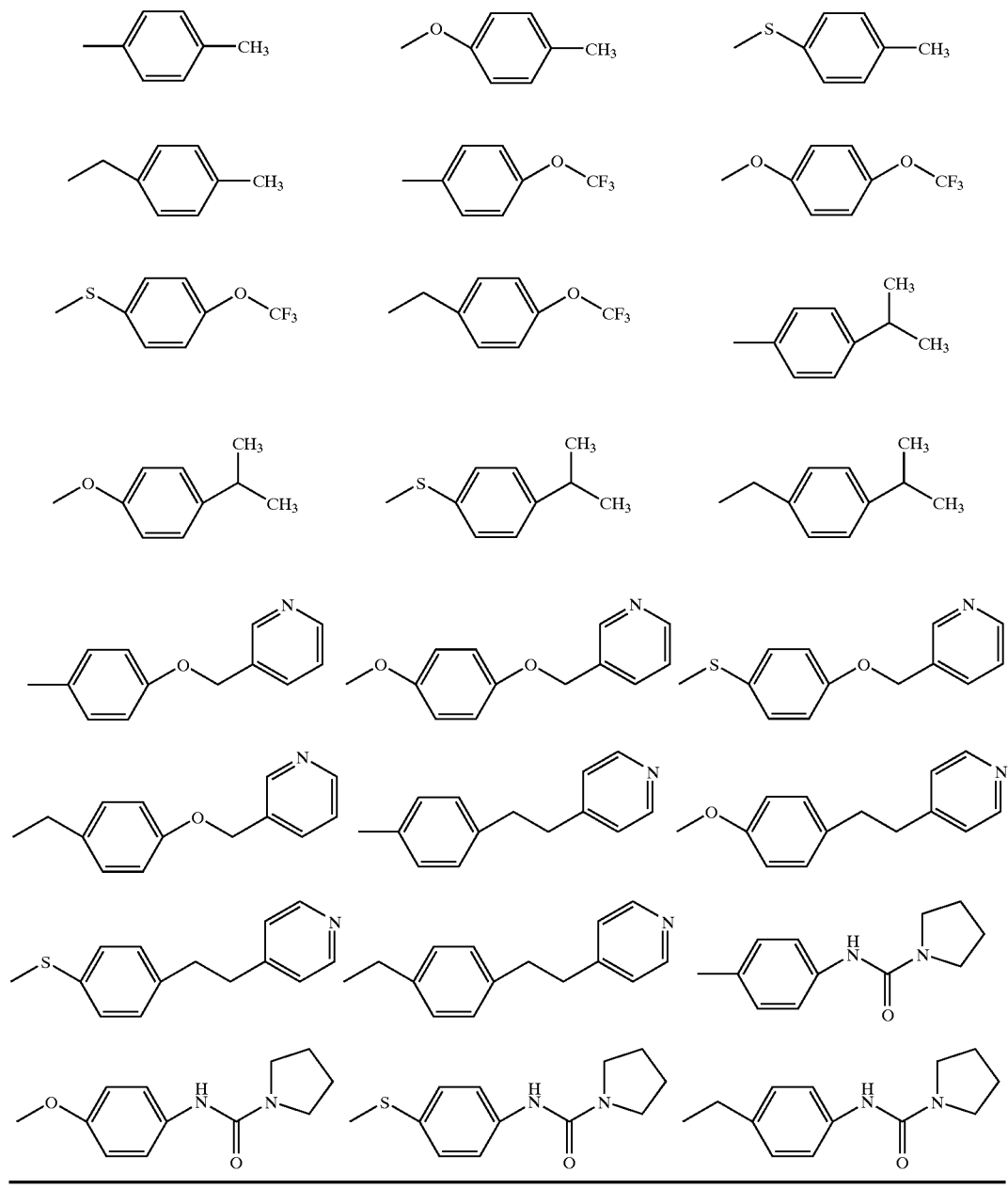

TABLE 47
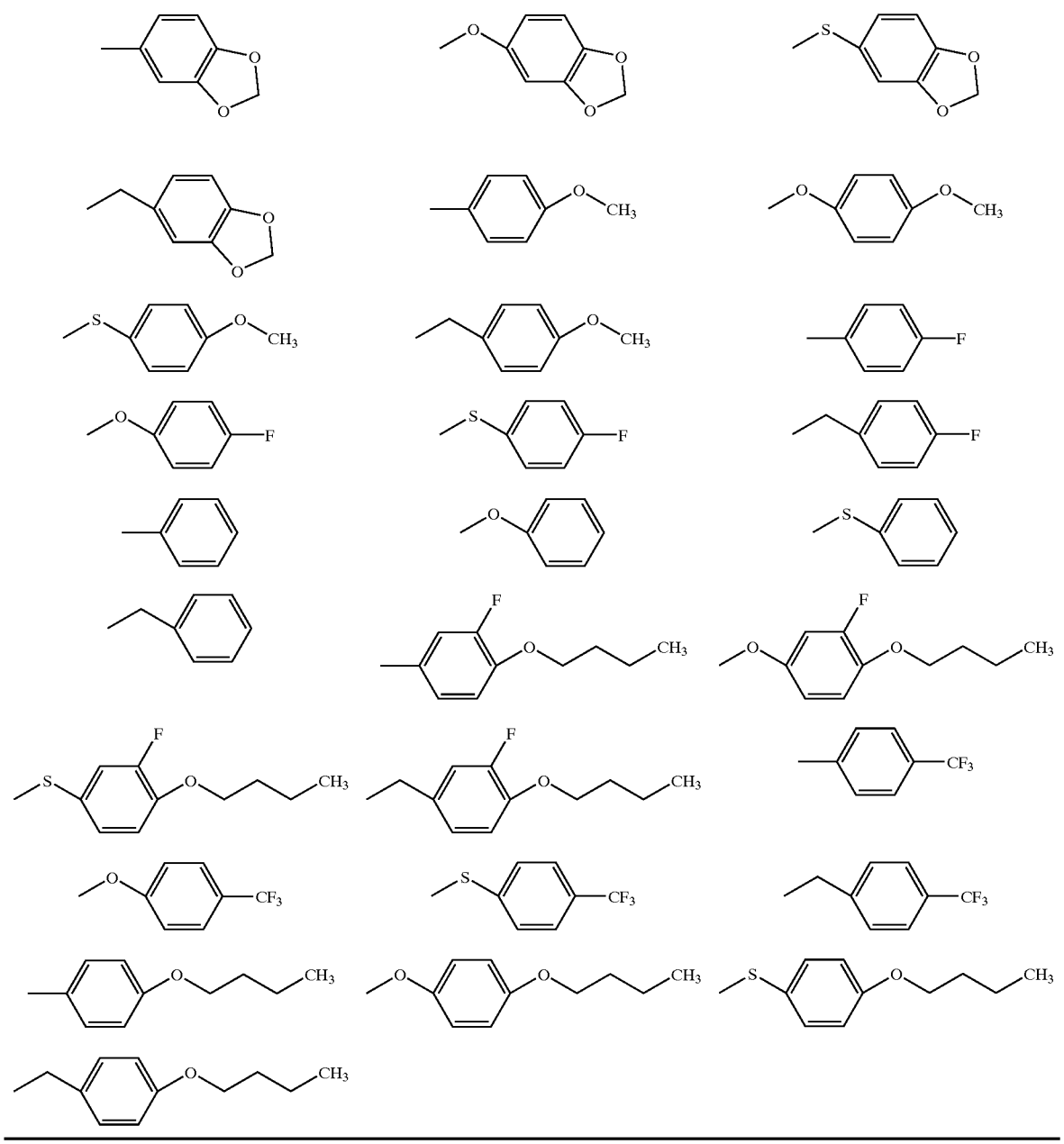

TABLE 48
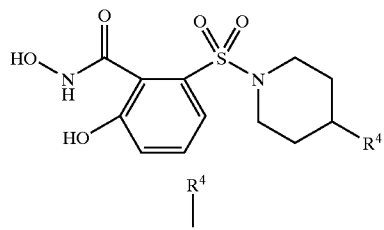
R⁴
| | | |
|---|---|---|
| 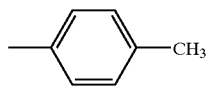 | 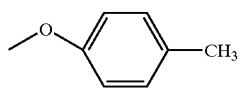 | 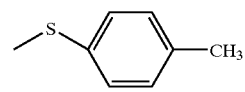 |
| 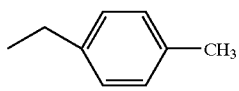 | 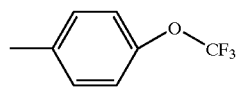 | 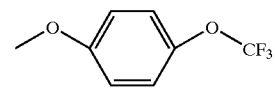 |
| 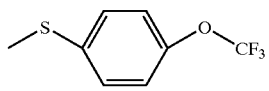 | 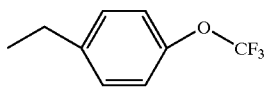 | 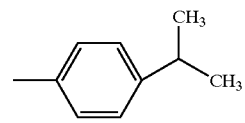 |
| 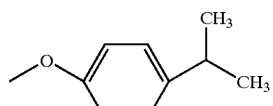 | 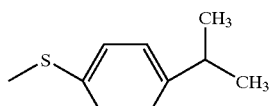 | 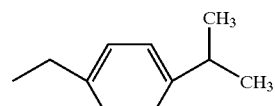 |
| 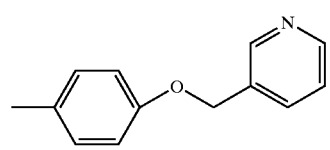 | 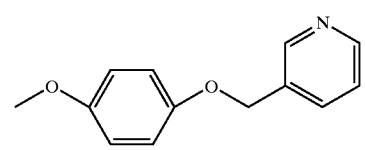 | 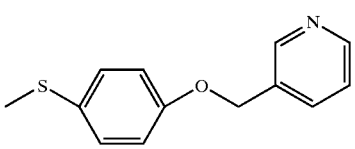 |
| 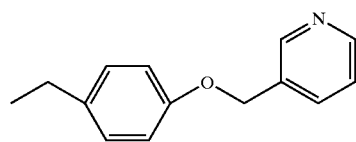 | 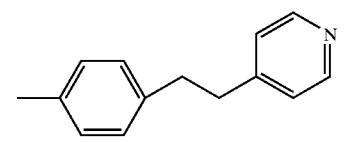 | 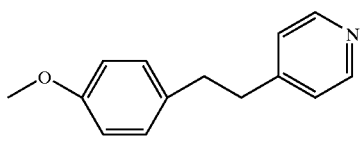 |
| 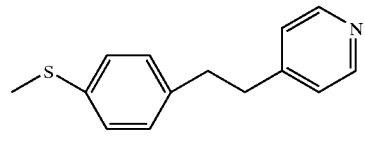 | 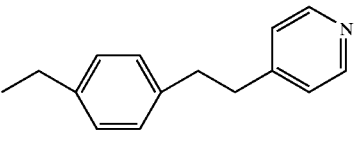 | 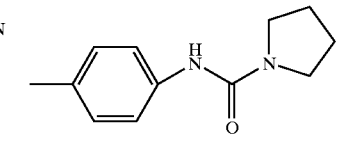 |
| 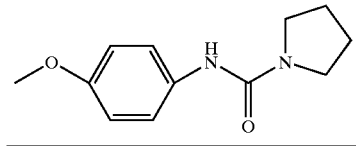 | 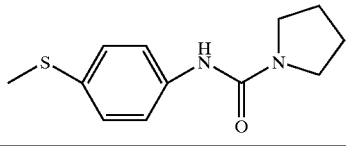 | 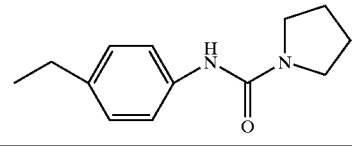 |

TABLE 49
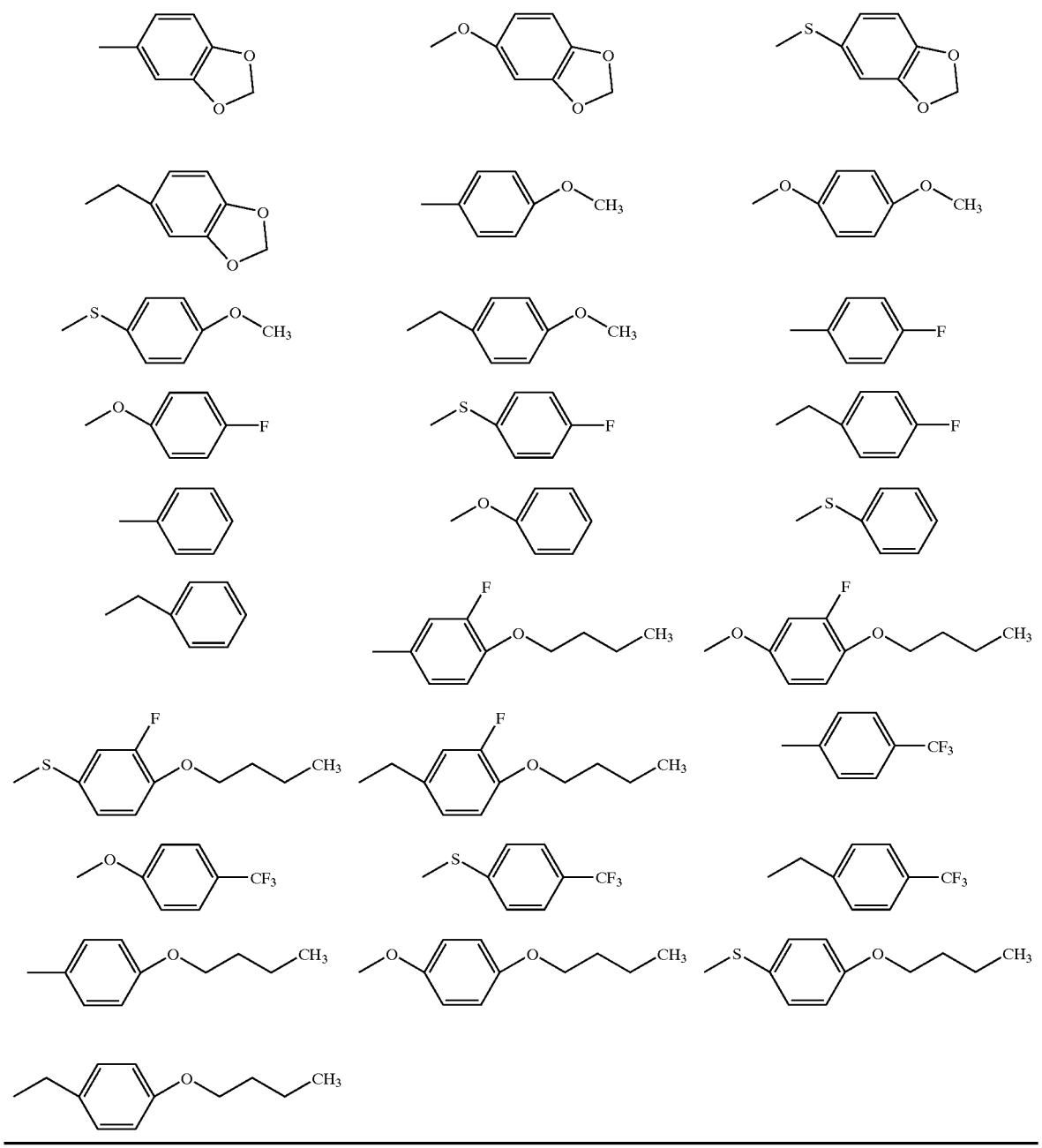

TABLE 50
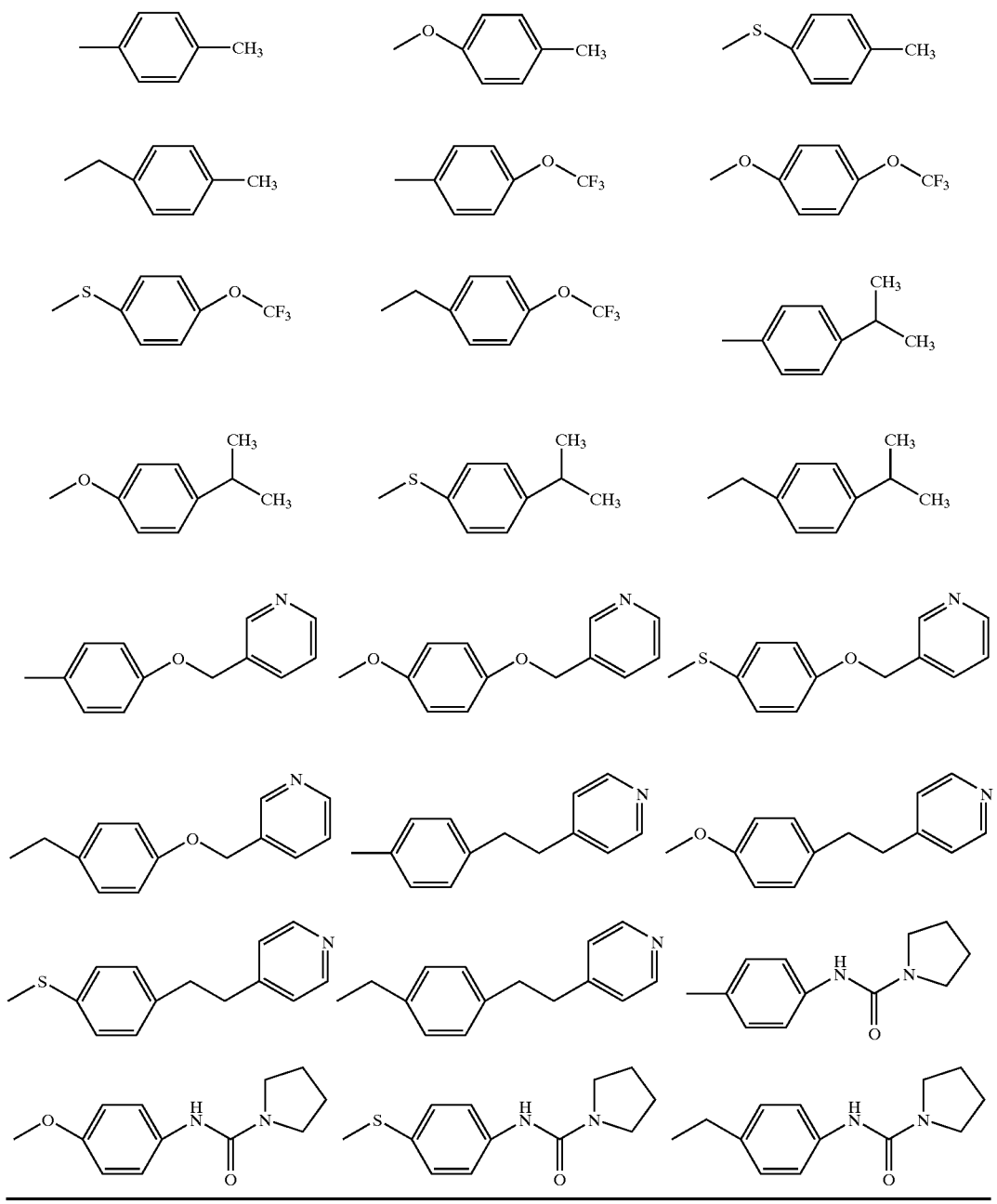

TABLE 51
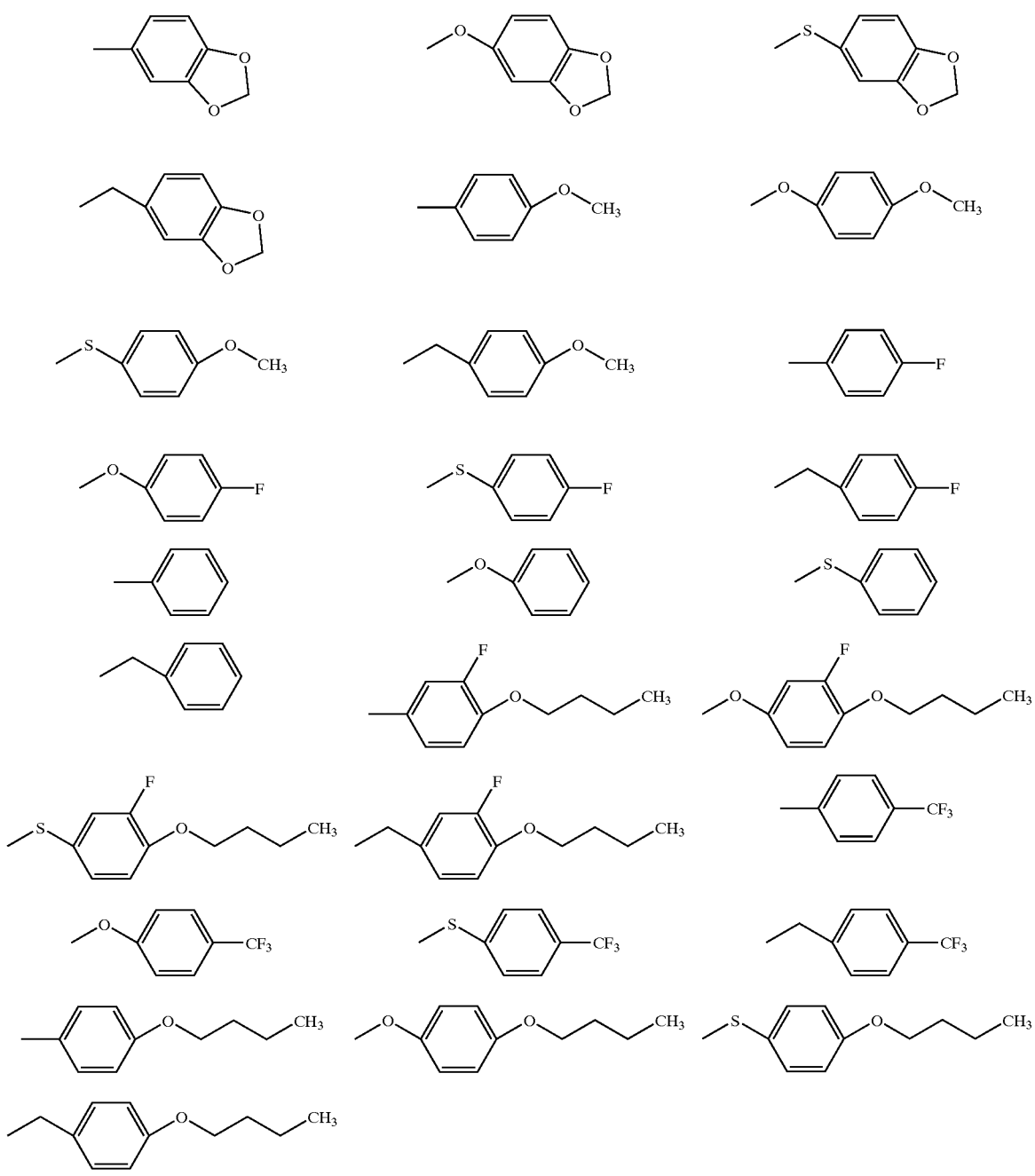

TABLE 52
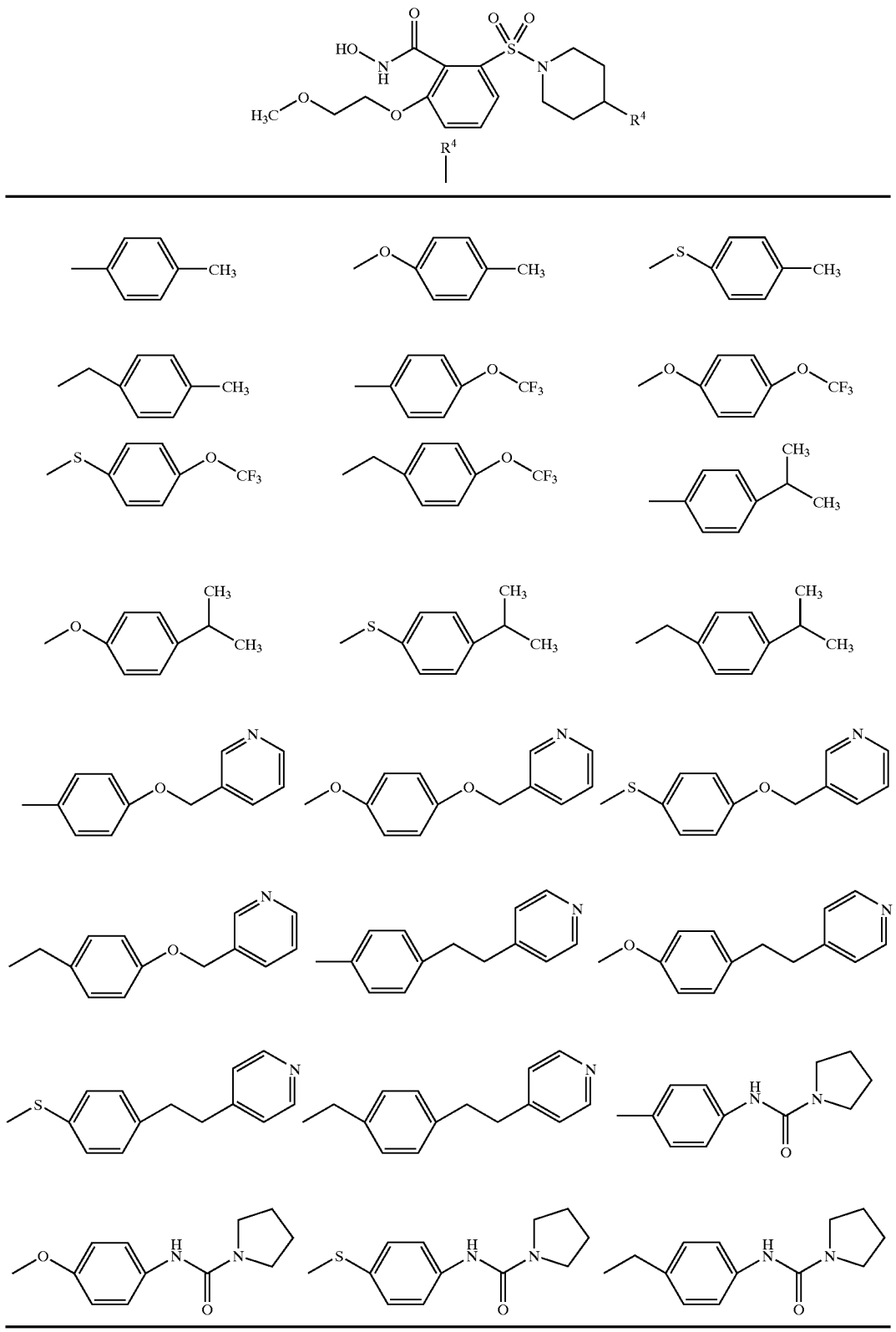

TABLE 53
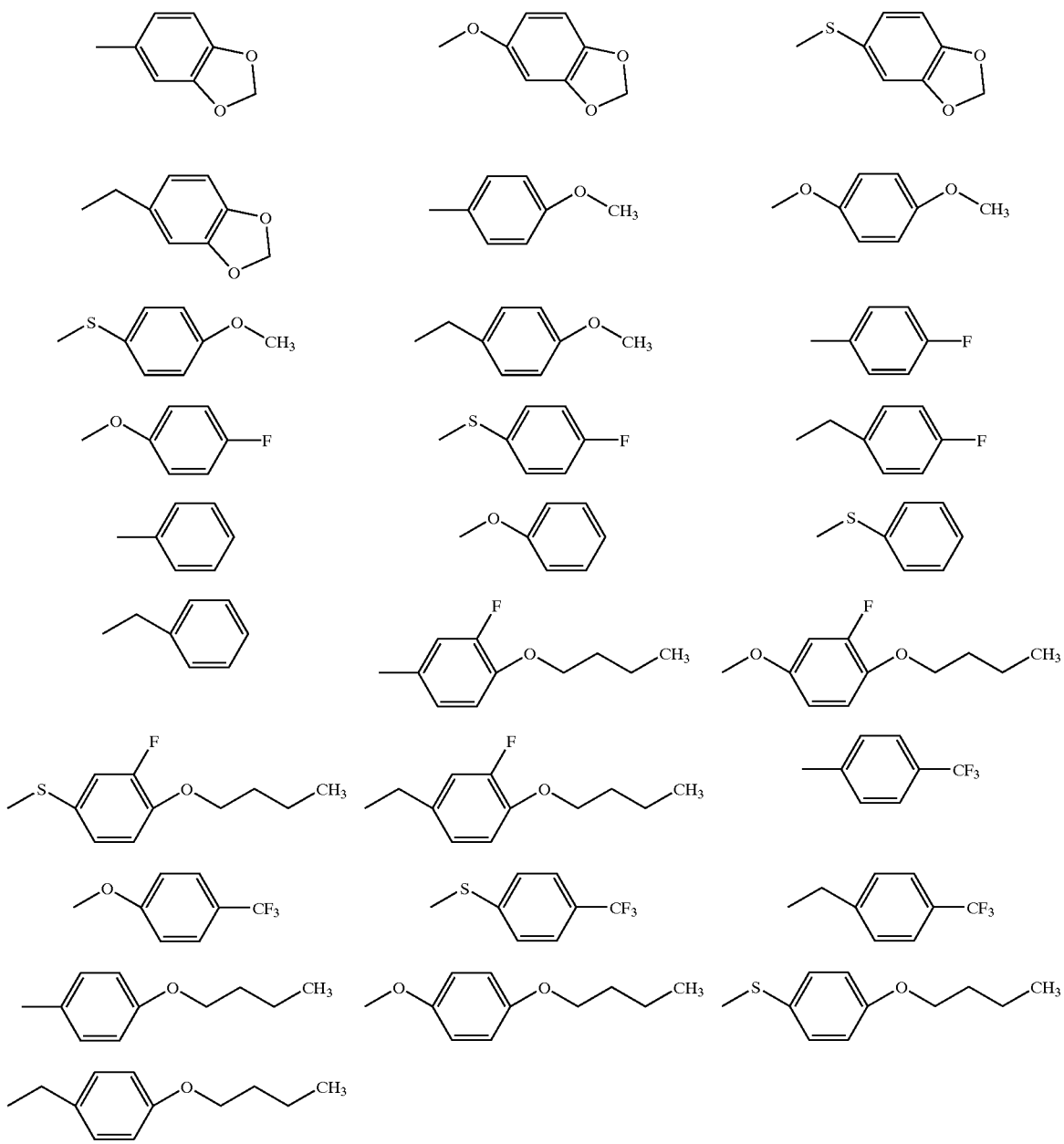

TABLE 54
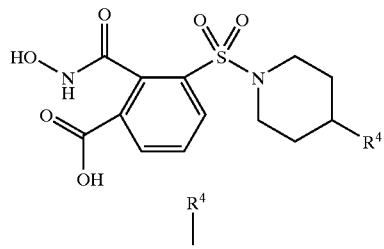
| | | |
|---|---|---|
| 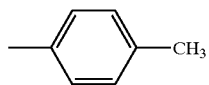 | 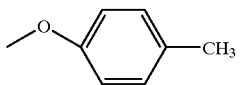 | 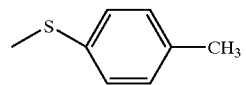 |
| 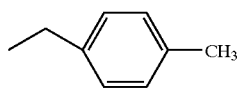 | 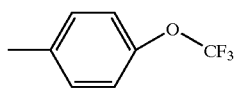 | 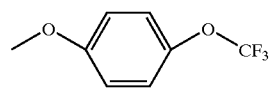 |
| 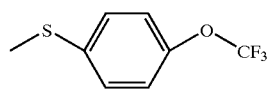 | 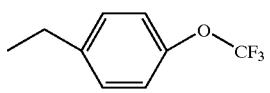 | 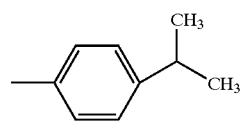 |
| 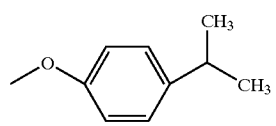 | 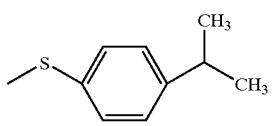 | 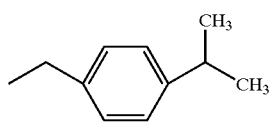 |
| 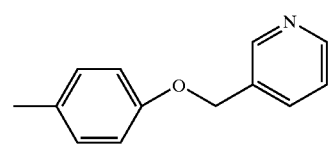 | 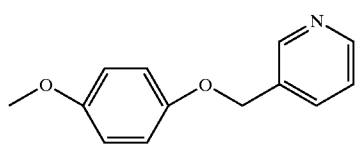 | 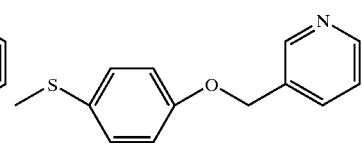 |
| 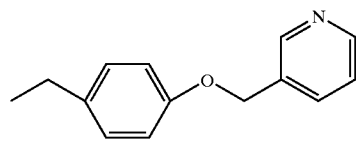 | 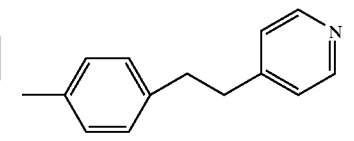 | 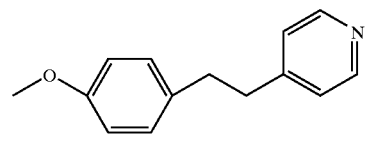 |
| 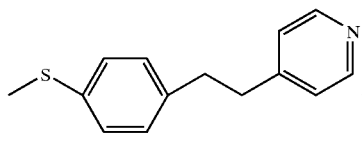 | 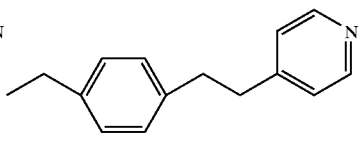 | 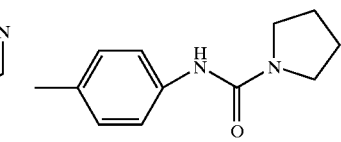 |
| 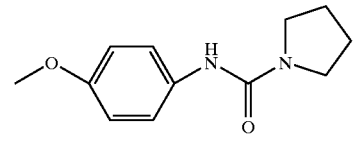 | 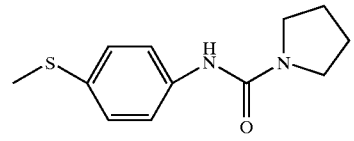 | 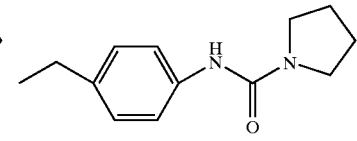 |

TABLE 55
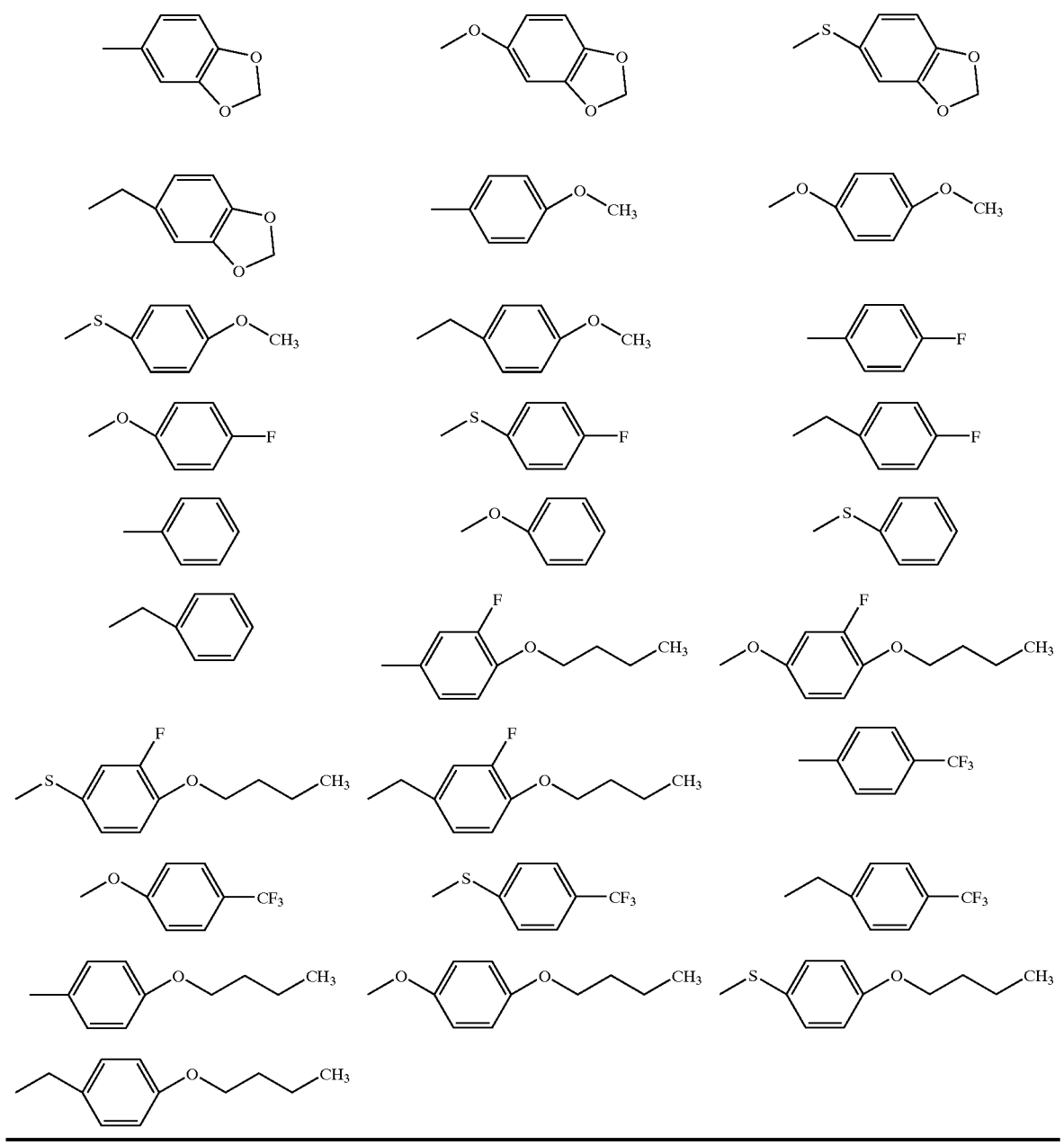

TABLE 56
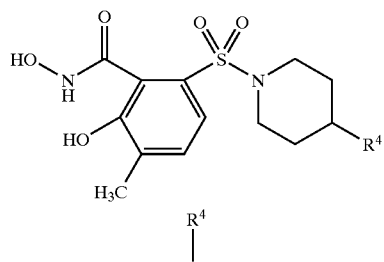
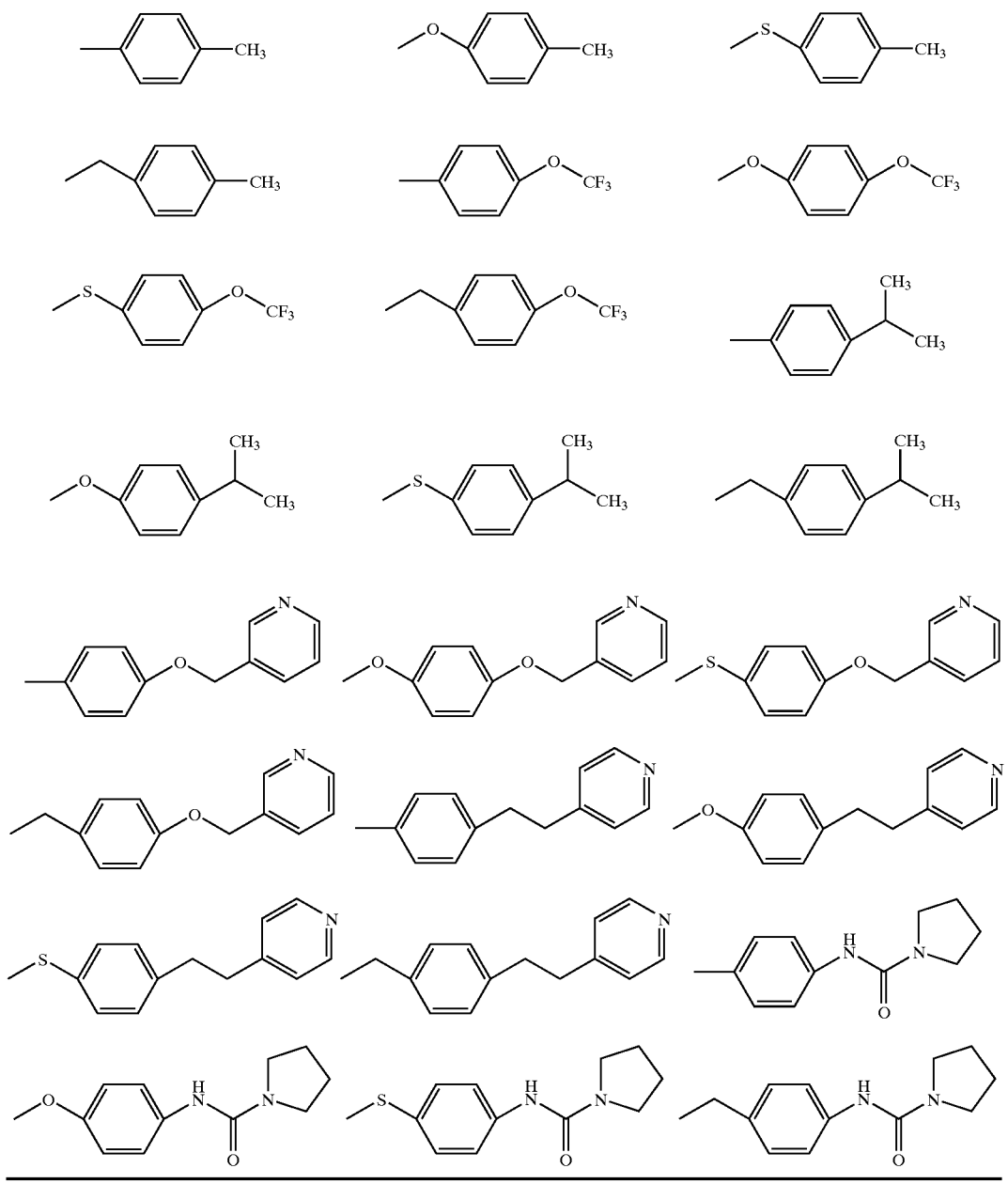

TABLE 57
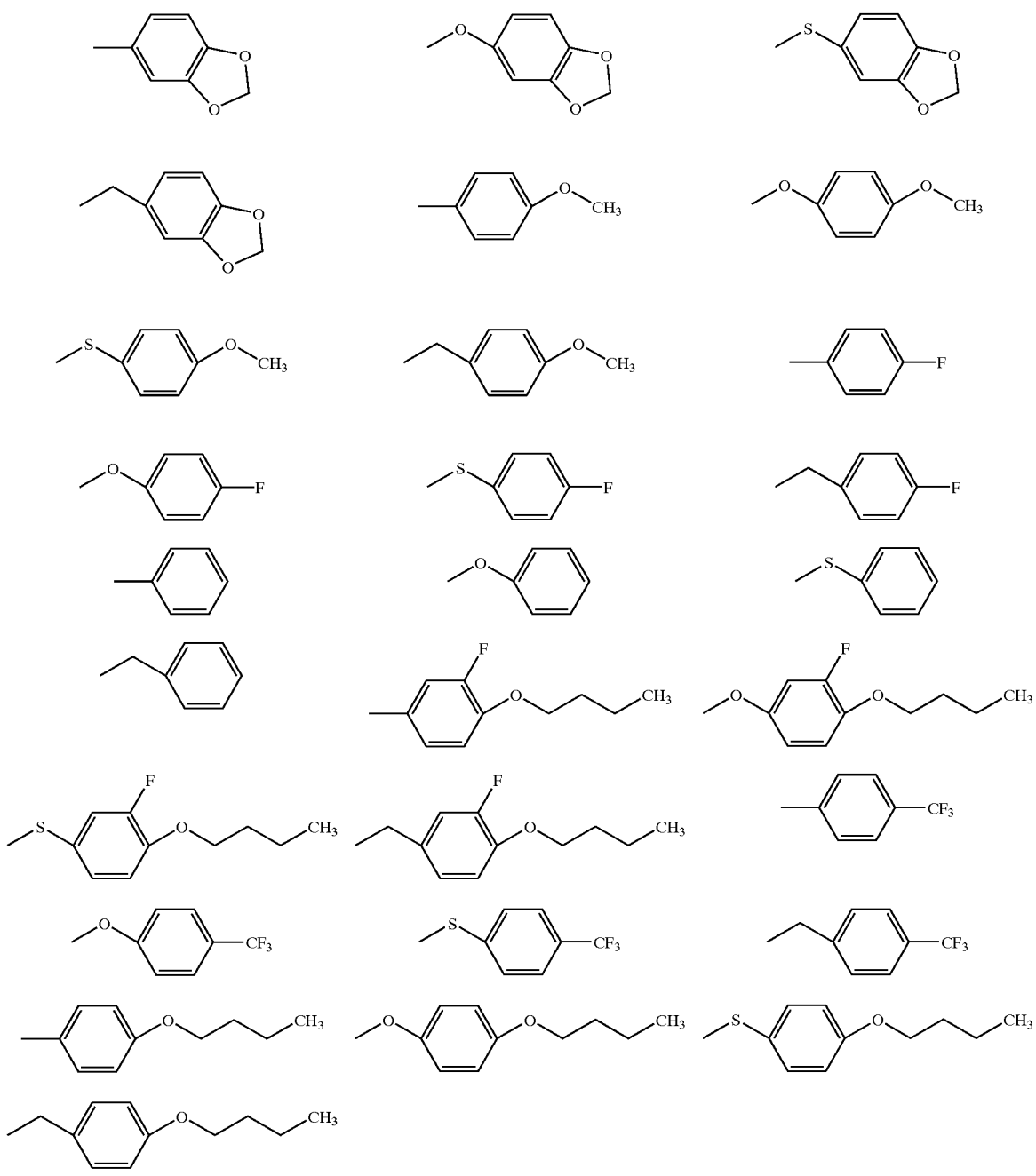

TABLE 58
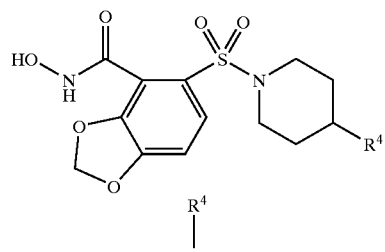
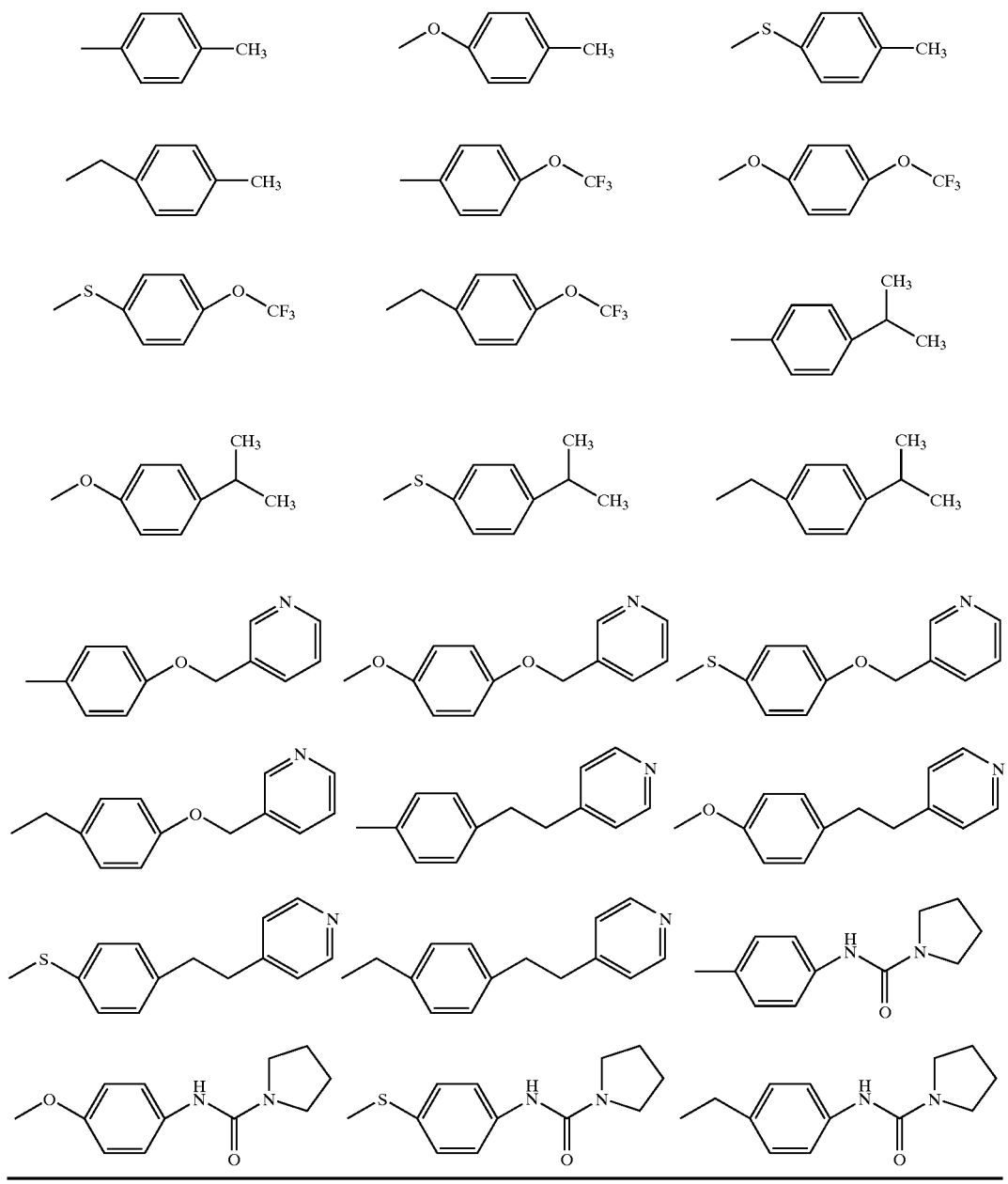

TABLE 59
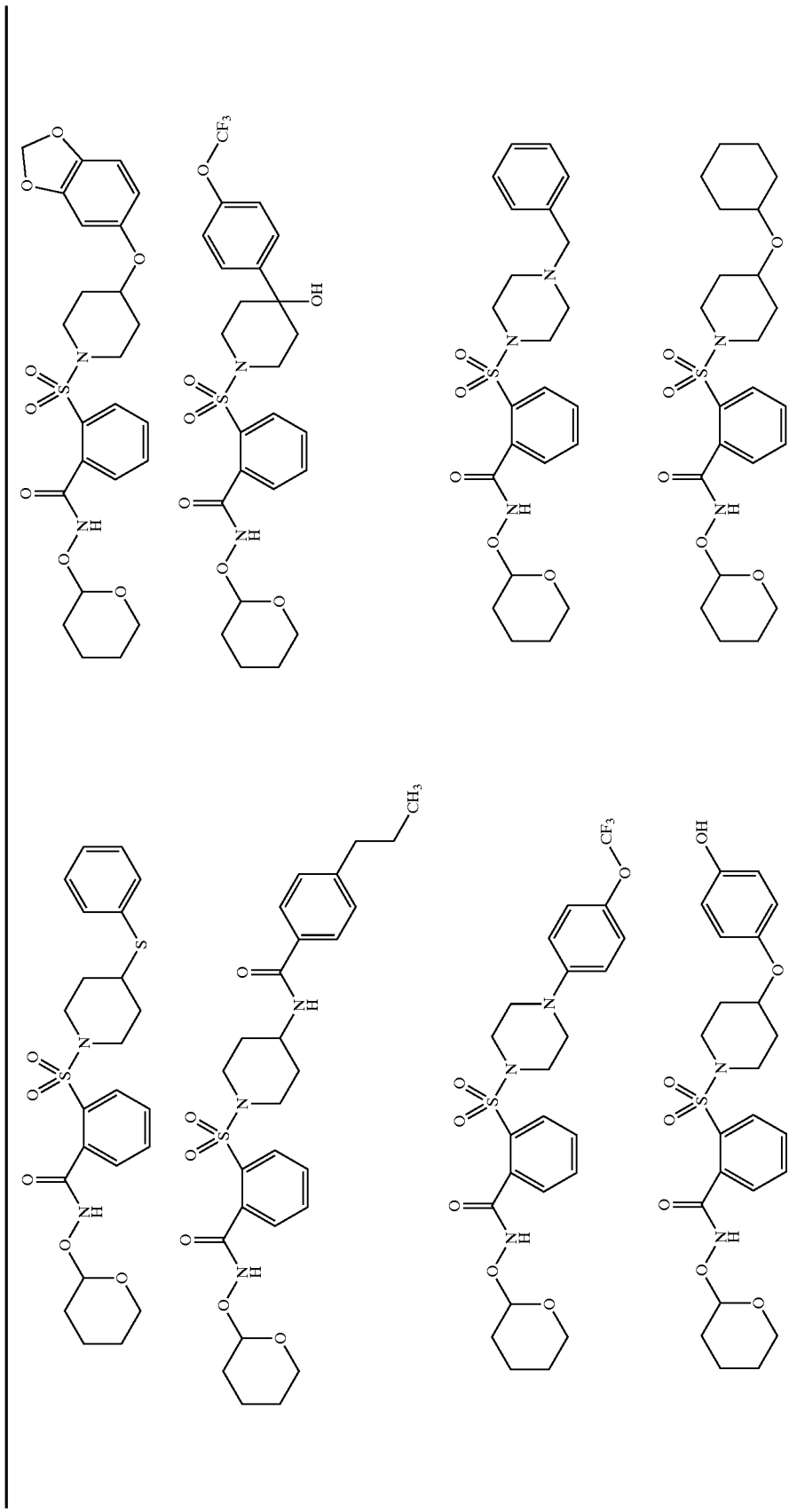

TABLE 59-continued
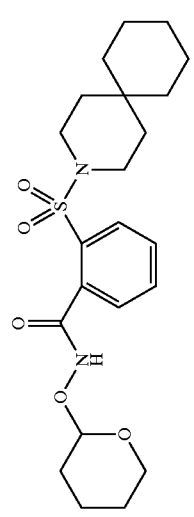 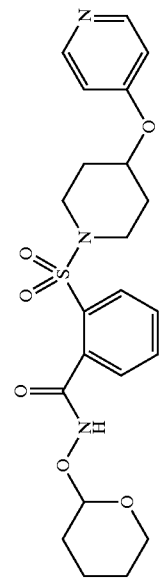
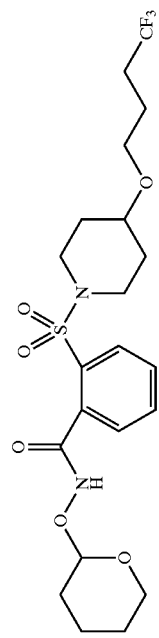 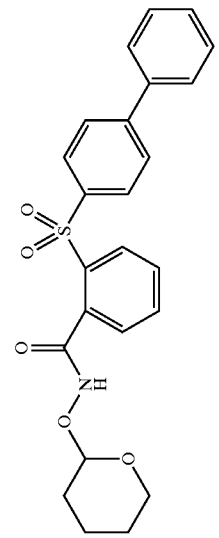

TABLE 60
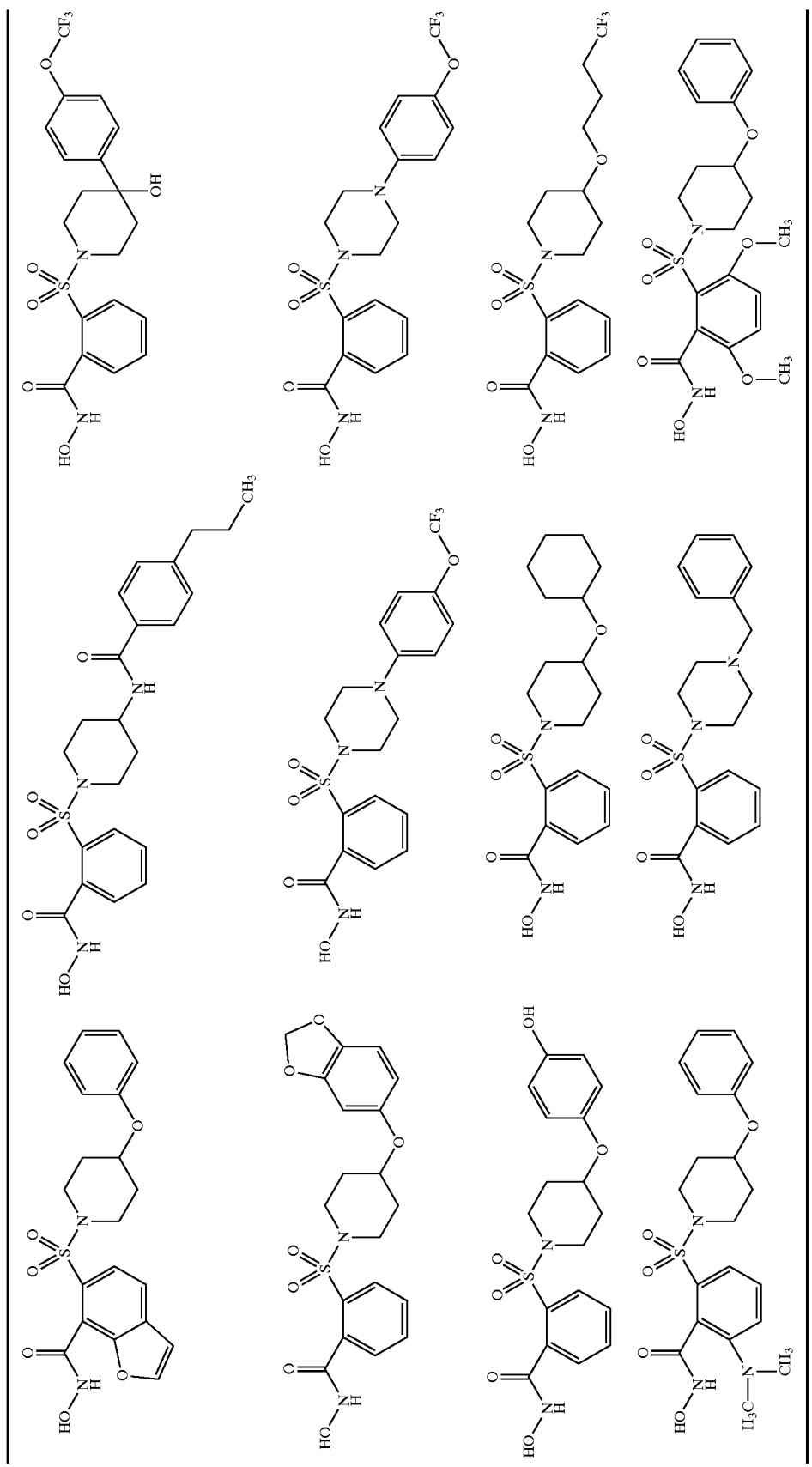

TABLE 61
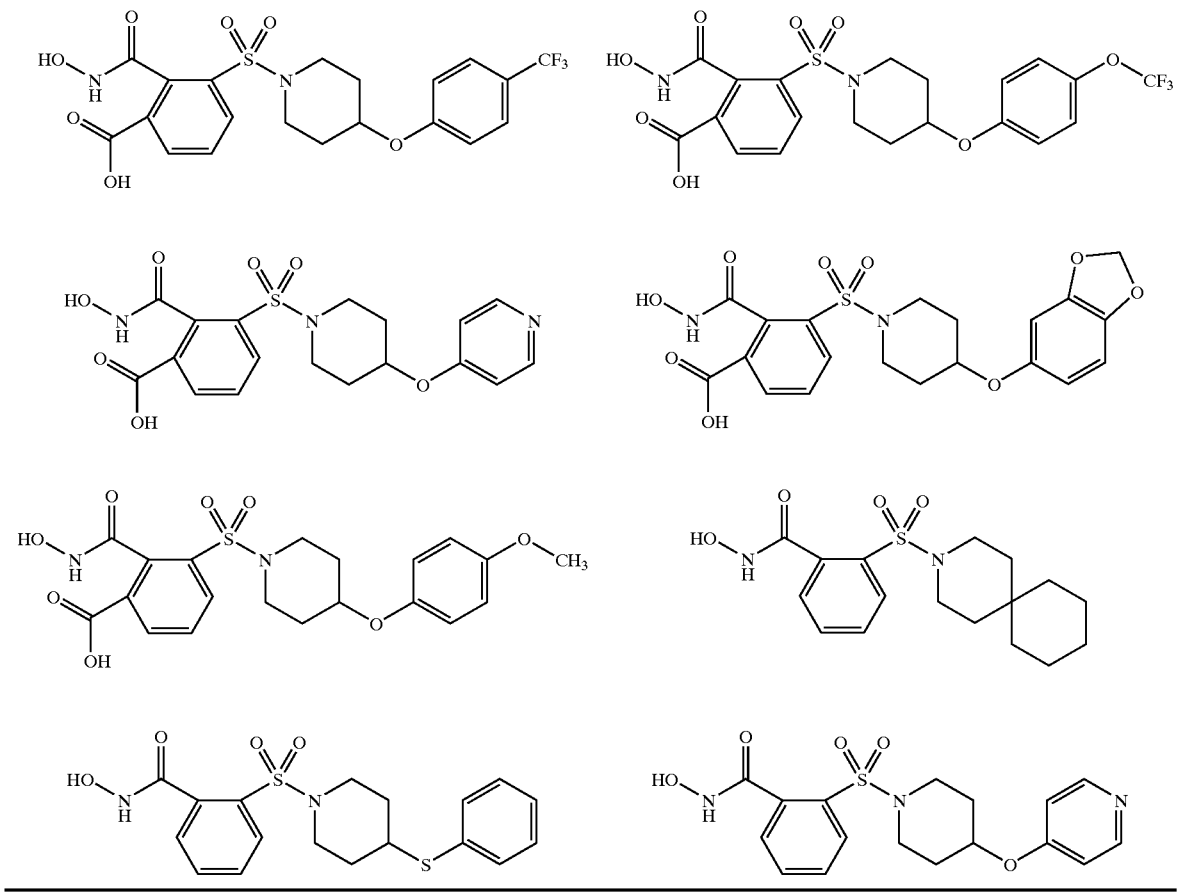
TABLE 62
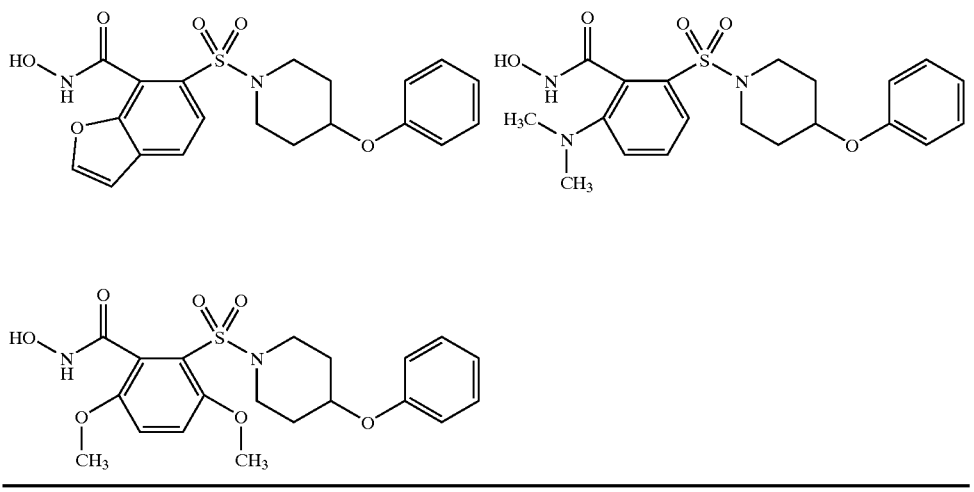

TABLE 63
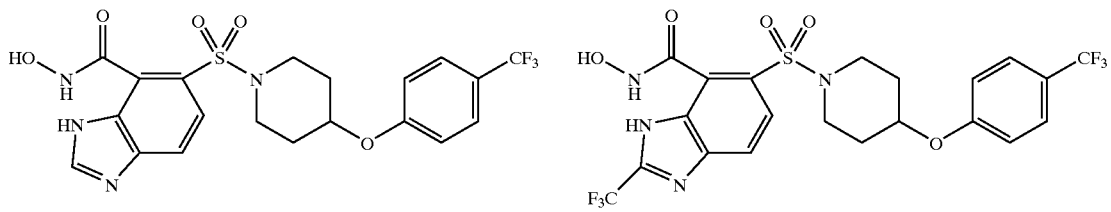
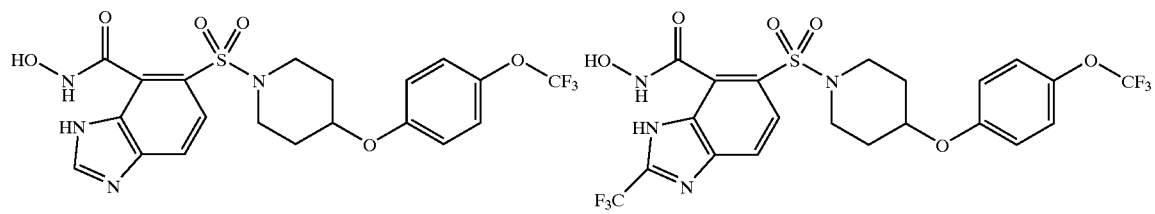
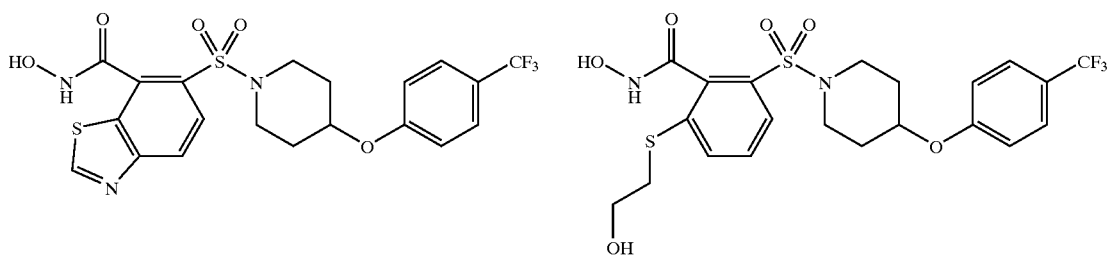
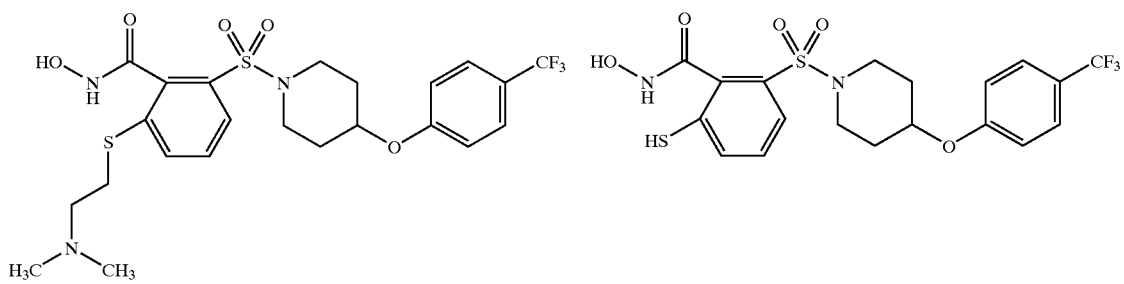
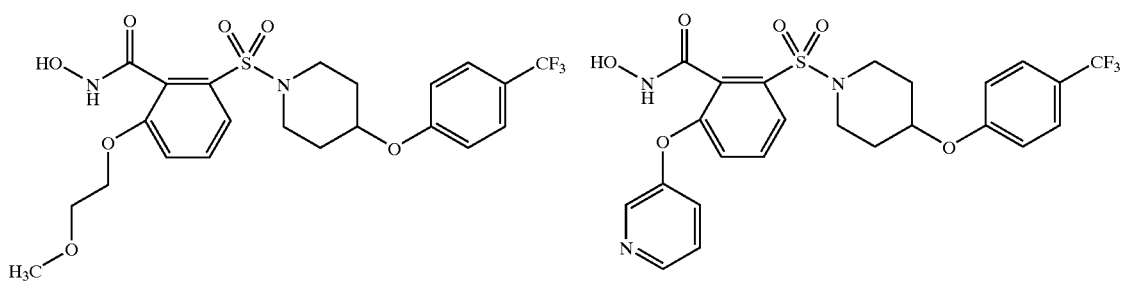

TABLE 63-continued
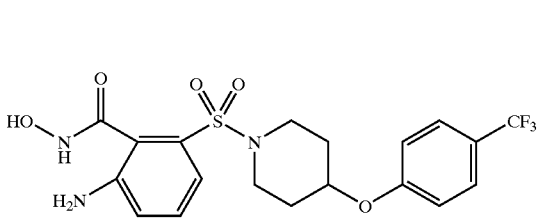
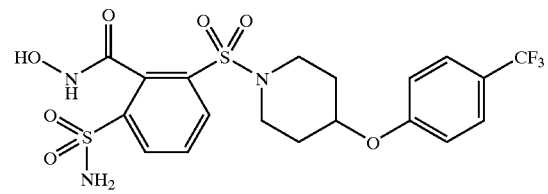
TABLE 64
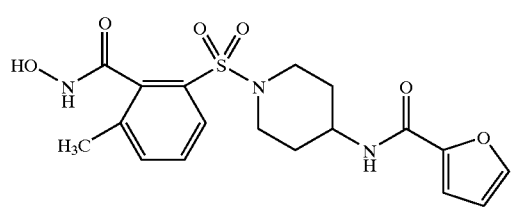
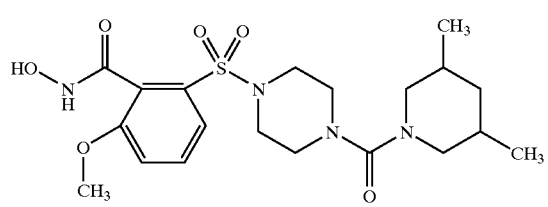
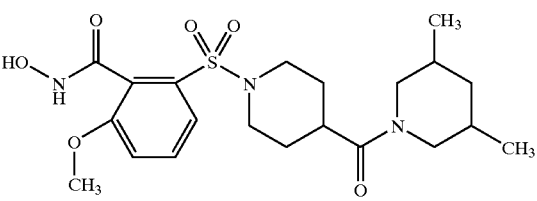
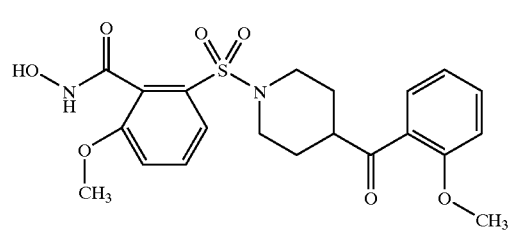
TABLE 64-continued
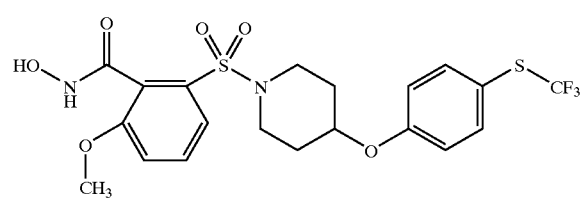
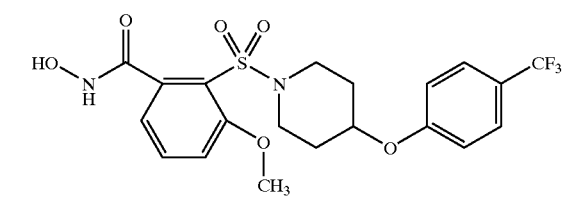
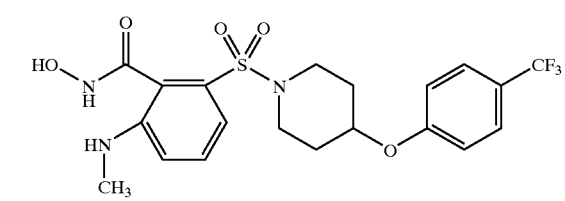
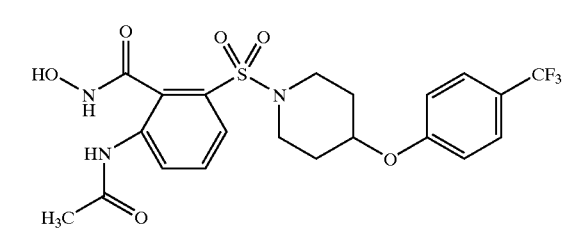

TABLE 65
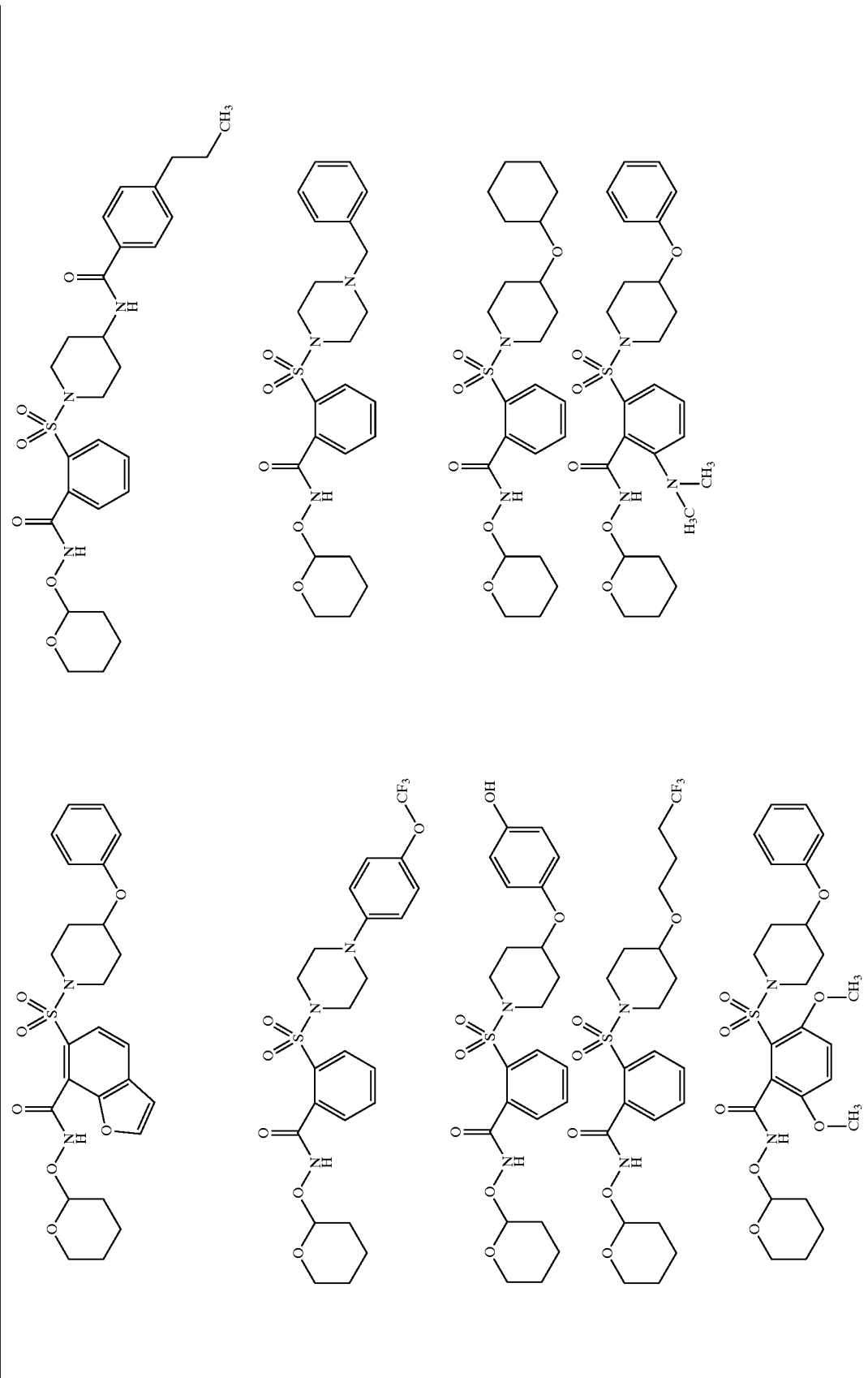

TABLE 66
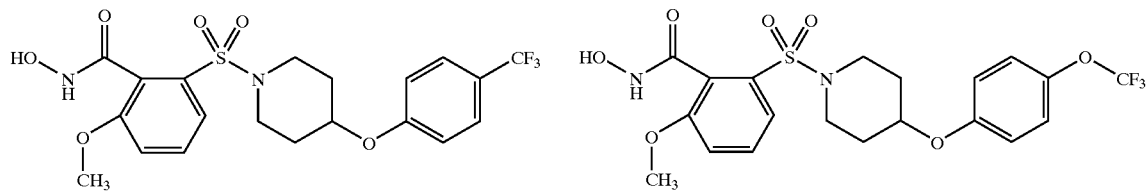
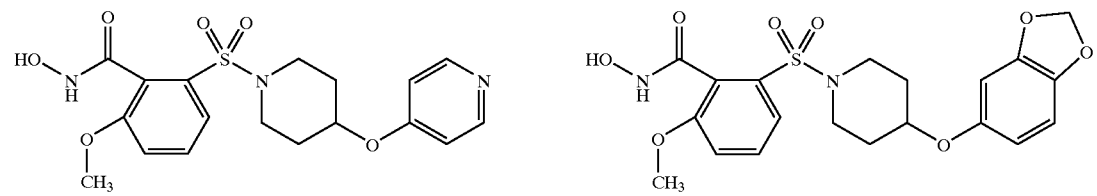
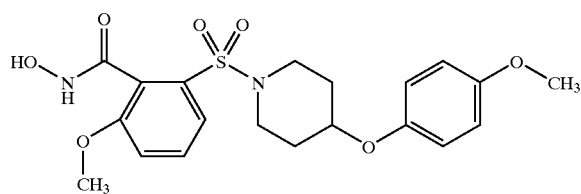

TABLE 67
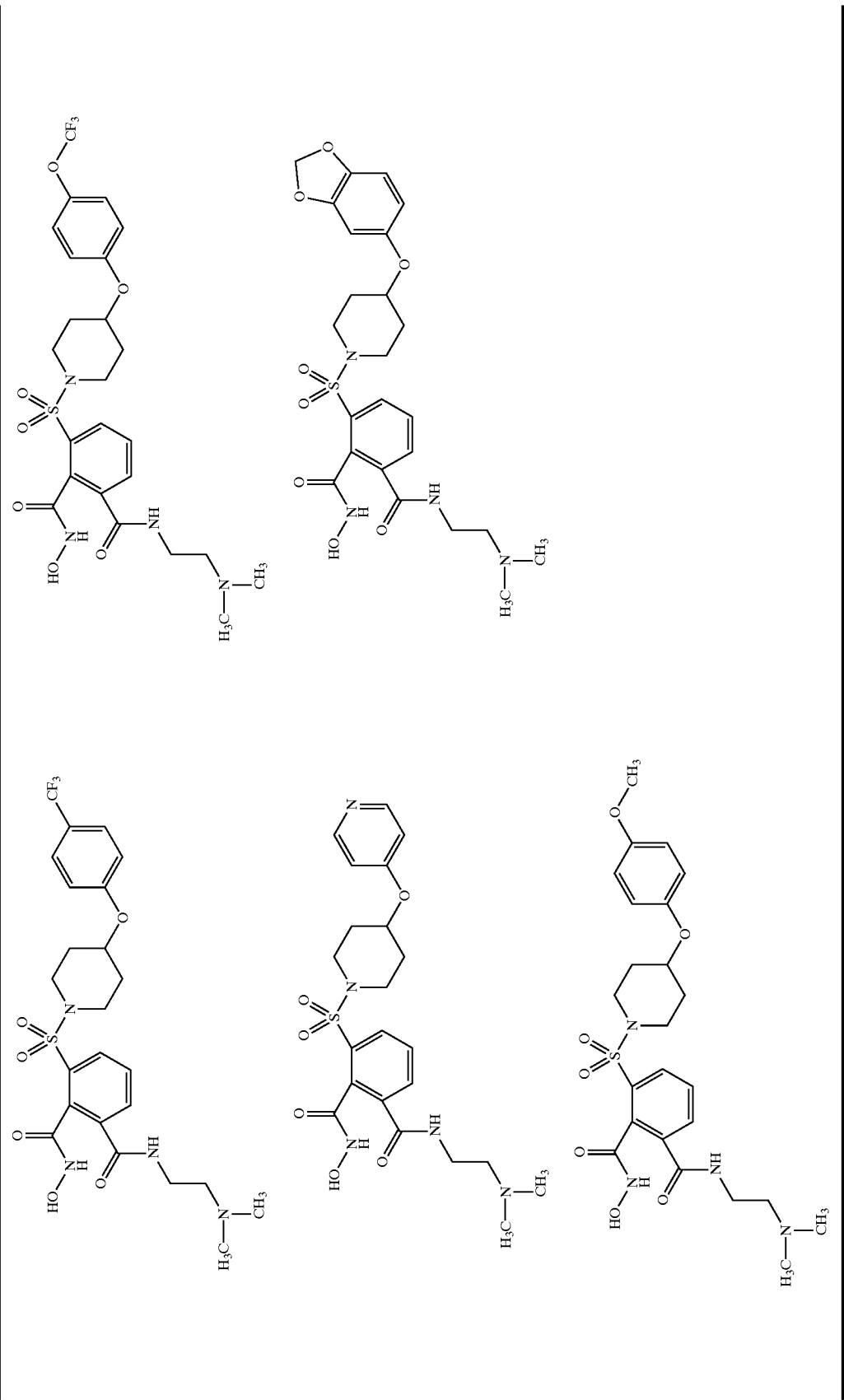

TABLE 68
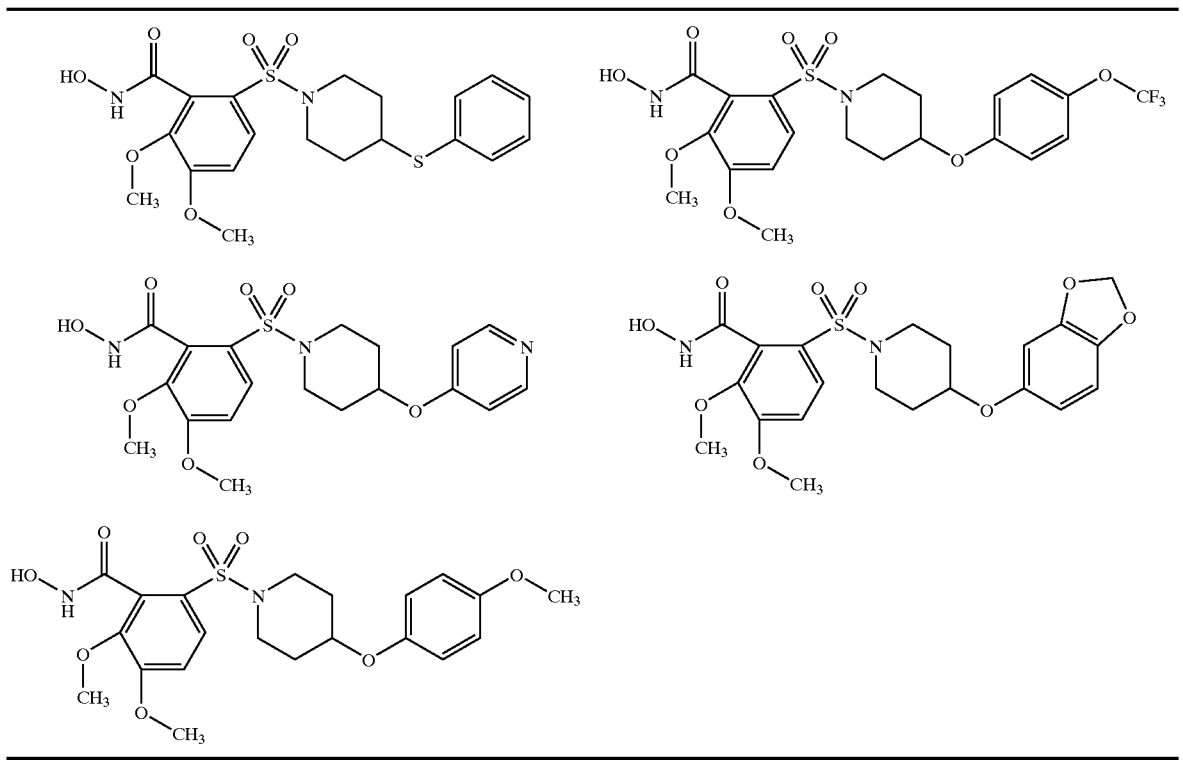
TABLE 69
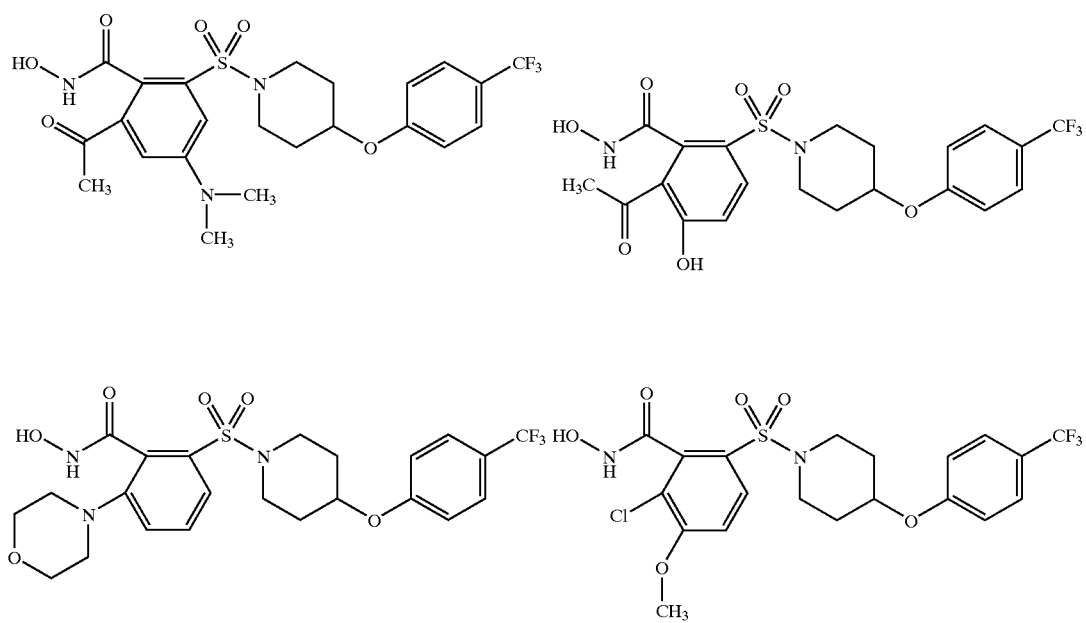

TABLE 69-continued
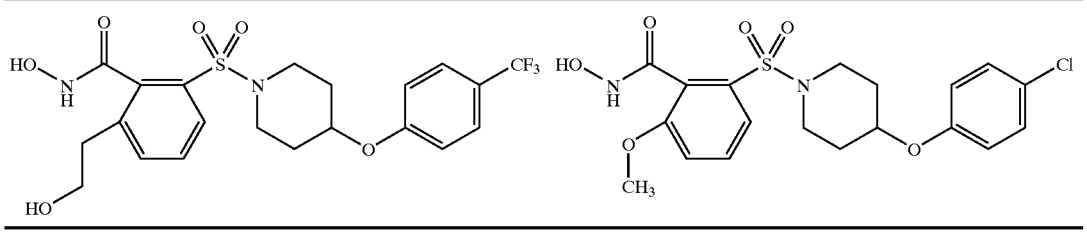
| TABLE 70 | TABLE 71 |
|---|---|
| 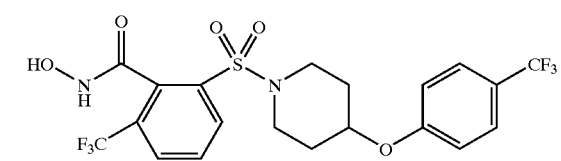 | 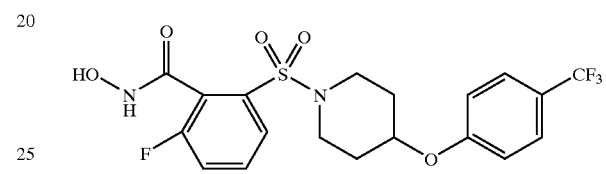 |
| 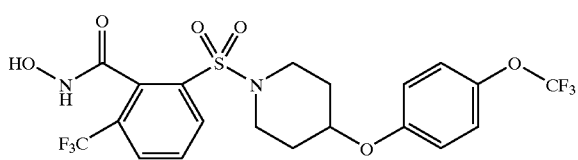 | 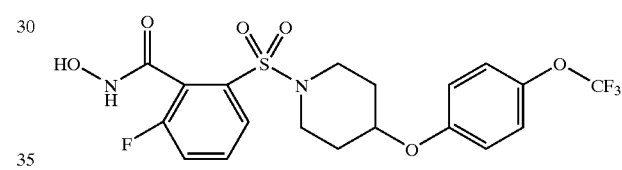 |
| 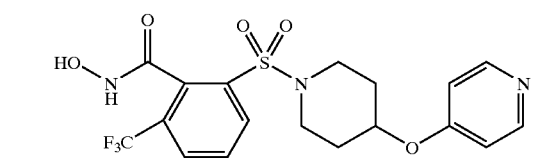 | 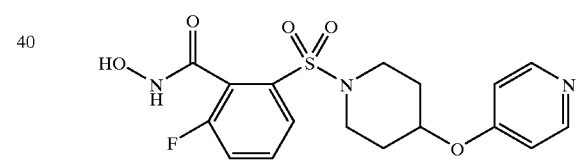 |
| 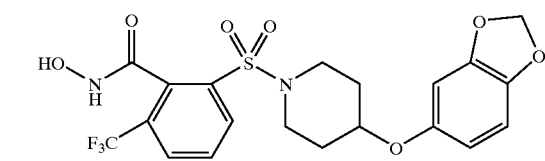 | 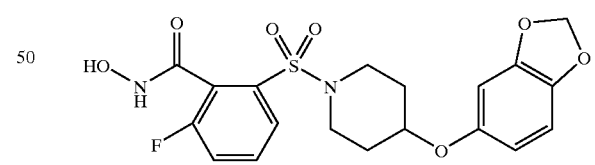 |
| 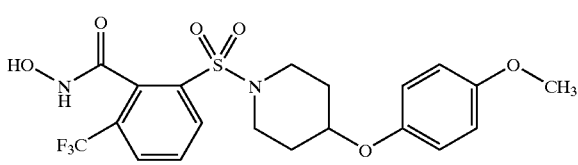 | 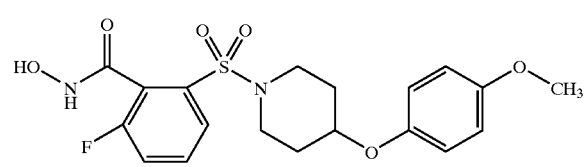 |

TABLE 72

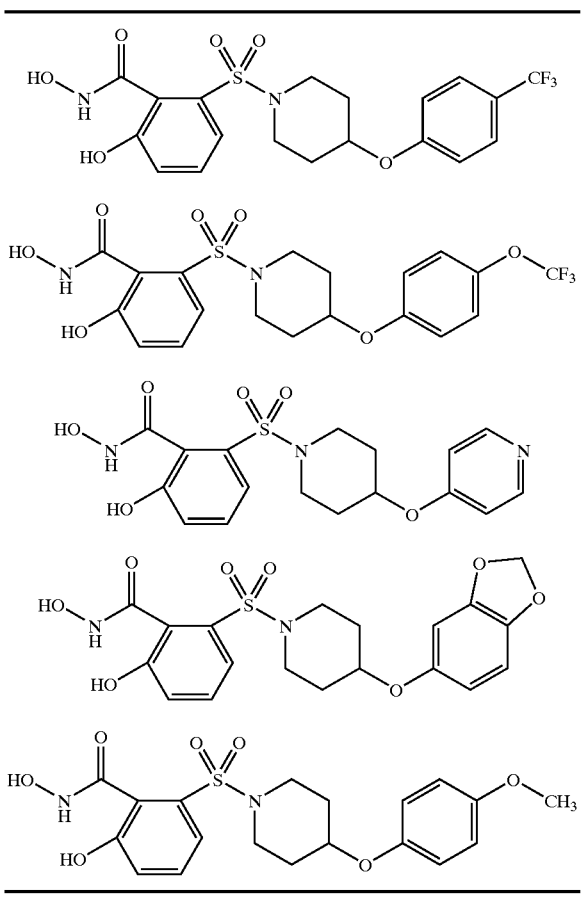

TABLE 73

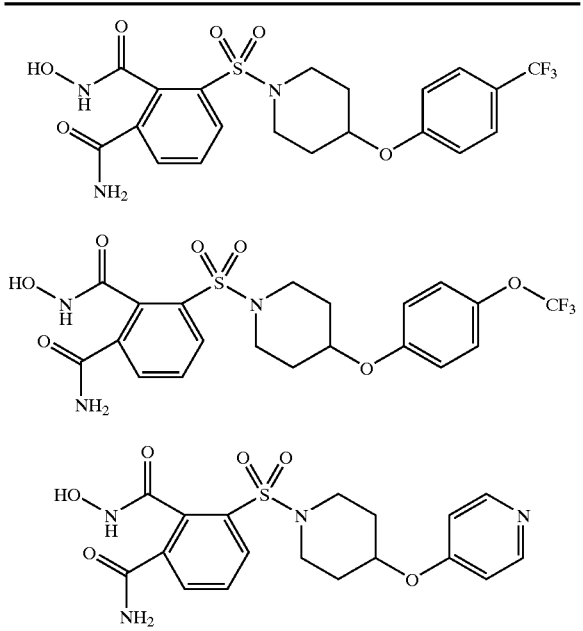

TABLE 73-continued

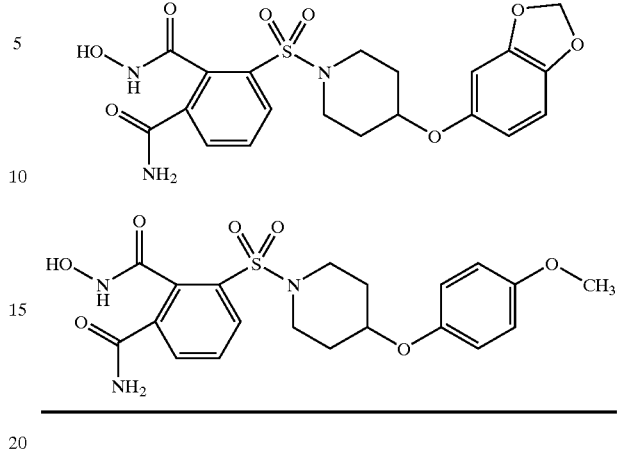

B. Salts of the Compounds of This Invention

The compounds of this invention can be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound Where a salt is intended to be administered to a patient (as opposed to, for example, being used in an in vitro context), the salt preferably is pharmaceutically acceptable. Pharmaceutically acceptable salts include salts commonly used to form alkali metal salts and to form addition salts of free acids or free bases. In general, these salts typically may be prepared by conventional means with a compound of this invention by reacting, for example, the appropriate acid or base with the compound.

Pharmaceutically-acceptable acid addition salts of the compounds of this invention may be prepared from an inorganic or organic acid. Examples of suitable inorganic acids include hydrochloric, hydrobromic acid, hydroionic, nitric, carbonic, sulfuric, and phosphoric acid. Suitable organic acids generally include, for example, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sulfanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically-acceptable base addition salts of the compounds of this invention include, for example, metallic salts and organic salts. Preferred metallic salts include alkali metal (group Ia) salts, alkaline earth metal (group IIa) salts, and other physiological acceptable metal salts. Such salts may be made from aluminum, calcium, lithium, magnesium, potassium, sodium, and zinc. Preferred organic salts can be made from tertiary amines and quaternary amine salts, such as trimethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$–$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), aralkyl halides (e.g., benzyl and phenethyl bromides), and others.

Particularly preferred salts of the compounds of this invention include hydrochloric acid (HCl) salts and trifluoroacetate ($CF_3COOH$ or TFA) salts.

C. Preventing or Treating Conditions Using the Compounds and Salts of This Invention One embodiment of this invention is directed to a process for preventing or treating a pathological condition associated with MMP activity in a host animal (typically a mammal, such as a human, companion animal, farm animal, laboratory animal, zoo animal, or wild animal) having or disposed to having such a condition. Such a condition may be, for example, tissue destruction, a fibrotic disease, pathological matrix weakening, defective injury repair, a cardiovascular disease, a pulmonary disease, a kidney disease, a liver disease, a bone disease, a central nervous system disease, or cancer. Specific examples of such conditions include osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermolysis bullosa, aortic aneurysm, weak injury repair, an adhesion, scarring, congestive heart failure, coronary thrombosis, emphysema, proteinuria, and Alzheimer's disease.

The condition may alternatively (or additionally) be associated with TNF-α activity. Examples of such a condition include inflammation (e.g. rheumatoid arthritis), autoimmune disease, graft rejection, multiple sclerosis, a fibrotic disease, cancer, an infectious disease (e.g., malaria, mycobacterial infection, meningitis, etc.), fever, psoriasis, a cardiovascular disease (e.g., post-ischemic reperfusion injury and congestive heart failure), a pulmonary disease, hemorrhage, coagulation, hyperoxic alveolar injury, radiation damage, acute phase responses like those seen with infections and sepsis and during shock (e.g., septic shock, hemodynamic shock, etc.), cachexia, and anorexia.

The condition may alternatively (or additionally) be associated with aggrecanase activity. Examples of such a condition include inflammation diseases (e.g., osteoarthritis, rheumatoid arthritis, joint injury, reactive arthritis, acute pyrophosphate arthritis, and psoriatic arthritis) and cancer.

In this patent, the phrase "preventing a condition" means reducing the risk of (or delaying) the onset of the condition in a mammal that does not have the condition, but is predisposed to having the condition. In contrast, the phrase "treating a condition" means ameliorating, suppressing, or eradicating an existing condition. The pathological condition may be (a) the result of pathological MMP and/or aggrecanase activity itself, and/or (b) affected by MMP and/or aggrecanase activity (e.g., diseases associated with TNF-α).

A wide variety of methods may be used alone or in combination to administer the hydroxamates and salt thereof described above. For example, the hydroxamates or salts thereof may be administered orally, parenterally, by inhalation spray, rectally, or topically.

Typically, a compound (or pharmaceutically acceptable salt thereof) described in this patent is administered in an amount effective to inhibit a target MMP(s) and/or aggrecanase. The target MMP is/are typically MMP-2, MMP-9, and/or MMP-13, with MMP-13 often being a particularly preferred target. The preferred total daily dose of the hydroxamate or salt thereof (administered in single or divided doses) is typically from about 0.001 to about 100 mg/kg, more preferably from about 0.001 to about 30 mg/kg, and even more preferably from about 0.01 to about 10 mg/kg (i.e., mg hydroxamate or salt thereof per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular hydroxamate or salt thereof employed; whether a drug delivery system is utilized; and whether the hydroxamate or salt thereof is administered as part of a drug combination. Thus, the dosage regimen actually employed can vary widely, and, therefore, can deviate from the preferred dosage regimen set forth above.

D. Pharmaceutical Compositions Containing the Compounds and Salts of This Invention This invention also is directed to pharmaceutical compositions comprising a hydroxamate or salt thereof described above, and to methods for making pharmaceutical compositions (or medicaments) comprising a hydroxamate or salt thereof described above.

The preferred composition depends on the method of administration, and typically comprises one or more conventional pharmaceutically acceptable carriers, adjuvants, and/or vehicles. Formulation of drugs is generally discussed in, for example, Hoover, John E., Remington's *Pharmaceutical Sciences* (Mack Publishing Co., Easton, Pa.: 1975). See also, Liberman, H. A. See also, Lachman, L., eds., *Pharmaceutical Dosage Forms* (Marcel Decker, New York, N.Y., 1980). Suitable methods of administration include, for example, oral administration, parenteral administration, rectal administration, topical administration, and administration via inhalation.

Solid dosage forms for oral administration include, for example, capsules, tablets, pills, powders, and granules. In such solid dosage forms, the hydroxamates or salts thereof are ordinarily combined with one or more adjuvants. If administered per os, the hydroxamates or salts thereof can be mixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the hydroxamate or salt thereof in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the carriers or diluents mentioned for use in the formulations for oral administration. The hydroxamates or salts thereof can be dissolved in water, polyethylene glycol, propylene glycol, ethanol, corn oil, cottonseed oil, peanut oil, sesame oil, benzyl alcohol, sodium chloride, and/or various buffers.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, such as cocoa butter; synthetic mono-, di-, or triglycerides; fatty acids; and/or polyethylene glycols.

Topical administration includes the use of transdermal administration, such as transdermal patches or iontophoresis devices.

Inhalation administration includes, for example, nasal sprays.

Other adjuvants and modes of administration known in the pharmaceutical art may also be used.

e. Preparation of Compounds

The following discussion describes exemplary chemical transformations that can be useful for preparing compounds of this invention. The reader also is referred to WIPO Int'l Publ. No. WO 00/69819. The reader is further referred to WIPO Int'l Publ. No. WO 98/38859.

These syntheses, as with all of the reactions discussed herein, can be carried out under a dry, inert atmosphere such as nitrogen ($N_2$) or argon if desired. Selected reactions known to those skilled in the art can be carried out under a dry atmosphere such as dry air, whereas other synthetic steps, like aqueous acid or base ester or amide hydrolyses, can be carried out under laboratory air.

Aryl and heteroaryl aryl compounds of this invention as defined above by W can be prepared in a similar manner as is known to those skilled in the art. It should be understood that the following discussion refers to both heteroaromatics and carbon aromatics even though only one may be specifically mentioned.

In general, the choices of starting material and reaction conditions can vary, as is well known to those skilled in the art. Usually, no single set of conditions is limiting because variations can be applied as required and selected by one skilled in the art. Conditions will also will be selected as desired to suit a specific purpose, such as small scale preparations or large scale preparations. In either case, the use of less safe or less environmentally sound materials or reagents will usually be minimized. Examples of such less desirable materials are diazomethane, diethyl ether, heavy metal salts, dimethyl sulfide, some halogenated solvents, benzene and the like. In addition, many starting materials can be obtained from commercial sources through catalogs or various other arrangements.

An aromatic compound of this invention where y is 1 can be prepared as illustrated (see, e.g., Scheme 1) by converting a carbonyl group bonded to an aromatic (e.g., benzene) ring ortho-substituted with a sulfide. The sulfide can be prepared via a nucleophilic displacement reaction of the ortho fluoride.

The nucleophile can be a thiol or thiolate anion prepared from a aryl thiol discussed below. A preferred thiol is 4-phenoxybenzenethiol converted in situ into its anion (thiolate) using potassium carbonate in iso-propyl alcohol at reflux temperature.

The carbonyl group can be an aldehyde, ketone, or carboxylic acid derivative, i.e., a protected carboxylic acid or hydroxamate. A preferred carbonyl group is an aldehyde and a preferred aldehyde is 2-flourobenzaldehyde (ortho-fluorobenzaldehyde). A ketone can be converted by oxidation into an acid and/or an acid derivative using reagents such as those discussed below for oxidation of a sulfide or other methods well known in the art. It is noted that this oxidation can accomplish the oxidation of a sulfide intermediate into the corresponding sulfone in the same reaction system, i.e., in the same pot, if desired.

The carbonyl group can then be homologated if desired by reaction with an anion to form an addition compound. An example of a homologation reagent is a tri-substituted methane compound such as tetraethyl dimethylammonium-methylenediphosphonate or trimethylorthoformate. Tetraethyl dimethylammoniummethylenediphosphonate is preferred. Hydrolysis of the reaction product can provide a phenylacetic substituted on the aromatic ring with a sulfide of this invention. Acid hydrolysis is preferred. Various suitable acids and bases are discussed below, although HCl is preferred.

The sulfide can then be oxidized to form a sulfone in one or two steps as discussed below. A preferred oxidizing agent is hydrogen peroxide in acetic acid. The carboxylic acid product or intermediate of this invention can then be converted into a protected derivative such as an ester or converted into an activated carboxyl group for reaction with hydroxylamine or protected hydroxylamine. The conversion of an acid into a hydroxamate is discussed below, as is the coupling process and removal of a protecting group if required.

The preferred protected hydroxamic acid derivative is the O-tetrahydropyranyl compound, and the preferred coupling procedure utilizes a diimide (EDC), hydroxybenzotriazol, and DMF solvent for the coupling reaction to form the intermediate hydroxybenzotriazol activated ester. A preferred reagent for removal of the THP protecting group is HCl.

Alkylation of the acid at the carbon alpha to the carbonyl group to form the compounds of this invention can be carried out by first forming an anion using a base. Suitable bases are discussed below, although preferred bases are strong bases that are either hindered and/or non-nucleophilic such as lithium amides, metal hydrides, and lithium alkyls.

Following or during formation of the anion, an alkylating agent (i.e., an electrophile) is added that undergoes a nucleophilic substitution reaction. Nonlimiting examples of such alkylating agents are haloalkanes, dihaloalkanes, haloalkanes also substituted by an activated ester group or activated esters and alkanes substituted with sulfate esters.

Activated ester groups are well known in the art and can include, for example, an activated ester of an alcohol or a halo compound, an ester of a haloalcohol such as a bromo-, iodo- or chloro-derivative of a tosylate, triflate or mesylate activated ester. Compounds wherein, for example, $R^2$ and $R^3$ are taken together as defined above, can be prepared using disubstituted alkylating agent, i.e., alkylating agents with two leaving groups in the same molecule. For example, 1,5-dihalo-diethylether or analogous reagents containing one or more sulfate ester leaving groups replacing one or more halogens can be used to form a pyran ring. A similar sulfur, nitrogen, or protected nitrogen alkylating agent can be used to form a thiapyran or piperidine ring. A thiapyran can be oxidized to form a sulfoxide or a sulfone using methods discussed herein. A leaving group in an electrophilic reagent, as is well known in the art, can be a halogen such as chlorine, bromine or iodine, or an active ester such as a sulfonate ester, e.g., toluenesulfonate (tosylate), triflate, mesylate and the like as discussed above.

The conversion of a cyclic amino acid, heterocycle, or alpha-amino acid defined by $R^2$ and $R^3$ that can include an amino acid (nitrogen heterocycle), which can be protected or unprotected, into a compound of this invention can be accomplished by alkylation or acylation. The carboxylic acid group can be protected with a group such as an alkyl ester such as methyl, ethyl, tert-butyl, and the like or a tetrahydropyranyl ester or an arylalkyl ester such as benzyl or it can remain as a carboxylic acid. A protected amino acid such as an ethyl ester is preferred. The substituent on the heterocycle group is as defined above and can include hydrogen, tert- and iso-butyloxycarbonyl groups. In addition, the amine can be considered as being a protected intermediate as well as being a product of this invention when the N-substituent is not hydrogen.

The nitrogen substituent on the amino acid portion of the compounds of this invention can be varied. In addition, that variation can be accomplished at different stages in the synthetic sequence based on the needs and objectives of the skilled person preparing the compounds of this invention. The nitrogen side chain variations can include replacing the hydrogen substituent with an alkyl, arylalkyl, alkene, or alkyne.

This can be accomplished by methods well known in the art such as alkylation of the amine with an electrophile such as halo- or sulfate ester (activated ester) derivative of the desired side chain. An alkylation reaction is typically carried out in the presence of a base such as those discussed above and in a pure or mixed solvent as discussed above. A preferred base is potassium carbonate and a preferred solvent is DMF.

The alkenes, arylalkenes, arylalkynes, and alkynes so formed can be reduced, for example, by hydrogenation with a metal catalyst and hydrogen, to an alkyl or arylalkyl compound of this invention and an alkyne or arylalkyne can be reduced to an alkene, arylalkene, arylalkane or alkane under catalytic hydrogenation conditions as discussed herein or a deactivated metal catalyst. Catalysts can include, for example, Pd, Pd on Carbon, Pt, $PtO_2$, and the like. Less robust catalysts (deactivated) include such things as Pd on $BaCO_3$ or Pd with quinoline or/and sulfur.

An alternative method for alkylation of the amine nitrogen is reductive alkylation. This process, well known in the art, allows treatment of the secondary amine with an aldehyde or ketone in the presence of a reducing agent such as borane, borane:THF, borane:pyridine, or lithium aluminum hydride. Alternatively, reductive alkylation can be carried out under hydrogenation conditions in the presence of a metal catalyst. Such catalysts, suitable hydrogen pressures, and suitable temperatures are well known in the art. A preferred reductive alkylation catalyst is borane:pyridine complex.

As discussed above, in the case where an intermediate is a carboxylic acid, standard coupling reactions well known in the art can be used to form the compounds of this invention, including protected intermediates. For example, the acid can be converted into an acid chloride, mixed anhydride, or activated ester and reacted with an alcohol, amine, hydroxylamine, or a protected hydroxylamine in the presence of base to form the amide, ester, hydroxamic acid, or protected hydroxamic acid. Suitable bases include N-methyl-morpholine, triethylamine, and the like.

Coupling reactions of this nature are well known in the art, particularly the art related to peptide and amino acid chemistry. Removal of the protecting group can be accomplished, if desired, using standard hydrolysis conditions such as base hydrolysis or exchange or acid exchange or hydrolysis.

The schemes below illustrate conversion of a carboxylic acid protected as an ester or amide into a hydroxamic acid derivative such as a O-arylalkylether or O-cycloalkoxyalkylether group, such as the THP group. Methods of treating an acid or acid derivative with hydroxylamine or a hydroxylamine derivative to form a hydroxamic acid or hydroxamate derivative are discussed above. Hydroxylamine can be used in an exchange reaction by treating a precursor compound where the carboxyl is protected as an ester or amide with one or more equivalents of hydroxylamine hydrochloride or hydroxylamine at room temperature or above to provide a hydroxamic acid directly. The solvent or solvents, usually protic or protic solvent mixtures, include those listed herein.

This exchange process can be further catalyzed by the addition of additional acid. Alternatively, a base (e.g., a salt of an alcohol used as a solvent, such as, for example, sodium methoxide in methanol) can be used to form hydroxylamine from hydroxylamine hydrochloride in situ which can exchange with an ester or amide. As mentioned above, exchange can be carried out with a protected hydroxylamine (e.g., tetrahydropyranyl-hydroxyamine (THPONH$_2$), benzylhydroxylamine (BnONH$_2$), O-(trimethylsilyl) hydroxylamine, and the like), in which case, the compounds formed are tetrahydropyranyl (THP), benzyl (Bn), or TMS hydroxamic acid derivatives. Removal of the protecting groups when desired (e.g., following further transformations in another part of the molecule or following storage) can be accomplished by standard methods well known in the art, such as acid hydrolysis of the THP group as discussed above or reductive removal of the benzyl group with hydrogen and a metal catalyst such as palladium, platinum, palladium on carbon, or nickel.

α-Amino acids or a-hydroxy carboxylic acids or protected carboxylic acids, hydroxamates or hydroxamic acid derivatives or intermediates (precursors) of this invention can be prepared by displacing, for example, a halogen, sulfate ester, or other electrophile, from the alpha carbon of an acid or a derivative as listed. Methods for the halogenation of acids, esters, acid chlorides, and the like are well known in the art and include, for example, the HVZ reaction, treatment with $CuCl_2$, N-bromo- or N-chloro-succinimide, $I_2$, carbon tetraiodide or bromide, and the like. The halogen can be displaced with a nucleophile in an $SN_2$ reaction. Nucleophiles can include hydroxide, ammonia, or amines.

The aryl or heteroaryl carboxylic acids of this invention where Y is 0 and z is 1 can be prepared from heteroaryl or aryl fused lactones. An example of a fused lactone is phthalide. A preferred starting material is phthalide. This compound can be treated with an thiol, thiolate, or metal —SH to undergo an $SN_2$ displacement at the methylene carbon to provide a sulfide or thiol compound of this invention or intermediate to a compound of this invention. A preferred thiol is 4-phenoxybenzenethiol that is used in the presence of potassium carbonate as a preferred base. The sulfide can be oxidized, before or after conversion of the acid to a hydroxamate or hydroxamic acid, to a sulfone of this invention. A preferred oxidizing agent is meta-chloroperbenzoic acid.

A preferred acid activating group is the chloride prepared by reaction of an acid with oxalyl chloride as a preferred reagent. A phthalide or a heteroaryl analog of a phthalide can be treated with a Lewis acid (e.g., zinc chloride or zinc bromide) along with a halogenating reagent (e.g., phosphorus trichloride, thionyl bromide and the like) to form an ortho-(haloalkyl)-aryl acid or ortho-(haloalkyl)heteroaryl acid derivative. Examples include bromomethyl acid bromides and chloromethyl acid chlorides. These carboxylic acids can be derivatized with protecting groups, hydroxamic acids, or hydroxamic acid precursors or hydrolyzed to the acid as required. A preferred hydroxamate-forming reagent is O-(trimethylsilyl)hydroxylamine (TMS-hydroxylamine), and removal of the TMS protecting group is preferably accomplished by acid hydrolysis using HCl.

Displacement ($SN_2$) of the halogen in this example by a thiol in the presence of base or a preformed thiolate can be accomplished as discussed and/or shown and as is well known in the art. Again, oxidation of the sulfide can be carried out before or after derivatization of the carboxylic acid as discussed to prepare the hydroxamic acids of this invention. Removal of the protecting groups can be carried out using acid hydrolysis or reduction as discussed elsewhere.

The alcohols of this invention can be protected or deprotected as required or desired. Protecting groups can include THP ethers, acylated compounds, and various silyl derivatives. These groups, including their protection and removal, are well known in the art.

Examples of bases that can be used include, for example, metal hydroxides, such as sodium, potassium, lithium or magnesium hydroxide; oxides, such as those of sodium, potassium, lithium, calcium or magnesium; metal carbonates, such as those of sodium, potassium, lithium, calcium or magnesium; metal bicarbonates, such as sodium bicarbonate or potassium bicarbonate; primary (I°), secondary (II°), or tertiary (III°) organic amines, such as alkyl amines, arylalkyl amines, alkylarylalkyl amines, heterocyclic amines, or heteroaryl amines; ammonium hydroxides; and quaternary ammonium hydroxides. As non-limiting examples, such amines can include triethyl amine, trimethyl amine, diisopropyl amine, methyldiisopropyl amine, diazabicyclononane, tribenzyl amine, dimethylbenzyl amine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine, and the like.

Non-limiting examples of ammonium hydroxides, usually made from amines and water, include ammonium hydroxide, triethyl ammonium hydroxide, trimethyl ammonium hydroxide, methyldiiosopropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiiospropyl ammonium hydroxide, benzylmethyldiisopropyl ammonium hydroxide, methyldiazabicyclononyl ammonium hydroxide, methyltribenzyl ammonium hydroxide, N,N dimethylmorpholinium hydroxide, N,N,N',N',-tetramethylpiperazenium hydroxide, and N-ethyl-N'-hexylpiperidinium hydroxide, and the like. Metal hydrides, amides, or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide, and the like, can also be suitable reagents. Organometallic deprotonating agents, such as alkyl or aryl lithium reagents (e.g., methyl, phenyl, butyl, iso-butyl, sec-butyl, or tertbutyl lithium), nodium or potassium salts of dimethylsulfoxide, Grignard reagents (e.g., methylmagnesium bromide or methymagnesium chloride), or organocadium reagents (e.g., dimethylcadium and the like) can also serve as bases for causing salt formation or catalyzing the reaction. Quaternary ammonium hydroxides or mixed salts are also useful for aiding phase transfer couplings or serving as phase transfer reagents. The preferred base for use in the alkylation reaction is lithium diisopropyl amide.

Reaction media in general can be comprised of a single solvent, mixed solvents of the same or different classes, or serve as a reagent in a single or mixed solvent system. The solvents can be protic, non-protic, or dipolar aprotic. Non-limiting examples of protic solvents include water, methanol (MeOH), denatured or pure 95% or absolute ethanol, isopropanol, and the like.

Typical non-protic solvents include acetone, tetrahydrofurane (THF), dioxane, diethylether, tert-butylmethyl ether (TBME), aromatics (e.g., xylene, toluene, or benzene), ethyl acetate, methyl acetate, butyl acetate, trichloroethane, methylene chloride, ethylenedichloride (EDC), hexane, heptane, isooctane, cyclohexane, and the like. Dipolar aprotic solvents include dimethylformamide (DMF), dimethylacetamide (DMAc), acetonitrile, nitromethane, tetramethylurea, N-methylpyrrolidone, and the like.

Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides, or thiols for making the products of this invention and the like. Room temperature or less or moderate warming (−10° C. to 60° C.) are the preferred temperatures of the reaction. If desired, the reaction temperature may be from about −78° C. to the reflux point of the reaction solvent or solvents. The preferred solvent for an alkylation reaction is tetrahydrofurane (THF).

Acids are used in many reactions during various synthesis. The Schemes below and this discussion illustrate using acid for removing a THP protecting group to produce a hydroxamic acid, removing a tert-butoxy carbonyl group, hydroxylamine/ester exchange, and the like. Acid hydrolysis of carboxylic acid protecting groups or derivatives is well known in the art. These methods, as is well known in the art, can use acid or acidic catalysts. The acid can be mono-, di-, or tri-protic organic or inorganic acids. Examples of acids include hydrochloric acid, phosphoric acid, sulfuric acid, acetic acid, formic acid, citric acid, succinic acid, hydrobromic acid, hydrofluoric acid, carbonic acid, phosphorus acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They can also be Lewis acids such as aluminum chloride, borontrifluoride, antimony pentafluoride, and the like.

Contemplated compounds can include compounds wherein a nitrogen of an amine is acylated to provide, for example, amino acid carbamates. Nonlimiting examples of these carbamates are the carbobenzoxycarbonyl (Z, CBZ, benzyloxycarbonyl), iso-butoxycarbonyl and tert-butoxycarbonyl (BOC, t-BOC) compounds. The materials can be made, as discussed above, at various stages in the synthesis based on the needs and decisions made by a person skilled in the art using methods well know in the art.

Useful synthetic techniques and reagents include those used in protein, peptide, and amino acid synthesis, coupling, and transformation chemistry. The use of the tert-butoxycarbonyl (BOC) and benzyloxycarbonyl (Z), as will as their synthesis and removal, are examples of such protection or synthesis schemes. Transformations of amino acids, amino esters, amino acid hydroxamates, amino acid hydroxamate derivatives, and amino acid amides of this invention or compounds used in this invention is discussed herein or/and shown in the schemes below. This includes, for example, active ester or mixed anhydride couplings wherein preferred bases, if required, are tertiary amines, such as N-methylmorpholine. Reagents for protection of the amine group of the protected amino acids include carbobenzoxy chloride, iso-butylchloroformate, tert-butoxycarbonyl chloride, di-tert-butyl dicarbonate and the like which are reacted with the amine in non-protic or dipolar aprotic solvents such as DMF or THF or mixtures of solvents.

Removal of protecting groups such as carbamates, silyl groups and benzyl, p-methoxybenzyl, or other substituted benzyl groups or diphenylmethyl (benzhydryl) or triphenylmethyl (trityl) can be carried out at different stages in the synthesis of the compounds of this invention as required by methods selected by one skilled in the art. These methods are well known in the art including the amino acid, amino acid coupling, peptide synthesis, and peptide mimetic synthesis art. Removal methods can include catalytic hydrogenation, base hydrolysis, carbonyl addition reactions, acid hydrolysis, and the like. Both the preparation and removal of protecting groups (e.g., carbamates, benzyl groups, and/or substituted arylalkyl groups) are discussed in Green, T., *Protecting Groups in Organic Chemistry*, 2 nd ed. (John Wiley & Sons, New York, 1991). A preferred method of removal of a BOC group is HCl gas in methylene chloride, which, following normal workup, provides directly an HCl salt of an aminoacid of this invention.

Sulfone compounds, such as those where $R^1$ is nitrobenzene, can be prepared as compounds of this invention by synthesis of a thiol, displacement of an electrophile by the nucleophilic thiol or thiolate, and oxidation of the product thiol ether to the sulfone. For example, displacement of the electrophilic group with a nitro-benzene thiol can yield a compound where $R^1$ is nitrobenzene, whose nitro group can be reduced to provide a useful amino compound wherein $R^1$ is an aniline. It should be noted that nitrobenzenethiol is an example and not to be considered as limiting or required. Oxidation of the thioether product can be carried out as discussed below when desired.

The reduction of nitro groups to amines is well known in the art, with a preferred method being hydrogenation. There is usually a metal catalyst such as Rh, Pd, Pt, Ni, or the like with or without an additional support such as carbon, barium carbonate, and the like. Solvents can be protic or non-protic pure solvents or mixed solvents as required. The reductions can be carried out at atmospheric pressure to a pressure of multiple atmospheres, with atmospheric pressure to about 40 pounds per square inch (psi) being preferred.

The resulting amino group can be alkylated if desired. It can also be acylated with, for example, an aroyl chloride, heteroaryl chloride, or other amine carbonyl forming agent to form an $R^1$ amide of this invention. The amino sulfone or thioether can also be reacted with a carbonic acid ester chloride, a sulfonyl chloride, a carbamoyl chloride, or an isocyanate to produce the corresponding carbamate, sulfonamides, or ureas of this invention. Acylation of amines of this type are well known in the art and the reagents are also well known.

Usually these reactions are carried out in aprotic solvents under an inert or/and dry atmosphere at about 45° C. to about −10° C. An equivalent of a non-competitive base is usually used with sulfonyl chloride, acid chloride, or carbonyl chloride reagents. Following or before this acylation step, synthesis of the hydroxamic acid products of this invention can proceed as discussed.

Other thiol reagents can also be used in the preparation of compounds of this invention. Examples are fluoroaryl, fluoroheteroaryl, azidoaryl or azidoheteroaryl, or heteroaryl thiol reagents. These thiols can be used a nucleophiles to as discussed above. Oxidation to the corresponding sulfone can then be carried out.

The sulfones, if substituted by a hydrazine or substituted hydrazine, can be oxidized to a hydrazone of this invention. The fluoro-substituted sulfone can be treated with a nucleophile such as ammonia, a primary amine, a quaternary ammonium or metal azide salt, or a hydrazine under pressure if desired, to provide an azido, amino, substituted amino or hydrazino group. Azides can be reduced to an amino group using, for example, hydrogen with a metal catalyst or metal chelate catalyst or by an activated hydride transfer reagent. The amines can be acylated as discussed above.

Methods of preparing useful aminethiol intermediates include protection of an aromatic or heteroaromatic thiol with trityl chloride to form the trityl thiol derivative, treatment of the amine with as reagent such as an aromatic or heteroaromatic acid chloride to form the amide, and removal of the trityl group with acid to form the thiol. Acylating agents include benzoyl chloride, and trityl removing reagents include triflouroacetic acid and triisopropylsilane.

The fluorine on the fluorosulfones of this invention can also be displaced with other aryl or heteroaryl nucleophiles to form compounds of this invention. Examples of such nucleophiles include salts of phenols, thiophenols, —OH containing aromatic heterocyclic compounds, or —SH containing heteroaryl compounds. Tautomers of such groups azo, hydrazo, —OH or —SH are specifically included as useful isomers.

A preferred method of preparing intermediates in the synthesis of the substituted sulfones is by oxidation of an appropriate acetophenone, prepared from a fluoroacetophenone, with for example, peroxymonosulfate, to form the corresponding phenol-ether. The phenol-ether is converted into its dimethylthiocarbamoyl derivative using dimethylthiocarbamoyl chloride, rearranged into the dimethylthiocarbamoyl derivative with heat to provide the thiol required for preparation of the thioether intermediate discussed and/or shown in the schemes.

The compounds of this invention, including protected compounds or intermediates, can be oxidized to the sulfones as shown in the schemes and/or discussed above. The selection of the stage of the alternative synthesis to implement this conversion of sulfides into the sulfones or sulfoxides can be carried out by one skilled in the art.

Reagents for this oxidation process may, in a non-limiting example, include peroxymonosulfate (OXONE®), hydrogen peroxide, meta-chloroperbenzoic acid, perbenzoic acid, peracetic acid, perlactic acid, tert-butyl peroxide, tert-butyl hydroperoxide, tert-butyl hypochlorite, sodium hypochlorite, hypochlorus acid, sodium meta-peroiodate, periodic acid, ozone, and the like. Protic, non-protic, dipolar aprotic solvents, either pure or mixed, can be chosen, for example, methanol/water. The oxidation can be carried out at temperature of from about –78° to about 50° C., and normally selected from about –10°C. to about 40° C.

Preparation of the sulfones can also be carried out in two steps by oxidizing a sulfide to a sulfoxide, followed by oxidizing the sulfoxide to the sulfone. This can occur in one pot or by isolation of the sulfoxide. This latter oxidation can be carried out in a manner similar to the oxidation directly to the sulfone, except that about one equivalent of oxidizing agent can be used preferably at a lower temperature such as about 0° C. Preferred oxidizing agents include peroxymonosulfate and meta-chloroperbenzoic acid.

A sulfonamide of this invention can be prepared in a similar manner using methods and procedures discussed hereinbefore. Aryl, substituted aryl, heteroaryl or substituted heteroaryl dicarboxylic anhydrides, imides (e.g., phthalic anhydrides or imides), their sulfonyl analogs or mixed carboxylic-sulfonic acid amides, imides (e.g., 1,2-benzenethiazole-3(2H)-one 1,1-dioxides) or anhydrides are useful starting material substrates. Reactions utilizing such substrates can be carried out before or after changes in the substitution patterns of the aryl or heteroaryl rings are made.

The sulfonamides can also be prepared from heterocyclic compounds such as saccharine, saccharine analogs, and saccharine homologs. Such compounds and methods are well known in the literature. For example, alkylation of sodium saccharine followed by ring opening or ring opening followed by alkylation permits coupling to form a protected hydroxamic acid derivative such as a THP (tetrahydropyranyl) or TMS (trimethylsilyl) derivative. Hydrolysis of the protecting group provides the hydroxamic acid. The sulfonamide nitrogen can be further alkylated, acylated, or otherwise treated to form various compounds at this stage of prior to coupling and deprotection.

As a non-limiting example, treatment of a mixed sulfonic/carboxylic anhydride (2-sulfobenzoic acid cyclic anhydride) with an alcohol or the salt of an alcohol or a protected hydroxamic acid provides a ring opened carboxylic acid derivative (ester or anhydride, respectively) as a sulfonic acid or salt. The carboxylic acid derivative so prepared is a product of this invention, and can be converted by standard procedures with reagents such as thionyl chloride, phosphorus pentachloride, or the like into a sulfonylhalide.

Reaction of the sulfonylhalide with a primary amine, secondary amine or ammonia with or without added base provides a sulfonamide or sulfonimide of this invention, a sulfonamide that can be alkylated to produce a sulfonamide of this invention or an intermediate to a sulfonamide of this invention. These imides or amides of sulfonamides can be alkylated as desired before or after opening to a benzoic acid substituted sulfonamide or phenylacetic acid substituted sulfonamide.

Compounds prepared as above with protected carboxyl groups are readily converted by exchange, combination exchange/hydrolysis or hydrolysis-coupling processes into the hydroxamic acids of this invention. The exchange/conversion of esters, amides, and protected hydroxylamines (protected hydroxamic acids) into hydroxamic acids is discussed herein. For example, a sulfonamide-ester can be hydrolyzed to a carboxylic acid that is coupled via a benzotriazole active ester with a THP-hydroxylamine reagent and then deprotected. Phenylacetic acid analogs of the above sulfo benzoic acid compounds can also be used in processes similar to those above to prepare the corresponding phenylacetic-derived compounds of this invention.

Aryl or heteroaryl 5- or 6-member ring thiolactones or dithiolactones are also desirable starting materials for the preparation of compounds of this invention. Such thiolactones can be opened to form protected carboxylic acid derivatives such as esters, amides or hydroxylamides before or after changes in the substitution patterns of the aryl or heteroaryl rings are made. Oxidation of the thiol function can be achieved prior to or following substitution changes depending upon the needs and wishes of the skilled chemist. Sulfur compounds can also be oxidized directly to sulfonyl chloride compounds using oxidizing agents whose mechanism involved putative positive chlorine species oxidizing agents and methods are discussed hereinabove. The sulfonic acid derivatives so obtained are then converted into the sulfonamides of this invention as previously discussed.

Changes in substitution patterns on the rings of the compounds of this invention can be carried out by processes well known in the art. Non-limiting examples of such processes include diazonium chemistry, aromatic ring substitution reactions or addition-elimination sequences, metallation reactions, and halogen metal exchange reactions.

A substituted or unsubstituted aryl or heteroaryl sulfonic acid, sulfonic acid derivative, or sulfonamide of this invention can be prepared starting with a halo-sulfonic acid or a sulfonic acid substituted in such a manner that the corresponding anion can be reacted with carbon dioxide, a carbonyl compound, isocyanate, a halogenating reagent, alkylating reagent, acylating reagent, a protected hydroxylamine isocyanate or isothiocyanate derivative to form a compound of this invention or an intermediate to a compound of this invention. An anion can be formed via, for example, direct metallation or metal-halogen exchange. The substituted or unsubstituted aryl or heteroaryl sulfonic acid, sulfonic acid derivative or sulfonamide can be prepared by sulfonation or chlorosulfonation of the substituted or unsubstituted aryl or heteroaryl compound. Metallation reactions as well as halogen-metal exchange reactions to form the salts of the corresponding anions or complexed anions can be carried out by direct treatment with a metal such as lithium, sodium, potassium, palladium, platinum or their complexes, and the like or treatment with a strong base such as tert-butyl lithium, sec-butyl lithium, and the like as discussed above. These intermediates are then quenched with a reagent such as is discussed elsewhere. The resulting carboxylic acids or carboxylic acid derivatives are converted into the sulfonamides of this invention by methods and processes known in the art and discussed herein.

Salts of the compounds or intermediates of this invention are prepared in the normal manner wherein acidic compounds are reacted with bases such as those discussed above to produce metal or nitrogen containing cation salts. Basic compounds, such as amines, can be treated with an acid to form an amine salt. It is noted that some compounds of this invention can be synthesized by biochemical processes, including mammalian metabolic processes. For example, methoxy groups can be converted by the liver in situ into alcohols and/or phenols. Where more than one methoxy group is present, either or both groups can be independently metabolized to hydroxy compounds. Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes well known in the art, for example by formation of diastereoisomeric salts by treatment with an optically active acid or base.

Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers.

Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases hydrolysis to the parent optically active drug is not necessary prior to dosing the patient since the compound can behave as a prodrug. The optically active compounds of Formula I can likewise be obtained by utilizing optically active starting materials.

In addition to the optical isomers or potentially optical isomers discussed above, other types of isomers are specifically intended to be included in this discussion and in this invention. Examples include cis isomers, trans isomers, E isomers, Z isomers, syn-isomers, anti-isomers, tautomers and the like. Aryl, heterocyclo or heteroaryl tautomers, heteroatom isomers and ortho, meta or para substitution isomers are also included as isomers. Solvates or solvent addition compounds such as hydrates or alcoholates are also specifically included both as chemicals of this invention and in, for example, formulations or pharmaceutical compositions for drug delivery.

Where a substituent is designated as, or can be, a hydrogen, the exact chemical nature of a substituent which is other than hydrogen at that position, e.g., a hydrocarbyl radical or a halogen, hydroxy, amino, and the like functional group, is not critical so long as it does not adversely affect the overall activity and/or synthesis procedure. For example, two hydroxyl groups, two amino groups, two thiol groups or a mixture of two hydrogen-heteroatom groups on the same carbon are known not to be stable without protection or as a derivative.

The chemical reactions described above are generally disclosed in terms of their broadest application to the preparation of the compounds of this invention. Occasionally, the reactions can not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Other compounds of this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

The following schemes further describe examples of suitable preparation methods for the compounds described in this patent.

Scheme 1
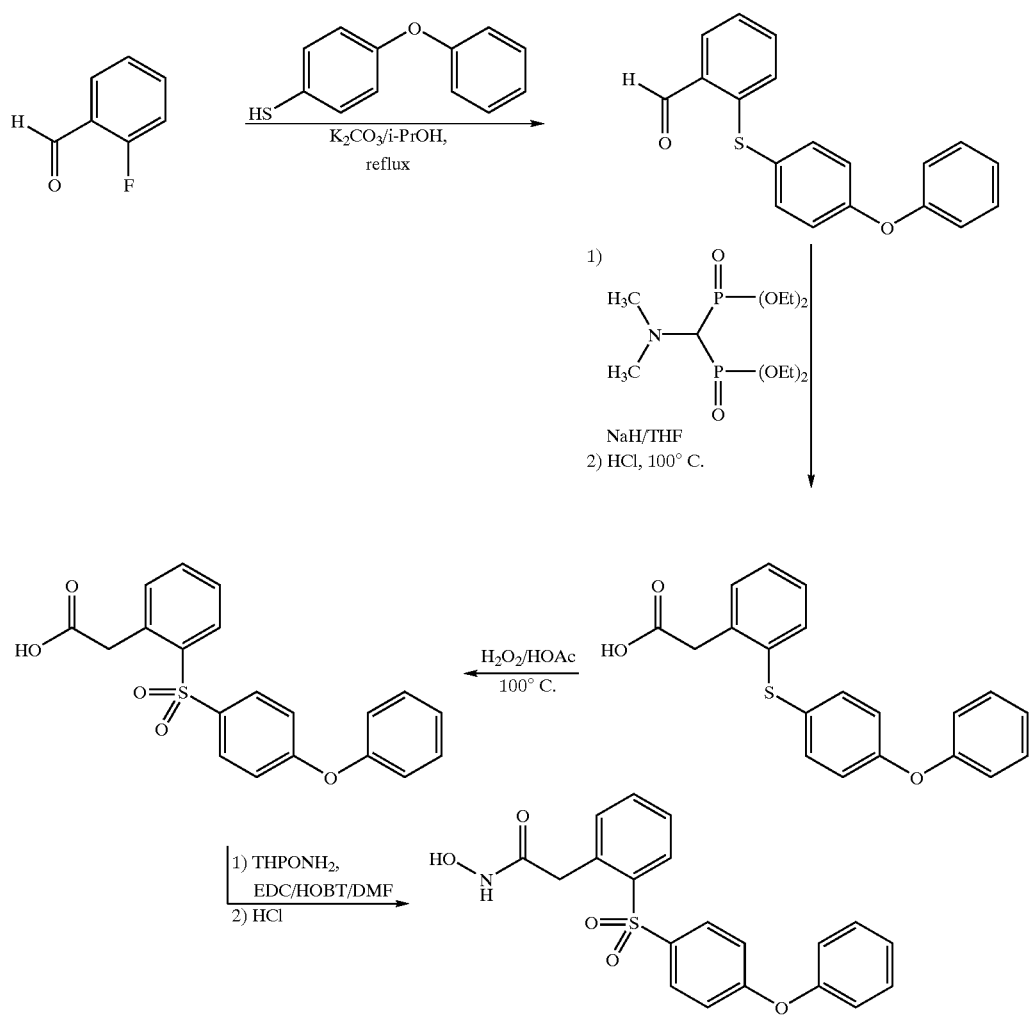
Scheme 2
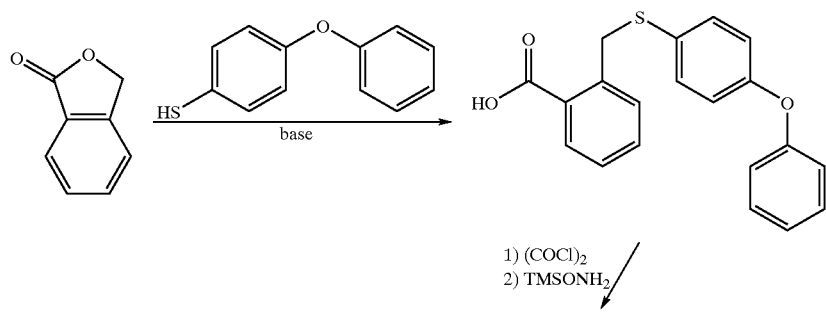

-continued
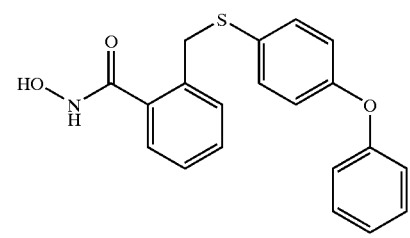
Oxidation ↓
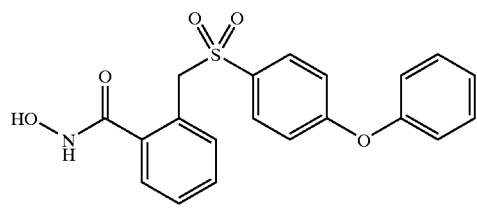
Scheme 3
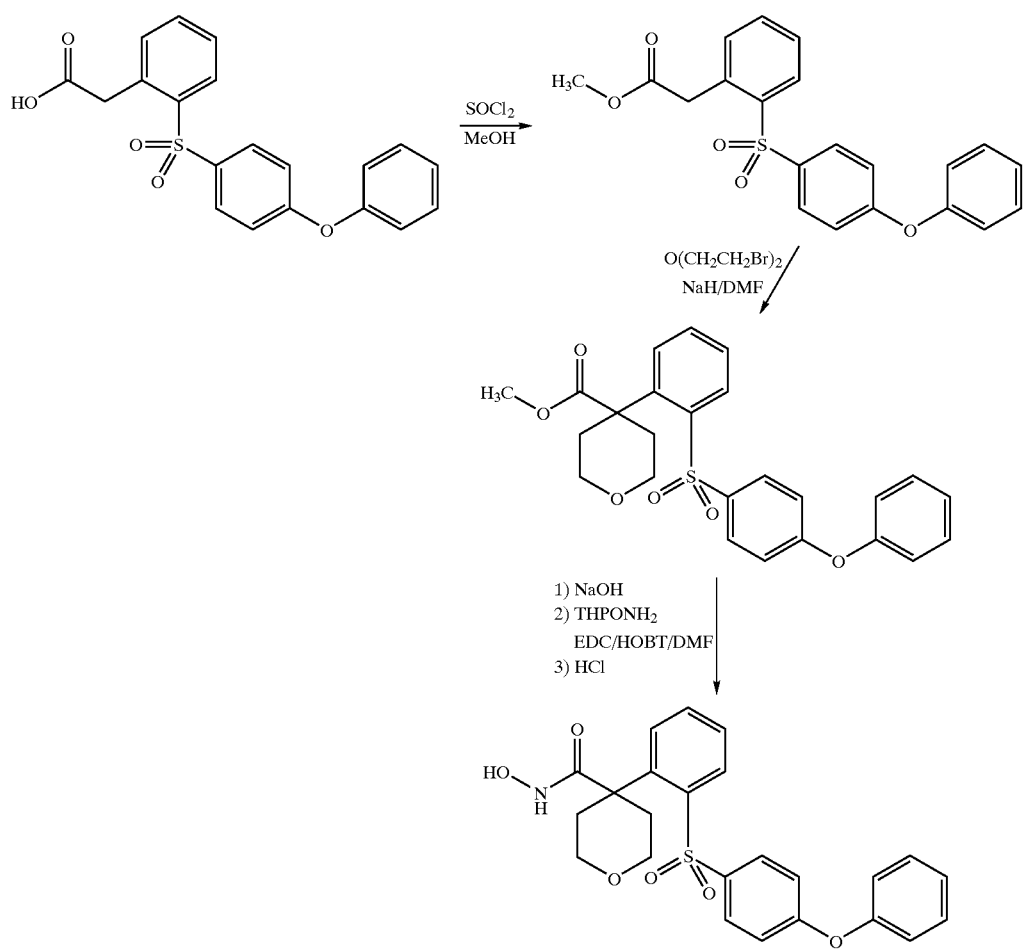

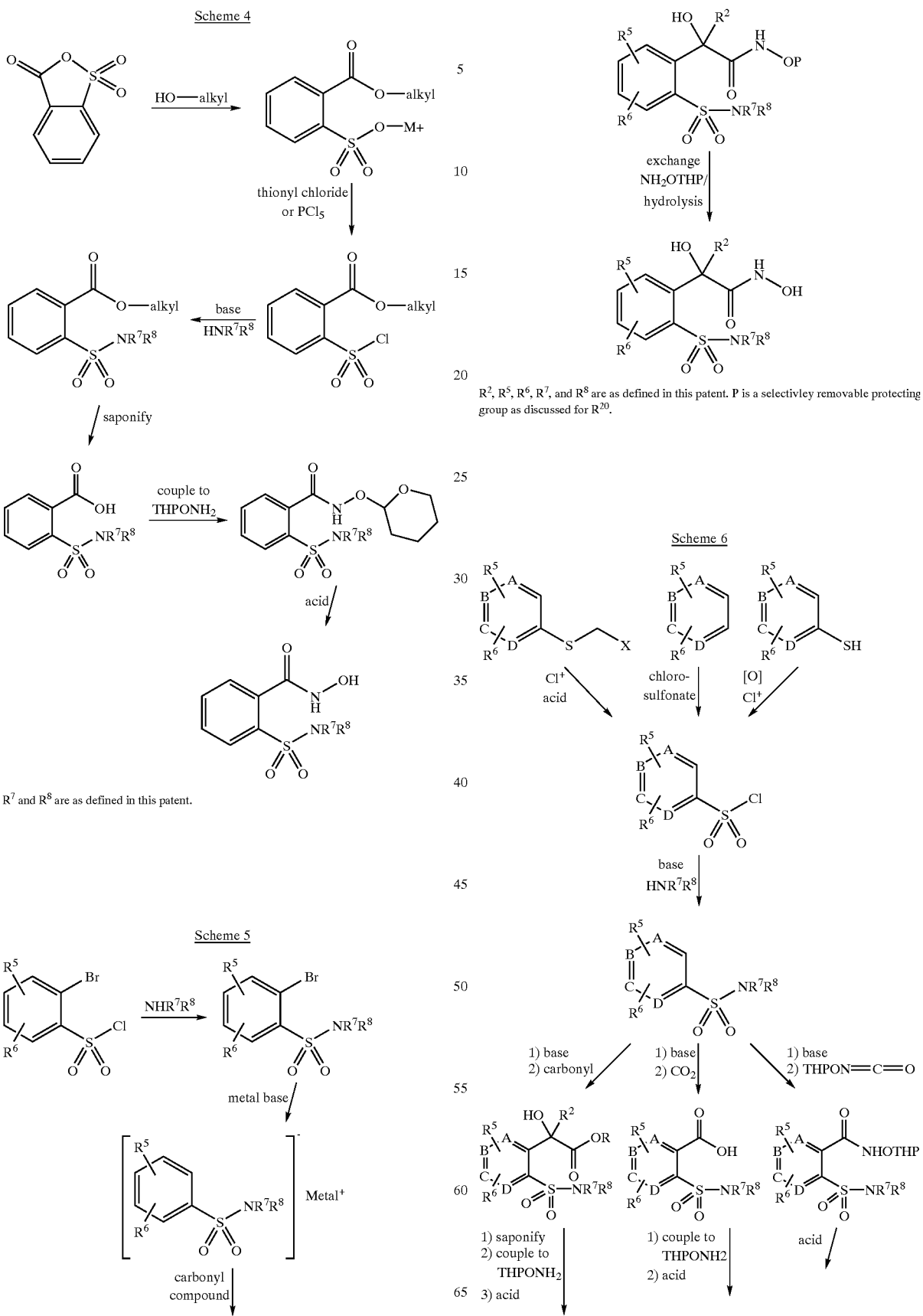

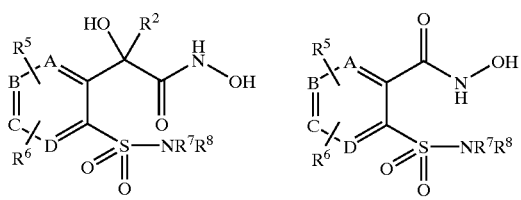
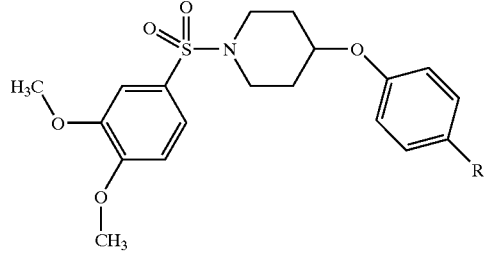
$R^2$, $R^5$, $R^6$, $R^7$, $R^8$, A, B, C, and D are as defined in this patent.
Scheme 7
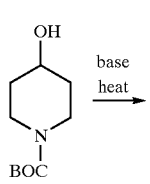 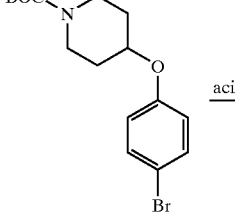 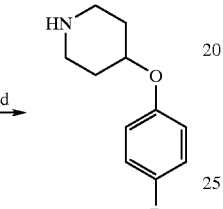
base, heat
acid
base, sulfonyl chloride compound
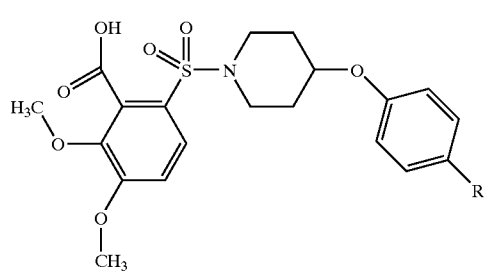
1) butyllithium
2) $CO_2$
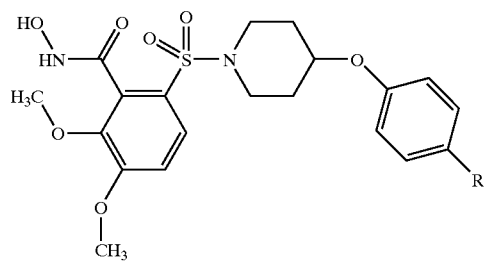
organometallic coupling
R may, for example, be selected from the -EY substituents described in this patent with respect to the -A-R-E-Y and G-A-R-E-Y substituents.
Scheme 8
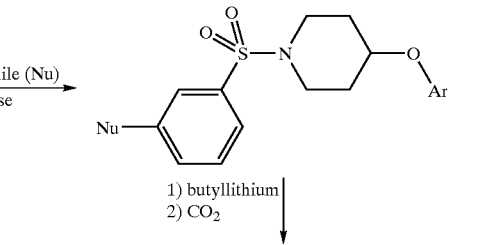
nucleophile (Nu)
base
1) butyllithium
2) $CO_2$
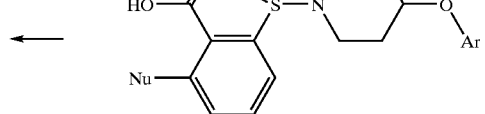
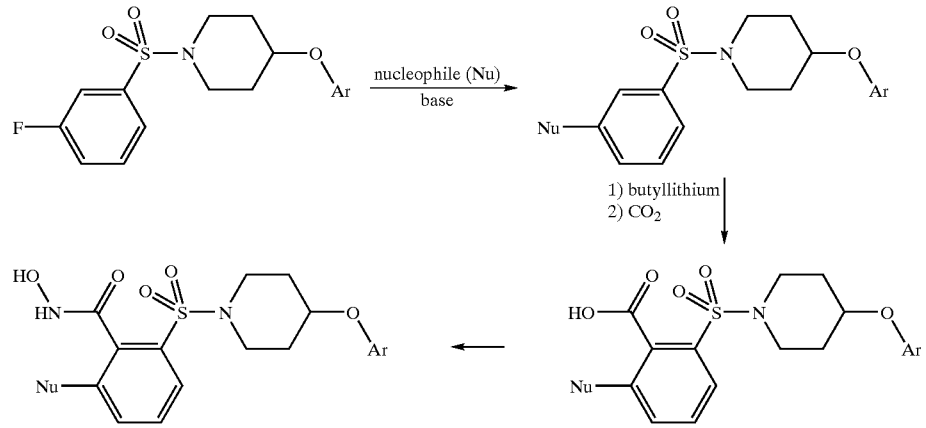

Scheme 9
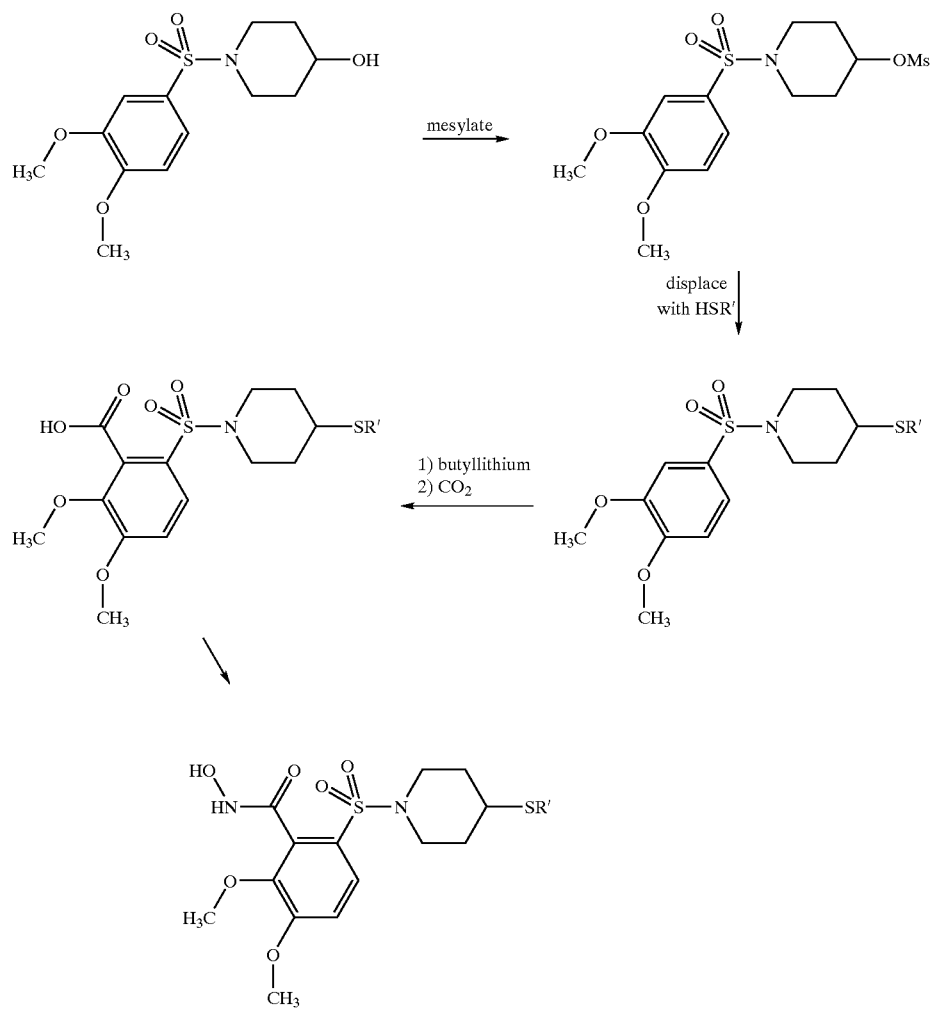
R' may, for example, be selected from the -REY substituents described in this patent with respect to the -A-R-E-Y and -G-A-R-E-Y substitutents.
Scheme 10
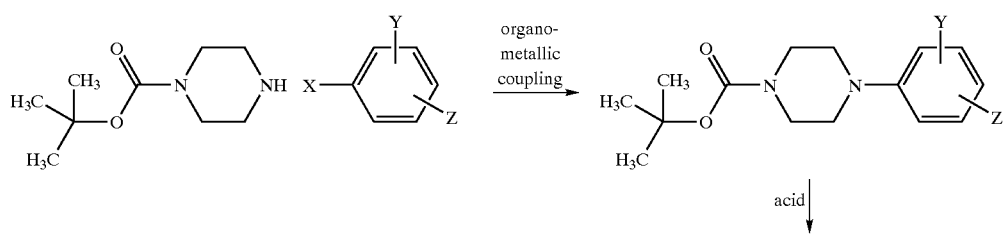

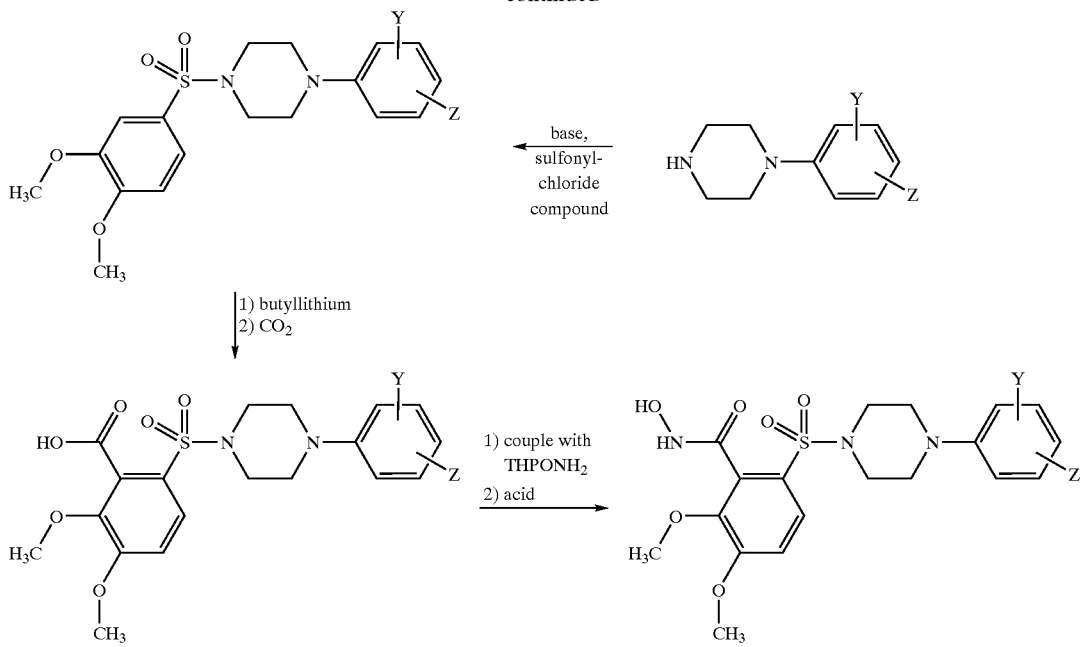

X is halogen. Y and Z may be a wide variety of substituents, one of which may, for example, be selected from the -EY substituents described in this patent with respec to the -A-R-E-Y and G-A-R-E-Y substituents.

f. Definitions

The term "hydrocarbyl" (alone or in combination) is used herein as a short hand term to include straight and branched chain aliphatic groups, as well as alicyclic groups that contain only carbon and hydrogen. Thus, alkyl, alkenyl, and alkynyl groups are contemplated, while aromatic hydrocarbons (e.g., phenyl and naphthyl groups), which strictly speaking are also hydrocarbyl groups, are referred to herein as aryl groups, as discussed hereinafter. Where a specific aliphatic hydrocarbyl substituent group is intended, that group is recited (e.g., $C_1$–$C_4$ alkyl, methyl, or dodecenyl). Preferred hydrocarbyl groups contain a chain of from 1 to about 12 carbon atoms, and more preferably from 1 to about 10 carbon atoms.

Alkyl groups include, for example, methyl, ethyl, n-propyl, isopropyl, n-butyl, isobutyl, sec-butyl, tert-butyl, pentyl, iso-amyl, hexyl, octyl, and the like. Alkenyl groups include, for example, ethenyl (vinyl), 2-propenyl, 3-propenyl, 1,4pentadienyl, 1,4-butadienyl, 1-butenyl, 2-butenyl, 3-butenyl, decenyl, and the like. Alkynyl groups include, for example, ethynyl, 2-propynyl, 3-propynyl, decynyl, 1-butynyl, 2-butynyl, 3-butynyl, and the like.

A particularly preferred hydrocarbyl is alkyl. As a consequence, a generalized, but more preferred substituent, can be recited by replacing the term "hydrocarbyl" with "alkyl" in any of the substituent groups enumerated herein.

Usual chemical suffix nomenclature is followed when using the term "hydrocarbyl" except that the usual practice of removing the terminal "yl" and adding an appropriate suffix is not always followed because of the possible similarity of a resulting name to one or more substituents. Thus, a hydrocarbyl ether is referred to as "hydrocarbyloxy" rather than "hydrocarboxy" as may possibly be more proper when following the usual rules of chemical nomenclature. On the other hand, a hydrocarbyl containing a —C(O)O— functionality is referred to as hydrocarboyl inasmuch as there is no ambiguity in using that suffix. As one skilled in the art will understand, a substituent that cannot exist (e.g., $C_1$-alkenyl group) is not intended to be encompassed by the term "hydrocarbyl".

The term "carbonyl" (alone or in combination) means —C(=O)—.

The term "thiol" or "sulfhydryl" (alone or in combination) means —SH.

The term "thio" or "thia" (alone or in combination) means a thiaether group, i.e., an ether group wherein the ether oxygen is replaced by a sulfur atom, as in a thiophenoxy group ($C_6H_5$—S—).

The term "amino" (alone or in combination) means an amine group or —$NH_2$. The term "mono-substituted amino" (alone or in combination) means an amine group wherein one hydrogen atom is replaced with a substituent, i.e., —N(H)(substituent). The term "di-substituted amine" (alone or in combination) means an amine group wherein both hydrogen atoms are replaced identical or different substituents, i.e., —N(substituent)$_2$. Amino groups, amines, and amides are classes that can be designated as primary (I°), secondary (II°), or tertiary (III°) or as unsubstituted, mono-substituted, or di-substituted depending on the degree of substitution of the amino nitrogen. The term "quaternary amine (IV°)" means a nitrogen that has 4 substituents and is positively charged and accompanied by a counter ion, i.e., —$N^+$(substituent)$_4$. The term "N-oxide" means a nitrogen that has 4 substituents, wherein one of the substituents is oxygen and the charges are internally compensated, —$N^+$(substituent)$_3$-$O^-$.

The term "cyano" (alone or in combination) means —C N (the "" symbol means a triple bond).

The term "azido" (alone or in combination) means —N=N=N— (the "=" symbol means a double bond).

The term "hydroxy" or "thydroxyl" (alone or in combination) means —OH.

The term "nitro" (alone or in combination) means —$NO_2$.

The term "azo" (alone or in combination) means —N=N—.

The term "hydrazino" (alone or in combination) means —N(H)—N(H)—. The hydrogen atoms of the hydrazino group can be independently replaced with substituents, and the nitrogen atoms can form acid addition salts or be quaternized.

The term "sulfonyl" (alone or in combination) means —S(O)$_2$—.

The term "sulfoxido" (alone or in combination) means —S(O)—.

The term "sulfonylamide" (alone or in combination) means —S(O)$_2$—N=, wherein the remaining 3 bonds (valences) are independently substituted.

The term "sulfinamido" (alone or in combination) means —S(O)—N=, wherein the remaining 3 bonds are independently substituted.

The term "sulfenamide" (alone or in combination) means —S—N=, wherein the remaining 3 bonds are independently substituted.

The term "hydrocarbyloxy" (alone or in combination) means a hydrocarbyl ether radical, wherein the term "hydrocarbyl" is as defined above. Hydrocarbyl ether radicals include, for example, methoxy, ethoxy, n-propoxy, isopropoxy, allyloxy, n-butoxy, iso-butoxy, sec-butoxy, tertbutoxy, and the like.

The term "cyclohydrocarbyl" (alone or in combination) means a cyclic structure that contains only carbon and hydrogen. Such a cyclic structure preferably contains from 3 to about 8 carbon atoms, and more preferably from about 3 to about 6 carbon atoms.

The term "cyclohydrocarbylhydrocarbyl" (alone or in combination) means a hydrocarbyl radical which is substituted by a cyclohydrocarbyl. Cyclohydrocarbylhydrocarbyl radicals include, for example, cyclopropyl, cyclobutyl, cyclopentenyl, cyclohexyl, cyclooctynyl, and the like.

The term "aryl" (alone or in combination) means a phenyl or naphthyl radical that optionally is substituted with one or more substituents selected from the group consisting of hydrocarbyl, hydrocarbyloxy, halogen, hydroxy, amino, nitro, and the like. Such radicals include, for example, unsubstituted phenyl, p-tolyl, 4-methoxyphenyl, 4-(tert-butoxy)phenyl, 4-fluorophenyl, 4-chlorophenyl, 4-hydroxyphenyl, and the like.

The term "arylhydrocarbyl" (alone or in combination) means a hydrocarbyl radical as defined above wherein one hydrogen atom is replaced by an aryl radical. Arylhydrocarbyls include, for example, benzyl, 2-phenylethyl, and the like.

The term "arylhydrocarbyloxycarbonyl" (alone or in combination) means —C(O)—O-arylhydrocarbyl. An example of an arylhydrocarbyloxycarbonyl radical is benzyloxycarbonyl.

The term "aryloxy" (alone or in combination) means aryl-O—.

The term "aromatic ring" (alone or in combination, such as "substituted-aromatic ring sulfonamide", "substituted-aromatic ring sulfinamide", or "substituted-aromatic ring sulfenamide") means aryl or heteroaryl as defined above.

The terms "hydrocarbyloyl" and "hydrocarbylcarbonyl" (alone or in combination) mean an acyl radical derived from a hydrocarbylcarboxylic acid. Examples include acetyl, propionyl, acryloyl, butyryl, valeryl, 4-methylvaleryl, and the like.

The term "cyclohydrocarbylcarbonyl" (alone or in combination) means an acyl group derived from a monocyclic or bridged cyclohydrocarbylcarboxylic acid (e.g., cyclopropanecarbonyl, cyclohexenecarbonyl, adamantanecarbonyl, and the like) or a benzofused monocyclic cyclohydrocarbylcarboxylic acid that is optionally substituted by, for example, a hydrocarbyloylamino group (e.g., 1,2,3,4-tetrahydro-2-naphthoyl, 2-acetamido-1,2,3,4-tetrahydro-2-naphthoyl, and the like).

The terms "arylhydrocarbyloyl" or "arylhydrocarbylcarbonyl" (alone or in combination) mean an acyl radical derived from an aryl-substituted hydrocarbylcarboxylic acid. Examples include phenylacetyl, 3-phenylpropenyl (cinnamoyl), 4-phenylbutyryl, (2-naphthyl)acetyl, 4-chlorohydrocinnamoyl, 4-aminocinnamoyl, 4-methoxycinnamoyl, and the like.

The terms "aroyl" and "arylcarbonyl" (alone or in combination) mean an acyl radical derived from an aromatic carboxylic acid. Examples include aromatic carboxylic acids, an optionally substituted benzoic or naphthoic acid (e.g., benzoyl, 4-chlorobenzoyl, 4-carboxybenzoyl, 4-(benzyloxycarbonyl)benzoyl, 2-naphthoyl, 6-carboxy-2-naphthoyl, 6-(benzyloxycarbonyl)-2-naphthoyl, 3-benzyloxy-2 naphthoyl, 3-hydroxy-2-naphthoyl, 3-(benzyloxyformamido)-2-naphthoyl, and the like), and the like.

The heterocyclyl (heterocyclo) or heterocyclohydrocarbyl portion of a heterocyclylcarbonyl, heterocyclyloxycarbonyl, heterocyclylhydrocarbyloxycarbonyl, heterocyclohydrocarbyl, or the like is a saturated or partially unsaturated monocyclic, bicyclic, or tricyclic heterocycle that preferably contains from 1 to 4 hetero atoms selected from the group consisting of nitrogen, oxygen, and sulphur. Such a heterocycle optionally is substituted on (a) one or more carbon atoms by a halogen, alkyl, alkoxy, oxo, and the like; (b) a secondary nitrogen atom (i.e., —NH—) by a hydrocarbyl, arylhydrocarbyloxycarbonyl, hydrocarbyloyl, aryl, or arylhydrocarbyl; and/or (c) on a tertiary nitrogen atom by oxido that is attached via a carbon atom. The tertiary nitrogen atom with 3 substituents can also form N-oxide, i.e., =N$^+$(O)$^-$. Such heterocyclyl groups include, for example, pyrrolidinyl, piperidinyl, piperazinyl, morpholinyl, thiamorpholinyl, and the like.

The term "heteroaryl" (alone or in combination) means an aromatic heterocyclic ring substituent that preferably contains from 1 to 4 hetero ring atoms, i.e., atoms other than carbon forming the ring. Those hetero ring atom(s) is (are independently) selected from the group consisting of nitrogen, sulfur, and oxygen. A heteroaryl group can contain a single 5- or 6-member ring or a fused ring system having two 6-member rings or a 5- and a 6-member ring. Heteroaryl groups include, for example, 6-member rings, such as pyridyl, pyrazyl, pyrimidinyl, and pyridazinyl; 5-member rings, such as 1,3,5-triazinyl, 1,2,4-triazinyl, 1,2,3-triazinyl, imidazyl, furanyl, thiophenyl, pyrazolyl, oxazolyl, isoxazolyl, thiazolyl, 1,2,3-oxadiazolyl, 1,2,4-oxadiazolyl, 1,2,5-oxadiazolyl, 1,3,4-oxadiazolyl, and isothiazolyl; 6-/5-member fused rings, such as benzothiofuranyl, isobenzothiofuranyl, benzisoxazolyl, benzoxazolyl, purinyl, and anthranilyl; and 6-/6-member fused rings, such as 1,2-benzopyronyl, 1,4-benzopyronyl, 2,3-benzopyronyl, 2,1-benzopyronyl, quinolinyl, isoquinolinyl, cinnolinyl, quinazolinyl, and 1,4-benzoxazinyl.

The heteroaryl portion of a heteroaroyl, heteroaryloxycarbonyl, heteroarylhydrocarbyloyl (heteroarylhydrocarbyl carbonyl) group, or the like is an aromatic monocyclic, bicyclic, or tricyclic heterocycle that contains the hetero atoms and is optionally substituted as defined above with respect to the definition of heterocyclyl.

The term "cyclohydrocarbylhydrocarbyloxycarbonyl" (alone or in combination) means cyclohydrocarbylhydrocarbyl-O—C(O)—.

The term "aryloxyhydrocarbyloyl" (alone or in combination) means aryl-O-hydrocarbyloyl.

The term "heterocyclyloxycarbonyl" (alone or in combination) means heterocyclyl-O—C(O)—.

The term "heterocyclylhydrocarbyloyl" (alone or in combination) is an acyl radical derived from a heterocyclyl-substituted hydrocarbylcarboxylic acid.

The term "heterocyclylhydrocarbyloxycarbonyl" means heterocyclyl-substituted hydrocarbyl-O—C(O)—.

The term "heteroaryloxycarbonyl" means an acyl radical derived from a carboxylic acid represented by heteroaryl-O—COOH.

The term "aminocarbonyl" (alone or in combination) means an amino-substituted carbonyl (carbamoyl) derived from an amino-substituted carboxylic acid, wherein the amino can be a primary, secondary, or tertiary amino group containing substituents selected from the group consisting of hydrogen, hydrocarbyl, aryl, aralkyl, cyclohydrocarbyl, cyclohydrocarbylhydrocarbyl, and the like.

The term "aminohydrocarbyloyl" (alone or in combination) means an acyl group derived from an amino-substituted hydrocarbylcarboxylic acid, wherein the amino can be a primary, secondary, or tertiary amino group containing substituents independently selected from the group consisting of hydrogen, alkyl, aryl, aralkyl, cyclohydrocarbyl, cyclohydrocarbylhydrocarbyl, and the like.

The term "halogen" (alone or in combination) means a fluorine radical (which may be depicted as —F), chlorine radical (which may be depicted as —Cl), bromine radical (which may be depicted as —Br), or iodine radical (which may be depicted as —I). Typically, a fluorine radical or chlorine radical is preferred, with a fluorine radical being particularly preferred.

The term "halohydrocarbyl" (alone or in combination) means a hydrocarbyl radical as defined above, wherein one or more hydrogens are replaced with a halogen. Halohydrocarbyl radicals include, for example, chloromethyl, 1-bromoethyl, fluoromethyl, difluoromethyl, trifluoromethyl, 1,1,1-trifluoroethyl, and the like.

The term "perfluorohydrocarbyl" (alone or in combination) means a hydrocarbyl group, wherein each hydrogen has been replaced by a fluorine atom. Perfluorohydrocarbyl groups include, for example, trifluoromethyl, perfluorobutyl, perfluoroisopropyl, perfluorododecyl, perfluorodecyl, and the like.

With reference to the use of the words "comprise" or "comprises" or "comprising" in this patent (including the claims), Applicants note that unless the context requires otherwise, those words are used on the basis and clear understanding that they are to be interpreted inclusively, rather than exclusively, and that Applicants intend each of those words to be so interpreted in construing this patent, including the claims below.

g. EXAMPLES

The following examples are merely illustrative, and not limiting to the remainder of this disclosure in any way.

Example 1

N-hydroxy-2-[[(4-phenoxyphenyl)-sulfonyl]methyl] benzamide

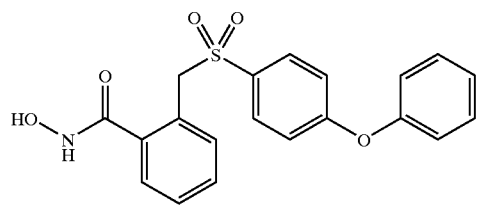

Part A: To a solution of phthalide (6.30 g, 47.0 mmol) in DMF (100 mL) was added $K_2CO_3$ (10.0 g, 49.4 mmol) and 4-(phenoxy)benzenethiol (9.59 g, 49.4 mmol), and the solution was heated to 100° C. for 2 hr. The solution was diluted with $H_2O$, and acidified with 1N HCl to a pH of 1. The resulting tan solid was collected and washed with $H_2O$. The solid was dissolved into ethyl ether and dried over $MgSO_4$. Concentration in vacuo and subsequent recrystallization (ethyl ether/hexane) provided the sulfide as a white solid (9.12 g, 58%). MS(CI) $MH^+$ calculated for $C_{20}H_{16}O_3S$: 337, found 337. Analytical calculation for $C_{20}H_{16}O_3S$: C, 71.41; H, 4.79; S, 9.53. Found: C, 71.28; H, 4.67; S, 9.19.

Part B: To a solution of the sulfide of Part A (3.00 g, 8.92 mmol) in dichloromethane (28 mL) and DMF (1 drop) was added oxalyl chloride (1.08 mL, 12.4 mmol), and the solution was stirred for 1 hr. After concentration in vacuo, the residue was dissolved into dichloromethane (16 mL) and then cooled to 0° C. Tetramethylsilyl hydroxylamine (2.55 mL, 20.8 mmol) was added, and the solution was stirred for 1.5 hr. The solution was diluted with dichloromethane; washed with 1 N HCl, $H_2O$, and saturated NaCl; and dried over $MgSO_4$. Chromatography (on silica, ethyl acetate/hexane/toluene) provide the hydroxylamine as a clear paste (970 mg, 31%).

Part C: To a solution of the hydroxylamine of Part B (970 mg, 2.76 mmol) in dichloromethane (25 mL) cooled to 0° C. was added 3-chloroperbenzoic acid (60%, 2.14 g, 7.45 mmol), and the solution was stirred for 3 hr at ambient temperature. The solution was diluted with ethyl ether; washed with saturated $Na_2SO_3$, saturated $NaHCO_3$, and saturated NaCl; and dried over $MgSO_4$. Reverse phase chromatography (on silica, acetonitrile/$H_2O$) provided the title compound as a white solid (345 mg, 33%). MS(CI) $MH^+$ calculated for $C_{20}H_{17}NO_5S$: 384, found 384. Analytical calculation for $C_{20}H_{17}NO_5S.00.3H_2O$: C, 61.70; H, 4.56; N, 3.60; S, 8.25. Found: C, 61.74; H, 4.42; N, 3.61; S, 8.31.

Example 2

N-hydroxy-2-[(4-phenoxyphenyl)-sulfonyl]
benzeneacetamide

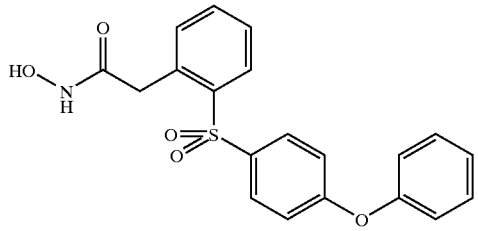

Part A: To a solution of 4-(phenoxy)-benzenethiol (6.06 g, 30.0 mmol) and K$_2$CO$_3$ (4.55 g, 33.0 mmol) in isopropanol (30 mL) was added 2-fluorobenzaldehyde (3.2 mL, 30.0 mmol). The solution was refluxed for 20 hr. The reaction was quenched by the addition of ice-H$_2$O, and extracted with CHCl$_3$. The organic layer was dried over MgSO$_4$. Filtration through a pad of silica gel provided the sulfide as a yellow solid (7.43 g, 81%).

Part B: A solution of NaH (60% dispersion in mineral oil, washed with hexane, 264 mg, 6.6 mmol) in THF (12 mL) was cooled to 0° C., and tetraethyl dimethylammoniummethylene diphosphonate (1.99 g, 6.0 mmol) was added. The solution was warmed to ambient temperature, and the sulfide of Part A (1.84 g, 6.0 mmol) was added. The solution was stirred for 4 hr at ambient temperature. The solution was then extracted with ethyl acetate, washed with H$_2$O, and dried over MgSO$_4$. Concentration in vacuo provided a brown oil. The oil was dissolved in 6M HCl (10 mL). The resulting solution was heated to 100° C. for 1 hr., and then extracted with CHCl$_3$. The organic layer was dried over MgSO$_4$. Concentration in vacuo provided the acid as an oil (918 mg, 48%).

Part C: To a solution of the acid of Part B (918 mg, 3 mmol) in acetic acid (30 mL) was added 30% H$_2$O$_2$ (1.2 mL, 12 mmol), and the solution was heated to 100° C. for 40 min. The solution was lyophilized, and chromatography (hexane/ethyl acetate) provided the sulfone as a foam (697 mg, 63%).

Part D: To a solution of the sulfone of Part C (695 mg, 1.89 mmol) in acetonitrile (2 mL) was added O-tetrahydropyranyl hydroxylamine (270 mg, 2.3 mmol). After 5 min, EDC (442 mg, 2.3 mmol) was added, and the solution was stirred for 3 hr. The solution was then concentrated in vacuo, and the residue was partitioned between ethyl acetate and H$_2$O. The organic layer was dried over MgSO$_4$. Chromatography (on silica gel, ethyl acetate/hexane) provided the THP-ether as a white foam (688 mg, 77%).

Part E: To a solution of the THP-ether of Part D (565 mg, 1.2 mmol) in methanol (10 mL) was added p-toluenesulfonic acid (25 mg), and the solution was stirred at ambient temperature for 2 hr. The solution was concentrated in vacuo and chromatography (chloroform/methanol) provided the title compound as a white solid (339 mg, 74%).

Example 3

N-hydroxy-2-[[4-(phenylmethyl)-1-piperidinyl]
sulfonyl]benzamide

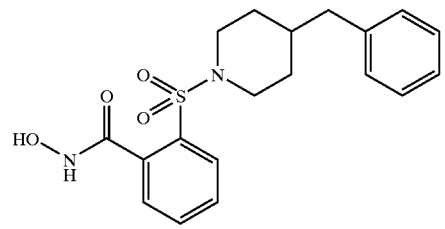

Part A: To a solution of 2-chlorosulfonylbenzoic acid ethyl ester (5.80 g, 23.0 mmol, prepared-per Nagasawa, et. al., *J. Med. Chem.*, 1995, 38, 1865–1871) in acetonitrile (50 mL) was added 4-benzylpiperidine (4.38 mL, 25 mmol), triethylamine (3.78 mL, 27 mmol), and 4-dimethylaminopyridine (50 mg). The solution was stirred for 4 hr at ambient temperature and concentrated in vacuo. The residue was dissolved into 1N HCl and extracted with ethyl acetate. The organic layer was dried over MgSO$_4$ and filtered through a pad of silica gel to provide the sulfonamide as an oil (7.45 g, 84%)

Part B: To a solution of the sulfonamide of Part A (1.08 g, 2.80 mmol) in methanol (50 mL) and H$_2$O (20 mL) was added KOH (2 g), and the solution was stirred for 3 hr at ambient temperature. The solution was concentrated in vacuo and the remaining aqueous solution was acidified with 1N HCl. The solution was extracted with chloroform and the organic layer was dried over MgSO$_4$ and filtered through a pad of silica gel. Concentration in vacuo provided the acid as a white foam (996 mg, quantitative yield).

Part C: To a solution of the acid of Part B (415 mg, 1.2 mmol) in acetonitrile (2 mL) was added O-tetrahydropyranyl hydroxylamine (200 mg, 1.7 mmol). After the solution was stirred for 5 min, EDC (325 mg, 1.7 mmol) was added, and the solution was stirred for 3 hr at ambient temperature. The solution was concentrated in vacuo, and the residue was dissolved into H$_2$O and extracted with ethyl acetate. The organic layer was dried over MgSO$_4$. Chromatography (on silica, ethyl acetate/hexane) provided the THP ether as a white solid (437 mg, 82%).

Part D: To a solution of the THP-ether of Part C (437 mg, 0.98 mmol) in methanol (5 mL) was added p-toluenesulfonic acid (40 mg), and the solution was stirred for 1 hr at ambient temperature. The solution was concentrated in vacuo. Chromatography (ethyl acetate, 1% NH$_4$OH) provided the title compound as an oil (122 mg, 34%).

Example 4

2-[([1,11-biphenyl]-4-ylmethyl)-sulfonyl]-N-
hydroxybenzamide

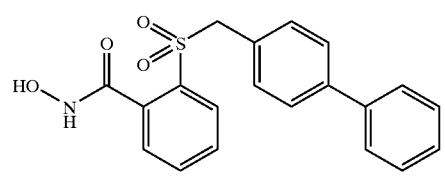

Part A: To a solution of thiosalicylic acid (5.00 g, 32.4 mmol) and 4-phenylbenzyl chloride (6.57 g, 32.4 mmol) in ethanol (81 mL) and H₂O (40 mL) was added K₂CO₃ (4.48 g, 32.4 mmol), and the solution was heated to reflux for 2 hr. Upon cooling to ambient temperature a white solid formed. To this mixture was added 1N HCl (200 mL), and vacuum filtration provided the sulfide as a white solid (7.32 g, 70%).

Part B: To a solution of the sulfide of Part A (1.00 g, 3.12 mmol) in formic acid (17 mL) heated to 50° C. was added 30% H₂O₂ (1.16 mL). The solution was stirred at 55° C. for 3 hr, followed by 40 hr at ambient temperature. The solution was concentrated, and reverse phase chromatography (acetonitrile/H₂O) provided the sulfone as a white solid (500 mg, 45%).

Part C: To a solution of the sulfone of Part B (500 mg, 1.42 mmol) in DMF (2.8 mL) was added O-tetrahydropyranyl hydroxylamine (173 mg, 1.48 mmol), N-hydroxybenzotriazole (211 mg, 1.56 mmol), and EDC (299 mg, 1.56 mmol), and the solution was stirred for 18 hr at ambient temperature. The solution was concentrated in vacuo and the residue was dissolved into H₂. The solution was extracted with ethyl acetate, and the organic layer was washed with 1 N HCl, saturated NaHCO₃, H₂O, and saturated NaCl, and then dried over MgSO₄. Concentrated in vacuo provided the ester as a white solid (571 mg, 89%). MS(CI) MH⁺ calculated for $C_{25}H_{25}NO_5S$: 452, found 452.

Part D: To a solution of the ester of Part C (570 mg, 1.26 mmol) in methanol (10 mL) was added p-toluenesulfonic acid (15 mg), and the solution was stirred at ambient temperature for 1.5 hr. The solution was concentrated in vacuo, and reverse phase chromatography (acetonitrile/H₂O) provided the title compound as a white solid (244 mg, 53%). MS(EI) M⁺ calculated for $C_{20}H_{17}NO_4S$: 367, found 367. Analytical calculation for $C_{20}H_{17}NO_4S$: C, 65.38; H, 4.66; N, 3.81. Found: C, 65.01; H, 4.64; N, 4.04.

Example 5

N-hydroxy-2-[[(4-phenoxyphenyl)-sulfonyl]amino]benzamide

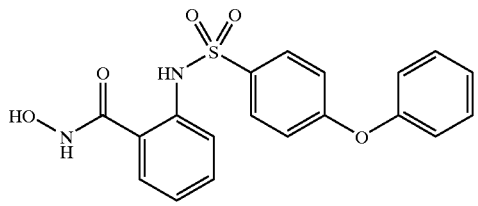

Part A: To a solution of isatoic anhydride (1.00 9, 6.13 mmol) in acetonitrile (3 mL) was added O-tetrahydropyranyl hydroxylamine (1.56 g, 6.74 mmol), and the solution was heated to reflux for 2 hr. The solution was concentrated in vacuo, and recrystallization of the residue (ethyl acetate/hexane) provided the THP-ether as a white solid (760 mg, 52%). MS(CI) MH⁺ calculated for $C_{12}H_{16}N_2O_3$: 237, found 237. Analytical calculation for $C_{12}H_{16}N_2O_3$: C, 61.00; H, 6.83; N, 11.86. Found: C, 60.82; H, 6.95; N, 11.76.

Part B: To a solution of 4-(phenoxy)benzene sulfonyl chloride (341 mg, 1.27 mmol, prepared per *J. Am. Chem. Soc.*, 1931, 93, 1112–1115) in pyridine (2 mL) cooled to 0° C. was added the THP-ether of Part A (300 mg, 1.27 mmol), and the solution was stirred at 0° C. for 3 hr. The solution was concentrated in vacuo, and the residue was dissolved in 1 N HCl and extracted with ethyl acetate. The organic layer was washed with 1 N HCl, H₂O, and saturated NaCl, and then dried over MgSO₄. Chromatography (on silica gel, ethyl acetate/hexane) provided the sulfone as a white solid (321 mg, 54%). MS(CI) MH⁺ calculated for $C_{24}H_{24}N_2O_6S$: 469, found 469. Analytical calculation for $C_{24}H_{24}N_2O_6S$: C, 61.53; H, 5.16; N, 5.98; S, 6.84. Found: C, 61.10; H, 4.93; N, 5.86; S, 6.41.

Part C: Into a solution of the sulfone of Part B (320 mg, 0.68 mmol) in methanol (3 mL) cooled to 0° C. was bubbled HCl gas for 5 min. The solution was concentrated in vacuo, and the residue was triturated with ethyl ether. Collection by vacuum filtration provided the title compound as a pink solid (163 mg, 62%). MS(CI) MH⁺ calculated for $C_{19}H_{16}N_2O_6S$: 385, found 385. Analytical calculation for $C_{19}H_{16}N_2O_6S \cdot 0.2H_2O$: C, 58.81; H, 4.26; N, 7.22; S, 8.26. Found: C, 58.88; H, 4.37; N, 6.98; S, 7.83.

Example 6

N-hydroxy-2-[[(4-methoxyphenyl)sulfonyl]methyl]-benzamide

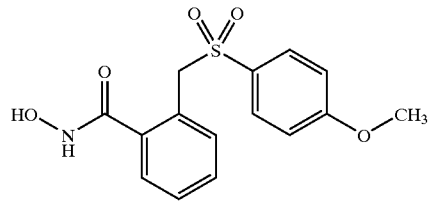

Part A: A 500 mL round bottom flask equipped with magnetic stir bar and N₂ inlet was charged with 1.5 mL (1.7 g, 12.0 mM) 4-methoxybenzenethiol and 2.5 g (10.9 mM) methyl (2-bromomethyl)benzoate in acetone (100 mL). The solution was treated with 1.8 g (13.1 mM) potassium carbonate, and heated at 55° C. in an oil bath. The reaction mixture was stirred at 55° C. for 17 hr, then concentrated in vacuo. The residue was partitioned between EtOAc and H₂O, and the resulting layers were separated. The aqueous layer was extracted with EtOAc (1×), and the organic phases were combined; washed with 5% citric acid solution, saturated sodium bicarbonate solution, and brine; dried over Na₂SO₄; and concentrated in vacuo to yield 3.3 g of product suitable for the next reaction.

Part B: A 500 mL round bottom flask equipped with magnetic stir bar and N₂ inlet was charged with 3.1 g (10.8 mM) of product from Part A in 90 mL MeOH. The solution was then treated with 15 mL water and 13.9 g (22.6 mM) Oxone®. The reaction mixture was stirred for 17 hr, and then filtered. The filter cake was washed with MeOH, and the filtrate was concentrated in vacuo. The residue was partitioned between EtOAc and H₂O, the layers were separated, and the aqueous layer was extracted with EtOAc (2×). The organic phases were combined, washed with saturated sodium bicarbonate solution and brine, dried (MgSO₄), and concentrated in vacuo to yield the 3.3 g of crude product. This was chromatographed on silica gel using 25–45% ethyl acetate/hexane to yield 2.1 g of pure product, m/z=321 (M+H).

Part C: A 250 mL round bottom flask equipped with magnetic stir bar and N₂ inlet was charged with 2.1 g (6.6 mM) of product from Part B in acetic acid (25 mL) and conc. HCl solution (25 mL), and the solution was heated to reflux for 24 hr. The reaction mixture was concentrated in vacuo. Two aliquots of toluene were added and stripped, and then dried under high vacuum to yield 2.0 g of product suitable for the next reaction.

Part D: A 2-necked, 50 mL round bottom flask equipped with addition funnel, thermometer, magnetic stir bar, and N₂ inlet was charged with 1.0 mL of DMF in 10 mL CH₂Cl₂. The solution was cooled in an ice bath, treated with 3.5 mL (0.9 g, 6.9 mM) of a 2.0 M oxalyl chloride solution in CH₂C₁₂, and then treated with a solution of 1.0 g (3.3 mM) of product from Part C in 5 mL DMF. The bath was removed, and the reaction was stirred for 1 hr. That reaction mixture was added to a 2-necked, 100 mL round-bottomed flask equipped with addition funnel, thermometer, magnetic stir bar, and N₂ inlet and containing a cooled solution of 2.1 mL (1.1 g, 37.7 mM) of 50% aqueous hydroxylamine in THF (25 mL). The bath was then removed and the reaction mixture was stirred for 2 hr. The reaction was filtered, the filtrate was concentrated in vacuo, the residue was partitioned between EtOAc/water, the layers were separated, the aqueous layer was extracted with EtOAc (1×), and the organic phases were combined and washed with water and brine, dried over Na₂SO₄, and concentrated in vacuo to yield 1.3 g of crude product. That material was chromatographed on silica gel using 80% ethyl acetate/hexane to yield 0.5 g of pure product, m/z=328 (M+Li).

Example 7

N-hydroxy-2-[(4-methoxyanilino)sulfonyl]benzamide

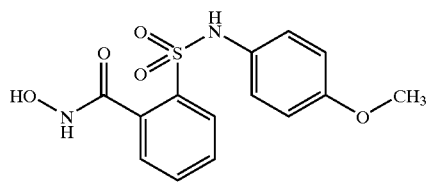

Part A: A 3-necked, 100 mL round bottom flask equipped with addition funnel, thermometer, magnetic stir bar, and N₂ inlet was charged with 0.5 g (4.3 mM) of p-anisidine and 1.8 mL (1.3 g, 12.8 mM) triethylamine in CH₂C₁₂ (20 mL). The solution was cooled in an ice bath, then treated with a solution of 1.0 g (4.3 mM) methyl (2-chlorosulfonyl)benzoate in CH₂C₁₂ (10 mL). The reaction mixture was stirred for 17 hr, then concentrated in vacuo. The residue was partitioned between EtOAc and H₂O, and the layers were separated. The organic phase was washed with 5% citric acid solution, saturated sodium bicarbonate solution, and brine, and then dried over Na₂SO₄ and concentrated in vacuo to yield 0.9 g of crude product. This was chromatographed on silica gel using 20–30% ethyl acetate/hexane to yield 0.7 g of pure product, m/z=328 (M+Li).

Part B: A 100 mL round bottom flask equipped with magnetic stir bar and N₂ inlet was charged with 0.7 g (2.1 mM) of the product from Part A and 0.7 g (10.2 mM) of hydroxylamine hydrochloride in 10 mL MeOH. The reaction mixture was cooled to 0° C. and charged with 0.4 g (16.4 mM) of sodium metal. After stirring for 17 hr, the reaction was concentrated in vacuo, the residue was slurried in 20 mL of water and then acidified using 2 N HCl solution. The aqueous slurry was extracted with EtOAc (3×). The organic layers were combined, washed with brine, dried over Na₂SO₄, and concentrated in vacuo to yield 0.6 g of crude product. The addition of methylene chloride to the crude product precipitated an off-white solid. Filtration gave 0.2 g of pure product, m/z=323 (M+Li).

Example 8

N-hydroxy-2-[(benzylamino)sulfonyl]benzamide

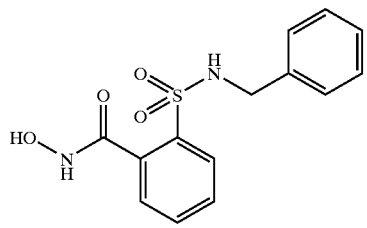

Part A: A 3-necked 100 mL round bottom flask equipped with an addition funnel, thermometer, magnetic stir bar, and N₂ inlet was charged with 0.5 mL (0.5 g, 4.3 mM) of benzylamine and 1.8 mL (1.3 g, 12.8 mM) triethylamine in CH₂Cl₂ (20 mL). The solution was cooled in an ice bath, and then treated with a solution of 1.0 g (4.3 mM) methyl (2-chlorosulfonyl)benzoate in CH₂Cl₂ (10 mL). The reaction mixture was stirred for 2 hr, and then concentrated in vacuo. The residue was partitioned between EtOAc and H₂O, and the layers were separated. The organic phase was washed with 5% citric acid solution, saturated sodium bicarbonate solution, and brine; dried over Na₂SO₄; and concentrated in vacuo to yield 0.9 g of crude product. This was chromatographed on silica gel using 20% ethyl acetate/hexane to yield 0.7 g of pure product, m/z=312 (M+Li).

Part B: A 100 mL round bottom flask equipped with magnetic stir bar and N₂ inlet was charged with 0.7 g (2.1 mM) of the product from Part A and 0.7 g (10.6 mM) of hydroxylamine hydrochloride in 10 mL MeOH. The reaction was cooled to 0° C. and charged with 0.4 g (17.0 mM) of sodium metal. After stirring for 17 hr, the reaction was concentrated in vacuo, the residue was slurried in 20 mL of water, then acidified using 2 N HCl solution. The aqueous slurry was extracted with EtOAc (3×). The organic layers were combined and washed with brine, dried over Na₂SO₄, and concentrated in vacuo to yield 0.3 g of crude product. The addition of methylene chloride to the crude product precipitated a white solid. Filtration gave 0.1 g of pure product, m/z=307 (M+H).

Example 9

Preparation of N-Hydroxy-2-[[4-(phenyl)-1-piperidinyl]sulfonyl]benzamide

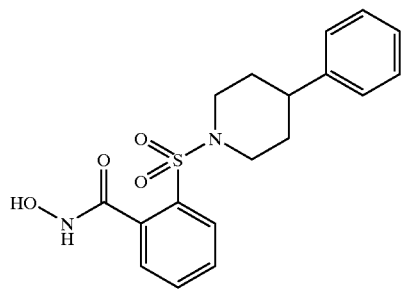

Part A: 2-carboethoxybenzenesulfonyl chloride (3.72 g, 15 mmol) was dissolved in methylene chloride (60 mL). 4-phenylpiperidine (2.89 g, 18 mmol) was added, followed by triethylamine (2.5 mL, 18 mmol) and 4-(dimethylamino)

piperidine (100 mg). After 5 hr, the mixture was diluted with 10% aqueous HCl (100 mL). The organic layer was separated and dried over magnesium sulfate.(MgSO$_4$) The solution was filtered through a silica pad and concentrated, affording the ester sulfonamide as an oil (3.27 g, 63%).

Part B: The ester sulfonamide from Part A (938 mg, 2.51 mmol) was stirred for 20 hr at ambient temperature in the presence of KOH (940 mg, 17 mmol), ethanol (15 mL), and water (5 mL). The mixture was diluted with water (20 mL) and acidified using concentrated HCl to a pH of approximately 4. The product was extracted using chloroform (2×100 mL), and the combined organic layers were dried using anhydrous MgSO$_4$. Concentration afforded carboxylic acid (768 mg, 89%), which was carried on to the next step.

Part C: To a solution of the acid from Part B (764 mg, 2.2 mmol) dissolved in acetonitrile (15 mL) was added O-tetrahydropyranyl hydroxylamine (351 mg, 3.0 mmol) and N-hydroxybenzotriazole (405 mg, 3.0 mmol), followed by 1-(3-dimethylaminopropyl)-3-ethylcarbodiimide hydrochloride (600 mg, 3 mmol). The reaction was stirred for 16 hr and then concentrated. The residue was diluted with half saturated brine (15 mL) and extracted with ethyl acetate (100 mL). The organic phase was dried using MgSO$_4$ and concentrated. The residue was purified by silica gel chromatography affording, on concentration, the desired THP-protected hydroxamate as a white foam (833 mg, 82%).

Part D: The THP-protected hydroxamate from Part C (833 mg, 1.8 mmol) was dissolved in absolute methanol (3 mL). Acetyl chloride (0.28 mL, 4 mmol) was added drop-wise. After 3 hr, the reaction was concentrated, and the residue was subjected to purification by chromatography, affording the title compound (430 mg, 66%) as a white foam. Anal. calculated for $C_{18}H_{20}N_2O_4S(H_2O)$: C, 57.08; H, 5.81; N, 7.40. Found: C, 57.02; H, 5.61; N, 6.90.

Example 10

Preparation of N,2-dihydroxy-2-methyl-2-[(4-phenyl-1-piperidinyl)sulfonyl]benzeneacetamide

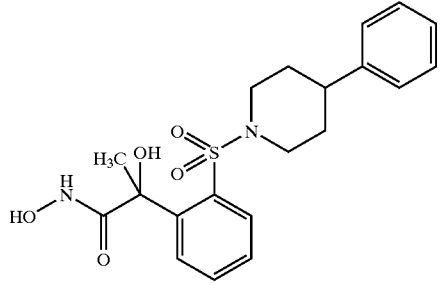

Part A: 2-bromobenzenesulfonyl chloride (2.56 g, 10 mmol) was added to a solution of 4-phenylpiperidine (1.61 g, 10 mmol), triethylamine (2.0 mL, 14 mmol), 4-dimethylaminopyridine (75 mg), and acetonitrile (20 mL). After 24 hr, water (100 mL) was added. The mixture was extracted with ethyl acetate (100 ml, then 50 mL). The combined organic layers were dried over MgSO$_4$, filtered through silica, and concentrated to afford the bromo sulfonamide as a white solid (3.47 g, 96%).

Part B: The bromo sulfonamide (359 mg, 1 mmol) was dissolved in dry tetrahydrofuran (2 mL) and cooled to −78° C. t-Butyllithium (0.68 mL, 1.7 M in pentane) was added drop-wise, and the anion was permitted to form over 15 min. Ethyl pyruvate (0.11 mL, 1.15 mmol) was added. The cooling bath was removed. When the reaction reached ambient temperature, the mixture was quenched with water (10 mL) and extracted with ethyl acetate (100 mL). The organic layer was dried over MgSO$_4$, filtered through silica, concentrated, and chromatographed to afford the desired hydroxy ester as a glass (163 mg 40%).

Part C: The hydroxy ester from Part B (134 mg. 0.33 mmol) was stirred in the presence of KOH (134 mg, 2.4 mmol) in ethanol (1 mL) and water (1 mL). After 4 hr, the mixture was heated at 50° C. for 1 hr, then cooled, neutralized with dilute HCl, concentrated, and azeotroped to dryness with acetonitrile to afford the crude hydroxy acid, which was used directly as is. The hydroxy acid was diluted with acetonitrile (1 mL). O-Tetrahydropyranylhydroxylamine (117 mg, 1.0 mmol) and N-hydroxybenzotriazole (13S mg, 1.0 mmol) were added, followed by 1-(3-dimethylaminopropyl)-3-ethylcarbodiimide hydrochloride (191 mg, 1 mmol). The reaction was stirred overnight (about 18 hr), then diluted with water (10 mL) and extracted with ethyl acetate (SO mL). The organic layer was dried over ethyl acetate, and concentrated and chromatographed to afford the THP-protected hydroxamate as a glass (80 mg, 48%).

Part D: The THP-protected hydroxamate from Part C (80 mg) was diluted with absolute methanol (4 mL), and toluenesulfonic acid (6 mg) was added. After 3 hr, the reaction mixture was concentrated, and the residue was chromatographed using 1:1 hexane:ethyl acetate 1% NH$_4$OH. The title compound was isolated as a white foam (40 mg, 60%). Analysis calculated for $C_{20}H_{24}N_2O_5S(1.33\ H_2O)$: C, 53.75; H, 5.90; N, 6.27. Found: C, 53.80; H, 5.65; N, 5.84.

Example 11

Preparation of N-hydroxy-2-[[3-[(4-methoxybenzoyl)amino]-1-pyrrolidinyl]sulfonyl]benzamide

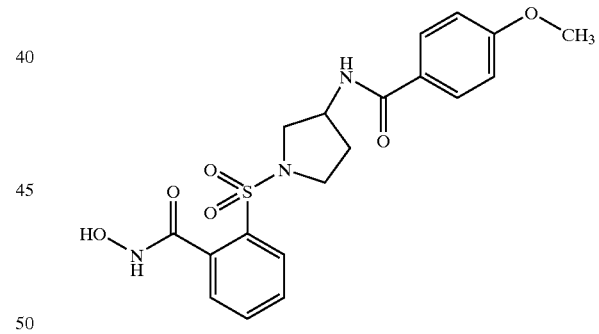

Part A: 3-aminopyrrolidine (636 mg, 4 mmol), triethylamine (2.7 mL, 20 mmol), and 4-(dimethylamino)pyridine (75 mg) were suspended in acetonitrile. After 10 min, the reaction was chilled to 0° C. 4-methoxybenzoyl chloride (0.54 mL, 4 mmol) was added drop-wise. After 30 min, 2-carboethoxybenzenesulfonyl chloride (0.996 g, 4.0 mmol) was introduced drop-wise by syringe. The mixture was stirred at 0° C. for 1 hr, and then at ambient temperature for 2 hr. Water was added (50 mL). The mixture was extracted using ethyl acetate (2×50 mL). The organic layer was dried over MgSO$_4$, filtered through silica, and concentrated. The residue was purified using silica gel chromatography using 1:1 ethyl acetate:hexane to ethyl acetate as eluant. The desired amide sulfonamide was isolated as a foam (282 mg, 16%).

Part B: The amide sulfonamide from Part A (272 mg, 0.63 mmol) was combined with KOH (156 mg, 2.8 mmol), ethanol (3 mL), and water (2 mL) and the resulting reacting mixture was brought to reflux. After 40 min, the reaction mixture was permitted to cool, and acetic acid (0.1 mL) and absolute ethanol (20 mL) were added. Concentration followed by chromatography (9:1 ethyl acetate:methanol to methanol; 20 g silica gel) afforded the desired acid as a crystalline solid (229 mg, 96?6). The acid (229 mg, 0.57 mmol) was dissolved in acetonitrile (1 mL). O-tetrahydropyranyl hydroxylamine (117 mg, 1.0 mmol) and N-hydroxybenzotriazole (135 mg, 1.0 mmol) were added, followed by 1-(3-dimethylaminopropyl)-3-ethylcarbodiimide hydrochloride (191 mg, 1 mmol). The mixture was stirred at ambient temperature overnight (about 18 hr), then concentrated and chromatographed (ethyl acetate to 9:1 ethyl acetate: methanol), affording the THP-protected hydroxamate as a white crystalline solid (98 mg, 33%).

Part C: The THP-protected hydroxamate (76 mg,0.15 mmol) was dissolved in methanol (2 mL). Acetyl chloride (0.01 mL, 1 mmol) was added. After 30 min, the solution was concentrated, and then azeotroped with chloroform/acetonitrile affording the title compound as a solid (65 mg, quantitative.). MS (EI) MH$^+$: calculated for $C_{19}H_{21}N_3O_6S$: 420, found 420.

Example 12

Preparation of N-hydroxy-2-[[4-[4-(trifluoromethoxy)phenoxy]-1-piperidinyl]sulfonyl]benzamide

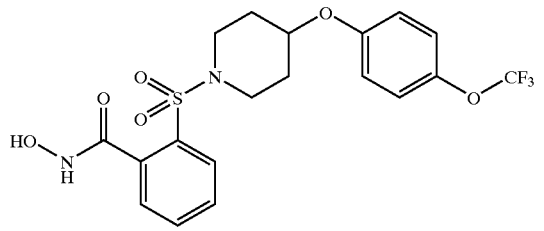

Part A: Diethyl azodicarboxylate (4.11 g, 23.6 mmol) was added at ambient temperature under $N_2$ to a mixture of N-(tert butyloxycarbonyl)-4-piperidinol (4.31 g, 21.4 mmol, prepared according to Wells, Kenneth M.; et al; *Tetrahedron Lett.*, 1996, 37, 6439–6442), 4-trifluoromethoxyphenol (4.20 g, 23.6 mmol), and triphenylphosphine (6.19 g, 23.6 mmol) in THF (200 mL). After 1.5 hr, the reaction mixture was concentrated. The residue was diluted with ethyl ether, filtered, and purified by chromatography (on silica, methyl tert-butyl ether/hexane) to afford the impure BOC-amine as an off-white solid (5.23 g). To the off-white solid cooled to 0° C. under $N_2$ was added a solution of 4 N HCl in dioxane (36.1 mL, 145 mmol). After 2 hr, the reaction mixture was concentrated and diluted with ethyl ether to give a white solid. The white solid was diluted with $H_2O$ (15 mL), and a solution of $NaHCO_3$ (1.68 g, 20.0 mmol) in water (10 mL) was added. The precipitate was extracted into ethyl ether. The organic layer was washed with brine, dried over $MgSO_4$, and concentrated to give the amine as a white solid (1.93 g, 34%); MS MH$^+$ calculated for $C_{12}H_{14}NO_2F_3$:262, found 262.

Part B: A solution of the amine of Part A (1.90 g, 7.28 mmol), ethyl 2-chlorosulfonylbenzoate (1.70, 6.85 mmol), triethylamine (1.15 mL, 8.22 mmol), and 4-dimethylaminopyridine (10 mg) in acetonitrile (20 mL) was stirred under $N_2$ at ambient temperature for 18 hr. After concentrating the solution, the residue was diluted with $H_2O$ and extracted into ethyl acetate. The organic layer was washed with 1.0 N $KHSO_4$, saturated $NaHCO_3$, $H_2O$, and brine, and then dried over $MgSO_4$ and concentrated to a yellow oil. Chromatography (on silica, ethyl acetate/hexane) provided the sulfonamide as a white solid (1.59 g, 51%); MS MH$^+$ calculated for $C_{21}H_{22}NO_6F_3S$:474, found 474.

Part C: A solution of the sulfonamide of Part B (1.45 g, 3.17 mmol) and KOH (1.77 g, 31.7 mmol) in a mixture of MeOH (30 mL), $H_2O$ (10 mL), and THF (10 mL) was heated at reflux for 1.5 hr. After the solution was concentrated in vacuo, the residue was triturated with ethyl ether, dissolved into $H_2O$, acidified with concentrated HCl, and extracted into ethyl acetate. The organic layer was washed with brine, dried over $MgSO_4$, and concentrated in vacuo to provide the acid as a clear oil (1.04 g, 74%); Anal. calculated for- $C_{19}H_{18}NO_6F_3S$: C, 51.23; H, 4.07; N, 3.14; S, 7.20. Found: C, 51.34; H, 3.78; N, 3.15; S, 7.30.

Part D: A solution of the acid of Part C (0.97 g, 2.18 mmol), N-hydroxybenzotriazole (0.89 g, 6.50 mmol), 4-methylmorpholine (0.71 mL, 6.50 mmol), O-tetrahydro-2H-pyran-2-yl-hydroxylamine (0.51 g, 4.36 mmol), and 1-(3-dimethylaminopropyl)-3 ethylcarbodiimide hydrochloride (1.25 g, 6.50 mmol) in DMF (19 mL) was stirred at ambient temperature under $N_2$ for 20 hr. The mixture was concentrated in vacuo, diluted with water, and extracted with ethyl acetate. The organic layer was washed with 1.0 N $KHSO_4$, saturated $NaHCO_3$, $H_2O$, and brine, and then dried over $MgSO_4$ and concentrated in vacuo to afford the THP-protected hydroxamate as a white solid (1.05 g, 88%): Anal. calculated. for $C_{24}H_{27}N_2O_7F_3S$: C, 52.94; H, 5.00; N, 5.14; S, 5.89. Found: C, 52.80; H, 4.84; N, 5.23; S, 6.14.

Part E: The THP-protected hydroxamate of Part D (1.01 g, 1.86 mmol) was dissolved in methanol (10 mL). Acetyl chloride (0.36 mL, 5.0 mmol) was added. After 1 hr, the solution was concentrated, and the residue was subjected to chromatography (1:1 hexane:ethyl acetate; 1% $NH_4OH$ to ethyl acetate; 1% $NH_4OH$) affording the title compound as foam (643 mg, 75%). Anal. calculated for $C_{19}H_{19}F_3N_2O_6S$: C, 49.56; H, 4.13; N, 6.09. Found: C, 49.27; H, 3.72; N, 5.87.

Example 13

Preparation of N-hydroxy-2-[[4-[4-(trifluoromethyl)phenoxy]-1-piperidinyl]sulfonyl]benzamide

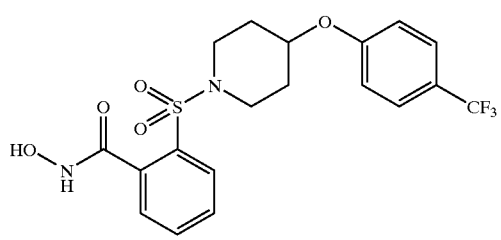

Part A: A solution of N-(tert-butyloxycarbonyl)-4-piperidinol (5.00 g, 2.48 mmol), 4-fluorobenzo-trifluoride (3.46 mL, 2.73 mmol), and cesium carbonate (12.1 g, 3.72 mmol) in DMF (60 mL) was heated at 120° C. under $N_2$ for 2 days. The mixture was concentrated, diluted with $H_2O$, and extracted with ethyl acetate. The organic layer was washed with $H_2O$ and brine, dried with $MgSO_4$, and concentrated in vacuo. Chromatography (on silica, ethyl acetate/hexane) provided the BOC-aminoether as a white solid (6.97 g, 81%); Anal. calculated. for $C_{17}H_{22}NO_3F_3$: C, 59.12; H, 6.42; N, 4.06. Found: C, 59.29; H, 6.47; N, 3.99.

Part B: A solution of the BOC-aminoether of Part A (4.00 g, 11.6 mmol) and p-toluenesulfonic acid (6.61 g, 34.7 mmol) in $CH_2Cl_2$ (30 mL) at ambient temperature under $N_2$ was stirred for 3 hr and then concentrated in vacuo. The residue was partitioned between aqueous $NaHCO_3$ and ethyl acetate. The organic layer was dried over $MgSO_4$, and concentrated to provide the free amine as a clear, yellow oil (1.57 g, 55%); MS MH+ calculated. for $C_{12}H_{14}NOF_3$: 246, found 246.

Part C: A solution of the amine of Part B (1.57 g, 6.40 mmol), ethyl 2-chlorosulfonylbenzoate (1.57 g, 6.03 mmol), triethylamine (1.00 mL, 7.24 mmol), and 4-dimethylaminopyridine (10 mg) in acetonitrile (20 mL) was stirred under $N_2$ at ambient temperature for around 1.5 hr. After concentrating the solution, the residue was diluted with $H_2O$ and extracted into ethyl acetate. The organic layer was washed with 1.0 N $KHSO_4$, saturated $NaHCO_3$, $H_2O$, and brine, and then dried over $MgSO_4$ and concentrated to provided the sulfonamide as a clear, yellow oil (2.52 g, 92%); MS MH$^+$ calculated for $C_{21}H_{22}NO_5F_3S$: 458, found 458.

Part D: A solution of the sulfonamide of Part C (2.50 g, 5.46 mmol) and KOH (3.06 g, 54.6 mmol) in a mixture of MeOH (49 mL) and $H_2O$ (24 mL) was heated at reflux for 4 hr. After the solution was concentrated in vacuo, the residue was triturated with ethyl ether, dissolved into $H_2O$, acidified with concentrated HCl, and extracted into ethyl acetate. The organic layer was washed with 1.0 N $KHSO_4$, $H_2O$, and brine; dried over $MgSO_4$; and concentrated in vacuo to provide the acid as an oil (2.17 g, 93%); MS MH$^+$ calculated for $C_{19}H_{18}NO_5F_3S$: 430, found 430.

Part E: A solution of the acid of Part D (2.10 g, 4.89 mmol), N-hydroxybenzotriazole (1.97 g, 14.6 mmol), 4-methylmorpholine (1.61 mL, 14.6 mmol), O-tetrahydro-2H-pyran-2-yl-hydroxylamine (1.1S g, 9.79 30 mmol), and 1-(3-dimethylaminopropyl)-3-ethylcarbodiimide hydrochloride (2.80 g, 14.6 mmol) in DMF (43 mL) was stirred at ambient temperature under $N_2$ for about 18 hr. The mixture was concentrated in vacu, diluted with water, and extracted into ethyl acetate. The organic layer was washed with 1.0 N $KHSO_4$, $H_2O$, and brine, and then dried over $MgSO_4$ and concentrated in vacu. Chromatography (on silica, ethanol/$CHCl_3$) provided the THP-protected hydroxamate as a white solid (2.09 g, 81%): MS MH$^+$ calculated for $C_{24}H_{27}N_2O_6F_3S$: 529, found 529.

Part F: To a solution of the THP-protected hydroxamate of Part C (1.80 g, 3.41 mmol) in methanol (24 mL) was added acetyl chloride (0.73 mL, 10.2 mmol) and the solution was stirred at ambient temperature under $N_2$ for 1.5 hr. The solution was concentrated in vacuo and chromatography (on silica, MeOH/$CHCl_3$) provided the title compound as an off white solid (1.18 g, 78%): Anal. calculated. for $C_{19}H_{19}N_2O_5F_3S.0.2\%H_2O$: C, 50.94; H, 4.36; N, 6.25; S, 7.16. Found: C, 50.88; H, 4.31; N, 6.20; S, 7.43. MS MH$^+$ calculated. for $C_{19}H_{19}N_2O_5F_3S$: 445, found 445.

Example 14

Preparation of N-hydroxy-2-[[4-[[4-(trifluoromethyl)phenyl]methoxy]-1-piperidinyl]sulfonyl]benzamide

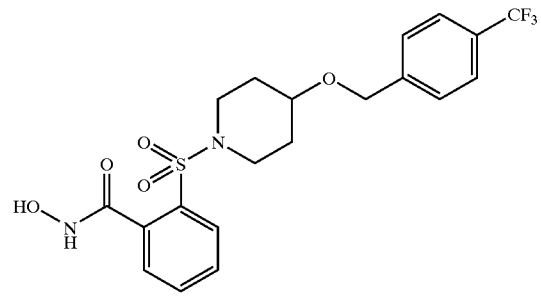

Part A: A solution of 4-(trifluoromethyl)benzyl bromide (2.00 mL, 12.9 mmol) in THF (6 mL) was added drop-wise under $N_2$ to a -52° C. mixture of N-(tert-butyloxycarbonyl)-4-piperidinol (2.85 g, 14.9 mmol) and 60% sodium hydride (0.600 g, 14.9 mmol) in THF (15 mL), and then stirred at ambient temperature for about 20 hr. The reaction mixture was quenched with a saturated $NH_4Cl$ solution, concentrated in vacuo, diluted with $H_2O$, and extracted with ethyl acetate. The organic layer was washed with 1.0 N HCl, a saturated $NaHCO_3$ solution, $H_2O$, and brine, and then dried over $MgSO_4$ and concentrated in vacuo to provide the BOC-aminoether as an off-white solid (3.35 g, 72%); MS MH$^+$ calculated for $C_{18}H_{24}NO_3F_3$: 360, found 360.

Part B: A 0° C. solution of the BOC-aminoether of Part A (3.35 g, 9.32 mmol) in ethyl acetate (40 mL) was saturated with HCl (gas), and then stirred at ambient temperature for 1 hr. After concentrating in vacuo and triturating with ethyl ether, the crude free base was partitioned between aqueous $NaHCO_3$ and ethyl ether. The organic layer was washed with $H_2O$, and brine, dried over $MgSO_4$, and concentrated in vacuo to provide the amine as a clear, yellow oil (2.11 g, 87%), which had a proton NMR spectrum consistent for the desired product.

Part C: A solution of the amine of Part B (2.11 g, 8.14 mmol), ethyl 2-chlorosulfonylbenzoate (2.65 g, 10.7 mmol), triethylamine (1.75 mL, 12.6 mmol), and 4-dimethylaminopyridine (50 mg) in acetonitrile (25 mL) was stirred under $N_2$ at ambient temperature for about 18 hr. After concentrating the solution, the residue was diluted with 1.0 N $KHSO_4$ and extracted into ethyl acetate. The organic layer was washed with 1.0 N $KHSO_4$, saturated $NaHCO_3$, $H_2O$, and brine, and then dried over $MgSO_4$ and concentrated to a yellow oil. Chromatography (on silica, ethyl acetate/hexane) provided the sulfonamide as a clear oil (2.48 g, 65%); MS MH$^+$ calculated for $C_{22}H_{24}NO_5F_3S$: 472, found 5 472.

Part D: A solution of the sulfonamide of Part C (2.10 g, 4.45 mmol) and KOH (2.49 g, 44.5 mmol) in a mixture of MeOH (40 mL), H2O (20 mL), and THF (4 mL) was heated at reflux for 1.5 hr. After the solution was concentrated in vacuo, the residue was triturated with ethyl ether, dissolved into $H_2O$, acidified with concentrated HCl, and extracted into ethyl acetate. The organic layer was washed with 1.0 N $KHSO_4$, $H_2O$, and brine, dried over $MgSO_4$, and concentrated in vacuo to provide the acid as a white solid (2.08 g, 1.06%); Anal. Calculated for $C_{20}H_{20}NO_5F_3S$: C, 54.17; H, 4.55; N, 3.16; S, 7.23. Found: C, 54.29; H, 4.68; N, 3.11; S, 7.19.

Part E: A solution of the acid of Part D (2.00 20 g, 4.51 mmol), N-hydroxybenzotriazole (1.83 g, 13.5 mmol), 4-methylmorpholine (1.48 mL, 13.5 mmol), O-tetrahydro-2H-pyran-2-yl-hydroxylamine (1.06 g, 9.02 mmol), and 1-(3-dimethylaminopropyl)-3 ethylcarbodiimide hydrochloride (2.59 g, 13.5 mmol) in DMF (40 mL) was stirred at ambient temperature under $N_2$ for about 20 hr. The mixture was concentrated in vacuo, diluted with $H_2O$, and extracted into ethyl acetate. The organic layer was washed with saturated $NaHCO_3$, $H_2O$, and brine, and then dried over $MgSO_4$ and concentrated in vacuo to provide the THP-protected hydroxamate as a white solid (2.01 g, 82%): Anal. calculated. for $C_{25}H_{29}N_2O_6F_3S$: C, 55.34; H, 5.39; N, 5.16; S, 5.91. Found: C, 55.36; H, 5.63; N, 5.20; S, 6.12.

Part F: To a solution of the THP-protected hydroxamate of Part E (2.00 g, 3.69 mmol) in methanol (25.9 mL) was added acetyl chloride (0.78 mL, 11.1 mmol), and the solution was stirred at ambient temperature under $N_2$ for 1.5 hr. The solution was concentrated in vacuo and chromatography (on silica, $MeOH/CHCl_3$) provided the title compound as an off-white solid (1.07 g, 63%): Anal. calculated. for $C_{20}H_{21}N_2O_5F_3S$: C, 52.40; H, 4.62; N, 6.11; S, 6.99. Found: C, 52.53; H, 4.74; N, 6.25; S, 7.16. MS MH+ calculated. for $C_{20}H_{21}N_2O_5SF_3$: 459, found 459.

Example 15

Preparation of N-hydroxy-2-[[(4-phenoxyphenyl)-amino]sulfonyl]benzamide

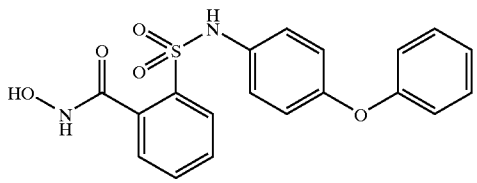

Part A: A solution of 4-phenoxyaniline (3.43 g, 18.5 mmol), ethyl 2-chlorosulfonylbenzoate (4.25 g, 17.1 mmol), triethylamine (2.81 mL, 20.1 mmol), and 4-dimethylaminopyridine (50 mg) in acetonitrile (40 25 mL) was stirred under $N_2$ at ambient temperature for about 18 hr. After concentrating the solution, the residue was diluted with 1.0 N $KHSO_4$ and extracted into ethyl acetate. The organic layer was washed with 1.0 N $KHSO_4$, $H_2O$, and brine, and then dried over $MgSO_4$ and concentrated in vacuo. Chromatography (on silica, ethyl acetate/hexane) provided the sulfonamide as a tan solid (4. 94 g, 73%); Anal. calculated for $C_{21}H_{19}NO_5S$: C, 63.46; H, 4.82; N, 3.52; S, 8.07. Found: C, 63.36; H, 4.78; N, 3.45; S, 8.31. MS M+ calculated for $C_{21}H_{19}NO_5S$: 397, found 397.

Part B: A solution of the sulfonamide of Part A (3.00 g, 7.55 mmol) and KOH (4.23 g, 75.5 mmol) in a mixture of MeOH (68 mL), THF (8 mL), and $H_2O$ (33 mL) was heated at reflux for 2 hr. After the solution was concentrated in vacuo, the residue was triturated with ethyl ether, dissolved into $H_2O$, acidified with concentrated HCl, and extracted into ethyl acetate. The organic layer was washed with 1.0 N HCl, $H_2O$, and brine; dried over $MgSO_4$; and concentrated in vacuo to provide the acid as a tan solid (2.31 g, 83%); Anal. calculated. for $C_{19}H_{15}NO_5S$: C, 61.78; H, 4.09; N, 3.79; S, 8.68. Found: C, 61.66; H, 4.22; N, 3.73; S, 8.70. MS M+ calculated for $C_{19}H_{15}NO_5S$: 369, found 369.

Part C: A solution of the acid of Part B (2.30 g, 6.23 mmol), N-hydroxybenzotriazole (2.52 g, 18.6 mmol), 4-methylmorpholine (2.04 mL, 18.6 mmol), O-tetrahydro-2H-pyran-2-yl-hydroxylamine (1.46 g, 12.5 mmol), and 1-(3-dimethylaminopropyl)-3-ethylcarbodiimide hydrochloride (3.57 g, 18.6 mmol) in DMF (55 mL) was stirred at ambient temperature under $N_2$ for about 18 hr. The mixture was diluted with $H_2O$, and extracted into ethyl acetate. The organic layer was washed with saturated $NaHCO_3$, $H_2O$, and brine, and then dried over $MgSO_4$ and concentrated in vacuo to provide the saccharin compound as a white solid (2.13 g, 97%): Anal. calculated. for $C_{19}H_{13}NO_4S$: C, 64.95; H, 3.73; N, 3.99; S, 9.13. Found: C, 64.98; H, 3.82; N, 4.17; S, 9.07. MS MH+ calculated for $C_{19}H_{13}NO_4S$: 352, found 352.

Part D: A solution of the saccharin of Part C (0.500 g, 1.42 mmol) and O-tetrahydro-2H-pyran-2-yl-hydroxylamine (0.183 g, 1.56 mmol) in dioxane (2 mL) under $N_2$ was stirred for 6 days at ambient temperature and 1 day at 50° C. The solution was concentrated and chromatography provided the THP-protected hydroxamate as a white solid (0.285 g, 43%); MS MH+ calculated for $C_{24}H_{24}N_2O_6S$: 469, found 469.

Part E: To a solution of the THP-protected hydroxamate of Part D (0.275 g, 0.587 mmol) in methanol (5 mL) was added acetyl chloride (0.150 mL, 2.13 mmol), and the solution was stirred at ambient temperature under $N_2$ for 2 hr. The solution was concentrated in vacuo and chromatography (on silica, $MeOH/CHCl_3$) provided the title compound as an off-white solid (1.18 g, 78%). The proton NMR was consistent for the desired product.

Example 16

Preparation of N-hydroxy-2,3-dimethoxy-6-[[4-[4-trifluoromethyl)phenoxy]-1-piperidinyl)sulfonyl]benzamide

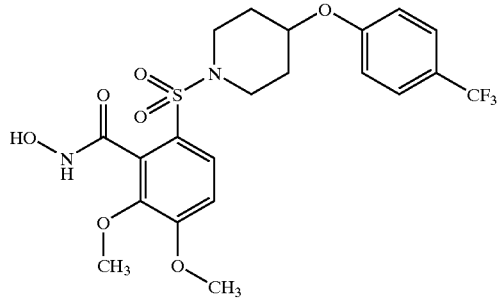

Part A: The piperidine from Example 13, Part B (as the hydrochloride) (1.12 g, 4.0 mmol) was dissolved in a mixture of acetonitrile (6 ml), triethylamine (1.3 mL, 9.0 mmol), and N,N-dimethylaminopyridine (80 mg). 3,4-dimethoxybenzenesulfonyl chloride (947 mg, 4.0 mmol) was added, and the mixture was stirred at ambient temperature for 6 hr. The reaction mixture was concentrated, and the residue was extracted with ethyl acetate (100, then 25 mL). The combined organic layers were dried over $MgSO_4$, filtered through silica, and concentrated to afford the desired sulfonamide as a white solid (1.05 g, 59%).

Part B: The sulfonamide from Part A (1.05 g, 2.38 mmol) was dissolved in tetrahydrofuran (20 mL) and then cooled to 0° C. t-Butyllithium (1.7 M in pentane 2.8 mL) was added drop-wise. Fifteen min after complete addition of the base, the solution was rapidly saturated with dry $CO_2$ gas. After an additional 15 min, the solution was acidified with a minimum of concentrated HCl. The reaction mixture was concentrated and azeotroped with absolute ethanol, and the residue was subjected to silica gel chromatography using 8:1 ethyl acetate:methanol, affording the desired acid as a glass (279 mg, 24%).

Part C: The acid from Part B (231 mg, 0.47 mmol) was dissolved in methylene chloride (4 mL). N,N-Dimethylformamide (2 drops) was added, followed by oxalyl chloride (0.35 mL, 4 mmol). The reaction was stirred for 1.5 hr at ambient temperature, during which time gas was evolved. The reaction mixture was concentrated and dried in vacuo, affording crude acid chloride, which was used as is. To the acid chloride was added a solution of O-tetrahydropyranylhydroxylamine (234 mg, 2.0 mmol) and pyridine (0.5 mL, 6.0 mmol) in acetonitrile (2–3 mL). The reaction was stirred at ambient temperature for 16 hr, and then was diluted with $H_2O$ (3 mL). The mixture was extracted with ethyl acetate (100 mL, then 50 mL). The combined organic layers were dried over $MgSO_4$, filtered through a silica pad, and concentrated, affording 376 mg of crude THP-protected hydroxamate. The THP-protected hydroxamate was used directly without purification and was diluted with absolute methanol (10 mL). Acetyl chloride (0.36 mL, 5.0 mmol) was added drop-wise. After 2.5 hr, the mixture was concentrated, and the residue was chromatographed (ethyl acetate:1% $NH_4OH$). The desired hydroxamate was obtained as a glass (121 mg, 51% from acid). MS MH$^+$ calculated for $C_{21}H_{23}F_3N_2O_7S$: 505, found 505.

Example 17

Preparation of N-hydroxy-2-[[3-[4-(trifluoromethyl) phenoxy]-1-pyrrolidinyl]sulfonyl]benzamide

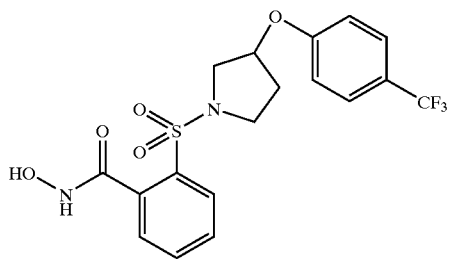

Part A: Diethyl azodicarboxylate (2.03 mL, 12.9 mmol) was added under $N_2$ to a solution of 1-(tert-butoxycarbonyl)-3-hydroxypyrrlidine (2.31 g, 12.3 mmol), p-trifluoromethylphenol (2.09 g, 12.9 mmol), and triphenylphosphine (3.38 g, 12.9 mmol) in anhydrous THF (40 mL) at ambient temperature. After stirring for 2 hr, the reaction was concentrated in vacuo. The residue was diluted with ether, filtered through a silica gel bed, concentrated, and purified by flash chromatography (on silica, ethyl acetate/hexane) to afford the BOC-protected amine as a white solid (1.85 g, 45%); Anal. Calculated for $C_{16}H_2ONO_3F_3$: C, 58.00; H, 6.08; N, 4.23. Found: C, 57.86; H, 6.17; N, 3.92.

Part B: To the BOC-protected amine of Part A (1.75 g, 5.28 mmol) was added a solution of 4 N HCl in dioxane (13.2 mL, 52.8 mmol). After 1 hr, the reaction mixture was concentrated, diluted with ethyl ether, and concentrated to give an oil. The oil was dissolved in $H_2O$ and saturated $NaHCO_3$ solution was added until the pH value was 8. The mixture was extracted with ethyl acetate. The organic layer was washed with $H_2O$ and brine, dried over $MgSO_4$, and concentrated in vacuo to give the amine as a clear, yellow oil (0. 75 g, 61%); MS MH' calculated for $C_{11}H_{12}NOF_3$:231, found 232.

Part C: A solution of the amine of Part B (0.680 g, 2.94 mmol), ethyl 2-chlorosulfonylbenzoate (0.688, 2.77 mmol), triethylamine (0.46 mL, 3.3 mmol), and 4-dimethylaminopyridine (10 mg) in acetonitrile (10 mL) was stirred under $N_2$ at ambient temperature for 18 hr. After concentrating in vacuo, the residue was diluted with $H_2O$ and extracted with ethyl acetate. The organic layer was washed with 1.0 N $KHSO_4$, saturated $NaHCO_3$, $H_2O$, and brine, and dried over $MgSO_4$ and concentrated to a yellow oil. Chromatography (on silica, ethyl acetate/hexane) provided the sulfonamide as a clear, colorless oil (0.95 g, 76%); MS MH$^+$ calculated for $C_{20}H_{20}NO_5F_3S$: 443, found 444. Anal. Calculated for $C_{20}H_{20}NO_5F_3S$: C, 54.17; H, 4.55; N, 3.16; S, 7.23. Found: C, 53.82; H, 4.35; N, 3.13.

Part D: A solution of the sulfonamide of Part C (0.85 g, 1.9 mmol) and KOH (1.07 g, 10 19.2 mmol) in a mixture of MeOH (17 mL) and $H_2O$ (8 mL) was heated at reflux for 4 hr. After the solution was concentrated in vacuo, the residue was dissolved into $H_2O$, acidified with concentrated HCl, and extracted into ethyl acetate. The organic layer was washed with $H_2O$ and brine, dried over $MgSO_4$, and concentrated in vacuo to provide the acid as a clear, colorless wax (0.74 g, 93%); MS MH$^+$ calculated for $C_{18}H_{16}NO_5F_3S$: 415, found 416.

Part E: A solution of the acid of Part D (0.690 20 g, 1.56 mmol), N-hydroxybenzotriazole (0.629 g, 4.65 mmol), 4-methylmorpholine (0.51 mL, 4.7 mmol), O-tetrahydro-2H-pyran-2-yl-hydroxylamine (0.340 g, 2.90 mmol), and 1-(3-dimethylaminopropyl)-3-ethylcarbodiimide hydrochloride (0.891 g, 4.65 mmol) 25 in DMF (13 mL) was stirred at ambient temperature under $N_2$ for 3 days. The mixture was concentrated in vacuo, diluted with 1.0 N $KHSO_4$, and extracted with ethyl acetate. The organic layer was washed with 1.0 N $KHSO_4$, saturated $NaHCO_3$, $H_2O$, and brine; dried over $MgSO_4$; and concentrated in vacuo. Chromatography on silica, with ethyl acetate/hexane as eluant, afforded the THP-protected hydroxamate as a white foam (0.575 g, 71.6%): Anal. calculated for $C_{23}H_{25}N_2O_6F_3S$: C, 53.69; H, 4.90; N, 5.44; S, 6.23. Found: C, 53.48; H, 4.95; N, 5.37; S, 6.35.

Part F: To a solution of the THP-protected hydroxamate of Part E (0.500 g, 0.972 mmol) in methanol (6 mL) was added acetyl chloride (0.24 mL, 3.5 mmol), and the solution was stirred at ambient temperature under $N_2$ for 4.5 hr. The solution was concentrated in vacuo and chromatography (on silica, MeOH/CHCl$_3$) provided the title compound as a white solid (0.325 g, 77.8%): MS MH$^+$ calculated. for $C_{18}H_{17}N_2O_5SF_3$: 430, found 431.

Example 18

Preparation of N-alpha-dihydroxy-2-[[4-[4-(trifluoromethyl)phenoxy]-1-piperidinyl]sulfonyl] benzeneacetamide

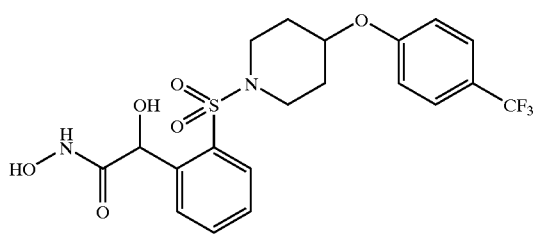

Part A: A mixture of 4-[(4-trifluoromethyl)-phenoxypiperidine hydrochloride (the hydrochloride from the product of Example 13, Part B, 2.50 g, 8.87 mmol), 2-bromobenenesulfonyl chloride (2.16 g, 8.45 mmol), triethylamine (2.51 mL, 18.0 mmol), and 4-(dimethylamino)pyridine (20 mg) in acetonitrile (25 mL) was stirred at ambient temperature under $N_2$ for 18 hr, concentrated in vacuo, and partitioned between $H_2O$ and ethyl acetate. The organic layer was washed with 1.0 N $KHSO_4$, saturated $NaHCO_3$, $H_2O$, and brine; dried over $MgSO_4$; and concentrated in vacuo. The oil was purified by chromatography (on silica, ethyl acetate/hexane) to provide the bromide as a clear oil (3.38 g, 82.8%): MS+ calculated. for $C_{18}H_{17}NO_3SF_3Br$: 464, found 464.

Part B: To a −78° C. solution of the sulfonamide from Part A (3.68 g, 7.93 mmol) in anhydrous THF (40 mL) under $N_2$ was added 1.7 M tert-butyl lithium (9.35 mL, 15.9 mmol). The reaction was maintained at −78° C. for 1 hr, warmed up to −30° C., and then cooled down to −78° C. A 50% ethyl glyoxalate solution in toluene was added dropwise while maintaining the reaction mixture at a temperature below −50° C. The solution was warmed up slowly to ambient temperature, stirred 2 days at ambient temperature, poured into a saturated $NH_4Cl$ solution, diluted with $H_2O$, and extracted with ethyl acetate. The organic layer was washed with $H_2O$ and brine, dried over $MgSO_4$, and concentrated in vacuo. Chromatography on silica with ethyl acetate/hexane as eluant provided the ester as a yellow oil (1.55 g, 40%); Anal. calculated. for $C_{22}H_{24}NO_6F_3S$: C, 54.20; H, 4.96; N, 2.87. Found: C, 54.18; H, 4.72; N, 2.77. MS MH+ calculated for $C_{22}H_{24}NO_6F_3S$: 487, found 488.

Part C: A solution of the ester of Part B (1.35 g, 2.77 mmol) and KOH (1.55 g, 27.7 mmol) in a mixture of MeOH (24.5 mL) and $H_2O$ (14.7 mL) was stirred at ambient temperature for 1 hr. The solution was concentrated in vacuo, dissolved into a mixture of $H_2O$ and acetonitrile, acidified with concentrated HCl, and extracted with ethyl acetate. The organic layer was washed with 1.0 N $KHSO_4$, $H_2O$, and brine; dried over $MgSO_4$; and concentrated in vacuo to provide the acid as a wax (1.09 g, 85.8%); Anal. calculated. for $C_{20}H_{20}NO_6F_3S$: C, 52.29; H, 4.39; N, 3.05; S, 6.98. Found: C, 52.06; H, 4.41; N, 2.90; S, 5 7.11.

Part D: A solution of the acid of Part C (1.00 g, 2.18 mmol), N-hydroxybenzotriazole (0.876 g, 6.48 mmol), 4-methylmorpholine (0.712 mL, 6.48 mmol), O-tetrahydro-2H-pyran-2-yl-hydroxylamine (0.474 g, 4.05 mmol), and 1-(3-dimethylaminopropyl)-3-ethylcarbodiimide hydrochloride (1.24 g, 6.48 mmol) in DMF (15 mL) was stirred at ambient temperature under $N_2$ for 18 hr. The mixture was concentrated in vacuo, diluted with $H_2O$, and extracted with ethyl acetate. The organic layer was washed with 1.0 N $KHSO_4$, saturated $NaHCO_3$, $H_2O$, and brine; dried over $MgSO_4$; and concentrated in vacuo. Chromatography on silica with ethyl acetate/hexane as eluant provided the THP-protected hydroxamate as a white solid (0.81 g, 66%): Anal. calculated. for $C_{25}H_{29}N_2O_7F_3S$: C, 53.76; H, 5.23; N, 5.02; S, 5.74. Found: C, 53.73; H, 5.39; N, 4.85; S, 5.72.

Part E: A solution of the THP-protected hydroxamate of Part D (0.800 g, 1.43 mmol) and acetyl chloride (0.36 mL, 5.2 mmol) in methanol (15 mL) was stirred at ambient temperature under $N_2$ for 1.5 hr. The solution was concentrated in vacuo and purified by preparatory HPLC ($CH_3CN$/$H_2O$) to provide the title compound as a white solid (0.310 g, 45%). Anal. calculated. for $C_{20}H_{21}N_2O_6SF_3$·0.2%$H_2O$: C, 50.25; H, 4.51; N, 5.86; S, 6.71. Found: C, 50.18; H, 4.52; N, 5.82; S, 6.58

Example 19

Preparation of 2-flouro-N-hydroxy-6-[[4-[4-(trifluoromethyl)phenoxy]-1-piperidinyl]sulfonyl] benzamide

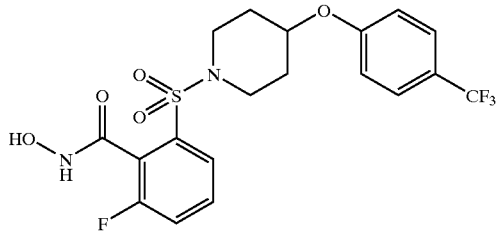

Part A: A solution of the piperidine from Example 13, Part B (as the hydrochloride, 2.0 g, 10 6.72 mmol), 3-flourobenzenesulphonyl chloride (1.19 g, 6.11 mmol), triethylamine (2.13 mL, 15.3 mmol), and 4-dimethylaminopyridine (10 mg) in acetonitrile (10 mL) was stirred under argon at ambient temperature for 18 hr. After concentrating the solution, the residue was diluted with $H_2O$ and extracted into ethyl acetate. The organic layer was washed with saturated $NaHSO_4$, $H_2O$, and brine; dried over $MgSO_4$; and concentrated to an oil. Chromatography (on silica, 20% ethyl acetate/hexane) provided the sulfonamide as a viscous oil (2.35 g, 95%); MS H+ calculated for $C_{18}H_{17}NSO_3F_4$: 404, found 404.

Part B: t-Butyl lithium (3.5 mL, 5.96 mmol) was added to a solution of the sulfonamide of Part A (1.2 g, 2.98 mmol) in dry THF (10 mL) at 0° C. The solution was stirred at this temperature for 15 min. Carbon dioxide was bubbled into the reaction mixture for 7 min at 0° C., and the mixture was stirred for 0.5 hr. Water was added to the solution. The mixture was acidified to pH=1.0 with 1 N HCl, and concentrated in vacuo to give an oil. Chromatography (on silica, 1% acetic acid/5% methanol/ethyl acetate) provided the acid as a white powder (0.970 mg, 73%). MS H+ calculated for $C_{19}H_{16}NSO_5F_4$:448, found 448.

Part C: A solution of the acid of Part B (880 mg,1.97 mmol), N-hydroxybenzotriazole (319 mg, 2.36 mmol), 4-methylmorpholine (0.649 mL, 5.91 mmol), O-tetrahydro-2H-pyran-2-yl-hydroxylamine (346 mg, 2.95 10 mmol), and 1-(3-dimethylaminopropyl)-3-ethylcarbodiimide hydrochloride (528 mg, 2.76 mmol) in DMF (10 mL) was stirred at ambient temperature under argon for 18 hr, followed by stirring at 60° C. for 24 hr. The mixture was concentrated in vacuo, diluted with $H_2O$, and extracted with ethyl acetate. The organic layer was washed with brine, dried over $MgSO_4$, and concentrated in vacuo to give a solid. Chromatography on a C-18 reverse phase column eluting with acetonitrile/$H_2O$ afforded the THP-protected hydroxamate as a white solid (240 mg, 30%).

Part D: To a solution of the THP-protected hydroxamate of Part C (230 mg, 0.422 mmol) in dioxane (5 mL) was added 4 N HCl (1 nmL), and the solution was stirred at ambient temperature under argon for 1 hr. The solution was concentrated in vacuo to give an oil. Chromatography on a C-18 reverse phase column, eluting with acetonitrile/$H_2O$ afforded the titled hydroxamate as a white foam (180 mg, 92%).

Example 20

Preparation of 2-chloro-N-hydroxy-6-[[4-[4-(trifluoromethyl)phenoxy]-1-piperidinyl]sulfonyl]benzamide

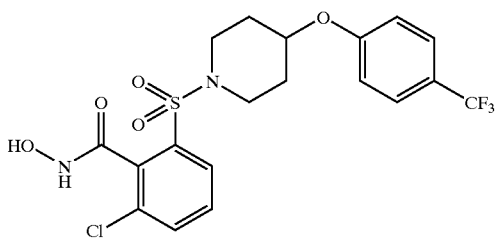

Part A: A solution of the amine of piperidine from Example 13, Part B (as the hydrochloride, 2.00 g, 6.72 mmol), 3-chlorobenzenesulphonyl chloride (1.29 g, 6.11 mmol), triethylamine (2.2 mL, 15.3 mmol), and 4-dimethylaminopyridine (10 mg) in acetonitrile (10 mL) was stirred under argon at ambient temperature for 18 hr. After concentrating the solution, the residue was diluted with $H_2O$ and extracted into ethyl acetate. The organic layer was washed with saturated $NaHSO_4$, $H_2O$, and brine; and dried over $MgSO_4$; and concentrated to an oil. Chromatography (on silica, 20% ethyl acetate/hexane) provided the sulfonamide as a viscous oil (2.44 g, 95%); MS H+ calculated for $C_{18}H_{17}NSO_3F_3Cl$:419, found 419.

Part B: t-Butyl lithium (3.4 mL, 5.7 mmol) was added to a solution of the sulfonamide of Part A (1.2 g, 2.9 mmol) in dry THF (10 mL) at 0° C. The solution was stirred at this temperature for 15 min. Carbon dioxide was bubbled into the reaction mixture for 7 min at 0° C., and then the reaction was stirred for 1.5 hr. Water was added to the solution, which was then acidified to pH=1.0 with 1 N HCl and then concentrated in vacuo to give an oil. Chromatography (on silica, 1% acetic acid/5% methanol/ethyl acetate) provided the acid as a white powder (320 mg, 24%).

Part C: Oxalyl chloride (0.154 mL) was added to a solution of the acid of Part B (410 mg, 0.88 mmol) in methylene chloride (4 mL) at ambient temperature, and the solution was stirred under argon for 1 hr. The solution was concentrated in vacuo to give the acid chloride. To the acid chloride in DMF (5 mL) was added 4-methylmorpholine (0.200 mL, 1.77 mmol), O-tetrahydro-2H-pyran-2-yl-hydroxylamine (155 mg, 1.30 mmol), and the reaction mixture was stirred at ambient temperature under argon for 4 hr. The mixture was diluted with $H_2O$, and extracted with ethyl acetate. The organic layer was washed with brine, dried over $MgSO_4$, and concentrated in vacuo to give an oil. Chromatography on a C-18 reverse phase column eluting with acetonitrile/$H_2O$ afforded the THP-protected hydroxamate as a white foam (260 mg, 52%).

Part D: To a solution of the THP-protected hydroxamate of Part C in dioxane was added 4 N HCl, and the was solution stirred at ambient temperature under argon for 1 hr. The solution was concentrated in vacuo to give a semi-solid. Chromatography (on silica, 60% ethyl acetate/hexane) provided the title compound.

Example 21

Preparation of N-hydroxy-2-[[4-(4-pyridinyloxy)-1-piperidinyl]sulfonyl]benzamide, monohydrochloride

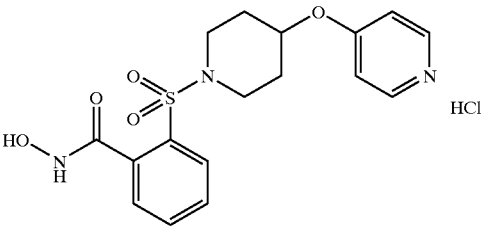

Part A: To a solution of N—BOC-4-hydroxypiperidine (3.00 g, 14.9 mmol) in dimethylsulfoxide (10 mL) are sequentially added 4-chloropyridine hydrochloride (2.35 g, 15.6 mmol) and potassium-t-butoxide (30.5 mL of a 1.0 M solution in tetrahydrofuran, 30.5 mmol). After 16 hr at ambient temperature, the reaction mixture is diluted with diethyl ether (100 mL) and washed with $H_2O$ (3×) and brine, and then dried over sodium sulfate ($Na_2SO_4$). Concentration of the organic solution gives the desired 4-pyridyloxypiperidine (4.24 g, 100%) as a white solid. Analytical calculation for $C_{15}H_{22}N_2O_3$: C 64.73; H, 7.97; N, 10.06. Found: C, 64.48; H, 8.14; N, 9.82.

Part B: A solution of HCl in 1,4-dioxane (20 mL of a 4 N solution, 80 mmol) is added to a solution of pyridyloxypiperidine of Part A (3.81 g, 13.7 mmol) in 1,4-dioxane (28 mL) at ambient temperature. After 1 hr, the suspension is concentrated and the residue triturated with hot isopropanol. The resulting solid is dried at 50° C. under vacuum to afford the desired piperidine hydrochloride salt as a white powder (3.03 g, 88%). Analytical calculation for $C_{10}H_{14}N_2O$, HCl: C, 47.82; H, 6.42; N, 11.15. Found: C, 47.40; H, 6.64; N, 11.04.

Part C: The solid piperidine hydrochloride from Part B.(450 mg, 1.79 mmol) was added to a solution of 2-carboxyethoxy-benzenesulfonyl chloride (580 mg, 2.33 mmol) in acetonitrile (5 mL), followed by the addition of neat triethylamine (0.95 mL, 7.16 mmol) and dimethylaminopyridine (10 mg, 0.08 mmol). Additional acetonitrile (10 mL) was added, along with methylene chloride (3 mL) to aid in dissolution. After 16 hr at ambient temperature, $H_2O$ (100 mL) was added and the mixture is extracted twice with ethyl acetate. The combined organic extracts are washed successively with $H_2O$ (3×) and brine, and then dried over sodium sulfate. Concentration produced a residue (0.49 g) that was chromatographed on silica gel eluting with ethanol/ethyl acetate (4/96) to afford the desired aryl sulfonamide (462 mg, 66%) as a pale yellow foam. Analytical calculation for $C_{19}H_{22}N_2O_5S$-3/4$H_2O$: C, 56.49; H, 5.86; N, 6.93. Found: C, 56.36; H, 5.88; N, 6.68.

Part D: Sodium hydroxide (10 equivalents) is added to a solution of the aryl sulfonamide of Part C in ethanol, $H_2O$, and tetrahydrofuran, and the solution is heated to 60° C. for 24 hr. The solution is cooled, and then diluted with $H_2O$ followed by 10% aqueous HCl to bring the pH to 3. The resulting solution is extracted with ethyl acetate. The organic extracts are combined and washed with $H_2O$ and brine, and dried over sodium sulfate to afford the desired carboxylic acid.

Part E: To a solution of the carboxylic acid of Part D in N,N-dimethylformamide are added 4 methylmorpholine (6.0 equivalents), N-hydroxybenzotriazole (1.2 equivalents), and 1-[3-(dimethylamino)propyl]-3-ethylcarbodiimide hydrochloride (1.3 equivalents), followed by O-(tetrahydro-2H-pyran-2-yl)hydroxylamine (1.3 equivalents). After stirring for 2 days at ambient temperature, the solution is concentrated. Water is added and the mixture is extracted with ethyl acetate. The organic extracts are washed with H$_2$O and brine, and dried over sodium sulfate. Concentration affords a residue that is chromatographed on silica gel eluting with ethyl acetate/hexane (20/80 to 90/10) as eluate to afford the THP-protected hydroxamate derivative.

Part F: To a solution of the THP-protected hydroxamate of Part E in 1,4-dioxane is added 4 N HCl in 1,4-dioxane (10 equivalents), and the solution is permitted to stir at ambient temperature for 3 hr. Concentration gives a residue that is then triturated with diethyl ether to afford the title compound.

Example 22

Preparation of N-hydroxy-2,3-dimethoxy-6-[[4-[(2'-methoxy[1,1'-biphenyl]-4-yl)-oxy-1-piperidinyl]sulfonyl]benzamide

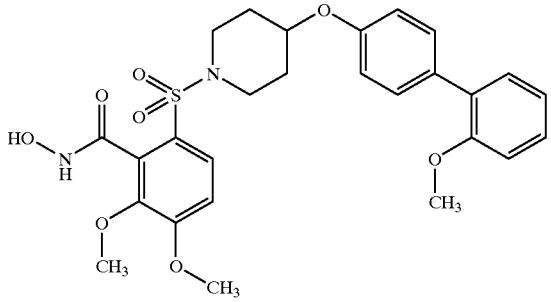

Part A: To a solution of N—BOC-4-hydroxypiperidine (25 mmol, 5.0 g) in 1 methyl-2-pyrrolidinone (20 mL) was added hexane-washed NaH (26 mmol, 1.01 g). The mixture was stirred at ambient temperature for 15 min, and then heated to 65° C. for 30 min. Bromo-4-fluorobenzene (25 mmol, 4.38 g) was added, and the solution was heated at 120° C. for 24 hr. The reaction mixture was permitted to cool to ambient temperature, diluted with H$_2$O (100 mL), and was extracted with ethyl acetate (150 mL). The organic layer was washed with brine (50 mL), dried over MgSO$_4$, and concentrated in vacuo to afford an oil, which was further purified by passage through silica pad, eluting with ethyl acetate. 7.28 g (820–.) were obtained. MS calculated for C$_{16}$H$_{22}$NO$_3$Br: 356, found 356.

Part B: To a solution of the bromide of part A (20 mmol, 7.2 g) in dioxane (20 mL) was added 4N HCl (50 mL). The solution was stirred at ambient temperature for 2 hr and then concentrated to give a solid. The solid was triturated with diethyl ether, affording the desired piperidine hydrochloride (5.8 g 99%).

Part C: To a solution of 3,4dimethoxybenzenesulfonyl chloride (18 mmol, 4.26 g) in acetonitrile (75 mL) was added the hydrochloride from part B (20 mmol, 5.8 g), followed by triethylamine (36 mmol, 7.5 mL) and N,N dimethylaminopyridine (100 mg). The solution was stirred at ambient temperature for 75 hr. The mixture was diluted with H$_2$O (200 mL) and extracted with ethyl acetate (300 mL). The ethyl acetate layer was washed with brine (100 mL), and dried over MgSO$_4$. Concentration followed by chromatography (1:1 hexane:ethyl acetate) provided the desired sulfonamide as a solid (5.45 g, 66%). MS calculated for C$_{19}$H$_{22}$BrNSO$_5$ 456, found 456.

Part D: To a solution of the compound of Part C (2.96 g, 6.49 mmol) in ethylene glycol dimethyl ether (30 mL) at ambient temperature under N$_2$ was added tetrakis(triphenylphosphine)palladium(0) (0.375 g, 0.325 mmol). After stirring for 5 min, 2-methoxyphenylboronic acid (1.18 g, 7.79 mmol) was added, followed by a solution of sodium carbonate (0.954 g, 9.00 mmol) in H$_2$O (18 mL). The mixture was refluxed for 1.5 hr, and then stirred overnight (about 18 hr) at ambient temperature. The mixture was diluted with H$_2$O (50 mL) and extracted with methylene chloride (50 mL). The solution was filtered through a silica bed and concentrated in vacuo to a black solid. Chromatography (on silica, acetone/hexane) provided the biphenyl as a white solid (2.69 g, 86% yield); Anal. calc'd for C$_{26}$H$_{29}$NO$_6$S: C, 64.58; H, 6.04; N, 2.90; S, 6.63. Found: C, 64.30; H, 6.16; N, 2.86; S, 6.90. M S (EI) MH+ calc'd. for C$_{26}$H$_{29}$NO$_6$S 484, found 484.

Part E: To a solution of the biphenyl of Part D (2.85 g, 5.89 mmol) in THF (80 mL) at −80° C. under N$_2$ was added a solution of 1.6 M n-butyllithium in hexane (5.17 25 mL, 8.27 mmol). After stirring at ambient temperature for 30 min, the solution was cooled to −80° C. and CO$_2$ was bubbled into the solution for 7 min. The solution was diluted with 1N HCl (50 mL) and extracted with ethyl acetate (3×50 mL). The organic layer was washed with H$_2$O (2×50 mL) and brine (50 mL), dried with MgSO$_4$, and concentrated in vacuo to provide the carboxylic acid as a tan solid (3.00 g, 96% yield)); Anal. calc'd for C$_{27}$H$_{29}$NO$_8$S: C, 61.47; H, 5.54; N, 2.65; S, 6.08'. Found: C, 61.46; H, 5.94; N, 2.48; S, 5.70. MS (EI) MH+ calc'd. for C$_{27}$H$_{29}$NO$_8$S 528, found 528.

Part F: To a solution of the carboxylic acid of Part E (2.92 g, 5.53 mmol) and DMF (2 drops, catalytic amount) in 1,2-dichloroethane(50 mL) was added oxalyl chloride (4.07 mL, 46.7 mmol). After stirring for 1.5 hr at ambient temperature under N$_2$, the solution was concentrated in vacuo to a yellow oil. To the oil were added N-methylmorpholine (1.57 mL, 14.2 mmol), O-(tetrahydro-2H-pyran-2-yl)hydroxylamine (1.66 g, 14.2 mmol), and 1,2-dichloroethane (19 mL). After stirring for about 20 hr at ambient temperature under N$_2$, the mixture was diluted with H$_2$O (150 mL) and extracted with ethyl acetate (3×50 mL). The organic layer was washed with 1N HCl (50 mL), saturated NaHCO$_3$ (50 mL), H$_2$O (50 mL), and brine (50 mL); dried with MgSO$_4$; and concentrated in vacuo to a tan solid. Chromatography (on silica, ethyl acetate/hexane) provided the 0-protected hydroxamate as a white solid (2.41 g, 69% yield); MS (EI) MH+ calc'd. for C$_{32}$H$_{38}$N$_2$O$_9$S 627, found 627.

Part G: To a solution of acetyl chloride (2.61 mL, 38.1 mmol) in MeOH (39 mL) was added the O-protected hydroxamate of Part F (2.39 g, 3.81 mmol) and stirred at ambient temperature under N$_2$ for 1.5 hr. The solution was concentrated, triturated with ether, concentrated again, and dried to give a white solid. Chromatography (on silica, MeOH/CHCl$_3$) provided the title compound as a white solid (1.36 g, 66% yield). Anal. calc'd for C$_{27}$H$_{30}$N$_2$O$_8$S: C, 59.77; H, 5.57; N, 5.16; S, 5.91. Found: C, 57.60; H, 5.17; N, 5.04; S, 5.67. MS (EI) MH+ calc'd. for C$_{27}$H$_{30}$N$_2$O$_8$S 543

Example 23

Preparation of N-hydroxy-2-(2-methoxyethoxy)-6-[[4-[4-(trifluoromethyl)phenoxy]-1-piperidinyl]sulfonyl]benzamide

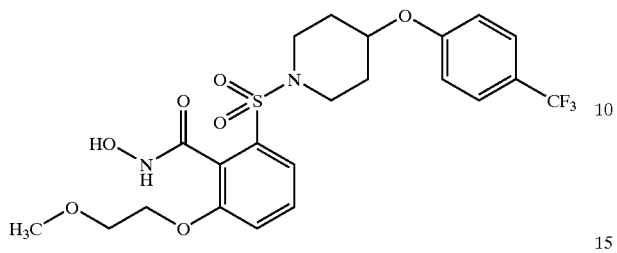

Part A: A solution of 1-[(3-fluorophenyl)-sulfonyl]-4-[4-(trifluoromethyl)phenoxypiperidine (7.00 g, 17.4 mmol), 60% NaH (1.13 g, 28.2 mmol) and 2-methoxy-1-ethanol (2.19 mL, 27.7 mmol) in 1-methyl-2-pyrrolidinone (10 mL) was heated at 120° C. for 5 hr. The solution was diluted with $H_2O$ (300 mL) and extracted with ethyl acetate (3×100 mL). The organic layer was washed with $H_2O$ (2×100 mL) and brine (100 mL), dried with $MgSO_4$, and concentrated in vacuo to a brown paste. Recrystallization from methyl tert-butyl ether/hexane provided the ether as a white solid (6.59 g, 83% yield). The proton NMR spectrum was consistent for the desired ether.

Part B: To a solution of the ether of Part A (6.59 g, 14.3 mmol) in THF (120 mL) at −10° C. under $N_2$ was added a solution of 1.7M t-butyllithium in pentane (16.B mL, 26.8 mmol). After stirring at −60° C. for 30 min, $CO_2$ was bubbled into the solution for 7 min. The resulting solution was poured into a solution of 1N HCl (100 mL) and $H_2O$ (500 mL), and extracted with ethyl acetate (3×100 mL). The organic layer was washed with 1N HCl (100 mL), $H_2O$ (2×100 mL), and brine (100 mL); dried with $MgSO_4$; and concentrated in vacuo. Chromatography (acetic acid/MeOH/$CHCl_3$) provided the carboxylic acid as a yellow oil (4.67 g, 64% yield)); Anal. calc'd for $C_{22}H_{24}NO_7F_3S$: C, 52.48; H, 4.80; N, 2.78; S, 6.37. Found: C, 52.49; H, 4.70; N, 2.69; S, 6.31. MS (EI) MH+ calc'd for $C_{22}H_{24}NO_7F_3S$ 504, found 504.

Part C: To a solution of the carboxylic acid of Part B (5.45 g, 10.8 mmol) and DMF (4 drops, catalytic amount) in dichloromethane (99 mL) was added oxalyl chloride (8.03 mL, 92.0 mmol). After stirring for 2 hr at ambient temperature, the solution was concentrated in vacuo to a dark brown mixture. To the mixture were added N-methylmorpholine (4.76 mL, 43.3 mmol), O-(tetrahydro-2H-pyran-2-yl)hydroxylamine (5.07 g, 43.3 mmol), and dichloromethane (77 mL). After stirring for about 4 hr at ambient temperature, the solution was washed with $H_2O$, 1.0 N HCl, saturated $NaHCO_3$, $H_2O$, and brine; dried with $MgSO_4$; and concentrated in vacuo to a paste. Chromatography (on silica, MeOH/ethyl acetate) provided the O-protected hydroxamate as a pink solid (5.23 g, 80% yield); Anal. calc'd for $C_{27}H_{33}N_2O_8F_3S$: C, 53.81; H, 5.52; N, 4.65; S, 5.32. Found: C, 53.67; H, 5.43; N, 4.77; S, 5.17. MS (EI) MH+ calc'd. $C_{27}H_{33}N_2O_8F_3S$ for 603, found 603.

Part D: A solution of acetyl chloride (5.90 mL, 86.3 mmol) in MeOH (89 mL) was added to the O-protected hydroxamate of Part C (5.20 9, 8.63 mmol) and stirred at ambient temperature for 3 hr. The solution was concentrated, triturated with ether, and concentrated to give an off-white solid. Chromatography (on silica, MeOH/methylene chloride) provided the title compound as a white solid (2.25 g, 50% yield); Anal. calc'd for $C_{22}H_{25}N_2O_7S$: C, 50. 96; H, 4.86; N, 5.40; S, 6.18. Found: C, 50.57; H, 4.91; N, 5.37; S, 6.08.MS (EI) MH+ calc'd. for $C_{22}H_{25}N_2O_7S$ 519, found 519.

Example 24

Preparation of N-hydroxy-2,3-dimethoxy-6-[[4-(phenylthio)-1-piperidinyl]sulfonyl]benzamide

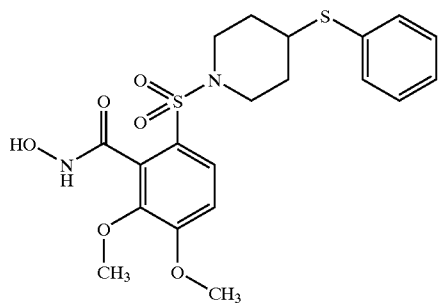

Part A: 4-Hydroxypiperidine (55 mmol, 5.56 g) was diluted with acetonitrile (100 mL), triethylamine (55 mmol, 7.7 mL), and N,N-dimethyl-aminopyridine (500 mg). 3,4-Dimethoxy-benzenesulfonyl chloride (50 mmol, 11.84 g) was added. The mixture was stirred overnight (about 18 hr), and then concentrated by rotary evaporation. The residue was diluted with $H_2O$ (100 mL) and extracted with dichloromethane (2×150 mL). The combined organic phases were dried using $MgSO_4$, filtered through a silica plug, and concentrated to afford the desired alcohol as a foam (7.31 g, 51%).

Part B: The alcohol from Part A (6.39 g, 22.4 mmol) was combined with methylene chloride (65 mL) and triethylamine (3.46 mL, 25 mmol). The solution was chilled to 0° C. Methanesulfonyl chloride (1.79 mL, 23 mmol) was added. The reaction was stirred at ambient temperature for 4 hr, and then diluted to 150 ml with additional methylene chloride, washed with $H_2O$ (2×25 mL). The organic phase was dried over $MgSO_4$, filtered through silica, and concentrated to provide the mesylate as a white solid (3.51 g, 41%).

Part C: 60% NaH in mineral oil (324 mg, 8.1 mmol) was washed with hexanes. The washed hydride was covered with N,N-dimethylformamide (12 mL) and chilled to 0° C. Thiophenol (0.83 mL, 8.1 mmol) was added, and the mixture was stirred for 20 min. Solid mesylate from Part B above, (3.0 g, 7.9 mmol) was added. Mesylate displacement was slow at ambient temperature; the reaction was warmed at 55° C. for 3 hr. Work-up comprised of azeotropic removal of the DMF assisted by toluene, followed by chromatography of the residue, affording 1.45 g (44%) of the sulfide as a white foam.

Part D: The sulfide was dissolved in tetrahydrofuran (24 mL) and cooled to 0° C. T-BuLi (1.7 M in pentane, 4.1 mL) was added over 1 min. After 15 min, the reaction was quenched with $CO_2$ gas. After 10 min, the mixture was acidified using concentrated HCl, concentrated, and chromatographed to give the desired acid as a foam (1.067 g, 70%)

Part E: The acid from Part C was diluted with methylene chloride (15 mL). Three drops of N,N-dimethylformamide were added, followed by oxalyl chloride (0.35, 4 mmol). The reaction was stirred at ambient temperature for 2 hr, and then concentrated. The crude acid chloride was added using about 3 mL of methylene chloride to a mixture of tetrahydropyranhydroxylamine (0.47 g, 4 mmol-), pyridine (0.47 ml, 6 mmol), and acetonitrile (3 mL). The mixture was stirred overnight (about 18 hr), and then subjected to aqueous extraction (50 mL methylene chloride/50 mL H$_2$O). The organic phase was dried over MgSO$_4$, concentrated, and chromatographed to afford the O—THP hydroxamate as a foam (619 mg). The O—THP hydroxamate (614 mg) was diluted with dry methanol (20 mL). Acetyl chloride (0.6 mL, 8 mmol) was added. After 1 hr, the mixture was concentrated and chromatographed, affording the desired hydroxamate as a foam (428 mg, 31%). MS (EI) MH+ calculated for C$_{20}$H$_{24}$N$_2$O$_6$S$_2$: 453, found 453.

Example 25

Preparation of 6-[[4-(butoxy-3-fluorophenyl)-1-piperazinyl]sulfonyl]-N-hydroxy-2,3-dimethoxybenzamide

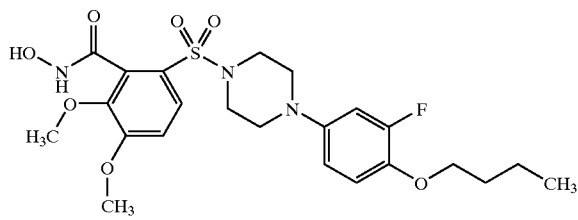

Part A: 4-bromo-2-fluoro-phenol (19.1 g; 100 mmol), cesium carbonate (39.1 g; 120 mmol), tetrabutylammonium iodide (900 mg), and bromobutane (12.8 mL; 120 mmol) were suspended in N-methylpyrrolidinone (20 mL) and warmed to 85° C. During the course of reaction, an additional 20 mL of N-methylpyrrolidinone was added to facilitate stirring. After 2 hr, the mixture was allowed to cool, diluted with water (400 mL), and extracted with 1:1 hexane:ethyl acetate (400 mL; then 100 mL). The combined organic phases were dried over magnesium sulfate, filtered through a silica plug, and concentrated to afford the desired aryl ether as an oil (23.72 g; 96%). The product was characterized by nuclear magnetic resonance.

Part B: The aryl ether from Part A (23.75 g; 96 mmol) was combined with t-butoxycarbonylpiperazine (21.39 g; 115 mmol), rac-2,2'-bis(diphenylphosphino)-1,1'binaphthyl (2.36 g; 3.8 mmol), sodium t-butoxide (12.0 g; 125 mmol), 1,4-dioxane (75 mL), and tris(dibenzylideneacetone) dipalladium (0) (1.10 g; 1.2 mmol). The stirred mixture was lowered into an oil bath set to 50° C., and the temperature of the bath was raised over about 30 min to 100° C. At that point, thin layer chromatography indicated that the reaction was complete. The mixture was allowed to cool, and then diluted with water (500 mL) and extracted with dichloromethane (2×300 mL). The combined organic layers were dried using magnesium sulfate. Filtration through a silica plug followed by concentration afforded the desired aryl BOC piperazine as a dark oil (33.8 g, 95%) which was carried directly into the next step. The product was characterized by nuclear magnetic resonance.

Part C: The aryl BOC piperazine from Part B was diluted with dry methanol (700 mL). Acetyl chloride (17 mL) was added over 10 min. The solution was warmed to reflux. After 1 hr, the reaction was allowed to cool to ambient temperature. The reaction was poured into dry ether (1.6 L). The desired aryl piperazine dihydrochloride precipitate was collected by filtration and dried in vacuo, affording 26.23 g of white crystalline product (81%). Elemental anal. calc'd. for C$_{14}$H$_{21}$FN$_2$O (2HCl): C, 51.65; H, 7.07: N, 8.61. Found: C, 51.89; H, 7.03: N, 8.52.

Part D: The aryl piperazine from Part C (1.63 g 5 mmol) was diluted with triethylamine (2.24 mL; 16 mmol) and acetonitrile (50 mL). N,N-4-dimethylaminopyridine (50 mg) was added, followed by 3,4-dimethoxybenzenesulfonylchloride (1.165 g; 4.9 mmol). The mixture was stirred for 2.5 hr at ambient temperature, and was then concentrated. The residue was diluted with water (100 mL) and extracted with ethyl acetate (100, then 50 mL). The combined organic layers were dried over magnesium sulfate, filtered through silica, and concentrated to afford the desired aryl sulfonamide (2.03 g; 92%) as a white solid.

Part E: The aryl sulfonamide (1.34 g; 2.96 mmol) from Part D was dissolved in dry tetrahydrofuran (30 mL) and cooled to 0° C. t-BuLi (1.7 M in pentane; 3.53 mL, 6 mmol) was added, dropwise. After 15 min, excess CO$_2$ gas was bubbled through the reaction mixture. Hydrogen chloride (conc. aq., ca. 1 mL) was added. The mixture was then concentrated and subjected to silica gel chromatography. The desired carboxylic acid was obtained as a dark foam (462 mg; 31%).

Part F: The carboxylic acid from Part E (460 mg; 0.93 mmol) was dissolved in methylene chloride (5 mL). N,N-dimethylformamide (ca. 3 drops) and oxalyl chloride (0.18 mL; 2 mmol) were added. After 1.5 hr, the solvent was removed, and the acid chloride was dried in vacuo. The acid chloride was transferred into a solution of O-(tetrahydro-2H-pyran-2yl)hydroxylamine (234 mg; 2 mmol) and pyridine (0.2 mL; 2.5 mmol) in acetonitrile (5 mL) using a minimum of methylene chloride (ca. 3 mL). The reaction was stirred 16 hr, diluted with water (50 mL), and extracted with ethyl acetate (2×50 mL). The combined organic phase was dried over magnesium sulfate, concentrated, and chromatographed to afford the THP-hydroxamate as a white foam (320 mg; 59%).

Part G: The THP-hydroxamate from Part F (310 mg; 0.52 mmol) was diluted with methanol (20 mL). Acetyl chloride (0.5) was added. After 30 min, the reaction was concentrated and the residue was subjected to column chromatography (ethyl acetate: 5% NH$_4$OH), affording the title aryl hydroxamate as a white foam (171 mg; 63%). MS MH$^+$ calc'd. for C$_{23}$H$_{30}$FN$_3$O$_7$S 512, found 512.

Example 26

Preparation of N-hydroxy-2,3-dimethoxy-6-[[4-(4-trifluoromethoxy)phenyl]-1-piperazinyl]sulfonyl]benzamide

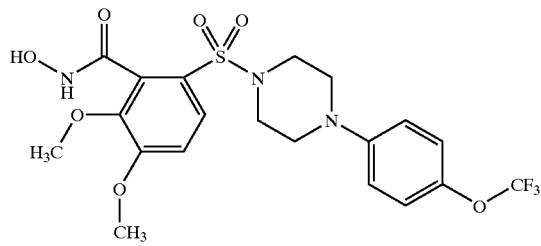

Part A: To a mixture of 1-tert-butoxycarbonylpiperazine (3.00 g, 16.1 mmol), 1-bromo-4-(trifluoromethoxy)benzene (3.23 g, 13.4 mmol), sodium tert-butoxide (1.80 g, 18.8 mmol), and rac-2,2'-bis(diphenylphosphino)-1,1'binaphthyl (0.250 g, 0.402 mmol) in 1,4-dioxane (29 mL) was added tris(dibenzylideneacetone)dipalladium (0) (0.123 g, 0.134 mmol). After 1.5 hr of heating at 83° C., the mixture was cooled to ambient temperature, diluted with water (300 mL), and extracted with ethyl acetate (3×100 mL). The organic layer was washed with water (100 mL) and brine (100 mL), dried over magnesium sulfate, concentrated in vacuo, and purified by medium pressure chromatography (ethyl acetate/ hexane) to afford the BOC-protected piperazine as an off white solid (4.72 g, 102% yield). MS MH$^+$ calc'd. for $C_{16}H_{21}N_2O_3F_3$ 347, found 347. Anal. Calc'd. for $C_{16}H_{21}N_2O_3F_3$: C, 55.49; H, 6.11: N, 8.09. Found: C, 55.52; H. 6.01: N, 8.06.

Part B: To a solution of the BOC-protected piperazine of Part A (4.62 g, 13.3 mmol) in methanol (26 mL) was added a solution of acetyl chloride (4.56 mL, 66.7 mmol) in methanol (26 mL). After stirring at ambient temperature for 4 hr, the mixture was poured into diethyl ether (600 ml). The solid was collected by filtration and dried in a 50° C. vacuum oven to give the piperazine hydrochloride salt as a white solid (3.75 g, 88% yield). MS MH$^+$ calc'd. for $C_{11}H_{13}N_2OF_3$ 247, found 247.

Part C: The aryl piperazine from Part B (2.23 g; 7 mmol) was diluted with triethylamine (3.5 mL; 25 mmol) and acetonitrile (100 mL). N,N-4-dimethylaminopyridine (100 mg) was added, followed by 3,4-dimethoxybenzenesulfonylchloride (1.63 g; 6.9 mmol). The mixture was stirred for 4 hr at ambient temperature, and then concentrated. The residue was diluted with water (50 mL) and extracted with ethyl acetate (2×100 mL). The combined organic layers were dried over magnesium sulfate, filtered through silica, and concentrated to afford the desired aryl sulfonamide (2.78 g; 90%) as a white solid. The structure was verified by nuclear magnetic resonance.

Part D: The aryl sulfonamide (1.15 g; 2.58 mmol) from Part C was dissolved in dry tetrahydrofuran (20 mL) and cooled to 0° C. t-BuLi (1.7 M in pentane; 2.9 mL; 5 mmol) was added, dropwise. After 15 min, excess CO$_2$ gas was bubbled through the reaction mixture. Hydrogen chloride (conc. aq., ca. 1 mL) was added. The mixture was concentrated and subjected to silica gel chromatography (ethyl acetate: 5% NH$_4$OH). The desired carboxylic acid was obtained as a dark foam (1.59 g; ~quant.)

Part E: The carboxylic acid from Part D (1.59 g; ~2.6 mmol) was dissolved in methylene chloride (20 mL). N,N-dimethylformamide (ca. 3 drops) and oxalyl chloride (0.46 mL; 5.2 mmol) were added. After 1.5 hr, the solvent was removed, and the acid chloride was dried in vacuo. The acid chloride was transferred into a solution of O-(tetrahydro-2H-pyran-2-yl)hydroxylamine (351 mg; 3 mmol) and pyridine (0.48; 6 mmol) in acetonitrile (3 mL) using a minimum of methylene chloride (ca. 3 mL). The reaction was stirred 16 hr, diluted with water (100 mL); and extracted with ethyl acetate (2×100). The combined organic phase was dried over magnesium sulfate and concentrated. The residue was purified by chromatography, affording THP-hydroxamate as a white foam (419 mg; 28%).

Part F: The THP-hydroxamate from Part E (418 mg; 0.73 mmol) was diluted with methanol (50 mL). Acetyl chloride (1 mL) was added. After 30 min, the reaction was concentrated and the residue was subjected to column chromatography (ethyl acetate: 5% NH$_4$OH), affording the title aryl hydroxamate as a white foam (296 mg; 78%). MS MH$^+$ calc'd. for $C_{20}H_{22}F_3N_3O_7S$ 506, found 506.

The following analogs were made in good yield using procedures similar to those above:

Example 27

6-[[4-[(3'-dimethoxy[1,1'-biphenyl]-4-yl)-1-piperidinyl]sulfonyl]-N-hydroxy-2,3-dimethoxybenzamide

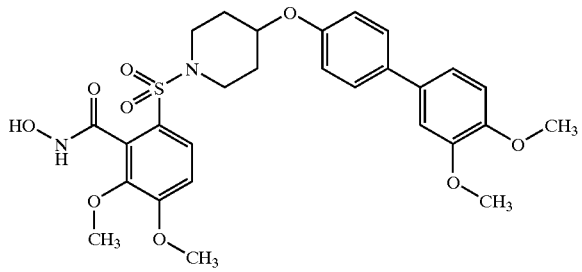

MS (EI) MH+ calculated for $C_{28}H_{32}N_2O_9S$: 573, found 573.

Example 28

N-hydroxy-2,3-dimethoxy-6-[[4-[4-(trifluoromethyl) phenyl]-1-piperazinyl]sulfonyl]benzamide

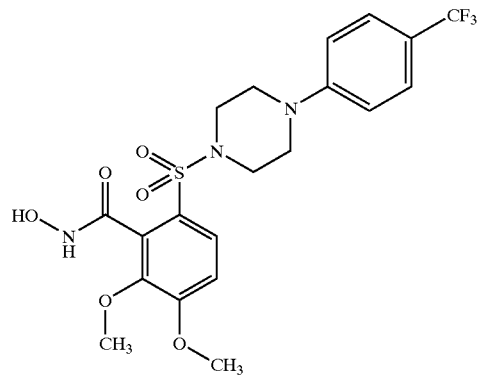

MS (EI) calculated for $C_{20}H_{22}F_3N_3O_6S$: 490, found 490.

Example 29

N-Hydroxyl-2,3-dimethoxy-6-[[4-[[3'-(trifluoromethyl)[1,1'-biphenyl]-4-yl]oxy]-1-piperidinyl]sulfonyl]benzamide

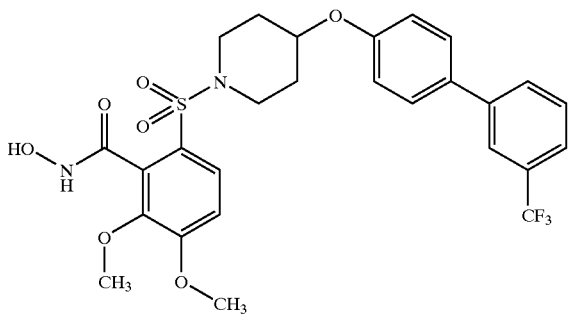

MS (EI) calculated for $C_{27}H_{27}F_3N_2O_7S$: 581, found 581.

Example 30

6-[[4-(1,1'-biphenyl]-4-yloxy)-1-piperidinyl]sulfonyl]-N-hydroxy-2,3-dimethoxybenzamide

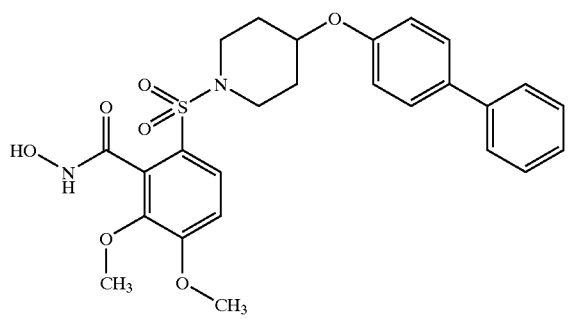

Example 31

2-[[4-(2,3-dihydro-2-oxo-1H-benzimidazol-1-yl)-1-piperidinyl]sulfonyl]-N-hydroxybenzamide

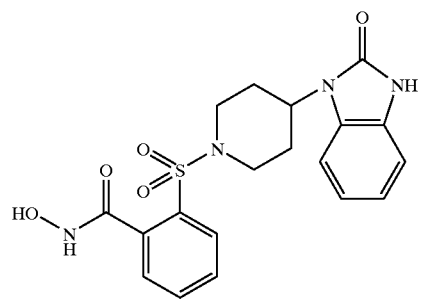

MS (EI) calculated for $C_{19}H_{20}N_4O_5S$: 417, found 417.

Example 32

2,3-dihydro-N-hydroxy-6-[(4-methoxy-1-piperidinyl)sulfonyl]-1,4-benzodioxin-5-carboxamide

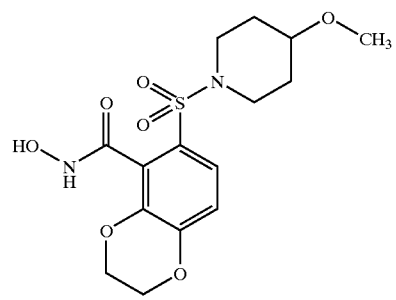

MS (EI) calculated for $C_{15}H_{20}N_2O_7S$: 372, found 373.

Example 33

2,3-dihydro-N-hydroxy-6-[[4-[4-(trifluoromethyl)phenoxy-1-piperidinyl]sulfonyl-1,4-benzodioxin-5-carboxamide

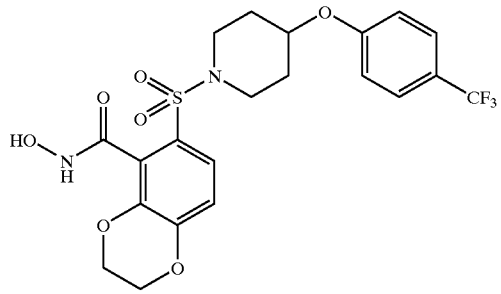

MS (EI) calculated for $C_{21}H_{21}F_3N_2O_7S$: 502, found 503.

Example 34

2,5-dichloro-N-hydroxy-4-[[4-(4-(trifluoromethyl)phenoxy]-1-piperidinyl]sulfonyl]-3-thiophenecarboxamide

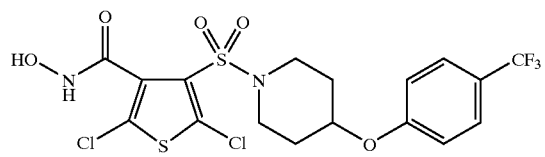

Example 35

N-hydroxy-2,3-dimethoxy-6-[[4-[4-(trifluoromethoxy)phenoxy]-1-piperinyl]sulfonylbenzamide

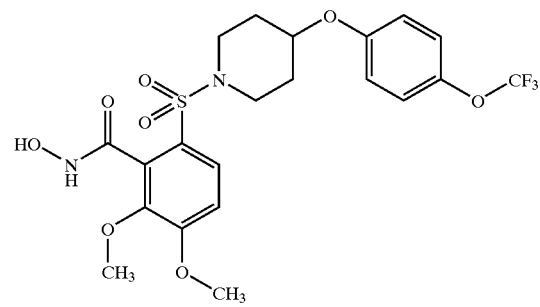

Example 36

N-Hydroxy-2,3-dimethoxy-6-[[4-(2-methoxyphenoxy)-1-piperidinyl]-sulfonyl]benzamide

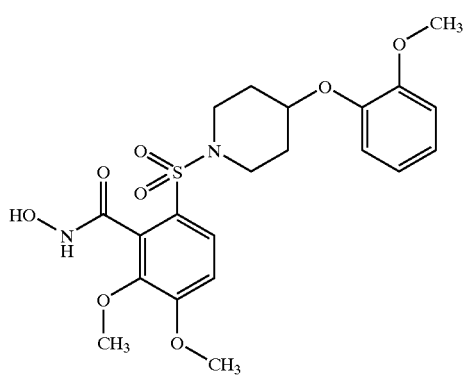

Anal. Calc'd for $C_{21}H_{16}N_2O_8S$: C, 50.07; H, 5.62; N, 6.00. Found: C, 53.77; H, 5.64; N, 5.79.

Example 37

N-Hydroxy-3,6-dimethoxy-2-[[4-(trifluoromethyl)phenoxy]-1-piperidinyl]sulfonyl]benzamide

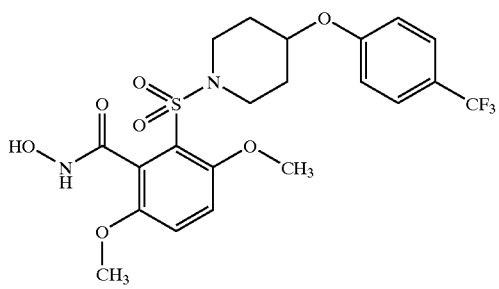

Example 38

N-Hydroxyl-5-[[4-[4-(trifluoromethyl)-phenoxy-1-piperidinyl]sulfonyl-1,3-benzodioxole-4-carboxamide

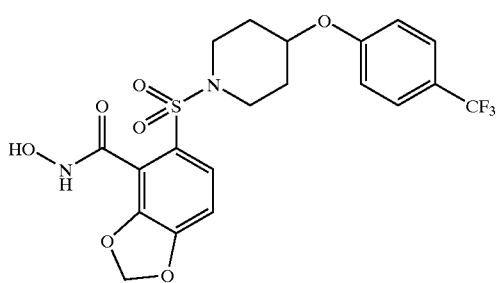

MS (EI) calculated for $C_{20}H_{19}F_3N_2O_7S$: 489, found 489.

Example 39

6-[[4-[(2', 5'-dimethoxy[1,1'-biphenyl]-4-yl)oxy]-1-piperidinyl]sulfonyl]-N-hydroxy-2,3-dimethoxybenzamide

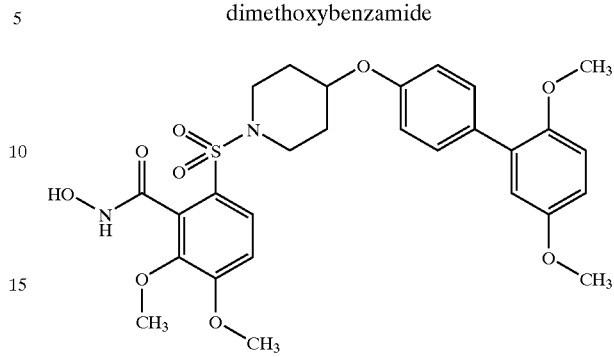

Anal. calc'd for $C_{28}H_{32}N_2O_9S$: C, 58.73; H, 5.63; N, 4.89. Found: C, 58.55; H, 5.82; N, 4.81.

Example 40

N-Hydroxy-2,3-dimethoxy-6-[[4-[[2'-(trifluoromethyl)[1,1'-biphenyl]-4-yl]oxy]-1-piperidinyl]sulfonyl]benzamide

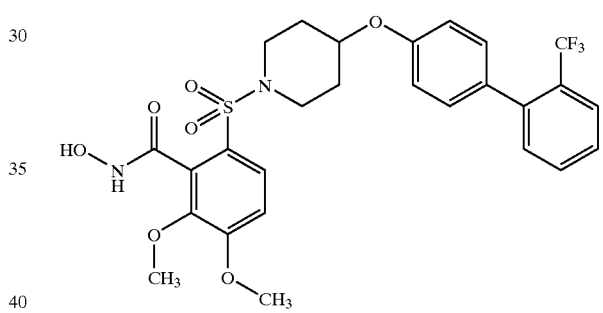

Anal. calc'd for $C_{27}H_{27}F_3N_2O_7S$: C, 55.86; H, 4.69; N, 4.83. Found: C, 55.77; H, 4.75; N, 4.77.

Example 41

N-Hydroxy-2,3-dimethoxy-6-[[4-[[2'-(trifluoromethyl)[1,1'-biphenyl]-4-yl]-1-piperidinyl]sulfonyl]benzamide

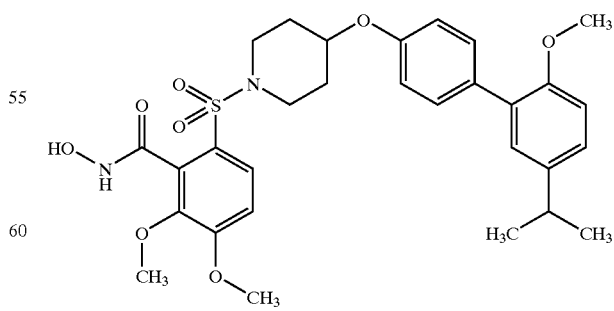

Anal. calc'd for $C_{30}H_{36}N_2O_8S$: C, 61.63; H, 6.21; N, 4.79. Found: C, 61.36; H, 6.29; N, 4.64.

Example 42

6-[[4-[(2'-ethoxy[1,1-biphenyl]-4-yl)oxy-1-piperidinyl]sulfonyl]-N-hydroxyl-2,3-dimethoxybenzamide

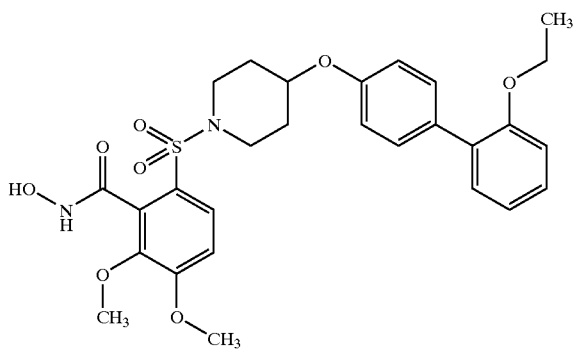

Anal. calc'd for $C_{28}H_{32}N_2O_8S$: C,60.42; H,5.79; N, 5.03. Found: C, 60.30; H, 5.94; N, 4.88.

Example 43

N-hydroxy-2,3-dimethoxy-6-[[4-(4-methoxyphenyl)-1-piperazinyl]sulfonyl]-benzamide, monohydrochloride

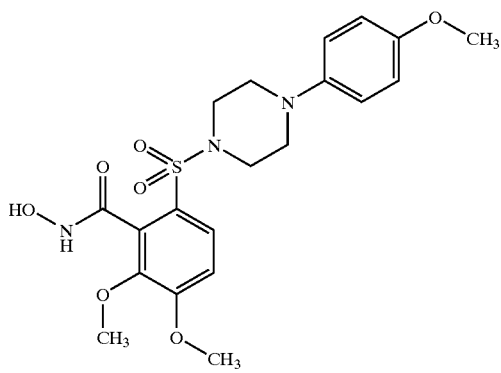

MS (EI) MH+ calc'd for $C_{20}H_{25}N_3O_7S$ (free base): 452, found 452.

Example 44

N-hydroxyl-2-[[4-(2-pyridinyloxy)-1-piperidinyl]sulfonyl]benzamide, monohydrochloride

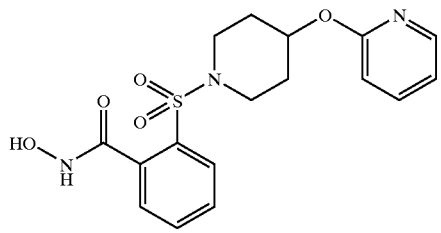

MS (EI) MH+ calculated for $C_{17}H_{19}N_3O_7S$ (free base) 378, found 378.

Example 45

5-[(4-butoxy-1-piperidinyl)sulfonyl]-N-hydroxy-1,3-benzodioxole-4-carboxamide

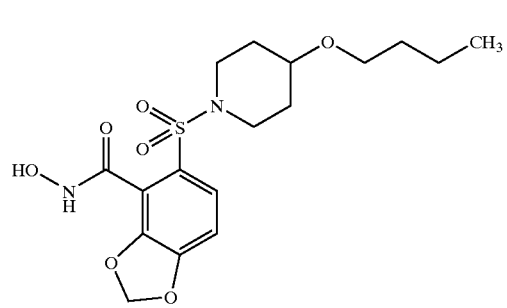

Anal. calc'd for $C_{17}H_{24}N_2O_7S$: C, 50.99; H,6.04; N, 7.00. Found: C, 50.97; H, 6.27; N, 6.88.

Example 46

5-[(4-heptyloxy-1-piperidinyl)sulfonyl]-N-hydroxy-1,3-benzodioxole-4-carboxamide

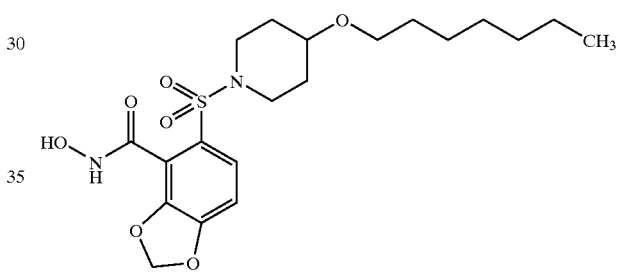

Anal. calc'd for $C_{20}H_{30}N_2O_7S$: C,54.28; H,6.33; N, 6.33. Found: C,53.91; H, 7.10; N, 6.25.

Example 47

N-Hydroxy-2,3-dimethoxy-6-[[4-(4-methoxyphenoxy-1-piperidinyl]-sulfonyl]benzamide

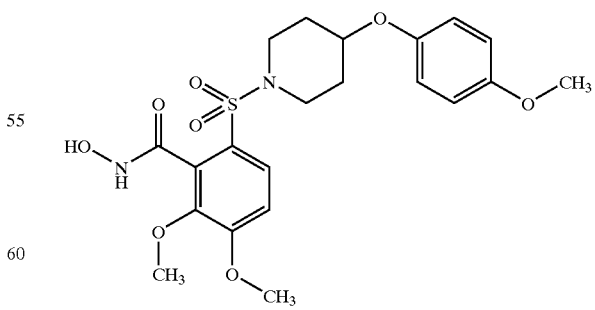

Anal. calc'd for $C_{21}H_{26}N_2O_8S$: C, 54.07; H, 5.62; N, 6.00. Found: C, 53.69; H, 5.87; N, 5.79.

Example 48

6-[[4-(4-chlorophenoxy)-1-piperidinyl]-sulfonyl]-N-hydroxy-2,3-dimethoxybenzamide

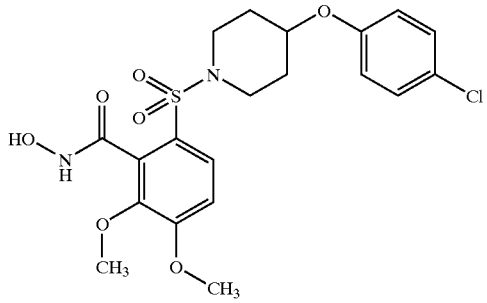

Anal. calc'd for $C_{20}H_{23}ClN_2O_8S$: C,51.01; H, 4.92; N, 5.95. Found: C, 50.62; H, 4.93; N, 5.92.

Example 49

N-hydroxy-2,3-dimethoxy-G-[(4-phenoxy-1-piperidinyl)sulfonyl]benzamide

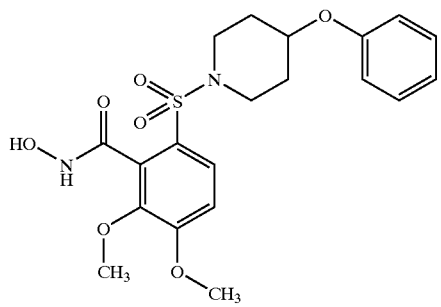

MS (EI) calculated for $C_{20}H_{24}N_2O_7S$: 436, found 437.

Example 50

N-hydroxy-2-[(tetrahydro-2H-pyran-4-yl)oxy]-6-[[4-(trifluoromethyl)phenoxy]-1-piperidinyl]sulfonyl]benzamide

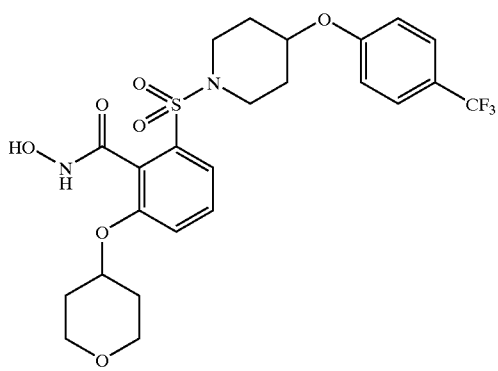

Anal. calc'd for $C_{24}H_{27}F_3N_2O_7S$: C, 52.94; H, 5.00; N, 5.14. Found: C,52.64; H, 4.92; N, 5.02.

Example 51

5-[[4-((1,3-benzodioxol]-5-yloxy)-1-piperidinyl]sulfonyl]-N-hydroxy-1,3-benzodioxole-4-carboxamide

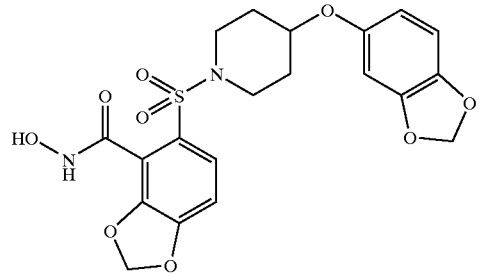

Example 52

6-[[4-(1,3-benzodioxole-5-yloxy)-1-piperinyl]sulfonyl]-N-hydroxy-2,3-dimethoxybenzamide

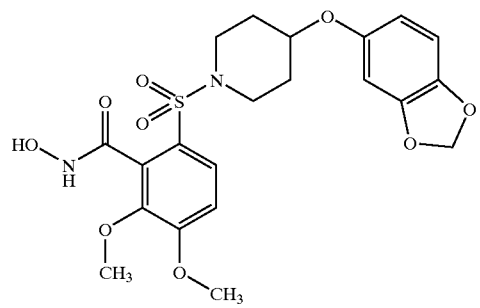

MS (EI) calculated for $C_{21}H_{24}N_2O_9S$:481, found 481.

Example 53

2-[(4-benzoyl-1-piperazinyl)sulfonyl]-N-hydroxybenzamide

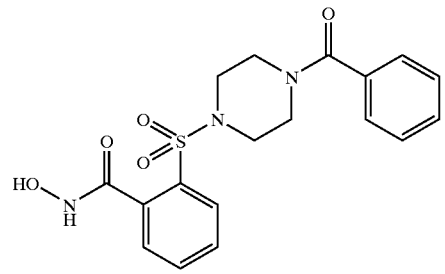

MS (EI) MH+ calculated for $C_{18}H_{19}N_3O_5S$: 390, found 390.

Example 54

N-hydroxy-2,3-dimethoxy-6-[[4-(phenylmethyl)-1-piperazinyl]sulfonyl]benzamide, monohydrochloride

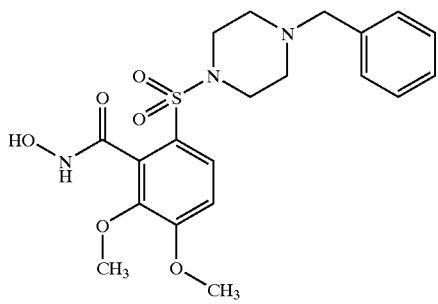

MS (EI) MH+ calculated for $C_{20}H_{25}N_3O_6S$ (free base) 436, found 436.

Example 55

N-hydroxy-2,3-dimethoxy-6-[[4-[[4-(trifluoromethoxy)phenyl]methyl]-1-piperazinyl]sulfonyl]benzamide, monohydrochloride

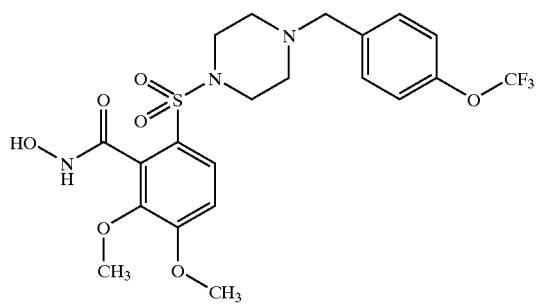

MS (EI) MH+ calculated for $C_{21}H_{24}F_3N_3O_7S$: 520, found 520.

Example 56

6-[[4-(4-butoxyphenoxy)-1-piperidinyl]-sulfonyl]-N-hydroxy-2,3-dimethoxybenzamide

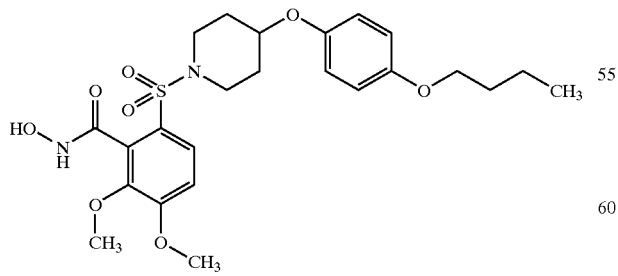

MS (EI) MH+ calculated for $C_{24}H_{32}N_2O_8S$: 509, found 509.

Example 57

N-Hydroxy-2-[[4-(4-pyridinyloxy)-1-piperidinyl]sulfonyl]benzamide, monohydrochloride

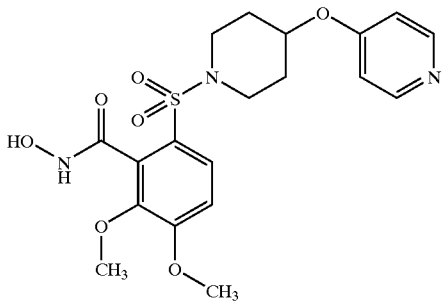

MS (EI) MH+ calculated for $C_{17}H_{19}N_3O_5S$ (free base): 378, found 378.

Example 58

6-[[4-(4-butoxy-3-methylphenyl)-1-piperazinyl]sulfonyl]-N-hydroxy-2,3-dimethoxybenzamide, monohydrochloride

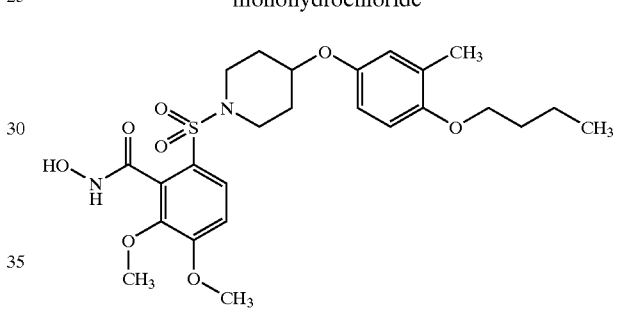

MS (EI) MH+ calculated for $C_{24}H_{33}N_3O_7S$ (free base): 508, found 508.

Example 59

N-hydroxy-2,3-dimethoxy-6-[[4-(3-methoxyphenoxy-1-piperidinyl]sulfonyl]benzamide

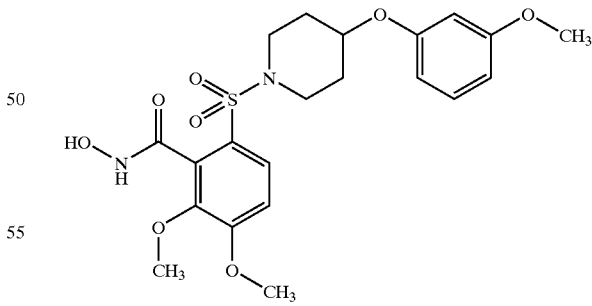

Anal. calc'd for C21H26N2O8S: C, 54.07; H, 5.62; N, 6.00. Found: C, 53.77; H, 5.64; N, 5.79.

Example 60

In Vitro MMP Inhibition

Several hydroxamates and salts thereof were assayed for MMP inhibition activity by an in vitro assay generally following the procedures outlined in Knight et al., *FEBS Lett.*, 296(3), 263 (1002).

Recombinant human MMP-1, MMP-2, MMP-3, MMP-8, MMP-9, MMP-13, and MMP-14 were used in this assay. These enzymes were prepared in the Assignee's laboratories following usual laboratory procedures. Specifics for preparing and using these enzymes can be found in the scientific literature describing these enzymes. See, e.g., *Enzyme Nomenclature* (Academic Press, San Diego, Calif., 1992) (and the citations therein). See also, Frije et al., *J Biol. Chem.*, 26(24), 16766–73 (1994).

The MMP-1 was obtained from MMP-1 expressing transfected HT-1080 cells provided by Dr. Harold Welgus of Washington University in St. Louis, Mo. The MMP-1 was activated using 4-aminophenylmercuric acetate (APMA), and then purified over a hydroxamic acid column.

The MMP-2 was obtained from MMP-2 expressing transfected cells provided by Dr. Gregory Goldberg of Washington University.

The MMP-9 was obtained from MMP-9 expressing transfected cells provided by Dr. Gregory Goldberd.

The MMP-13 was obtained as a proenzyme from a full-length cDNA clone using baculovirus, as described by V. A. Luckow, "Insect Cell Expression Technology," *Protein Engineering: Principles and Practice*, pp. 183–218 (edited by J. L. Cleland et al., Wiley-Liss, Inc., 1996). The expressed proenzyme was first purified over a heparin agarose column, and then over a chelating zinc chloride column. The proenzyme was then activated by APMA for use in the assay. Further details on baculovirus expression systems may be found in, for example, Luckow et al., *J Virol.*, 67, 4566–79 (1993). See also, O'Reilly et al, *Baculovirus Expression Vectors: A Laboratory Manual* (W. H. Freeman and Co., New York, N.Y., 1992). See also, King et al., *The Baculovirus Expression System: A Laboratory Guide* (Chapman & Hall, London, England, 1992).

The enzyme substrate was a methoxycoumarin-containing polypeptide having the following sequence:

MCA-ProLeuGlyLeuDpaAlaArgNH$_2$

Here, "MCA" is methoxycoumarin and "Dpa" is 3-(2,4-dinitrophenyl)-L-2,3-diaminopropionyl alanine. This substrate is commercially available from Baychem (Redwood City, Calif.) as product M-1895.

The subject hydroxamate (or salt thereof) was dissolved at various concentrations using 1% dimethyl sulfoxide (DMSO) in a buffer containing 100 mM Tris-HCl, 100 mM NaCl, 10 mM CaCl$_2$, and 0.05% polyethyleneglycol (23) lauryl ether at a pH of 7.5. These solutions were then compared to a control (which contained an equal amount of DMSO/buffer solution, but no hydroxamate compound) using Microfluor™ White Plates (Dynatech, Chantilly, Va.). More specifically, the MMPs were activated with APMA or trypsin. Then the various hydroxamate/DMSO/buffer solutions and control solutions were introduced into separate plates at room temperature with the activated MMP. After 10 minutes, 4 um of the MMP substrate was added to each plate. The plates were then incubated for 5 minutes at room temperature. In the absence of inhibitor activity, a fluorogenic peptide was cleaved at the gly-leu peptide bond of the substrate, separating the highly fluorogenic peptide from a 2,4-dinitrophenyl quencher, resulting in an increase of fluorescent intensity (excitation at 328 nm/emission at 415). Inhibition was measured as a reduction in fluorescent intensity as a function of inhibitor concentration using a Perkin Elmer (Norwalk, Conn.) L550 plate reader. The IC$_{50}$'s were then calculated from these measurements. The results are set forth in the following Tables A and B.

Inhibition Table A
(IC$_{50}$ values in nM)

| Example # | MMP-1 | MMP-2 | MMP-13 |
|---|---|---|---|
| 1 | >10,000 | 10 | 45 |
| 2 | 900 | 0.3 | 2 |
| 3 | >10,000 | 148 | 1,000 |
| 4 | >10,000 | >10,000 | >10,000 |
| 5 | >10,000 | 3500 | >10,000 |
| 6 | >10,000 | — | 4,000 |
| 7 | >10,000 | — | >10,000 |
| 8 | >10,000 | — | >10,000 |
| 9 | >10,000 | 45.0 | 1,500 |
| 10 | >10,000 | 70.0 | 520 |
| 11 | >10,000 | 2,300 | 2,200 |
| 12 | >10,000 | 2.2 | 33.0 |
| 13D | >10,000 | 3,300 | 3,800 |
| 13 | >10,000 | 1.3 | 28.5 |
| 14 | >10,000 | 35 | 900 |
| 15 | >10,000 | 3,500 | 9,000 |
| 16 | >10,000 | 2.4 | 2.7 |
| 17 | >10,000 | 1,800 | 2,000 |
| 18 | — | — | — |
| 19 | >10,000 | 5.0 | 12.3 |
| 20 | >10,000 | 1.8 | 14.8 |
| 21 | >10,000 | 5.9 | 63 |

Inhibition Table B
(IC50 Values in nM)

| Example | MMP-1 | MMP-2 | MMP-3 | MMP-8 | MMP-9 | MMP-13 | MMP-14 |
|---|---|---|---|---|---|---|---|
| 22 | >10,000 | 15.5 | 170 | 800 | 300 | 5.5 | 2,500 |
| 23 | >10,000 | 1.0 | | | | 4.3 | |
| 24 | >10,000 | 0.9 | 400 | 107 | 10.0 | 3.0 | 25.4 |
| 25 | >10,000 | 0.4 | 294 | 252 | 22.1 | 8.5 | >10,000 |
| 26 | >10,000 | 0.4 | 1460 | 7.1 | 40.1 | 17.9 | 416 |
| 27 | >10,000 | 3.3 | 100 | 115 | 370 | 2.6 | 1,700 |
| 28 | >10,000 | 6.5 | 1,750 | 37.2 | 970 | 40 | 1,920 |
| 29 | >10,000 | 3.3 | 300 | 210 | 520 | 3.0 | 690 |
| 30 | >10,000 | 0.4 | | | | 1.8 | |
| 31 | >10,000 | 370 | | | | 2,000 | |
| 32 | >10,000 | >10,000 | | | | >10,000 | |
| 33 | >10,000 | 1.4 | | | | 7.7 | |
| 34 | >10,000 | 110 | | | | 730 | |
| 35 | >10,000 | 0.9 | 100 | | 1.5 | 5.0 | 360 |
| 36 | >10,000 | 330 | | | | 2,500 | |
| 37 | >10,000 | 21 | | | | 110 | |
| 38 | >10,000 | 3.0 | 600 | 12.2 | 8.0 | 18.0 | 300 |
| 39 | — | — | | | | — | |
| 40 | | 20 | | 1,700 | | 82 | |
| 41 | | 120 | | 400 | | 100 | |
| 42 | | 80 | | 4,400 | | 50 | |
| 43 | >10,000 | 6.0 | 8,000 | 120 | 470 | 100 | 4,000 |
| 44 | >10,000 | 42 | | | | 1,200 | |
| 45 | >10,000 | 200 | | | | 3,700 | |
| 46 | >10,000 | 206 | | | | 330 | |
| 47 | >10,000 | 1.8 | 900 | 11.4 | 3.0 | 13.9 | 300 |
| 48 | >10,000 | 0.3 | | | | 1.5 | |
| 49 | >10,000 | 1.1 | | | | 6.7 | |
| 50 | >10,000 | 1.0 | | | | 2.2 | |
| 51 | >10,000 | 1.1 | | | | 19 | |
| 52 | >10,000 | 1.1 | 1,300 | 12.2 | 9.0 | 18.6 | 270 |
| 53 | >10,000 | 1,000 | | | | 6,700 | |
| 54 | | 1,500 | | >10,000 | | 4,000 | |
| 55 | >10,000 | 240 | | | | 1,900 | |
| 56 | >10,000 | 0.8 | 31.6 | 70.0 | 2.0 | 1.6 | 200 |
| 57 | >10,000 | 5.9 | | | | 63 | |

-continued

Inhibition Table B
(IC50 Values in nM)

| Example | MMP-1 | MMP-2 | MMP-3 | MMP-8 | MMP-9 | MMP-13 | MMP-14 |
|---|---|---|---|---|---|---|---|
| 58 | >10,000 | 9.0 | | | | 20.0 | |
| 59 | >10,000 | 12.1 | | | | 250 | |

Example 61

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, Kenyon, B M, et al., "A Model of Angiogenesis in the Mouse Cornea," *Investigative Ophthalmology & Visual Science*, Vol. 37, No. 8 (July 1996).

In this assay, uniformly sized Hydron™ pellets containing BFGF and sucralfate are prepared and surgically implanted into the stroma mouse corneal adjacent to the temporal limbus. The pellets are formed by making a suspension of 20 $\mu$L sterile saline containing 10 $\mu$g recombinant bFGF, 10 mg of sucralfate and 10 $\mu$L of 12% Hydron™ in ethanol. The slurry is then deposited on a 10×10 mm piece of sterile nylon mesh. After drying, the nylon fibers of the mesh are separated to release the pellets.

The corneal pocket is made by anesthetizing a 7 week old C57B1/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet is placed on the corneal surface at the base of the pocket with a jeweler's forceps. The pellet is then advanced to the temporal end of the pocket. Antibiotic ointment is then applied to the eye.

Mice are dosed on a daily basis for the duration of the assay. Dosing of the animals is based on bioavailability and overall potency of the compound. An exemplary dose is 50 mg/kg bid, po. Neovascularization of the corneal stroma begins at about day 3, and is permitted to continue under the influence of the assayed compound until day 5. At day 5, the degree of angiogenic inhibition is scored by viewing the neovascular progression with a slit lamp microscope.

The mice are anesthetized and the studied eye is once again proposed. The maximum vessel length of neovascularization, extending from the limbal vascular plexus toward the pellet is measured. In addition, the contiguous circumferential zone of neovascularization is measured as clock hr, where 30 degrees of arc equals 1 clock hr. The area of angiogenesis is calculated as follows.

area(0.4×clock *hr*×3.14×vessel length (in *mm*))

The studied mice are thereafter compared to control mice and the difference in the area of neovascularization is recorded. A contemplated compound typically exhibits about from 25% to about 75% inhibition, whereas the vehicle control exhibits 0% inhibition.

Example 62

In Vitro Aggrecanase Inhibition

Assays for measuring the potency ($IC_{50}$) of a compound toward inhibiting aggrecanase are known in the art.

One such assay, for example, has been reported in European Patent Application Publ. No. EP 1 081 137 A1. In that assay, primary porcine chondrocytes from articular joint cartilage are isolated by sequential trypsin and collagenase digestion followed by collagenase digestion overnight and are plated at $2\times10^5$ cells per well into 48 well plates with 5 $\mu$Ci/ml$^{35}$S (1000 Ci/mmol) sulphur in type 1 collagen coated plates. Cells are allowed to incorporate label into their proteoglycan matrix (approximately 1 week) at 37° C. under an atmosphere of 5% $CO_2$. The night before initiating the assay, chondrocyte monolayers are washed 2 times in DMEM/1% PSF/G and then allowed to incubate in fresh DMEM/1% FBS overnight. The next morning, chondrocytes are washed once in DMEM/1% PSF/G. The final wash is allowed to sit on the plates in the incubator while making dilutions. Media and dilutions are made as described in the following Table C:

TABLE C

| | |
|---|---|
| control media | DMEM alone |
| IL-1 media | DMEM + IL-1 (5 ng/ml) |
| drug dilutions | Make all compound stocks at 10 mM in DMSO. Make a 100 $\mu$M stock of each compound in DMEM in 96-well plate. Store in freezer overnight. The next day, perform serial dilutions in DMEM with IL-1 to 5 $\mu$M, 500 nM, and 50 nM. Aspirate final wash from wells and add 50 $\mu$M of compound from above dilutions to 450 $\mu$L of IL-1 media in appropriate wells of the 48 well plates. Final compound concentrations equal 500 nM, 50 nM, and 5 nM. All samples completed in triplicate with control and IL-1 alone on each plate. |

Plates are labeled and only the interior 24 wells of the plate are used. On one of the plates, several columns are designated as IL-1 (no drug) and control (no IL-1, no drug). These control columns are periodically counted to monitor 35S-proteoglycan release. Control and IL-1 media are added to wells (450 $\mu$L) followed by compound (50 $\mu$L) so as to initiate the assay. Plates are incubated at 37° C. with 5% $CO_2$ atmosphere. At 40–50% release (when CPM from IL-1 media is 4–5 times control media) as assessed by liquid scintillation counting (LSC) of media samples, the assay is terminated (about 9 to about 12 hours). Media is removed from all wells and placed into scintillation tubes. Scintillate is added and radioactive counts are acquired (LSC). To solubilize cell layers, 500 $\mu$L of papain digestion buffer (0.2 M Tris, pH 7.0, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC). The percent of released counts from the total present in each well is determined. Averages of the triplicates are made with control background subtracted from each well. The percent of compound inhibition is based on IL-1 samples as 0% inhibition (100% of total counts).

Another assay for measuring aggrecanase inhibition has been reported in WIPO Int'l Publ. No. WO 00/59874. That assay reportedly uses active aggrecanase accumulated in media from stimulated bovine cartilage (BNC) or related cartilage sources and purified cartilage aggrecan monomer or a fragment thereof as a substrate. Aggrecanase is generated by stimulation of cartilage slices with interleukin-1 (IL-1), tumor necrosis factor alpha (TNF-α), or other stimuli. To accumulate BNC aggrecanase in culture media, cartilage reportedly is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. To decrease the amounts of matrix metalloproteinases released into the media during aggrecanase accumulation, agents which inhibit MMP-1, -2, -3, and -9 biosynthesis are included during stimulation. This BNC conditioned media containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, et al., *Biochem J,* 306:799–804 (1995)). This antibody reportedly recognizes aggrecan fragments with the N-terminus, 374ARGSVIL, generated upon cleavage by aggrecanase. The BC-3 antibody reportedly recognizes this neoepitope only when it is at the N-terminus and not when it is present internally within aggrecan fragments or within the aggrecan protein core. Only products produced upon cleavage by aggrecanase reportedly are detected. Kinetic studies using this assay reportedly yield a Km of 1.5+/−0.35 μM for aggrecanase. To evaluate inhibition of aggrecanase, compounds are prepared as 10 mM stocks in DMSO, water, or other solvents and diluted to appropriate concentrations in water. Drug (50 μL) is added to 50 μL of aggrecanase-containing media and 50 μL of 2 mg/ml aggrecan substrate and brought to a final volume of 200 μL in 0.2 M Tris, pH 7.6, containing 0.4 M NaCl and 40 mM CaCl$_2$. The assay is run for 4 hr at 37° C., quenched with 20 mM EDTA, and analyzed for aggrecanase-generated products. A sample containing enzyme and substrate without drug is included as a positive control and enzyme incubated in the absence of substrate serves as a measure of background. Removal of the glycosaminoglycan side chains from aggrecan reportedly is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 μg GAG) for 2 hr at 37° C. and then with keratanase (0.1 units/10 μg GAG) and keratanase II (0.002 units/10 μg GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 μL of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A compound or salt thereof, wherein: the compound corresponds in structure to Formula 15.1:

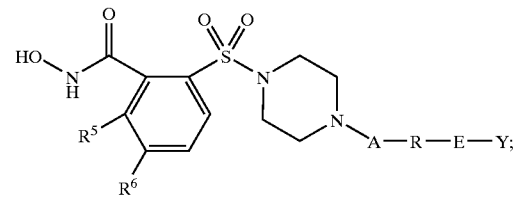

15.1

A is selected from the group consisting of:
a bond,
—O—,
—S—,
—S(O)—,
—S(O)$_2$—,
—N(R$^k$)—,
—C(O)—N(R$^k$)—,
—N(R$^k$)—C(O)—,
—C(O)—O-,
—O—C(O)—,
—O—C(O)—O—,
—C(H)=C(H)—,
—C≡C—,
—N=N—,
—N(H)—N(H)—,
—N(H)—C(O)—N(H)—,
—C(S)—N(R$^k$)—,
—N(R$^k$)—C(S)—,
—C(H)$_2$—,
—O—C(H)$_2$—O—,
—C(H)$_2$—O—,
—S—C(H)$_2$—, and
—C(H)$_2$—S—;

R is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and heterocycloalkylthioalkyl, wherein:
the aryl, heteroaryl, cycloalkyl, or heterocycloalkyl is each optionally and independently substituted with up to two substituents selected from the group consisting of halogen, nitro, hydroxy, amino, alkyl, perfluoroalkyl, trifluoromethylalkyl, hydroxyalkyl, alkoxy, perfluoroalkoxy, perfluoroalkylthio, alkoxycarbonylalkyl, C$_1$-C$_2$-alkylenedioxy, hydroxycarbonylalkyl, hydroxycarbonylalkylamino, alkanoylamino, and alkoxycarbonyl;

E is absent or selected from the group consisting of:
a bond,
—C(O)—,
—C(O)—R$^g$—,
—R$^g$—C(O)—, —C(O)—N(R$^k$)—,
—N(R$^k$)—C(O)—,
—S(O)$_2$—,
—S(O)$_2$—R$^g$—,
—R$^g$—S(O)$_2$—,
—N(R$^k$)—S(O)$_2$—, and
—S(O)$_2$—N(R$^k$)—;

Y is absent when B is absent, or Y is selected from the group consisting of hydrogen, hydroxy, nitrile, nitro, alkyl, haloalkyl, aminoalkyl, alkoxy, perfluoroalkoxy, cycloalkyl, aryl, aralkyl, heteroaryl, aryloxy, aralkoxy, heteroaryloxy, heteroaralkyl, R$^g$-oxyalkyl, perfluoroalkylthio, alkenyl, heterocycloalkyl, and alkoxycarbonyl, wherein:
  the aryl, heteroaryl, or heterocycloalkyl optionally is substituted with up to two substituents independently selected from the group consisting of halogen, nitro, nitrile, alkyl, haloalkyl, alkoxy, and aminoalkanoyl, aralkyl, and aryl, wherein:
    the amino nitrogen optionally is substituted with up to two substituents independently selected from alkyl and aralkyl;

as to R$^5$ and R$^6$:
  R$^5$ and R$^6$ are not both hydrogen, and are independently selected from the group consisting of hydrogen, halogen, nitro, hydroxy, cyano, alkyl, haloalkyl, hydroxyalkyl, acylalkyl, cycloalkyl, alkoxy, haloalkoxy, and N(R$^b$)(R$^c$)-alkyl, or
  R$^5$ and R$^6$, together with the atoms to which they are bonded, form a 5 or 6 membered alkylene dioxy ring;

R$^b$ and R$^c$ are independently selected from the group consisting of hydrogen, alkyl, haloalkyl, carboxyalkyl, hydroxyalkyl, aminoalkyl, alkenyl, alkynyl, alkoxyalkyl, bisalkoxyalkyl, perfluoroalkoxyalkyl, alkanoyl, haloalkanoyl, hydroxyalkanoyl, thioalkanoyl, alkoxycarbonyl, alkoxycarbonylalkyl, aminocarbonyl, alkyliminocarbonyl, cycloalkyl, cycloalkylalkyl, aryl, arylalkyl, aryloxyalkyl, aryloxycarbonyl, arylsulfonyl, aralkanoyl, aroyl, aryliminocarbonyl, heterocyclo, heterocycloalkyl, heterocycloalkyl-carbonyl, heteroaryl, heteroaryloxyalkyl, heteroarylalkoxyalkyl, heteroarylthioalkyl, alkylsulfonyl, heteroarylsulfonyl, heterocycloiminocarbonyl, arylthioalkyl, alkylthioalkyl, arylthioalkenyl, alkylthioalkenyl, heteroarylalkyl, aminoalkylcarbonyl, aminosulfonyl, and aminoalkylsulfonyl, wherein any amino nitrogen of R$^b$ or R$^c$ is:
  unsubstituted,
  substituted with 1 or 2 R$^d$ substituents, or
  substituted with substituents such that the substituents, taken together with the amino nitrogen, form either:
    a saturated or partially saturated heterocyclo optionally substituted with up to three R$^d$ substituents, or
    a heteroaryl optionally substituted with up to three R$^f$ substituents;

each R$^d$ and R$^e$ is independently selected from the group consisting of hydrogen, alkyl, alkenyl, arylalkyl, aryl, alkanoyl, aroyl, arylalkylcarbonyl, alkoxycarbonyl, and arylalkoxycarbonyl;

each R$^f$ is independently selected from the group consisting of halogen, cyano, nitro, hydroxy, alkyl, alkoxy, aryl, and —N(R$^d$)(R$^e$);

R$^g$ is selected from the group consisting of hydrogen, halogen, hydroxy, cyano, amino, carboxy, alkyl, perfluoroalkyl, trifluoroalkyl, alkenyl, alkenyloxy, alkynyl, alkynyloxy, aldehydo, alkoxy, alkoxyalkyl, alkoxycarbonyl, alkanoyl, alkylthio, cycloalkyl, cycloalkenyl, aryl, heteroaryl, heterocyclo, aroyl, heteroaroyl, aryloxy, heteroaryloxy, alkoxyaryl, alkoxyheteroaryl, alkylenedioxy, aryloxyalkyl, arylthio, alkoxycarbonyloxy, aryloxycarbonyl, arylalkoxycarbonyl, arylalkoxycarbonylamino, aryloxycarbonyloxy, —N(R$^h$)(R$^i$), N(R$^h$)(R$^i$)-carbonyloxy, N(R$^h$)(R$^i$)-carbonyl, N(R$^h$)(R$^i$)-alkanoyl, hydroxyaminocarbonyl, —N(R$^h$)(R$^i$)-sulfonyl, N(R$^h$)(R$^i$)-carbonyl-N(R$^h$)—, trifluoromethylsulfonyl-N(R$^h$)—, heteroarylsulfonyl-N(R$^h$)—, arylsulfonyl-N(R$^h$)—, arylsulfonyl-N(R$^h$)-carbonyl, alkylsulfonyl-N(R$^h$)—, arylcarbonyl-N(R$^h$)-sulfonyl, and alkylsulfonyl-N(R$^h$)-carbonyl;

each R$^h$ is independently selected from the group consisting of alkyl, haloalkyl, hydroxyalkyl, carboxyalkyl, unsubstituted aminoalkyl, substituted aminoalkyl, alkenyl, alkynyl, alkoxyalkyl, alkoxycarbonyl, arylalkyl, alkanoyl, haloalkanoyl, unsubstituted aminoalkanoyl, substituted aminoalkanoyl, aryl, arylalkoxycarbonyl, aroyl, heteroaryl, and heterocyclo, wherein: each such group (including the substituents of any substituted amino alkyl or aminoalkanoyl) optionally is substituted by up to two R$^j$ substituents R$^1$ is selected from the group consisting of alkyl, haloalkyl, hydroxyalkyl, carboxyalkyl, unsubstituted aminoalkyl, substituted aminoalkyl, alkoxyalkyl, alkoxycarbonyl, alkenyl, alkynyl, alkanoyl, haloalkanoyl, unsubstituted aminoalkanoyl, substituted aminoalkanoyl, aryl, arylalkyl, arylalkoxycarbonyl, aroyl, heteroaryl, and heterocyclo, wherein:
  each R$^i$ group may be optionally and independently substituted with up to two R$^j$ substituents;

each R$^j$ is independently selected from the group consisting of alkyl, haloalkyl, hydroxyalkyl, carboxyalkyl, unsubstituted aminoalkyl, substituted aminoalkyl, alkenyl, alkynyl, alkoxyalkyl, alkoxycarbonyl, alkanoyl, haloalkanoyl, unsubstituted aminoalkanoyl, substituted aminoalkanoyl, aryl, arylalkyl, arylalkoxycarbonyl, aroyl, heteroaryl, and heterocyclo, wherein: the substituents of the substituted aminoalkyl or substituted aminoalkanoyl are independently selected from the group consisting of alkyl, alkenyl, alkoxycarbonyl, aryl, arylalkyl, aryloxycarbonyl, heteroaryl, and heteroarylalkyl; and R$^k$ is selected from the group consisting of hydrogen, alkyl, alkenyl, alkoxycarbonyl, aryl, arylalkyl, aryloxycarbonyl, heteroaryl, heteroarylalkyl, N(R$^c$)(R$^d$)-carbonyl, N(R$^c$)(R$^d$)-sulfonyl, N(R$^c$)(R$^d$)-alkanoyl, and N(R$^c$)(R$^d$)-alkylsulfonyl.

2. A compound or salt thereof according to claim 1, wherein:
Y is absent or selected from the group consisting of hydrogen, hydroxy, nitrile, nitro, alkyl, aminoalkyl, alkoxy, perfluoroalkoxy, cycloalkyl, aryl, aralkyl, heteroaryl, aryloxy, aralkoxy, heteroaryloxy, heteroaralkyl, perfluoroalkylthio, alkenyl, heterocycloalkyl, and alkoxycarbonyl, wherein:
  the aryl, heteroaryl, or heterocycloalkyl optionally is substituted with 1 or 2 substituents independently selected from the group consisting of halogen, nitro, nitrile, alkyl, perfluoroalkyl, alkoxy, amino, alkanoyl, aralkyl, and aryl, wherein:

the amino nitrogen optionally is substituted with 1 or 2 substituents independently selected from alkyl and aralkyl; and $R^b$ and $R^c$ are independently selected from the group consisting of hydrogen, alkyl, perfluoroalkyl, trifluoromethylalkyl, carboxyalkyl, hydroxyalkyl, aminoalkyl, alkenyl, alkynyl, alkoxyalkyl, bisalkoxyalkyl, perfluoroalkoxyalkyl, alkanoyl, haloalkanoyl, hydroxyalkanoyl, thiolalkanoyl, alkoxycarbonyl, alkoxycarbonylalkyl, aminocarbonyl, alkyliminocarbonyl, cycloalkyl, cycloalkylalkyl, aryl, arylalkyl, aryloxyalkyl, aryloxycarbonyl, arylsulfonyl, aralkanoyl, aroyl, aryliminocarbonyl, heterocyclo, heterocycloalkyl, heterocycloalkylcarbonyl, heteroaryl, heteroaryloxyalkyl, heteroarylalkoxyalkyl, heteroarylthioalkyl, alkylsulfonyl, heteroarylsulfonyl, heterocycloiminocarbonyl, arylthioalkyl, alkylthioalkyl, arylthioalkenyl, alkylthioalkenyl, heteroarylalkyl, aminoalkylcarbonyl, aminosulfonyl, and aminoalkylsulfonyl, wherein any amino nitrogen of $R^b$ or $R^c$ is:

unsubstituted, substituted with 1 or 2 $R^d$ substituents, or substituted with substituents such that the substituents, taken together with the amino nitrogen, form either:
a saturated or partially saturated heterocyclo optionally substituted with 1, 2, or 3 $R^d$ substituents, or
a heteroaryl optionally substituted with 1, 2, or 3 $R^f$ substituents.

3. A compound or salt thereof according to claim 1, wherein $R^5$ and $R^6$, together with the atoms to which they are bonded, form a 5 or 6 membered alkylene dioxy ring.

4. A compound or salt thereof according to claim 1, wherein $R^5$ and $R^6$ are not both hydrogen, and are independently selected from the group consisting of hydrogen, halogen, nitro, hydroxy, cyano, alkyl, haloalkyl, hydroxyalkyl, acylalkyl, cycloalkyl, alkoxy, haloalkoxy, and $N(R^b)(R^c)$-alkyl.

5. A compound or salt thereof according to claim 4, wherein $R^5$ and $R^6$ are hydrogen.

6. A compound or salt thereof according to claim 4, wherein $R^6$ is hydrogen.

7. A compound or salt thereof according to claim 6, wherein $R^5$ is selected from the group consisting of halogen, nitro, hydroxy, cyano, alkyl, haloalkyl, hydroxyalkyl, acyl alkyl, cycloalkyl, alkoxy, haloalkoxy, and $N(R^b)(R^c)$-alkyl.

8. A compound or salt thereof according to claim 4, wherein $R^5$ and $R^6$ are independently selected from the group consisting of halogen, nitro, hydroxy, cyano, alkyl, haloalkyl, hydroxyalkyl, acylalkyl, cycloalkyl, alkoxy, haloalkoxy, and $N(R^b)(R^c)$-alkyl.

9. A compound or salt thereof according to claim 8, wherein R is phenyl optionally substituted with 1 or 2 substituents selected from the group consisting of halogen, nitro, hydroxy, amino, alkyl, perfluoroalkyl, trifluoromethylalkyl, hydroxyalkyl, alkoxy, perfluoroalkoxy, perfluoroalkylthio, alkoxycarbonylalkyl, $C_1$–$C_2$-alkylenedioxy, hydroxycarbonylalkyl, hydroxycarbonylalkylamino, alkanoylamino, and alkoxycarbonyl.

10. A compound or salt thereof according to claim 9, wherein $R^5$ and $R^6$ are alkoxy.

11. A compound or salt thereof according to claim 10, wherein $R^5$ and $R^6$ are methoxy.

12. A compound or salt thereof according to claim 11, wherein the compound corresponds in structure to Formula 0.1:

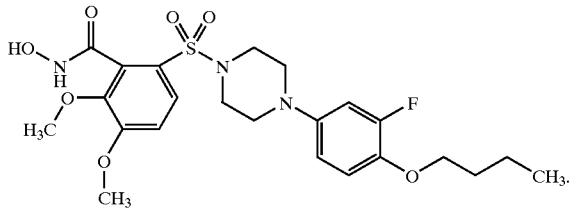

13. A compound or salt thereof according to claim 11, wherein the compound corresponds in structure to Formula 0.1:

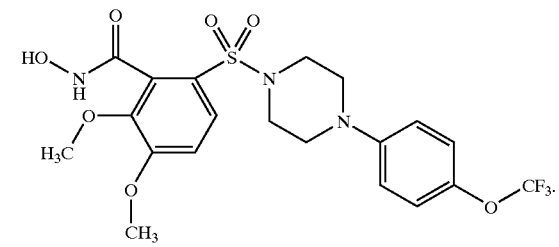

14. A process for treating a pathalogical condition treatable by the inhibition of matrix metalloprotease activity in an animal, wherein:

the process comprises administering a compound described in claim 1 or a pharmaceutically acceptable salt thereof to the animal in an amount effective to treat the condition; and the condition is selected from the group consisting of tissue destruction, a fibrotic disease, matrix weakening, defective injury repair, a cardiovascular disease, a pulmonary disease, a central nervous system disease, and cancer.

15. A process according to claim 14, wherein:

$R^5$ and $R^6$ are not both hydrogen, and are independently selected from the group consisting of hydrogen, halogen, nitro, hydroxy, cyano, alkyl, haloalkyl, hydroxyalkyl, acylalkyl, cycloalkyl, alkoxy, haloalkoxy, and $N(R^b)(R^c)$-alkyl, or $R^5$ and $R^6$, together with the atoms to which they are bonded, form a 5 or 6 membered alkylene dioxy ring.

16. A process according to claim 15, wherein the condition is selected from the group consisting of osteoarthritis, rheumatoid arthritis, septic arthritis, tumor invasion, tumor metastasis, tumor angiogenesis, a gastric ulcer, a corneal ulcer, periodontal disease, multiple sclerosis, weak injury repair, an adhesion, scarring, congestive heart failure, coronary thrombosis, emphysema, proteinuria, and Alzheimer's disease.

17. A process according to claim 15, wherein the condition is selected from the group consisting of a decubitis ulcer, fibrotic lung disease, otosclerosis, atherosclerosis, dilated cardiomyopathy, epidermolysis bullosa, and aortic aneurysm.

18. A process according to claim 15, wherein the compound corresponds in structure to a formula selected from the group consisting of:

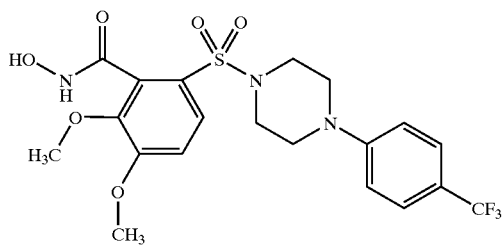

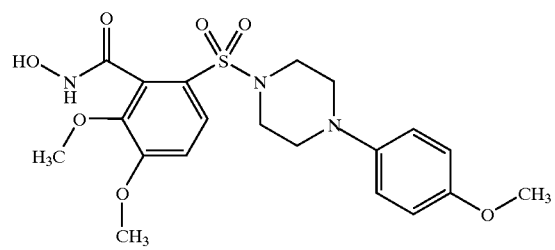

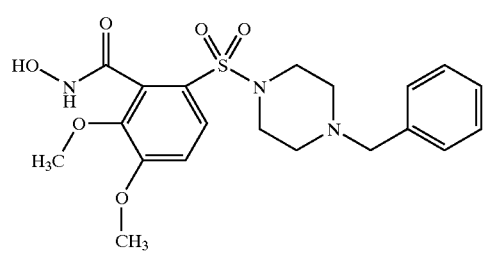

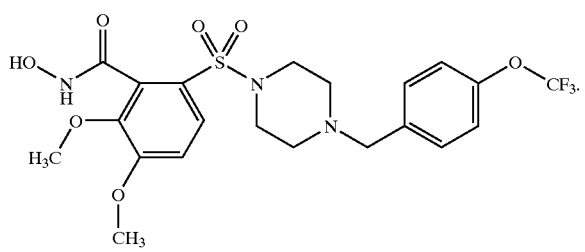

19. A process according to claim 15, wherein the compound corresponds in structure to a formula selected from the group consisting of:

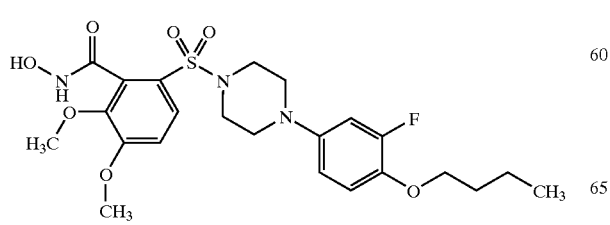

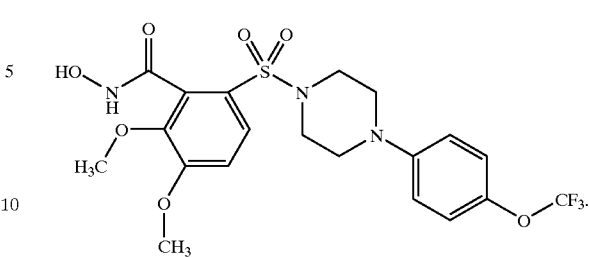

20. A process for treating a kidney or liver disease in an animal, wherein the process comprises administering a compound described in claim 1, or a pharmaceutically acceptable salt thereof to the animal in an amount effective to prevent or treat the disease.

21. A process according to claim 20, wherein the disease comprises liver cirrhosis.

22. A process according to claim 20, wherein the compound corresponds in structure to a formula selected from the group consisting of:

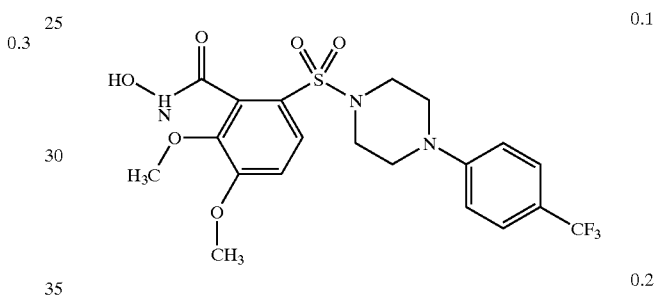

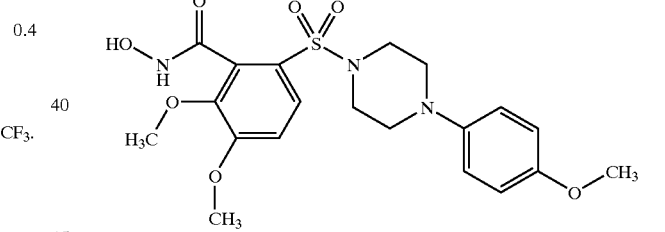

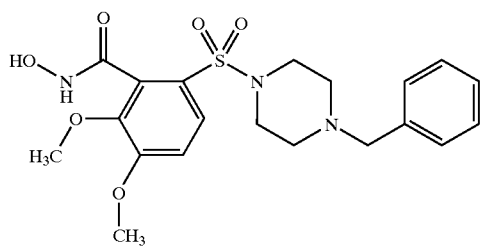

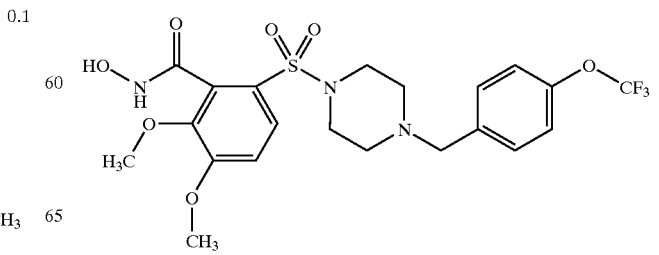

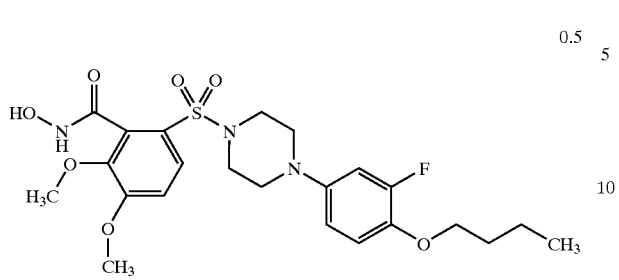

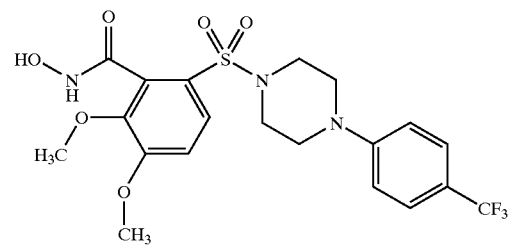

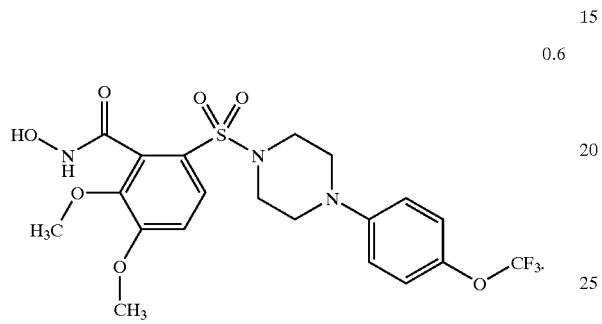

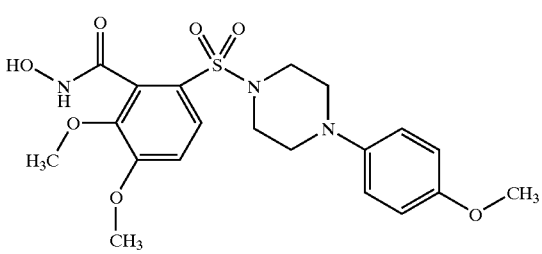

23. A process for treating a pathalogical condition treatable by the inhibition of matrix metalloprotease activity in an animal, the process comprising administering a compound described in claim 1 for a pharmaceutically-acceptable salt thereof to the animal in an amount effective to inhibit matrix metalloprotease-2, matrix metalloprotease-9, and/or matrix metalloprotease-13.

24. A process according to claim 23, wherein:

$R^5$ and $R^6$ are independently selected from the group consisting of hydrogen, halogen, nitro, hydroxy, cyano, alkyl, haloalkyl, hydroxyalkyl, acylalkyl, cycloalkyl, alkoxy, haloalkoxy, and $N(R^b)(R^c)$-alkyl, or $R^5$ and $R^6$, together with the atoms to which they are bonded, form a 5 or 6 membered alkylene dioxy ring.

25. A process according to claim 24, wherein matrix metalloprotease-2, matrix metalloprotease-9, or matrix metalloprotease-13 is inhibited selectively over matrix metalloprotease-1 or matrix metalloprotease-14.

26. A process according to claim 25, wherein matrix metalloprotease-2, matrix metalloprotease-9, or matrix metalloprotease-13 is inhibited selectively over matrix metalloprotease-1 and matrix metalloprotease-14.

27. A process according to claim 25, wherein matrix metalloprotease-2 is inhibited selectively over matrix metalloprotease-1 and matrix metalloprotease-14.

28. A process according to claim 26, wherein matrix metalloprotease-9 is inhibited selectively over matrix metalloprotease-1 and matrix metalloprotease-14.

29. A process according to claim 26, wherein matrix metalloprotease-13 is inhibited selectively over matrix metalloprotease-1 and matrix metalloprotease-14.

30. A process according to claim 24, wherein the compound corresponds in structure to a formula selected from the group consisting of:

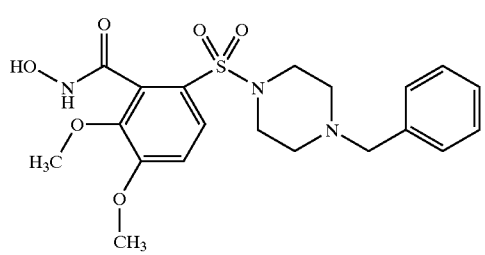

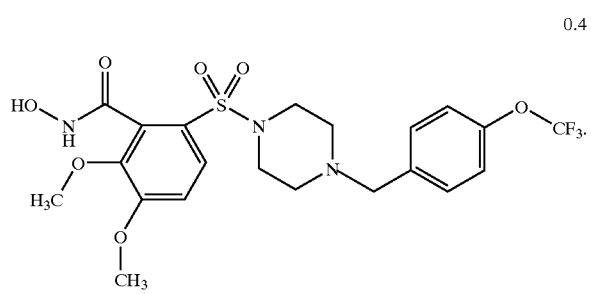

31. A process according to claim 25, wherein the compound corresponds in structure to a formula selected from the group consisting of:

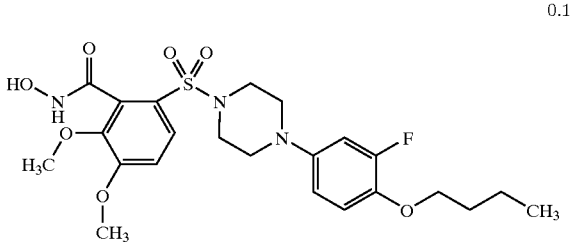

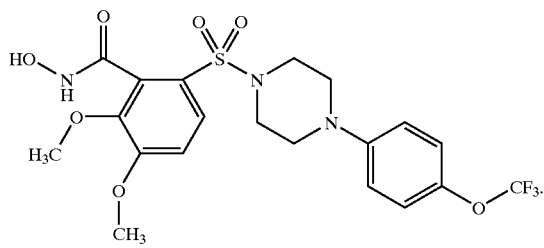

0.2

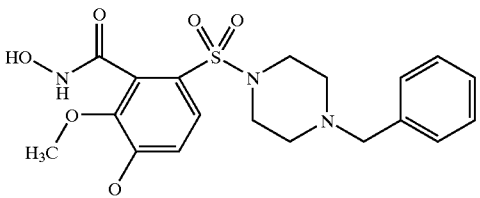

0.3

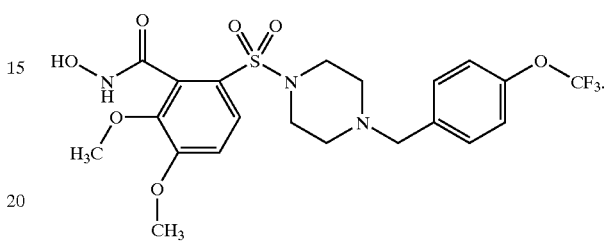

0.4

32. A process for treating a pathalogical condition treatable by the inhibition of TNF-α activity in an animal, wherein the process comprises administering a compound described in claim 1 or a pharmaceutically-acceptable salt thereof to the animal in an amount effective to treat the condition.

33. A process according to claim 32, wherein:

R⁵ and R⁶ are not both hydrogen, and are independently selected from the group consisting of hydrogen, halogen, nitro, hydroxy, cyano, alkyl, haloalkyl, hydroxyalkyl, acylalkyl, cycloalkyl, alkoxy, haloalkoxy, and N(R^b)(R^c)-alkyl, or R⁵ and R⁶, together with the atoms to which they are bonded, form a 5 or 6 membered alkylene dioxy ring.

34. A process according to claim 33, wherein the condition is selected from the group consisting of inflammation, a pulmonary disease, a cardiovascular disease, an autoimmune disease, graft rejection, a fibrotic disease, cancer, an infectious disease, fever, psoriasis, hemorrhage, coagulation, radiation damage, acute-phase responses of shock and sepsis, anorexia, and cachexia.

35. A process according to claim 33, wherein the compound corresponds in structure to a formula selected from the group consisting of:

36. A process according to claim 33, wherein the compound corresponds in structure to a formula selected from the group consisting of:

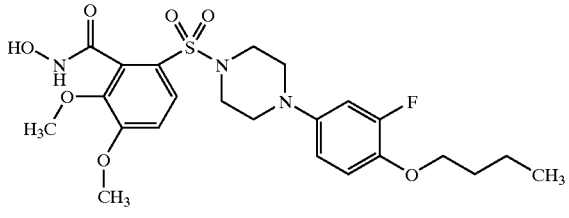

0.1

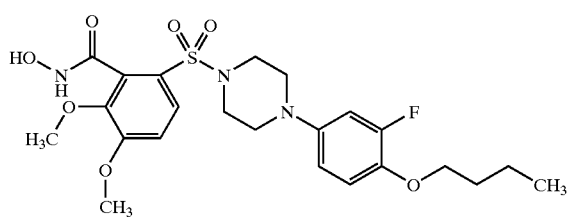

0.1

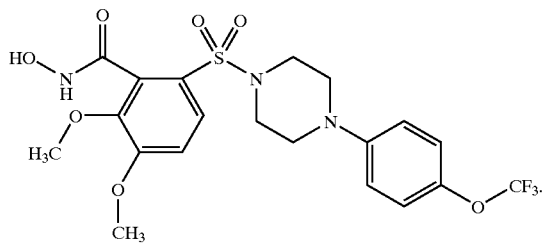

0.2

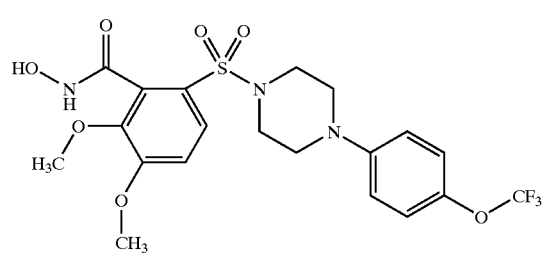

0.2

37. A process for treating osteoarthritis in an animal, wherein the process comprises administering a compound described in claim 1 or a pharmaceutically acceptable salt thereof to the animal in an amount effective to treat osteoarthritis.

38. A process according to claim 37, wherein the compound corresponds in structure to a formula selected from the group consisting of:

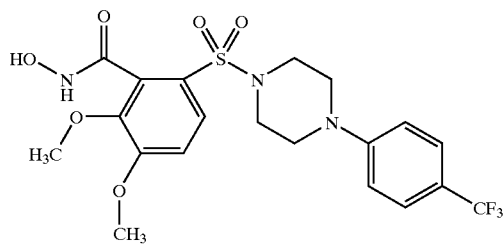
61.1
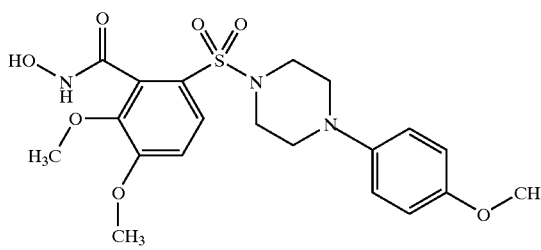
61.2
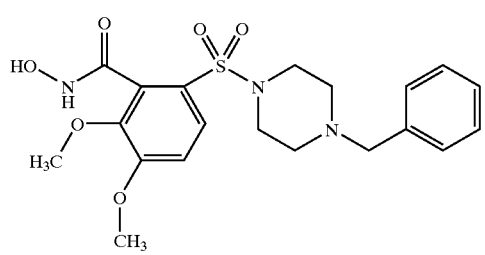
61.3
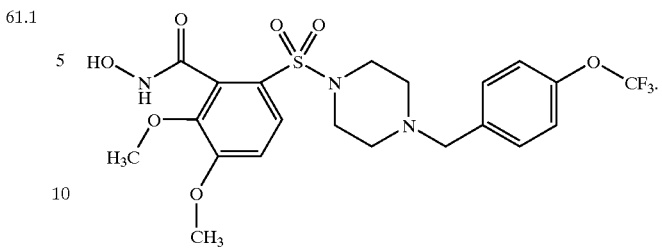
61.4
39. A process according to claim 37, wherein the compound corresponds in structure to a formula selected from the group consisting of:
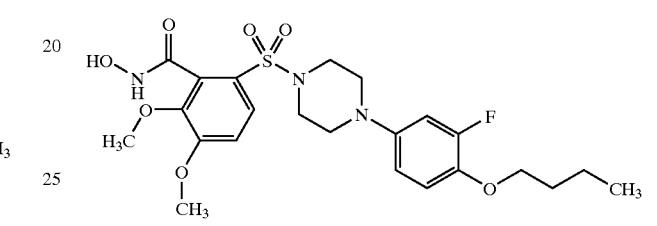
62.1
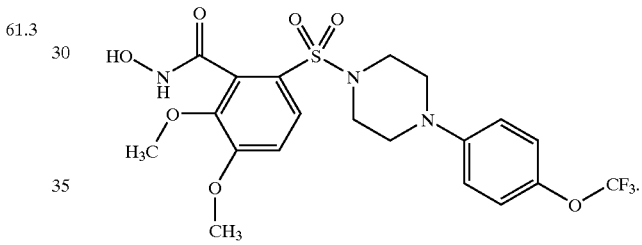
62.2
* * * * *